US006960651B2

(12) United States Patent
Kirst et al.

(10) Patent No.: US 6,960,651 B2
(45) Date of Patent: Nov. 1, 2005

(54) TANGO 332 POLYPEPTIDES

(75) Inventors: Susan J. Kirst, Brookline, MA (US); Douglas A. Holtzman, Jamaica Plain, MA (US); Christopher C. Fraser, Lexington, MA (US); John D. Sharp, Arlington, MA (US); Thomas S. Barnes, Boston, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 143 days.

(21) Appl. No.: 10/188,495

(22) Filed: Jul. 2, 2002

(65) Prior Publication Data

US 2003/0175733 A1 Sep. 18, 2003

Related U.S. Application Data

(60) Division of application No. 09/596,194, filed on Jun. 16, 2000, now abandoned, which is a continuation-in-part of application No. 09/342,364, filed on Jun. 29, 1999, now abandoned.

(51) Int. Cl.[7] ........................ A61K 38/00; A61K 39/00
(52) U.S. Cl. .......................... 530/350; 530/300; 514/2; 514/8; 424/278.1; 424/192.1; 435/69.7; 435/440; 536/23.1
(58) Field of Search ......................... 514/2, 8; 530/300, 530/350; 536/23.1, 23.4; 435/69.7, 440, 320.1; 424/278.1, 192.1

(56) References Cited

U.S. PATENT DOCUMENTS 5,635,370 A 6/1997 Hockfield et al.

FOREIGN PATENT DOCUMENTS

| | | | |
|---|---|---|---|
| WO | WO 95/26201 | | 10/1995 |
| WO | WO 95/27785 | A1 | 10/1995 |
| WO | WO 98/52590 | * | 11/1996 |
| WO | WO 98/31800 | A3 | 7/1998 |
| WO | WO 98/39446 | A3 | 9/1998 |
| WO | WO 99/06554 | A3 | 2/1999 |
| WO | WO 99/14327 | A3 | 3/1999 |
| WO | WO 99/14328 | A3 | 3/1999 |
| WO | WO 00/05367 | A3 | 2/2000 |
| WO | WO 00/75317 | A2 | 12/2000 |

OTHER PUBLICATIONS

Yamada, H. et al. (1994) Molecular cloning of brevican, a novel brain proteoglycan of the aggrecan/versican family. J. Biol. Chem. vol. 269, pp. 10119–10126.*

Better, et al., "*Escherichia coli* Secretion of an Active Chimeric Antibody Fragment," Science, 240:1041–43 (May 20, 1988).

Houghten, et al., "The Use of Synthetic Peptide Combinatorial Libraries for the Identification of Bioactive Peptides," Bio Techniques, 13:412–21 (1992).

Inagaki, et al., "Identification of a member of mouse semaphoring family," FEBS Lett., 370:269–72 (1995).

Itoh; et al., "Cloning and expressions of three mammalian homologues of *Drosophila slit* suggest possible roles for *Slit* in the formation and maintenance of the nervous system," Molecular Brain Research, 62:175–86 (1998).

Kohler, et al., "Continuous cultures of fused cells secreting antibody of predefined specificity," Nature, 256:495–7 (1975).

Kulman, et al., "Primary structure and tissue distribution of two novel proline–rich •–carboxyglutamic acid proteins," Proc. Natl. Acad. Sci. USA, 94–9058–62 (Aug., 1997).

Liu, et al., "Chimeric mouse–human IgG1 antibody that can mediate lysis of cancer cells," Proc. Natl. Acad. Sci. USA, 84:3439–43 (May, 1987).

Liu, et al., Production of a Mouse–Human Chimeric Monoclonal Antibody to CD20 with Potent Fc–Dependent Biologic Activity, J. Immunol., 139:3521–6 (Nov. 15, 1987).

Miura, et al., "The Proteoglycan Lectin Domain Binds Sulfated Cell Surface Glycolipids and Promotes Cell Adhesion," J. Biol. Chem., 274:11431–8 (Apr. 16, 1999).

Nishimura, et al., "Recombinant Human–Mouse Chimeric Monoclonal Antibody Specific for Common Acute Lymphocytic Leukemia Antigen," Cancer Res., 47:999–1005 (Feb. 15, 1987).

Shaw, et al., "Mouse/Human Chimeric Antibodies to a Tumor–Associated Antigen: Biologic Acitivity of the Four Human IgG Subclasses," J. Natl. Cancer Inst., 80:1553–9 (Dec. 7, 1988).

Sun, et al., "Chimeric antibody with human constant regions and mouse variable regions directed against carcinoma–associated antigen 17–1A," Proc. Natl. Acad. Sci. USA, 84:214–18 (Jan., 1987).

(Continued)

*Primary Examiner*—Karen Cochrane Carlson
*Assistant Examiner*—Samuel W. Liu
(74) *Attorney, Agent, or Firm*—Millennium Pharmaceuticals Inc.

(57) ABSTRACT

The invention provides isolated nucleic acids encoding a variety of proteins and nucleic acids having diagnostic, preventive, therapeutic, and other uses. These nucleic acids and proteins are useful for diagnosis, prevention, and therapy of a number of human and other animal disorders. The invention also provides antisense nucleic acid molecules, expression vectors containing the nucleic acid molecules of the invention, host cells into which the expression vectors have been introduced, and non-human transgenic animals in which a nucleic acid molecule of the invention has been introduced or disrupted. The invention still further provides isolated polypeptides, fusion polypeptides, antigenic peptides and antibodies. Diagnostic, screening, and therapeutic methods utilizing compositions of the invention are also provided. The nucleic acids and polypeptides of the present invention are useful as modulating agents in regulating a variety of cellular processes.

15 Claims, 109 Drawing Sheets

OTHER PUBLICATIONS

Wood, et al., "The synthesis and in vivo assembly of functional antibodies in yeast," Nature, 314:446–9 (Apr., 1985).

Zhang, et al., "Expression of a Cleaved Brain–Specific Extracellular Matrix Protein Mediates Glioma Cell Invasion In Vivo," J. Neurosci., 18:2370–6 (Apr. 1, 1998).

Hofsteenge., et al., "Ribonuclease Inhibitor," created Jul. 1, 1989 (sequence) GenPept [online] Bethesda, MD, USA: National Center for Biotechnology Information [retrieved on Feb. 9, 2000]. Retrieved from the Internet: URL: http://www.ncbi.nlm.nih.gov/>. Swiss Prot Accession No. P10775.

Chen, et al., "Cricetulus griseus HT protein mRNA, complete cds," Mar. 7, 1996 (sequence) GenBank [online] Bethesda, MD, USA: National Center for Biotechnology Information [retrieved on Feb. 9, 2000]. Retrieved from the Internet: URL: http://www.ncbi.nlm.nih.gov/>. GenBank Accession No. U48852.

Giordano, et al., "Hepatocyte Growth Factor Receptor Precursor (Met Proto–Oncogene Tyrosine Kinase) (HGF–SF Receptor)," created Aug. 1, 1988 (sequence) GenPept [online] Bethesda, MD, USA: National Center for Biotechnology Information [retrieved on Feb. 9, 2000]. Retrieved from the Internet: URL: http://www.ncbi.nlm.nih.gov/>. Swiss Prot Accession No. P08581.

Maestrini, et al., "Plexin 4 Precursor (Transmembrane Protein Sex)," created Oct. 1, 1996 (sequence) GenPept [online] Bethesda, MD, USA: National Center for Biotechnology Information [retrieved on Feb. 9, 2000]. Retrieved from the Internet: URL: http://www.ncbi.nlm.nih.gov/>. Swiss Prot Accession No. P51805.

Inagaki, et al., "M–Sema F=a factor in neural network development [mice, neonatal brain, mRNA, 3503 nt]," Dec. 9, 1995 (sequence) GenBank [online] Bethesda, MD, USA: National Center for Biotechnology Information [retrieved on Feb. 9, 2000]. Retrieved from the Internet: URL: http://www.ncbi.nlm.nih.gov/>. GenBank Accession No. S79463.

Itoh., et al, "Homo sapiens mRNA for Slit–1 protein, complete cds," Feb. 6, 1999 (sequence) GenBank [online] Bethesda, MD, USA: National Center for Biotechnology Information [retrieved on Feb. 9, 2000]. Retrieved from the Internet: URL: http://www.ncbi.nlm.nih.gov/>. GenBank Accession No. AB017167.

Kitani, et al., "Efficiency of neural differentiation of mouse P19 embryonal carcinoma cells is dependent on the seeding density," Cell Transplant, 6(5):521–5 (1997)

Agrawal and Brauer, "Urokinase–type plasminogen activator regulates cranial neural cell migration in vitro," Dev Dyn., 207(3) (abstract only) (1996).

Goodman, et al., "Modulation of N–myc expression alters the invasiveness of neuroblastoma," Clin Exp Metastasis, 15(2) (abstract only) (1997).

* cited by examiner

```
GTCGACCCACGCGTCCGGGGAGCGCGGCTAAGAGTGCCGCACCGCCTCACAACCTGGGAACCGGAGAGTAGGGGCCGTC   79

GGCTGGCAAGAACCCGCCGTGCCTCCTCGGCAAGGGCCATCCGGTGCCACCCATGTCGCACTAGAGCAGAAGAGGGTGA  158

                                                      M   T   W   L   V           5
GTCCTGAACTGCAACCTGCACAGAGCTGCTCTGTACTGTCCCTGGTGGTCGCCGCC ATG ACC TGG TTG GTG     229

 L   L   G   T   L   L   C   M   L   R   V   G   L   G   T   P   D   S   E   G    25
CTG CTG GGG ACA CTG CTC TGC ATG CTG CGC GTT GGG TTA GGC ACC CCG GAC TCC GAG GGT  289

 F   P   P   R   A   L   H   N   C   P   Y   K   C   I   C   A   A   D   L   L    45
TTC CCG CCC CGT GCG CTC CAC AAC TGC CCC TAC AAA TGT ATC TGC GCT GCC GAC CTG CTA  349

 S   C   T   G   L   G   L   Q   D   V   P   A   E   L   P   A   A   T   A   D    65
AGC TGC ACT GGC CTA GGG CTG CAG GAC GTG CCA GCC GAG TTA CCT GCC GCT ACT GCG GAC  409

 L   D   L   S   H   N   A   L   Q   R   L   R   P   G   W   L   A   P   L   F    85
CTC GAC CTG AGC CAC AAC GCG CTC CAG CGC CTG CGC CCC GGC TGG TTG GCG CCC CTC TTC  469

 Q   L   R   A   L   H   L   D   H   N   E   L   D   A   L   G   R   G   V   F   105
CAG CTG CGC GCC CTG CAC CTA GAC CAC AAC GAA CTA GAT GCG CTG GGT CGC GGC GTC TTC  529

 V   N   A   S   G   L   R   L   L   D   L   S   S   N   T   L   R   A   L   G   125
GTC AAC GCC AGC GGC CTG AGG CTG CTC GAT CTA TCA TCT AAC ACG TTG CGG GCG CTT GGC  589
```

Fig. 1A

```
R   H   D   L   D   G   L   G   A   L   E   K   L   L   L   F   N   N   R   L    145
CGC CAC GAC CTC GAC GGG CTG GGG GCG CTG GAG AAG CTG CTT CTG TTC AAT AAC CGC TTG  649

V   H   L   D   E   H   A   F   H   G   L   R   A   L   S   H   L   Y   L   G    165
GTG CAC TTG GAC GAG CAT GCC TTC CAC GGC CTG CGC GCG CTC AGC CAT CTC TAC CTG GGC  709

C   N   E   L   A   S   F   S   F   D   H   L   H   G   L   S   A   T   H   L    185
TGC AAC GAA CTC GCC TCG TTC TCC TTC GAC CAC CTG CAC GGT CTG AGC GCC ACC CAC CTG  769

L   T   L   D   L   S   S   N   R   L   G   H   I   S   V   P   E   L   A   A    205
CTT ACT CTG GAC CTC TCC TCC AAC CGG CTG GGA CAC ATC TCC GTA CCT GAG CTG GCC GCG  829

L   P   A   F   L   K   N   G   L   Y   L   H   N   N   P   L   P   C   D   C    225
CTG CCG GCC TTC CTC AAG AAC GGC CTC TAC TTG CAC AAC AAC CCT TTG CCT TGC GAC TGC  889

R   L   Y   H   L   L   Q   R   W   H   Q   R   G   L   S   A   V   R   D   F    245
CGC CTC TAC CAC CTG CTA CAG CGC TGG CAC CAG CGG GGC CTG AGC GCC GTG CGC GAC TTT  949

A   R   E   Y   V   C   L   A   F   K   V   P   A   S   R   V   R   F   F   Q    265
GCG CGC GAG TAC GTA TGC TTG GCC TTC AAG GTA CCC GCG TCC CGC GTG CGC TTC TTC CAG 1009

H   S   R   V   F   E   N   C   S   S   A   P   A   L   G   L   K   R   P   E    285
CAC AGC CGC GTC TTT GAG AAC TGC TCG TCG GCC CCA GCT CTT GGC CTA AAG CGG CCG GAA 1069
```

Fig. 1B

```
 E   H   L   Y   A   L   V   G   R   S   L   R   L   Y   C   N   T   S   V   P   305
GAG CAC CTG TAC GCG CTG GTG GGT CGG TCC CTG AGG CTT TAC TGC AAC ACC AGC GTC CCG 1129

 A   M   R   I   A   W   V   S   P   Q   Q   E   L   L   R   A   P   G   S   R   325
GCC ATG CGC ATT GCC TGG GTT TCG CCG CAG CAG GAG CTT CTC AGG GCG CCA GGA TCC CGC 1189

 D   G   S   I   A   V   L   A   D   G   S   L   A   I   G   N   V   Q   E   Q   345
GAT GGC AGC ATC GCG GTG CTG GCC GAC GGC AGC TTG GCC ATA GGC AAC GTA CAG GAG CAG 1249

 H   A   G   L   F   V   C   L   A   T   G   P   R   L   H   H   N   Q   T   H   365
CAT GCG GGA CTC TTC GTG TGC CTG GCC ACT GGG CCC CGC CTG CAC CAC AAC CAG ACG CAC 1309

 E   Y   N   V   S   V   H   F   P   R   P   E   P   E   A   F   N   T   G   F   385
GAG TAC AAC GTG AGC GTG CAC TTT CCG CGC CCA GAG CCC GAG GCT TTC AAC ACA GGC TTC 1369

 T   T   L   L   G   C   A   V   G   L   V   L   V   L   L   Y   L   F   A   P   405
ACC ACA CTG CTG GGC TGT GCC GTG GGC CTT GTG CTC GTG CTG CTC TAC CTG TTC GCC CCA 1429

 P   C   R   C   C   R   R   A   C   P   L   P   P   L   A   P   N   T   Q   P   425
CCC TGC CGC TGC TGC CGC CGT GCC TGC CCG CTG CCG CCG CTG GCC CCA AAC ACC CAG CCC 1489

 A   P   R   A   E   P   H   K   S   S   V   L   S   T   T   P   P   D   A   P   445
GCT CCA AGA GCT GAG CCG CAC AAG TCC TCA GTA CTC AGC ACC ACA CCG CCA GAC GCA CCC 1549
```

Fig. 1C

```
 S   P   Q   G   Q   A   S   T   S   T   *                                     456
AGC CCG CAA GGC CAA GCG TCC ACA AGC ACG TAG                                   1582

TCTTTCTGGAGCCAGGCCGGAGGGGCCTCAATGGCCCGCGTGCAGCTGGCAGTAGCTGAGGAATTCGATCTCTACAACC 1661

CTGGAGGCCTGCAGCTGAAGGCTGGCTCTGAGTCCGCCAGCTCCATAGGCTCCGAGGGTCCCATGACAACCTAGACTGC 1740

CAGGGCTCCCCCACCCAGGCCCCCACCCTCTTGCTGCTCGCCCTGCTCCCTGCTTCGGTCCAGAGAACTGGCAGATACT 1819

GGTGGGAAGCACTGTGCCTGGCCCCCCAGCTTCCTGTATGGGCCTCGAAACACAATGGGCCTTCTCGCTCACTGGTAGA 1898

GACAGGGGTTGTGGTCCCCAACCTGCCTTCTGCTCTGCCCCTGCACAGGACCCAAAGGCCCCAGGCCCTGCAAGGTGTG 1977

CTAGTTCCTGCTTTCCCGCGGACTTCCTAGTGCCCAAATGCCCTGTGAGGCTGAGAGACCCAGGCCCCTGTGGCTTTCA 2056

ACACAGCACAGCTGTGGAAGTGGCTGTGTTCTTCTACAGCCTGTGGAAGAACCCCTGTAGCAGAGCCTCCCATCCACCC 2135

TCAGGGGCTGAGGCAGCTCTCGAGGAGTGGTGCTCAAGAGCTGACGCAGGGCCACCTCCCCTTCCCAAGGGGGTGGGAG 2214

GGAGTGGGCCCACAGGGAAAAGAAGGCGGCTCTGAAGGAAGATCTCGCCCACACCCCAGGACAGAAAGAGGAAACAAGC 2293

CCGCCCTCTGGTGAAATGGGACTCCCTCCATCCACCAACACCCAACCTCCTGAAAGCTTCACAACTTCACGCAGAGTCC 2372

GGTGGCAGGCACCAGGCAGGAAAGGCTCCTCAAGAGGTTCCTGGTGGTCTGGCCTAAGCCCCAGCCAGAGGCCCTGCTC 2451
```

Fig. 1D

```
TCTCTGGCCTGGGGCATCCACCCGTTGTTCTGAAGGCAGAGCCCATTCTGTGGGCTCACAAGACACAGTGAAGGGGATC 2530
ATGGCCTGCACCCCTGCTTTTCAGCAGTAAAAAGCCCGAAAAGCCTGGCGAGCATGGCCGAGCTGGGAGGGCCGAGCCG 2609
GAACTCCACGTCCCTCGAGAGCAGGAGCCTCTTAAGGGCTGGCACTGGTCTCAGCCTAATGGCTGAGGCGGTACCCTGG 2688
CTTCATATGCATCTCACTGCTCCCACTGCAGGGGGGCAGGGAAGGGGGGTCTGGGAGCCCTTCATGTGTGGGGGCCGAG 2767
CTGGGGGCCCCCATGGCCATCCTGGACCTCGCTGCTCCAGAGTTTAATAAAGGTAGCACATGCTTATTGCTAGAAAAAA 2846
AAAAAAAAAAAAAAAAAAAAAAAAAAAAAAAAAAAAAAAGGGCGGCCGC                               2895
```

Fig. 1E

```
          10        20        30        40        50        60        70
H MTWLVLLGTLLCMLRVGLGTPDSEGFPPRALHNCPYKCICAADLLSCTGLGLQDVPAELPAATADLDLSH
  :. : .    :   :     :  . .    :..:         :. :  .:  .   .::   :..:  ..
P MN-LDIHCEQLSDARWTELLPLLQQYEVVRLDDCGLTEEHCKDIGS--ALRANPSLTELCLRTNEL--GD
           10        20        30        40          50        60

         80        90       100           110       120        130
H NALQRLRPGWLAPLFQLRALHLDHNELDALGRGVFVNA----SGLRLLDLSSNTLRALGRHDL-DGLGA-
  .... . .:  .:  ... : :..  : . : ::. ..    . :: :.::.: : . : . : .:: .
P AGVHLVLQGLQSPTCKIQKLSLQNCSLTEAGCGVLPSTLRSLPTLRELHLSDNPLGDAGLRLLCEGLLDP
      70        80        90       100       110       120       130

        140        150       160       170       180       190       200
H ---LEKLLLFNNRLVHLD-EHAFHGLRALSHLYLGCNELASFSFDHLHGLSATHLLTLDLSSNRLGHISV
     :::: :   ::.  . :    :::    :     .::.  . :   : .....:  .:..      :.
P QCHLEKLQLEYCRLTAASCEPLASVLRATRAL----KELTVSNND--IGEAGARVLGQGLAD------SA
    140       150       160             170         180       190

         210        220       230       240       250       260
H PELAALPAFLKN-GLYLHNNPLPCDCRLYHLLQRWHQRGLSAVRDFAREYVCLAFKVPASRVR---FFQH
   .:..:   : : ::   :     :.     .   :  . : ... :  . . .: ..   ::::..   . .
P CQLETLR--LENCGLTPANCKDLCGIVASQASLRELDLGSNGLGDAGIAELCPGLLSPASRLKTLWLWEC
     200         210       220       230       240       250       260
```

Fig. 1G

```
  270        280        290              300        310        320
H SRVFENCSSA-PALGLKRPEEHLYALVGRSL-----RLYCNTSV-PAMRIAWVSPQQELLRAPGSRDGSI
   . .  .: .   .: :     : .:.: :     :: :.. . :. ... .  .     : :.   .. :.
P DITASGCRDLCRVLQAKETLKEL-SLAGNKLGDEGARLLCESLLQPGCQLESLWVKSCSLTAACCQHVSL
      270        280         290        300        310        320        330

330        340        350        360        370        380        390
H AVLADGSLAIGNVQEQHAGLFVCLATGPRLHHNQTHEYNVSVHFPRPEPEAFNTGFTTLLGCAVGLVLVL
   .  .  :    .. : ..  .  .  . : .. ..  ..    .   . :. :.: ..: .  . :.
P MLTQNKHL----LELQLSSNKLGDSGIQELCQALSQPGTTLRVLCLGDCEVTNSGCSSLAS--LLLANRS
           340        350        360        370        380         390

400        410        420        430         440        450
H LYLFAPPCRCCRRACPLPPLAPNTQPAPRAEPHK-SSVLSTTPPDAPSPQGQASTS-----T
  :  .. .  :   .  :. :..  ::.   :.    ..  :    ..  .  ..: .      .
P LRELDLSNNCVGDPGVLQLLGSLEQPGCALEQLVLYDTYWTEEVEDRLQALEGSKPGLRVIS
     400        410        420        430        440        450
```

Fig. 1H

```
ccg ttt ctc ttt aac cac ttg cac ggt ctg ggg tta acc cgc ctg cgg      48
Pro Phe Leu Phe Asn His Leu His Gly Leu Gly Leu Thr Arg Leu Arg
 1               5                   10                  15

act ctg gac ctc tcc tcc aac tgg ctg aaa cat atc tcc atc cct gag      96
Thr Leu Asp Leu Ser Ser Asn Trp Leu Lys His Ile Ser Ile Pro Glu
            20                  25                  30

ttg gct gca ctg cca act tat ctc aag aac agg ctc tac ctg cac aac     144
Leu Ala Ala Leu Pro Thr Tyr Leu Lys Asn Arg Leu Tyr Leu His Asn
        35                  40                  45

aac ccg ctg ccc tgt gac tgc agc ctc tac cac ctg ctc cgg cgc tgg     192
Asn Pro Leu Pro Cys Asp Cys Ser Leu Tyr His Leu Leu Arg Arg Trp
    50                  55                  60

cac cag cgg ggc ctg agt gcc ctg cat gat ttt gaa cgc gag tac aca     240
His Gln Arg Gly Leu Ser Ala Leu His Asp Phe Glu Arg Glu Tyr Thr
 65                  70                  75                  80

tgc ttg gtc ttt aag gtg tca gag tcc cga gtg cgc ttt ttt gag cac     288
Cys Leu Val Phe Lys Val Ser Glu Ser Arg Val Arg Phe Phe Glu His
                 85                  90                  95

agc cgg gtc ttc aag aac tgc tct gtg gct gca gct cca ggc tta gag     336
Ser Arg Val Phe Lys Asn Cys Ser Val Ala Ala Ala Pro Gly Leu Glu
            100                 105                 110
```

Fig. 1I

```
ctg cct gaa gag cag ctg cac gcg cag gtg ggc cag tcc ctg agg ctc      384
Leu Pro Glu Glu Gln Leu His Ala Gln Val Gly Gln Ser Leu Arg Leu
        115                 120                 125

ttc tgc aac acc agt gtg cct gcc act cgg gtg gcc tgg gtc tcc ccg      432
Phe Cys Asn Thr Ser Val Pro Ala Thr Arg Val Ala Trp Val Ser Pro
    130                 135                 140

aag aat gag ctg ctt gtg gcg cca gcc tct cag gat ggt agc atc gct      480
Lys Asn Glu Leu Leu Val Ala Pro Ala Ser Gln Asp Gly Ser Ile Ala
145                 150                 155                 160

gtg ttg gct gat ggc agc tta gcc ata ggc agg gtg caa gag cag cac      528
Val Leu Ala Asp Gly Ser Leu Ala Ile Gly Arg Val Gln Glu Gln His
                165                 170                 175

gca ggc gtc ttt gtg tgc ctg gcc agt ggg ccc cgc ctg cac cac aac      576
Ala Gly Val Phe Val Cys Leu Ala Ser Gly Pro Arg Leu His His Asn
            180                 185                 190

cag aca ctt gag tac aat gtg agt gtg caa aag gct cgc ccc gag cca      624
Gln Thr Leu Glu Tyr Asn Val Ser Val Gln Lys Ala Arg Pro Glu Pro
        195                 200                 205

gag act ttc aac aca ggc ttt acc acc ctg ctg ggc tgt att gtg ggc      672
Glu Thr Phe Asn Thr Gly Phe Thr Thr Leu Leu Gly Cys Ile Val Gly
    210                 215                 220
```

Fig. 1J

```
ctg gtg ctg gtg ttg ctc tac ttg ttt gca cca ccc tgt cgt ggc tgc      720
Leu Val Leu Val Leu Leu Tyr Leu Phe Ala Pro Pro Cys Arg Gly Cys
225                 230                 235                 240

tgt cac tgc tgt cag cgg gcc tgc cgc aac cgt tgc tgg ccc cgg gca      768
Cys His Cys Cys Gln Arg Ala Cys Arg Asn Arg Cys Trp Pro Arg Ala
                245                 250                 255

tcc agt cca ctc cag gag ctg agc gca cag tcc tcc atg ctt agc act      816
Ser Ser Pro Leu Gln Glu Leu Ser Ala Gln Ser Ser Met Leu Ser Thr
            260                 265                 270

acg cca cca gat gca ccc agc cgc aag gcc agt gtc cac aag cat gtg      864
Thr Pro Pro Asp Ala Pro Ser Arg Lys Ala Ser Val His Lys His Val
        275                 280                 285

gtc ttc ctg gag ccg ggc aag aag ggc ctc aat ggc cgt gtg cag ctc      912
Val Phe Leu Glu Pro Gly Lys Lys Gly Leu Asn Gly Arg Val Gln Leu
    290                 295                 300

gca gta cct cca gac tcc gat ctg tgc aac ccc atg ggc ttg caa ctc      960
Ala Val Pro Pro Asp Ser Asp Leu Cys Asn Pro Met Gly Leu Gln Leu
305                 310                 315                 320

aa                                                                   962
```

Fig. 1K

```
M    1 ....................PFLFNHLHGLGLTRLRTLDLSSNWLKHISI 30
                            | |.|||||  | | ||||||| | |||:
H  151 HAFHGLRALSHLYLGCNELASFSFDHLHGLSATHLLTLDLSSNRLGHISV 200

M   31 PELAALPTYLKNRLYLHNNPLPCDCSLYHLLRRWHQRGLSALHDFEREYT 80
       ||||||| :||| |||||||||||| |||||.|||||||||. || |||
H  201 PELAALPAFLKNGLYLHNNPLPCDCRLYHLLQRWHQRGLSAVRDFAREYV 250

M   81 CLVFKVSESRVRFFEHSRVFKNCSVAAAPGLELPEEQLHAQVGQSLRLFC 130
       || |||  ||||||:|||||.||| | | ||. ||| |:| ||.||||:|
H  251 CLAFKVPASRVRFFQHSRVFENCSSAPALGLKRPEEHLYALVGRSLRLYC 300

M  131 NTSVPATRVAWVSPKNELLVAPASQDGSIAVLADGSLAIGRVQEQHAGVF 180
       |||||| |:|||||. ||| || |.||||||||||||||| |||||||.|
H  301 NTSVPAMRIAWVSPQQELLRAPGSRDGSIAVLADGSLAIGNVQEQHAGLF 350

M  181 VCLASGPRLHHNQTLEYNVSVQKARPEPETFNTGFTTLLGCIVGLVLVLL 230
       ||||.||||||||| ||||||   ||||| ||||||||||| ||||||||
H  351 VCLATGPRLHHNQTHEYNVSVHFPRPEPEAFNTGFTTLLGCAVGLVLVLL 400

M  231 YLFAPPCRGCCHCCQRACRNRCWPRASSPLQELSA.QSSMLSTTPPDAPS 279
       ||||||||    ||.|||        . |       .||.||||||||||
H  401 YLFAPPCR....CCRRACPLPPLAPNTQPAPRAEPHKSSVLSTTPPDAPS 446

M  280 RKASVHKHVVFLEPGKKGLNGRVQLAVPPDSDLCNPMGLQL 320

H  447 PQGQASTST................................ 455
```

Fig. 1M

```
                                     M   A   W   T   K   Y   Q   L   F   L    10
GTCGACCCACGCGTCCGGCGAACCCCAGCGTCCGCCGAC ATG GCC TGG ACC AAG TAC CAG CTG TTC CTG    69

 A   G   L   M   L   V   T   G   S   I   N   T   L   S   A   K   W   A   D   N    30
GCC GGG CTC ATG CTT GTT ACC GGC TCC ATC AAC ACG CTC TCG GCA AAA TGG GCG GAC AAT   129

 F   M   A   E   G   C   G   G   S   K   E   H   S   F   Q   H   P   F   L   Q    50
TTC ATG GCC GAG GGC TGT GGA GGG AGC AAG GAG CAC AGC TTC CAG CAT CCC TTC CTC CAG   189

 A   V   G   M   F   L   G   E   F   S   C   L   A   A   F   Y   L   L   R   C    70
GCA GTG GGC ATG TTC CTG GGA GAA TTC TCC TGC CTG GCT GCC TTC TAC CTC CTC CGA TGC   249

 R   A   A   G   Q   S   D   S   S   V   D   P   Q   Q   P   F   N   P   L   L    90
AGA GCT GCA GGG CAA TCA GAC TCC AGC GTA GAC CCC CAG CAG CCC TTC AAC CCT CTT CTT   309

 F   L   P   P   A   L   C   D   M   T   G   T   S   L   M   Y   V   A   L   N   110
TTC CTG CCC CCA GCG CTC TGT GAC ATG ACA GGG ACC AGC CTC ATG TAT GTG GCT CTG AAC   369

 M   T   S   A   S   S   F   Q   M   L   R   G   A   V   I   I   F   T   G   L   130
ATG ACC AGT GCC TCC AGC TTC CAG ATG CTG CGG GGT GCA GTG ATC ATA TTC ACT GGC CTG   429

 F   S   V   A   F   L   G   R   R   L   V   L   S   Q   W   L   G   I   L   A   150
TTC TCG GTG GCC TTC CTG GGC CGG AGG CTG GTG CTG AGC CAG TGG CTG GGC ATC CTA GCC   489
```

Fig. 2A

```
 T   I   A   G   L   V   V   V   G   L   A   D   L   L   S   K   H   D   S   Q   170
ACC ATC GCG GGG CTG GTG GTC GTG GGC CTG GCT GAC CTC CTG AGC AAG CAC GAC AGT CAG  549

 H   K   L   S   E   V   I   T   G   D   L   L   I   I   M   A   Q   I   I   V   190
CAC AAG CTC AGC GAA GTG ATC ACA GGG GAC CTG TTG ATC ATC ATG GCC CAG ATC ATC GTT  609

 A   I   Q   M   V   L   E   E   K   F   V   Y   K   H   N   V   H   P   L   R   210
GCC ATC CAG ATG GTG CTA GAG GAG AAG TTC GTC TAC AAA CAC AAT GTG CAC CCA CTG CGG  669

 A   V   G   T   E   G   L   F   G   F   V   I   L   S   L   L   L   V   P   M   230
GCA GTT GGC ACT GAG GGC CTC TTT GGC TTT GTG ATC CTC TCC CTG CTG CTG GTG CCC ATG  729

 Y   Y   I   P   A   G   S   F   S   G   N   P   R   G   T   L   E   D   A   L   250
TAC TAC ATC CCC GCC GGC TCC TTC AGC GGA AAC CCT CGT GGG ACA CTG GAG GAT GCA TTG  789

 D   A   F   C   Q   V   G   Q   Q   P   L   I   A   V   A   L   L   G   N   I   270
GAC GCC TTC TGC CAG GTG GGC CAG CAG CCG CTC ATT GCC GTG GCA CTG CTG GGC AAC ATC  849

 S   S   I   A   F   F   N   F   A   G   I   S   V   T   K   E   L   S   A   T   290
AGC AGC ATT GCC TTC TTC AAC TTC GCA GGC ATC AGC GTC ACC AAG GAA CTG AGC GCC ACC  909

 T   R   M   V   L   D   S   L   R   T   V   V   I   W   A   L   S   L   A   L   310
ACC CGC ATG GTG TTG GAC AGC TTG CGC ACC GTT GTC ATC TGG GCA CTG AGC CTG GCA CTG  969
```

Fig. 2B

```
 G   W   E   A   F   H   A   L   Q   I   L   G   F   L   I   L   L   I   G   T   330
GGC TGG GAG GCC TTC CAT GCA CTG CAG ATC CTT GGC TTC CTC ATA CTC CTT ATA GGC ACT 1029

 A   L   Y   N   G   L   H   R   P   L   L   G   R   L   S   R   G   R   P   L   350
GCC CTC TAC AAT GGG CTA CAC CGT CCG CTG CTG GGC CGC CTG TCC AGG GGC CGG CCC CTG 1089

 A   E   E   S   E   Q   E   R   L   L   G   G   T   R   T   P   I   N   D   A   370
GCA GAG GAG AGC GAG CAG GAG AGA CTG CTG GGT GGC ACC CGC ACT CCC ATC AAT GAT GCC 1149

 S   *                                                                           372
AGC TGA                                                                         1155

GGTTCCCTGGAGGCTTCTACTGCCACCCGGGTGCTCCTTCTCCCTGAGACTGAGGCCACACAGGCTGGTGGGCCCCGAA 1234

TGCCCTATCCCCAAGGCCTCACCCTGTCCCCTCCCTGCAGAACCCCCAGGGCAGCTGCTGCCACAGAAGATAACAACAC 1313

CCAAGTCCTCTTTTTCTCACTACCACCTGCAGGGTGGTGTTACCCAGCCCCCACAAGCCTGAGTGCAGTGGCAGACCTC 1392

AGCTCTCTGGACCCCTCCTACAGCACTAGAGCTAAATCATGAAGTTGAATTGTAGGAATTTACCACCGTAGTGTATCTG 1471

AATCATAAACTAGATTATCATAAAAAAAAAAAAAAAAGGGCGGCCGC                                 1518
```

Fig. 2C

```
                                                                M   A   P   H   W        5
GTCGACCCACGCGTCCGCGGGACAGCTGGCCTGAAGCTCAGAGCCGGGGCGTGCGCC ATG GCC CCA CAC TGG       72

 A   V   W   L   L   A   A   R   L   W   G   L   G   I   G   A   E   V   W   W     25
GCT GTC TGG CTG CTG GCA GCA AGG CTG TGG GGC CTG GGC ATT GGG GCT GAG GTG TGG TGG   132

 N   L   V   P   R   K   T   V   S   S   G   E   L   A   T   V   V   R   R   F     45
AAC CTT GTG CCG CGT AAG ACA GTG TCT TCT GGG GAG CTG GCC ACG GTA GTA CGG CGG TTC   192

 S   Q   T   G   I   Q   D   F   L   T   L   T   L   T   E   P   T   G   L   L     65
TCC CAG ACC GGC ATC CAG GAC TTC CTG ACA CTG ACG CTG ACG GAG CCC ACT GGG CTT CTG   252

 Y   V   G   A   R   E   A   L   F   A   F   S   M   E   A   L   E   L   Q   G     85
TAC GTG GGC GCC CGA GAG GCC CTG TTT GCC TTC AGC ATG GAG GCC CTG GAG CTG CAA GGA   312

 A   I   S   W   E   A   P   V   E   K   K   T   E   C   I   Q   K   G   K   N    105
GCG ATC TCC TGG GAG GCC CCC GTG GAG AAG AAG ACT GAG TGT ATC CAG AAA GGG AAG AAC   372

 N   Q   T   E   C   F   N   F   I   R   F   L   Q   P   Y   N   A   S   H   L    125
AAC CAG ACC GAG TGC TTC AAC TTC ATC CGC TTC CTG CAG CCC TAC AAT GCC TCC CAC CTG   432

 Y   V   C   G   T   Y   A   F   Q   P   K   C   T   Y   V   V   S   A   A   L    145
TAC GTC TGT GGC ACC TAC GCC TTC CAG CCC AAG TGC ACC TAC GTC GTG AGT GCT GCC CTC   492
```

Fig. 3A

```
L   P   R   C   P   Q   P   P   A   L   L   T   L   L   W   T   R   G   C   G    165
CTA CCT CGG TGT CCC CAG CCC CCC GCC CTC CTC ACC CTT CTC TGG ACT CGT GGA TGT GGC  552

P   Q   S   P   A   L   K   H   L   L   I   T   S   L   S   V   L   R   T   C    185
CCA CAG AGC CCT GCC CTT AAG CAT CTC CTC ATC ACC TCT CTC TCT GTC CTT AGA ACA TGC  612

S   P   S   L   W   S   M   E   S   L   K   M   G   R   A   S   V   P   M   T    205
TCA CCT TCA CTT TGG AGC ATG GAG AGT TTG AAG ATG GGA AGG GCA AGT GTC CCT ATG ACC  672

Q   L   R   A   M   L   A   F   L   W   M   V   S   C   T   R   P   H   S   T    225
CAG CTA AGG GCC ATG CTG GCC TTC TTG TGG ATG GTG AGC TGT ACT CGG CCA CAC TCA ACA  732

T   S   W   A   R   N   P   L   S   C   V   T   W   G   P   T   T   P   *        244
ACT TCC TGG GCA CGG AAC CCA TTA TCC TGC GTA ACA TGG GGC CCC ACC ACT CCA TGA      789

AGACAGAGTACCTGGCCTTTTGGCTCAACGAACCTCACTTTGTAGGCTCTGCCTATGTACCTGAGAGTGTGGGCAGCTT  868

CACGGGGGACGACGACAAGGTCTACTTCTTCTTCAGGGAGCGGGCAGTGGAGTCCGACTGCTATGCCGAGCAGGTGGTG  947

GCTCGTGTGGCCCGTGTCTGCAAGGGCGATATGGGGGGCGCACGGACCCTGCAGAGGAAGTGGACCACGTTCCTGAAGG 1026

CGCGGCTGGCATGCTCTGCCCCGAACTGGCAGCTCTACTTCAACCAGCTGCAGGCGATGCACACCCTGCAGGACACCTC 1105
```

Fig. 3B

CTGGCACAACACCACCTTCTTTGGGGTTTTTCAAGCACAGTGGGGTGACATGTACCTGTCGGCCATCTGTGAGTACCAG 1184

TTGGAAGAGATCCAGCGGGTGTTTGAGGGCCCCTATAAGGAGTACCATGAGGAAGCCCAGAAGTGGGACCGCTACACTG 1263

ACCCTGTACCCAGGCCCTGGTTGTGATGGCTGCCCAGCCCCGCCATGCCGGGGCCTACCACTGCTTTTCAGAGGAGCAG 1342

GGGGCGCGGCTGGCTGCTGAAGGCTACCTTGTGGCTGTCGTGGCAGGCCCGTCGGTGACCTTGGAGGCCCGGGCCCCCC 1421

TGGAAAACCTGGGGCTGGTGTGGCTGGCGGTGGTGGCCCTGGGGGCTGTGTGCCTGGTGCTGCTGCTGCTGGTGCTGTC 1500

ATTGCGCCGGCGGCTGCGGGAAGAGCTGGAGAAAGGGGCCAAGGCTACTGAGAGGACCTTGGTGTACCCCCTGGAGCTG 1579

CCCAAGGAGCCCACCAGTCCCCCCTTCCGGCCCTGTCCTGAACCAGATGAGAAACTTTGGGATCCTGTCGGTTACTACT 1658

ATTCAGATGGCTCCCTTAAGATAGTACCTGGGCATGCCCGGTGCCAGCCCGGTGGGGGGCCCCCTTCGCCACCTCCAGG 1737

CATCCCAGGCCAGCCTCTGCCTTCTCCAACTCGGCTTCACCTGGGGGGTGGGCGGAACTCAAATGCCAATGGTTACGTG 1816

CGCTTACAACTAGGAGGGGAGGACCGGGGAGGGCTCGGGCACCCCCTGCCTGAGCTCGCGGATGAACTGAGACGCAAAC 1895

TGCAGCAACGCCAGCCACTGCCCGACTCCAACCCCGAGGAGTCATCAGTATGAGGGGAACCCCCACCGCGTCGGCGGGA 1974

AGCGTGGGAGGTGTAGCTCCTACTTTTGCACAGGCACCAGCTACCTCAGGGACATGGCACGGGCACCTGCTCTGTCTGG 2053

Fig. 3C

```
GACAGATACTGCCCAGCACCCACCCGGCCATGAGGACCTGCTCTGCTCAGCACGGGCACTGCCACTTGGTGTGGCTCAC 2132
CAGGGCACCAGCCTCGCAGAAGGCATCTTCCTCCTCTCTGTGAATCACAGACACGCGGGACCCCAGCCGCCAAAACTTT 2211
TCAAGGCAGAAGTTTCAAGATGTGTGTTTGTCTGTATTTGCACATGTGTTTGTGTGTGTGTATGTGTGTGTGCACGC 2290
GCGTGCGCGCTTGTGGCATAGCCTTCCTGTTTCTGTCAAGTCTTCCCTTGGCCTGGGTCCTCCTGGTGAGTCATTGGAG 2369
CTATGAAGGGGAAGGGGTCGTATCACTTTGTCTCTCCTACCCCCACTGCCCCGAGTGTCGGGCAGCGATGTACATATGG 2448
AGGTGGGGTGGACAGGGTGCTGTGCCCCTTCAGAGGGAGTGCAGGGCTTGGGGTGGGCCTAGTCCTGCTCCTAGGGCTG 2527
TGAATGTTTTCAGGGTGGGGGAGGGAGATGGAGCCTCCTGTGTGTTTGGGGGGAAGGGTGGGTGGGGCCTCCCACTTG 2606
GCCCCGGGGTTCAGTGGTATTTTATACTTGCCTTCTTCCTGTACAGGGCTGGGAAAGGCTGTGTGAGGGGAGAGAAGGG 2685
AGAGGGTGGGCCTGCTGTGGACAATGGCATACTCTCTTCCAGCCCTAGGAGGAGGGCTCCTAACAGTGTAACTTATTGT 2764
GTCCCCGCGTATTTATTTGTTGTAAATATTTGAGATTTTTATATTGA                                 2811
```

Fig. 3D

```
          10        20        30        40        50        60        70
M MAPHWAVWLLAAGLWGLGIGAEMWWNLVPRKTVSSGELVTVVRRFSQTGIQDFLTLTLTEHSGLLYVGAR
  :::::::::::: ::::::::.:::::::::::::::.:::::::::::::::::::::: .::::::::
H MAPHWAVWLLAARLWGLGIGAEVWWNLVPRKTVSSGELATVVRRFSQTGIQDFLTLTLTEPTGLLYVGAR
          10        20        30        40        50        60        70

          80        90       100       110       120       130       140
M EALFAFSVEALELQGAISWEAPAEKKIECTQKGKSNQTECFNFIRFLQPYNSSHLYVCGTYAFQPKCTYI
  ::::::.:::::::::::::::.:::.::.::::.::::::::::::::::.:::::::::::::::::.
H EALFAFSMEALELQGAISWEAPVEKKTECIQKGKNNQTECFNFIRFLQPYNASHLYVCGTYAFQPKCTYV
          80        90       100       110       120       130       140

         150       160       170       180       190       200       210
M NMLTFTLDRAEFEDGKGKCPYDPAKGHTGLLVDGELYSATLNNFLGTEPVILRYMGTHHSIKTEYLAFWL

H ----------------------------------------------------------------------

         220       230       240       250       260       270       280
M NEPHFVGSAFVPESVGSFTGDDDKIYFFFSERAVEYDCYSEQVVARVARVCKGDMGGARTLQKKWTTFLK
       :..:..:                  :
H -----VSAALLP------------------R---------------------------------------

         290       300       310       320       330       340       350
M ARLVCSAPDWKVYFNQLKAVHTLRGASWHNTTFFGVFQARWGDMDLSAVCEYQLEQIQQVFEGPYKEYSE
      :. :        :. ::                     :
H ----CPQPP---------ALLTL---------------------L------------------------
     150
```

Fig. 3F

```
             360        370        380        390        400        410        420
M QAQKWARYTDPVPSPRPGSCINNWHRDNGYTSSLELPDNTLNFIKKHPLMEDQVKPRLGRPLLVKKNTNF
      :.:           .:  .     ...:           ::               ::.   :..
H ----WTR-----------GCGPQ-------SPAL-----------KH--------------LLI---TSL
     160                        170

             430        440        450        460        470        480        490
M THVVADRVPGLDGATYTVLFIGTGDGWLLKAVSLGPWIHMVEELQVFDQEPVESLVLSQSKKVLFAGSRS
  .                          .:.. : . :             ..::: ....     . . .
H S--------------------------VLRTCSPSLW-------------SMESLKMGRA-----SVPMT
180                                    190                    200

             500        510        520        530        540        550        560
M QLVQLSLADCTKYRFCVDCVLARDPYCAWNVNTSRCVATTSGRSGSFLVQHVANLDTSKMCNQYGIKKVR
  ::  . ::     :     :      : :. .:  .:::
H QLRAM-LA------F-----L-------WMVSCTRPHSTTS-----------------------------
    210                           220
             570        580        590        600        610        620        630
M SIPKNITVVSGTDLVLPCHLSSNLAHAHWTFGSQDLPAEQPGSFLYDTGLQALVVMAAQSRHSGPYRCYS
                             :
H ----------------------------W-----------------------------------------

             640        650        660        670        680        690        700
M EEQGTRLAAESYLVAVVAGSSVTLEARAPLENLGLVWLAVVALGAVCLVLLLLVLSLRRRLREELEKGAK
                           ::.::               :..
H --------------------------ARNPLS---------------CVT---------------------
                           230
```

Fig. 3G

```
         710       720       730       740       750       760       770
M ASERTLVYPLELPKEPASPPFRPGPETDEKLWDPVGYYYSDGSLKIVPGHARCQPGGGPPSPPPGIPGQP
                                 :                         :: .:
H -------------------------------W-------------------------GPTTP--------
                                                          240

         780       790       800       810       820       830
M LPSPTRLHLGGGRNSNANGYVRLQLGGEDRGGSGHPLPELADELRRKLQQRQPLPDSNPEESSV

H ----------------------------------------------------------------
```

```
           10        20        30        40        50        60        70
M GGCACGAGGTGGCCGGAGTCAAACGCGAGGGCAGCGCCAGGGATTGGAGCTGCACGAAAGAGGGCTGCTG
  : :       :.::         :.::       :: :              :.::     ::.:.::::
H GTC-------GACC---------CACG-------CGTC--------------CGCG-----GGACAGCTG
                           10                                  20

           80        90       100       110       120       130       140
M GACTGAAGTTTAGACCCTGGGTGTCTGCCATGGCCCCACACTGGGCTGTCTGGCTGCTGGCAGCAGGGCT
  : :::::: : ::: :: ::: ::  :::::::::::::::::::::::::::::::::::::::.::::
H GCCTGAAGCTCAGAGCCGGGGCGTGCGCCATGGCCCCACACTGGGCTGTCTGGCTGCTGGCAGCAAGGCT
  30        40        50        60        70        80        90

          150       160       170       180       190       200       210
M GTGGGGCCTGGGCATCGGGGCTGAGATGTGGTGGAACCTTGTGCCCCGGAAGACAGTATCTTCTGGGGAG
  ::::::::::::::: :::::::::.::::::::::::::::::: :: ::::::::.::::::::::::
H GTGGGGCCTGGGCATTGGGGCTGAGGTGTGGTGGAACCTTGTGCCGCGTAAGACAGTGTCTTCTGGGGAG
 100       110       120       130       140       150       160

          220       230       240       250       260       270       280
M CTGGTCACAGTAGTGAGGCGGTTCTCCCAGACAGGCATCCAGGACTTCCTGACACTGACCCTGACAGAAC
  :::: :::.:::::. :::::::::::::::: :::::::::::::::::::::::::: :::::.::.:
H CTGGCCACGGTAGTACGGCGGTTCTCCCAGACCGGCATCCAGGACTTCCTGACACTGACGCTGACGGAGC
 170       180       190       200       210       220       230

          290       300       310       320       330       340       350
M ATTCTGGCCTTTTATATGTGGGGGCCCGAGAGGCGCTGTTTGCCTTCAGTGTAGAGGCTCTGGAGCTGCA
    .:::: ::: :.:: ::::: ::::::::::: :::::::::::::: .:.::::: :::::::::::
H CCACTGGGCTTCTGTACGTGGGCGCCCGAGAGGCCCTGTTTGCCTTCAGCATGGAGGCCCTGGAGCTGCA
 240       250       260       270       280       290       300
```

Fig. 3I

```
          360       370       380       390       400       410       420
M AGGAGCGATCTCTTGGGAGGCTCCAGCTGAGAAGAAAATTGAATGTACCCAGAAAGGGAAGAGCAACCAG
  ::::::::::: :::::::: :: :  ::::::::.: :::.:::: :::::::::::::::.:::::::
H AGGAGCGATCTCCTGGGAGGCCCCCGTGGAGAAGAAGACTGAGTGTATCCAGAAAGGGAAGAACAACCAG
  310       320       330       340       350       360       370

          430       440       450       460       470       480       490
M ACCGAATGCTTCAACTTCATCCGCTTCCTTCAGCCATACAATTCCTCCCATCTGTATGTCTGCGGCACCT
  :::::.::::::::::::::::::::: ::::: :::::: ::::::: ::::: ::::: :::::::
H ACCGAGTGCTTCAACTTCATCCGCTTCCTGCAGCCCTACAATGCCTCCCACCTGTACGTCTGTGGCACCT
  380       390       400       410       420       430       440

          500       510       520       530       540       550       560
M ATGCCTTCCAGCCCAAGTGCACCTACATCAACATGCTCACGTTCACCTTGGACCGTGCAGAATTTGAGGA
  : :::::::::::::::::::::::.::.                  ::.   ::::
H ACGCCTTCCAGCCCAAGTGCACCTACGTCG------------------TGA---GTGC------------
  450       460       470                       480
          570       580       590       600       610       620       630
M TGGGAAGGGTAAATGCCCATATGACCCAGCTAAGGGTCACACCGGACTCCTTGTGGACGGTGAGCTGTAC
               :::::.     :: : :: .: ::: : ::.: : ::       ::          :
H -------------TGCCCT-----CCTACCTCGGTGTC-C-CCAGCCCCC-------CG----------C
                  490             500           510

          640       650       660       670       680       690       700
M TCAGCCACACTCAATAACTTCCTGGGCACAGAGCCGGTTATCCTTCGATACATGGGGACCCACCACTCCA
   :. ::.::: :    ..::  ::::.:.:. .:                   ::: :: :::::
H CCT-CCTCACCC---TTCT--CTGGACTCGTGG------------------ATGTGG-CCCAC-------
  520            530        540                         550
```

Fig. 3J

```
.          710       720       730       740       750       760       770
M TCAAGACAGAGTACCTGGCTTTTTGGCTGAATGAACCCCACTTTGTAGGCTCTGCCTTTGTCCCTGAGAG
                   ::..::  ::  ::..::      :.: ::.:.: .   ::::  :: ::::: : :::
H ---------AGAGCCCTGCCCTTAAGC------ATCTCCTCATCAC---CTCTCTCTCTGTCC-TTAGA-
             560       570              580          590       600

           780       790       800       810       820       830       840
M TGTGGGAAGCTTCACGGGAGACGATGACAAGATCTACTTCTTCTTCAGTGAGCGGGCAGTGGAGTATGAC
                              :::.: ::. ::::. ::: .: ::::.   .: .:::::.:::
H --------------------------ACATGCTCACCTTCA-CTT-TG-GAGCA---TGGAGAGTTTGA-
                           610       620         630          640

           850       860       870       880       890       900       910
M TGCTATTCCGAGCAGGTGGTGGCTCGTGTGGCGAGAGTCTGTAAGGGTGACATGGGGGGAGCACGGACGC
                ::.:::      :.. :::.::.:::          :          :.  ::: :
H -------------AGATGG------GAAGGGCAAGTGTC-----------C----------CTATGACCC
                       650       660                           670

           920       930       940       950       960       970       980
M TGCAGAAGAAATGGACGACGTTCCTGAAGGCTCGGTTGGTGTGCTCAGCCCCTGACTGGAAGGTCTACTT
  .::..:.:.   . :   :.: ::: ::. :: : :   .: :::.:::.::: :  :::       :.::..
H AGCTAAGGGCCATGCTGGCCTTCTTGT-GGATGGTGAGCTGTACTCGGCCAC--ACT-------CAACAA
      680       690       700        710       720                 730

           990      1000      1010      1020      1030      1040      1050
M CAACCAGCTGAAGGCGGTGCACACCCTGCGGGGCGCCTCTTGGCACAACACCACCTTCTTCGGGGTTTTT
  :..::.:     :::.            :::..: ::. ::. :                :: ::     :..
H CTTCCTG-----GGCA------------CGGAAC-CCA-TTATC-------------CTGCG-----TAA
      740                          750                        760
```

Fig. 3K

```
           1060      1070      1080      1090      1100      1110      1120
M CAAGCGCGATGGGGCGATATGGACCTGTCTGCAGTTTGTGAGTACCAGTTGGAACAGATCCAGCAAGTGT
  ::       ::::::        ::   :             ::::       :   ::::
H CA-------TGGGGC--------CC---C-------------ACCA-------C---TCCA--------
             770                             780

           1130      1140      1150      1160      1170      1180      1190
M TTGAGGGTCCCTACAAGGAGTACAGTGAGCAAGCCCAGAAGTGGGCCCGCTATACTGACCCGGTACCCAG
   :::.:      :::  ::::::      :..:::   .. :::  : .: :. :: ::   :::   .:
H -TGAAG------ACA--GAGTAC------CTGGCC---TTTTGGCTCAACGAACCTCACTTTGTA---GG
   790              800                 810       820        830

           1200      1210      1220      1230      1240      1250      1260
M CCCTCGGCCTGGTTCGTGTATCAACAACTGGCACCGAGACAATGGCTACACCAGTTCCCTGGAACTGCCG
  :  :: ::::.     :::: :     :::.    :::. .. :::..:. ::     :  ::.:: .:
H C--TCTGCCTA-----TGTA-C-----CTGA----GAGT-GTGGCAGCTTCA----CGGGGGACGAC--
     840                     850            860       870           880

           1270      1280      1290      1300      1310      1320      1330
M GACAACACCCTCAACTTCATCAAGAAGCACCCCCTGATGGAGGACCAGGTGAAGCCTCGGTTGGGCCGCC
  ::::: . : .:..::::.:::.:.:::                ::.:  .:::.:: : ::.
H GACAAGGTCTACTTCTTCTTCAGGGAGC-------------GGGC--AGTGGAGTC-CGA----------
           890       900                      910         920

           1340      1350      1360      1370      1380      1390      1400
M CCCTACTTGTGAAGAAGAACACTAACTTCACACACGTGGTGGCCGACAGGGTCCCAGGGCTTGATGGTGC
    ::.::.              ..:  :. .:: ::::::::        ::          .::  ::
H --CTGCTA---------------TGC--CGAGCAGGTGGTGGC--------TC----------GTGTGGC
     930                        940                950
```

Fig. 3L

```
          1410      1420      1430      1440      1450      1460      1470
M CACCTATACAGTGTTGTTCATTGGTACAGGAGATGGCTGGCTGCTGAAGGCTGTGAGCCTGGGGCCCTGG
  :  :  . .:.:          ::. ::  :  :: ::::  :::           ::.      :  ::.:::::
H C--CGTGTCTG-------CAAGGG--C--GATATGGGGGGC--------GCA------C--GGACCCTG-
   960              970           980                     990

          1480      1490      1500      1510      1520      1530      1540
M ATCCACATGGTGGAGGAACTGCAGGTGTTTGACCAGGAGCCAGTGGAAAGTCTGGTGCTGTCTCAGAGCA
       ::     ::::::      :::   ::::: :. ::.:    ::: :     :: :   :.: :::
H -----CA-----GAGGAA------GTG---GACCACGTTCCTG----AAGGC----GCGG---CTG-GCA
      1000                   1010      1020                1030

          1550      1560      1570      1580      1590      1600      1610
M AGAAGGTGCTCTTTGCTGGCTCCCGCTCTCAGCTGGTTCAGCTGTCTCTGGCCGACTGCACAAAGTACCG
        ::::::      :: :::: .:: .::.: ::..:: ::.   .::..::::    .:    ::
H ------TGCTCT------GC-CCCGAACT-GGCAG-CTCTACT-TCA---ACCAGCTGCA---GG---CG
        1040              1050        1060          1070         1080

          1620      1630      1640      1650      1660      1670      1680
M TTTCTGTGTAGACTGTGTCCTGGCCAGGGACCCTTACTGTGCCTGGAATGTCAACACCAGCCGCTGTGTG
  .: :        ::.    ::::  ::::.  :::         ::::: :   :::::::: :  :: :: :
H ATGC-------ACA---CCCTG--CAGGACACCT-------CCTGGCA---CAACACCACCTTCTTTGGG
               1090        1100             1110        1120       1130

          1690      1700      1710      1720      1730      1740      1750
M GCCACCACCAGTGGTCGCTCGGGGTCCTTTCTGGTCCAACATGTGGCGAACTTGGACACTTCAAAGATGT
  :  .   . ::.     ::.:.: :           :::  .::::::. : ..:    :.: :.::..    ::.
H GTTT--TTCAA-----GCACAGTGG-------GGT--GACATGTACCTGTC---GGC-CATCTG---TGA
               1140             1150        1160          1170
```

Fig. 3M

```
        1760      1770      1780      1790      1800      1810      1820
M GTAACCAGTATGGCATTAAAAAAGTCAGATCTATTCCCAAGAACATCACCGTTGTGTCAGGCACAGACCT
  ::: ::::: :::        :::  :::::            :: :.  : ::: : :::
H GTA-CCAGT-TGG--------AAG--AGATC------------CAGCG--GGTGTTTGAGG---------
 1180                 1190                    1200        1210

        1830      1840      1850      1860      1870      1880      1890
M GGTCCTACCCTGCCACCTCTCGTCCAATTTGGCCCATGCCCACTGGACCTTCGGAAGCCAGGACCTGCCT
             :::         ::.::..::  .:.::   . ::     ::::::         ::.
H -----------GCC---------CCTATAAGGA--GTACC---ATGA-----GGAAGC---------CCA
                          1220      1230                1240

        1900      1910      1920      1930      1940      1950      1960
M GCAGAACAACCTGGCTCCTTTCTTTATGACACGGGACTCCAGGCGCTGGTGGTGATGGCCGCACAGTCCC
  : ::.. .:::  ::: :  .::    ::: : : :: :::::: ::::: :::::::: :: ::: :::
H GAAGTGGGACC--GCTAC--ACT----GACCCTGTAC-CCAGGCCCTGGTTGTGATGGCTGCCCAGCCCC
     1250          1260          1270       1280      1290      1300

        1970      1980      1990      2000      2010      2020      2030
M GTCACTCTGGACCCTATCGTTGCTATTCAGAGGAGCAGGGGACAAGACTGGCTGCAGAAAGCTACCTTGT
  : ::  : ::. :::: :. ::::.:::::::::::::::::.:. :.:::::::.:::.:::::::::
H GCCATGCCGGGGCCTACCACTGCTTTTCAGAGGAGCAGGGGGCGCGGCTGGCTGCTGAAGGCTACCTTGT
    1310      1320      1330      1340      1350      1360      1370

        2040      2050      2060      2070      2080      2090      2100
M TGCTGTCGTGGCCGGCTCGTCGGTGACACTGGAGGCACGGGCTCCCTTGGAAAACCTGGGGCTCGTGTGG
   :::::::::: ::: :::::::::  ::::::: ::::: ::: ::::::::::::::: ::::::
H GGCTGTCGTGGCAGGCCCGTCGGTGACCTTGGAGGCCCGGGCCCCCCTGGAAAACCTGGGGCTGGTGTGG
    1380      1390      1400      1410      1420      1430      1440
```

Fig. 3N

```
         2110      2120      2130      2140      2150      2160      2170
M CTCGCTGTGGTGGCCCTGGGGGCTGTGTGCCTGGTGCTGCTGCTGCTGGTCCTATCGCTCCGCCGGCGAC
  :: :: :::::::::::::::::::::::::::::::::::::::::::: ::.::. : ::::::::.:
H CTGGCGGTGGTGGCCCTGGGGGCTGTGTGCCTGGTGCTGCTGCTGCTGGTGCTGTCATTGCGCCGGCGGC
      1450      1460      1470      1480      1490      1500      1510

         2180      2190      2200      2210      2220      2230      2240
M TTCGAGAAGAGCTAGAAAAGGGTGCCAAGGCATCTGAGAGGACACTGGTGTACCCCTTGGAACTGCCCAA
  : ::.::::::::.::.::.:: ::::::::..::::::::::  ::::::::::: ::::.::::::::
H TGCGGGAAGAGCTGGAGAAAGGGGCCAAGGCTACTGAGAGGACCTTGGTGTACCCCCTGGAGCTGCCCAA
      1520      1530      1540      1550      1560      1570      1580

         2250      2260      2270      2280      2290      2300      2310
M GGAGCCTGCCAGTCCCCCCTTCCGTCCTGGCCCCGAAACTGATGAGAAACTTTGGATCCTGTCGGGTAC
  :::::: .:::::::::::::::: ::  : :: ::: :.:::::::::::::::::::::::::: :::
H GGAGCCCACCAGTCCCCCCTTCCGGCCCTGTCCTGAACCAGATGAGAAACTTTGGATCCTGTCGGTTAC
      1590      1600      1610      1620      1630      1640      1650

         2320      2330      2340      2350      2360      2370      2380
M TACTATTCGGATGGCTCTCTCAAGATTGTGCCTGGTCACGCCCGGTGCCAGCCTGGGGGTGGCCCCCTT
  ::::::::.:::::::: :: :::::.::.::::: :: :::::::::::::: :: :: ::::::::::
H TACTATTCAGATGGCTCCCTTAAGATAGTACCTGGGCATGCCCGGTGCCAGCCCGGTGGGGGCCCCCTT
      1660      1670      1680      1690      1700      1710      1720

         2390      2400      2410      2420      2430      2440      2450
M CCCCACCTCCTGGCATACCTGGCCAGCCTCTGCCTTCTCCAACTCGGCTCCACCTAGGAGGTGGTCGGAA
  : ::::::::.::::: ::.::::::::::::::::::::::::::::: :::::.::.::::: :::::
H CGCCACCTCCAGGCATCCCAGGCCAGCCTCTGCCTTCTCCAACTCGGCTTCACCTGGGGGGTGGCGGAA
      1730      1740      1750      1760      1770      1780      1790
```

Fig. 3O

```
         2460      2470      2480      2490      2500      2510      2520
M CTCAAATGCCAATGGTTATGTGCGTTTACAGTTGGGCGGAGAGGACCGAGGAGGATCTGGGCACCCACTG
  ::::::::::::::::: ::::: :::::. :.:: ::.:::::::.:::::.   :::::::: :::
H CTCAAATGCCAATGGTTACGTGCGCTTACAACTAGGAGGGGAGGACCGGGGAGGGCTCGGGCACCCCCTG
     1800      1810      1820      1830      1840      1850      1860

         2530      2540      2550      2560      2570      2580      2590
M CCTGAGCTCGCGGATGAATTACGACGGAAACTACAACAGCGCCAGCCGCTGCCTGACTCCAACCCAGAGG
  ::::::::::::::::: :. :::: :::::.::.::.::::::::.::::: ::::::::::: ::::
H CCTGAGCTCGCGGATGAACTGAGACGCAAACTGCAGCAACGCCAGCCACTGCCCGACTCCAACCCCGAGG
     1870      1880      1890      1900      1910      1920      1930

         2600      2610      2620      2630      2640      2650
M AGTCTTCAGTATGAGGGGACCCCCCCACCTCATTGGCGGGGGGGGTCTCATGGGAGGTGCA-CTCTTAA
  ::::.:::::::::::::::: ::::: ::: :.: :::::::..:      :.::::::::: : ::: ::
H AGTCATCAGTATGAGGGGAACCCCC-ACCGCGTCGGCGGGAAG------CGTGGGAGGTGTAGCTCCTA-
     1940      1950       1960      1970           1980      1990

2660      2670      2680      2690      2700      2710      2720
M CTTTTGCACAGGCACCAGCTACCTCAGGGACATGGCAGGGGCACTTGCTCTGCCTGGGACAGACACTGCC
  :::::::::::::::::::::::::::::::::::::: :::::: ::::::: :::::::::: ::::::
H CTTTTGCACAGGCACCAGCTACCTCAGGGACATGGCACGGGCACCTGCTCTGTCTGGGACAGATACTGCC
  2000      2010      2020      2030      2040      2050      2060

2730      2740      2750           2760      2770      2780      2790
M CATCATTTGCCCGGCCGTGAGGACCTGCTC-----AGCATGGGCACTGCCACTTGGTGTGGCTCACCAGG
  :: ::   .:::::::.:::::::::::::     :::: :::::::::::::::::::::::::::::
H CAGCACCCACCCGGCCATGAGGACCTGCTCTGCTCAGCACGGGCACTGCCACTTGGTGTGGCTCACCAGG
  2070      2080      2090      2100      2110      2120      2130
```

Fig. 3P

```
      2800      2810      2820       2830      2840      2850      2860
M ACTTCAGCCTCACAGGAGACA-CACCCTCCTCT--GTGAATTTGAGACATGTGGGACCCCAGCAGCCAAA
  .:. :::::::.:::.::.:: :. ::::::::  :::::: . ::::: : ::::::::::: ::::::
H GCACCAGCCTCGCAGAAGGCATCTTCCTCCTCTCTGTGAATCACAGACACGCGGGACCCCAGCCGCCAAA
  2140      2150      2160      2170      2180      2190      2200

     2870      2880      2890      2900        2910      2920
M ACTTTGCAAGGAAGAGGTTTCAAGATGTGGGCGTGTTTGTGCAT--ATATGTGTTGGTATGCATGTGGAA
  ::::: ::::: :::.:::::::::::::: :  ::: :::. .:  : ::::::: ::.:: .:::: :.
H ACTTTTCAAGGCAGAAGTTTCAAGATGTGTGTTTGTCTGTATTTGCACATGTGTTTGTGTGTGTGTGTAT
  2210      2220      2230      2240      2250      2260      2270

2930      2940      2950          2960      2970      2980      2990
M GAATGTGTGTGTGTGTGTGTG----TGTGTTGTAACTTTCCTGTCTCTATCACGTCTTCCCTTGGCCTGG
  :..:::::: . : : ::: :    ::::  .::.: ::::::: :::.::: ::::::::::::::::
H GTGTGTGTGCACGCGCGTGCGCGCTTGTGGCATAGCCTTCCTGTTTCTGTCAAGTCTTCCCTTGGCCTGG
  2280      2290      2300      2310      2320      2330      2340

   3000      3010      3020      3030      3040      3050      3060
M GGTCCTCCTGGTTGAGTCTTTGGAGCTATGAAGGGGAAGGGGGTCATAGCACTTTGCTTCTCCTACCCCC
  : :::::::::: ::::::.::::::::::::::::::::::: ::.:: :::::::  ::::::::::::
H G-TCCTCCTGGT-GAGTCATTGGAGCTATGAAGGGGAAGGGG-TCGTATCACTTTGTCTCTCCTACCCCC
   2350      2360      2370      2380       2390      2400      2410

   3070      3080      3090      3100      3110      3120      3130
M AGCTGTCCCAAGCTTTGGGGCAGTGATGTACATACGGGGAAGGGAAGGACAGGGTGTTGTACCCCTTTTG
  : ::: :::.:: : : :::::: :::::::::: ::.:..:::..:::::::::: :::.::::::: .:
H A-CTGCCCCGAG-TGTCGGGCAGCGATGTACATATGGAGGTGGGGTGGACAGGGTGCTGTGCCCCTTCAG
      2420      2430      2440      2450      2460      2470      2480
```

Fig. 3Q

```
     3140      3150      3160      3170      3180      3190      3200
M GGGGAGTGCGGGACTCGGGGGTGGGCCTAGCCCTGCTCCTAGGGCTGTGAATGTTTTCAGGCGGGGGTT
  .:::::::::.:::.::  ::::::::::::: ::::::::::::::::::::::::::::::: :::::: .
H AGGGAGTGCAGGGCT-TGGGGTGGGCCTAGTCCTGCTCCTAGGGCTGTGAATGTTTTCAGGGTGGGGGA
          2490       2500      2510      2520      2530      2540      2550

     3210      3220         3230      3240      3250      3260      3270
M GGGGGTGGAGATGGAACCTCCTGC---TTCAGGGGGAGGGGTGGCAGGGCCTCCCACTTGCCCTCCGGG
  :::     ::::::::.:::::::    :: .::::::.:::::::: .:::::::::::::: :: : :::
H GGG-----AGATGGAGCCTCCTGTGTGTTTGGGGGGAAGGGTGGGTGGGGCCTCCCACTTGGCCCCGGGG
               2560      2570      2580      2590      2600      2610

        3280      3290      3300        3310        3320      3330
M TTCGGTGGTATTTTATATTTGCGCTCTTC-TG-ACAGGGCTGGGAAGGG--TTGTTGGGGGAGGGAAGGG
  :::.:::::::::::::: ::::  ::::: :: :::::::::::::.::    ::: .:::::::.::::::
H TTCAGTGGTATTTTATACTTGCCTTCTTCCTGTACAGGGCTGGGAAAGGCTGTGTGAGGGGAGAGAAGGG
     2620      2630      2640      2650      2660      2670      2680

  3340      3350      3360      3370      3380      3390        3400
M AGGAGGTGGGCATGCTATGGATACTGGCCTATCCTCTCCCTGCTCTGGGAAAAGGGCT---AACAGTGTA
  ::..::::::: ::::.:::: : :::: ::  :::: ::.:: ::.:::..::::::   :::::::::
H AGAGGGTGGGCCTGCTGTGGACAATGGCATACTCTCTTCCAGCCCTAGGAGGAGGGCTCCTAACAGTGTA
     2690      2700      2710      2720      2730      2740      2750

     3410      3420      3430      3440      3450      3460      3470
M ACTTATTGTGTCCCCACATATTTATTTGTTGTAAATATTTGAGTATTTTTATATTGACAAATAAAATGGA
  ::::::::::::::.:.:::::::::::::::::::::::::: :::::::::::::
H ACTTATTGTGTCCCCGCGTATTTATTTGTTGTAAATATTTGAG-ATTTTTATATTGA-------------
     2760      2770      2780      2790       2800      2810
```

Fig. 3R

```
GTCGACCCACGCGTCCGCGGACGCGTGGGCGCGCGGGGGCCATCCAGACCCTGCGGAGAGCGAGGCCCGGAGCGTCGCC    79

GAGGTTTGAGGGCGCCGGAGACCGAGGGCCTGGCGGCCGAAGGAACCGCCCCAAGAAGAGCCTCTGGCCCGGGGGCTGC   158

                                              M   F   T   L   L   V   L   L        8
TGGAACATGTGCGGGGGGACACAGTTTGTTTGACAGTTGCCAGACT ATG TTT ACG CTT CTG GTT CTA CTC   228

 S   Q   L   P   T   V   T   L   G   F   P   H   C   A   R   G   P   K   A   S    28
AGC CAA CTG CCC ACA GTT ACC CTG GGG TTT CCT CAT TGC GCA AGA GGT CCA AAG GCT TCT   288

 K   H   A   G   E   E   V   F   T   S   K   E   E   A   N   F   F   I   H   R    48
AAG CAT GCG GGA GAA GAA GTG TTT ACA TCA AAA GAA GAA GCA AAC TTT TTC ATA CAT AGA   348

 R   L   L   Y   N   R   F   D   L   E   L   F   T   P   G   N   L   E   R   E    68
CGC CTT CTG TAT AAT AGA TTT GAT CTG GAG CTC TTC ACT CCC GGC AAC CTA GAA AGA GAG   408

 C   N   E   E   L   C   N   Y   E   E   A   R   E   I   F   V   D   E   D   K    88
TGC AAT GAA GAA CTT TGC AAT TAT GAG GAA GCC AGA GAG ATT TTT GTG GAT GAA GAT AAA   468

 T   I   A   F   W   Q   E   Y   S   A   K   G   P   T   T   K   S   D   G   N   108
ACG ATT GCA TTT TGG CAG GAA TAT TCA GCT AAA GGA CCA ACC ACA AAA TCA GAT GGC AAC   528
```

Fig. 4A

```
 R   E   K   I   D   V   M   G   L   L   T   G   L   I   A   A   G   V   F   L   128
AGA GAG AAA ATA GAT GTT ATG GGC CTT CTG ACT GGA TTA ATT GCT GCT GGA GTA TTT TTG  588

 V   I   F   G   L   L   G   Y   Y   L   C   I   T   K   C   N   R   L   Q   H   148
GTT ATT TTT GGA TTA CTT GGC TAC TAT CTT TGT ATC ACT AAG TGT AAT AGG CTA CAA CAT  648

 P   C   S   S   A   V   Y   E   R   G   R   H   T   P   S   I   I   F   R   R   168
CCA TGC TCT TCA GCC GTC TAT GAA AGG GGG AGG CAC ACT CCC TCC ATC ATT TTC AGA AGA  708

 P   E   E   A   A   L   S   P   L   P   P   S   V   E   D   A   G   L   P   S   188
CCT GAG GAG GCT GCC TTG TCT CCA TTG CCG CCT TCT GTG GAG GAT GCA GGA TTA CCT TCT  768

 Y   E   Q   A   V   A   L   T   R   K   H   S   V   S   P   P   P   P   Y   P   208
TAT GAA CAG GCA GTG GCG CTG ACC AGA AAA CAC AGT GTT TCA CCA CCA CCA CCA TAT CCT  828

 G   H   T   K   G   F   R   V   F   K   K   S   M   S   L   P   S   H   *       227
GGG CAC ACA AAA GGA TTT AGG GTA TTT AAA AAA TCT ATG TCT CTC CCA TCT CAC TGA      885

CTACCTTGTCATTTTGGTATAAGAAATTTGTGTTATTTGATAGGCCGGGCATGGTGGCTCATGCCTGTAATCCCAGCAC  964

TTTGGGAGGCCAGGAGTTCGAGACCAGCCTGGCCAACATGGTGAAACCCGGTCTCTACTAAAAATTCAAAAATTACCTA 1043

GGCGTCATGGGGCATGCCTGTAGTCCCACCTACTTGGGAGGCTGAAGCAGGAGAATTGCTCGAACCTGGGAGGCAGAGG 1122
```

Fig. 4B

```
TTGCAGTAAGCTGAGATCACGCCACTGCATTCCAGCCTGGGCGACAGAGCAAGACTCCATCTCAAAAATAAAATAAAAA 1201
AAGAAAGAAAGAAAAGAAGAAGAAAAGAGAAGAAGGAGAAGGAGATGAAGGAGGAGGAGGAGAAGGAGAAGAAGAA 1280
GAAGAAGAAGACCACAAAAGACATGACTATCCAACTTTTTATGACAAACTGCAAGGAATAAAGGAAGAATAAGTCCATG 1359
TACTGTACCACAGAAGTTCTGTCTGCATCTTGGACCTGAACTTGATCATTATCAGCTTGATAAGAGACTTTTTGACTCT 1438
ATATCCTTGCAGTTAAGAAGAAAGCACTTTTTTGTAATGTTTGTTTTAATGGTTCAAAAAAAATCTTTCTTATAAAGAG 1517
CATAGGTAGAATTAGTGAACTCTTTGGATCCTTTGTACAGATAAAGGTTATAGATTTCTTGTGTTGAATATTAAAAAAG 1596
CAAGGATGTCTAACCATTAAGATTATCCAAAGTCAGGCTGGGCGCAGTGGCTCACGCCTGTAATCCCAGCACTTTGGGA 1675
GGGATAGGTGGGCGGATCACCTGAGGTCAGGAGTTTGAGACCAGCCTGGCCAACATGGCAAAACCCCGTCTCTACAAAA 1754
ATACAAAAGAAATTAGCCAGACATGATGGCGGGTGCCTCTAATCCCAGCTACTGGGGAGGCTGAGGTGGGAGAATCGCT 1833
TGAACTCGGGAGGTGGAGGTTGTAGTGAGGCGAGATTGTGCCATTGCACTCCAACCTGGGCGACAGAGTGAGACTCCAT 1912
CTCAAAAAAAAAAAAAAAAAAAAGATTATCCAAAAAGATATTGGACCTACTCTTTCTTAGGATTTTTTTGGCGGGGGGT 1991
TAGAAATACTTCACAGAATTTGACATTTCAGTATAAATCTGTGACCTTAATATAATCACTTGGTTTTATATGTTAAATT 2070
ATTGCACAGCAGTCATCATATTTTGCAGAGTTTAGTTCTTAACTCTTGCTGTCAGTCATGTTTTATTATAGGTAGTGGG 2149
GTCAGTAGTTTTCTTCTTCTAAAAAATACTATTTGCTATGAAGTTAGTTCTTCAGAAGATACAAGTTTGCAATGAAAAG 2228
GATTTGCAAGGGTTGTTATGCTATCAAATAAACAGACCTAAAATCTAGGAGACACTAGAACTTAATGAAGTTGCCCCTG 2307
TTACTGATTAGTAAATACTCCCATCTTCGTTGCAAAATTATCTCTCTGTATAACTACATATGATTATTTTGAAATTTGT 2386
TAAACTTCATAAGTAATAGTTTGAGAATGTGGAAAAAGTAATTTGCTTTTCTGCTCTTAAAATAATATTGATTAATGTT 2465
ACCAGAAAAAAAAAAAAAAAAAAAGGGCGGCCGC 2498
```

Fig. 4C

```
GTCGACCCAC GCGTCCGCTG CGTTCTCACC CCTGGACCAC CCTGGGAGAA CAGTTGACCG    60
AAGTTTGTTT GGCAGTTGCT GCTGGACT  ATG TTT CTG CTT CTG GTG GTA CTC     112
                                Met Phe Leu Leu Leu Val Val Leu
                                 1               5

AGC CAG CTG CCC AGA CTT ACC CTC GCG GTT CCT CAT ACA AGA AGC CTA     160
Ser Gln Leu Pro Arg Leu Thr Leu Ala Val Pro His Thr Arg Ser Leu
     10                  15                  20

AAG AAT TCT GAA CAT GCC CCA GAA GGA GTC TTT GCA TCA AAA AAA GCA     208
Lys Asn Ser Glu His Ala Pro Glu Gly Val Phe Ala Ser Lys Lys Ala
 25                  30                  35                  40

GCA AGC ATC TTT ATG CAC CGT CGC CTC CTA TAC AAT AGA TTT GAT TTA     256
Ala Ser Ile Phe Met His Arg Arg Leu Leu Tyr Asn Arg Phe Asp Leu
                 45                  50                  55

GAA CTC TTC ACT CCC GGG AAC CTG GAG AGA GAG TGC TAT GAG GAG TTC     304
Glu Leu Phe Thr Pro Gly Asn Leu Glu Arg Glu Cys Tyr Glu Glu Phe
             60                  65                  70

TGT AGT TAT GAA GAA GCC AGA GAG ATC CTC GGG GAC AAC GAA GAA ATG     352
Cys Ser Tyr Glu Glu Ala Arg Glu Ile Leu Gly Asp Asn Glu Glu Met
         75                  80                  85
```

Fig. 4E

```
ATC ACA TTC TGG CGG GAA TAT TCA GTC AAA GGA CCA ACC ACA AGA TCA      400
Ile Thr Phe Trp Arg Glu Tyr Ser Val Lys Gly Pro Thr Thr Arg Ser
     90                  95                 100

GAT GTC AAC AAA GAG AAA ATT GAT GTT ATG GGC CTT CTG ACT GGC TTA      448
Asp Val Asn Lys Glu Lys Ile Asp Val Met Gly Leu Leu Thr Gly Leu
105                 110                 115                 120

ATT GCG GCT GGA GTA TTC TTG GTT GTT TTT GGC TTA CTT GGT TAC TAT      496
Ile Ala Ala Gly Val Phe Leu Val Val Phe Gly Leu Leu Gly Tyr Tyr
                125                 130                 135

CTG TGT ATC ACC AAG TGT AAT AGG CAG CCA TAT CAA GGT TCT TCA GCT      544
Leu Cys Ile Thr Lys Cys Asn Arg Gln Pro Tyr Gln Gly Ser Ser Ala
            140                 145                 150

GTC TAC ACA AGA AGG ACC AGG CAC ACA CCG TCC ATC ATT TTC AGA ACC      592
Val Tyr Thr Arg Arg Thr Arg His Thr Pro Ser Ile Ile Phe Arg Thr
        155                 160                 165

CAT GAG GAA GCT GTC TTG TCT CCA TCG TCA TCC TCA GAG GAC GCG GGA      640
His Glu Glu Ala Val Leu Ser Pro Ser Ser Ser Ser Glu Asp Ala Gly
    170                 175                 180
```

Fig. 4F

```
CTA CCT TCC TAT GAA CAG GCA GTA GCT CTG ACC AGA AAA CAC AGT GTC       688
Leu Pro Ser Tyr Glu Gln Ala Val Ala Leu Thr Arg Lys His Ser Val
185                 190                 195                 200

TCA CCA CCA CCT CCA TAT CCT GGG CCA GCA AAA GGA TTT AGG GTA TTT       736
Ser Pro Pro Pro Pro Tyr Pro Gly Pro Ala Lys Gly Phe Arg Val Phe
                205                 210                 215

AAA AAG TCA ATG TCA CTC CCA TCT CAC TAAGCCCACC TTGCCGCCTT             783
Lys Lys Ser Met Ser Leu Pro Ser His
            220                 225

GCTGTGGTCT GAATAATATG TTCTTCCTGA AACAACAACA ACAAAAAAAT TTGCCTGTTC      843
AGCTTTTTAT GACAAAGCAC AAGGAATAAA GGAACACTAT ATACAGAACA GAATTCACCA      903
CAGCCCCGCT TTCAGCTCTG CCCCCAACTG GATTGCTGTC TTGGTAAGAG ACTTCTACCG      963
TGCTTCCTCG AAGTTAAGAA GAAAGTGCCT TTTTGCAATG TAAACTGTAC TGGTTCAAAC     1023
ATTCTTGCTA CAGCTAGGTA CCTATAATCC CCACCTTCAG GAGACTTAGG CGGGAGGGAT     1083
GAGAGTTCAA GGCCAGCCTG GGCCCTGTCA GGACGCTGTC TCAAAACAAA GTTTGTTATC     1143
AATAGAATAA TTAGAATTAA CAAACTAGGA TTTTCAGTCT TAAGTCATGA TATTGGATCT     1203
TCTCTTCAGT AAGGTTTCTT TTTGGCTAGA AATACTTCAT AGAATTTGAC ATTTTGGTAT     1263
ACATCTGTGG CCTTGATACA ATGACTTGAT TTTCTGTTTT AATTAGTGCA GAGGATTCAG     1323
CAAATTTGCA GGTCTTCATT TTGTTCCCTC GCTATCCATC GATCATGTTT CAGTGTATTA     1383
AGAGGAGTCA GCCAGGCGTG GTGGCCCACA CCTGTGATCC CAGCACTTAG GGGGGCATAG     1443
GCAGGCAGAT CTCTGTGAGC TGAAGGACAG CCTGGCCTAC AAAGTCCAGG ACAACCGAGA     1503
CCACACAGAG AAACCTTGTC TTGAAAAACA AAACAAAAAC AAGAGAGAGA GAGAGAGAGA     1563
```

Fig. 4G

```
GAGAAAAGAG ATGTCAAGAG GTTTTTGTTT TTTTTTTTTT AAATTACTAT TTATGGGCCT   1623
CACTTGGAAA AGTGCTTGCC ATGCAAATAG AAGGACAGGA GTTCAATCCT CATTACCCAC   1683
ATTTGAAACA AATAACAAGA AAAACAAACC AAAAAACCAA AACAAACAAA ATCTTGAGAA   1743
CTTGAGTGAA TACCGGTAAC CTCAGGGCTA GGCACTGTAA CTGAATCAGG AGCCTCCAGA   1803
TCCAGGGAAA CGCTGTCTCA ACAAATAAAT AAATAAGTAA GTCAGTGAGG TGGTCTTTAA   1863
ACCCAGCACT TGAGAGCCAA AGGCAGGCAG AGCTCAGTGA GTTGGAGACC AGCCTGGTCT   1923
ACAAAGCAAG TTCTAAGGGA GCCAGGGCAC AGAGAAACCC TGTCTGAAGG AAAAAAAAAA   1983
AAAAAAAAAG GGCGGCCGC                                                2002
```

Fig. 4H

```
                                .         .         .         .         .
G       1 ATGTTTCTGCTTCTGGTGGTACTCAGCCAGCTGCCCAGACTTACCCTCGC 50
          ||||||  |||||||||  |||||||||| ||||||| | ||||||| |
H       1 ATGTTTACGCTTCTGGTTCTACTCAGCCAACTGCCCACAGTTACCCTGGG 50

                                .         .         .         .         .
G      51 GGTTCCTCAT...ACAAGAAGCCTAAAGAATTCTGAACATGCCCCAGAAG 97
          | ||||||||    ||||| | | ||||  |||| | |||||   |||||
H      51 GTTTCCTCATTGCGCAAGAGGTCCAAAGGCTTCTAAGCATGCGGGAGAAG 100

                                .         .         .         .         .
G      98 GAGTCTTTGCATCAAAAAAAGCAGCAAGCATCTTTATGCACCGTCGCCTC 147
           ||| ||| |||||||| ||| ||||| | | || || ||  | |||||
H     101 AAGTGTTTACATCAAAAGAAGAAGCAAACTTTTTCATACATAGACGCCTT 150

                                .         .         .         .         .
G     148 CTATACAATAGATTTGATTTAGAACTCTTCACTCCCGGGAACCTGGAGAG 197
          || || |||||||||||| | || |||||||||||||| ||||| || ||
H     151 CTGTATAATAGATTTGATCTGGAGCTCTTCACTCCCGGCAACCTAGAAAG 200

                                .         .         .         .         .
G     198 AGAGTGCTATGAGGAGTTCTGTAGTTATGAAGAAGCCAGAGAGATCCTCG 247
          ||||||| |||| ||  | || | |||||| ||||||||||||||  | |
H     201 AGAGTGCAATGAAGAACTTTGCAATTATGAGGAAGCCAGAGAGATTTTTG 250
```

Fig. 4I

```
                                  .         .         .         .         .
G      248 GGGACAACGAAGAAATGATCACATTCTGGCGGGAATATTCAGTCAAAGGA 297
            |||  | ||  ||| |||  |||| |||| |||||||||||  ||||||
H      251 TGGATGAAGATAAAACGATTGCATTTTGGCAGGAATATTCAGCTAAAGGA 300

                                  .         .         .         .         .
G      298 CCAACCACAAGATCAGATGTCAACAAAGAGAAAATTGATGTTATGGGCCT 347
           |||||||||| |||||||| ||||| |||||||||| ||||||||||||||
H      301 CCAACCACAAAATCAGATGGCAACAGAGAGAAAATAGATGTTATGGGCCT 350

                                  .         .         .         .         .
G      348 TCTGACTGGCTTAATTGCGGCTGGAGTATTCTTGGTTGTTTTTGGCTTAC 397
           ||||||||| |||||||| ||||||||||| |||||| ||||||| ||||
H      351 TCTGACTGGATTAATTGCTGCTGGAGTATTTTTGGTTATTTTTGGATTAC 400

                                  .         .         .         .         .
G      398 TTGGTTACTATCTGTGTATCACCAAGTGTAATAGGCAGCCATATCAAGGT 447
           |||| |||||||| |||||||| |||||||||||||  | | ||| | |
H      401 TTGGCTACTATCTTTGTATCACTAAGTGTAATAGGCTACAACATCCATGC 450

                                  .         .         .         .         .
G      448 TCTTCAGCTGTCTACACAAGAAGGACCAGGCACACACCGTCCATCATTTT 497
           |||||||| |||||   |||  ||   |||||||| || |||||||||||
H      451 TCTTCAGCCGTCTATGAAAGGGGG...AGGCACACTCCCTCCATCATTTT 497
```

Fig. 4J

```
                  .         .         .         .         .
G     498 CAGAACCCATGAGGAAGCTGTCTTGTCTCCAT...CGTCATCCTCAGAGG 544
          |||||  | |||||| |||| |||||||||||   || | ||    ||||
H     498 CAGAAGACCTGAGGAGGCTGCCTTGTCTCCATTGCCGCCTTCTGTGGAGG 547

                  .         .         .         .         .
G     545 ACGCGGGACTACCTTCCTATGAACAGGCAGTAGCTCTGACCAGAAAACAC 594
          | || ||| ||||||| |||||||||||||| ||  |||||||||||||||
H     548 ATGCAGGATTACCTTCTTATGAACAGGCAGTGGCGCTGACCAGAAAACAC 597

                  .         .         .         .         .
G     595 AGTGTCTCACCACCACCTCCATATCCTGGGCCAGCAAAAGGATTTAGGGT 644
          ||||| ||||||||||| |||||||||||||   ||||||||||||||||
H     598 AGTGTTTCACCACCACCACCATATCCTGGGCACACAAAAGGATTTAGGGT 647

                  .         .         .
G     645 ATTTAAAAAGTCAATGTCACTCCCATCTCAC 675
          ||||||||| || ||||| ||||||||||||
H     648 ATTTAAAAAATCTATGTCTCTCCCATCTCAC 678
```

Fig. 4K

```
G     1 MFLLLVVLSQLPRLTLAVPH.TRSLKNSEHAPEGVFASKKAASIFMHRRL  49
        || |||.||||| .||  ||  |  | |.|| | || ||. |. |.||||
H     1 MFTLLVLLSQLPTVTLGFPHCARGPKASKHAGEEVFTSKEEANFFIHRRL  50
                 .         .         .         .         .
G    50 LYNRFDLELFTPGNLERECYEEFCSYEEAREILGDNEEMITFWREYSVKG  99
        ||||||||||||||||||| || |.|||||||  | :. | ||.||| ||
H    51 LYNRFDLELFTPGNLERECNEELCNYEEAREIFVDEDKTIAFWQEYSAKG 100
                 .         .         .         .         .
G   100 PTTRSDVNKEKIDVMGLLTGLIAAGVFLVVFGLLGYYLCITKCNRQPYQG 149
        |||:|| |:||||||||||||||||||||:|||||||||||||||  :  
H   101 PTTKSDGNREKIDVMGLLTGLIAAGVFLVIFGLLGYYLCITKCNRLQHPC 150
                 .         .         .         .         .
G   150 SSAVYTRRTRHTPSIIFRTHEEAVLSP.SSSSEDAGLPSYEQAVALTRKH 198
        |||||  | |||||||||  ||| |||   | ||||||||||||||||||
H   151 SSAVY.ERGRHTPSIIFRRPEEAALSPLPPSVEDAGLPSYEQAVALTRKH 199
                 .         .
G   199 SVSPPPPYPGPAKGFRVFKKSMSLPSH 225
        ||||||||||  |||||||||||||||
H   200 SVSPPPPYPGHTKGFRVFKKSMSLPSH 226
```

Fig. 4L

```
GTCGACCCACGCGTCCGGAAATGTCGTTCTTCAGATTTAAAAAGAAAACCTTTACTGAATCAGCTGAGTGTTAATAATA    79

                                                     M   C   G   L   Q   F      6
CGAATTTCCTTTTCTTGCCAATTCTGATCTGAACAGAAAATCCAAGAACAGGGAT ATG TGT GGA TTA CAG TTT    152

 S   L   P   C   L   R   L   F   L   V   V   T   C   Y   L   L   L   L   L   H     26
TCT CTG CCT TGC CTA CGA CTG TTT CTG GTT GTT ACC TGT TAT CTT TTA TTA TTA CTC CAC    212

 K   E   I   L   G   C   S   S   V   C   Q   L   C   T   G   R   Q   I   N   C     46
AAA GAA ATA CTT GGA TGT TCG TCT GTT TGT CAG CTC TGC ACT GGG AGA CAA ATT AAC TGC    272

 R   N   L   G   L   S   S   I   P   K   N   F   P   E   S   T   V   F   L   Y     66
CGT AAC TTA GGC CTT TCG AGT ATT CCT AAG AAT TTT CCT GAA AGT ACA GTT TTT CTG TAT    332

 L   T   G   N   N   I   S   Y   I   N   E   S   E   L   T   G   L   H   S   L     86
CTG ACT GGG AAT AAT ATA TCT TAT ATA AAT GAA AGT GAA TTA ACA GGA CTT CAT TCT CTT    392

 V   A   L   Y   L   D   N   S   N   I   L   Y   V   Y   P   K   A   F   V   Q    106
GTA GCA TTG TAT TTG GAT AAT TCT AAC ATT CTG TAT GTA TAT CCA AAA GCC TTT GTT CAA    452

 L   R   H   L   Y   F   L   F   L   N   N   N   F   I   K   R   L   D   P   G    126
TTG AGG CAT CTA TAT TTT CTA TTT CTA AAT AAT AAT TTC ATC AAA CGC TTA GAT CCT GGA    512
```

Fig. 5A

```
 I   F   K   G   L   L   N   L   R   N   L   Y   L   Q   Y   N   Q   V   S   F   146
ATA TTT AAG GGA CTT TTA AAT CTT CGT AAT TTA TAT TTA CAG TAT AAT CAG GTA TCT TTT  572

 V   P   R   G   V   F   N   D   L   V   S   V   Q   Y   L   N   L   Q   R   N   166
GTT CCG AGA GGA GTA TTT AAT GAT CTA GTT TCA GTT CAG TAC TTA AAT CTA CAA AGG AAT  632

 R   L   T   V   L   G   S   G   T   F   V   G   M   V   A   L   R   I   L   D   186
CGC CTC ACT GTC CTT GGG AGT GGT ACC TTT GTT GGT ATG GTT GCT CTT CGG ATA CTT GAT  692

 L   S   N   N   N   I   L   R   I   S   E   S   G   F   Q   H   L   E   N   L   206
TTA TCA AAC AAT AAC ATT TTG AGG ATA TCA GAA TCA GGC TTT CAA CAT CTT GAA AAC CTT  752

 A   C   L   Y   L   G   S   N   N   L   T   K   V   P   S   N   A   F   E   V   226
GCT TGT TTG TAT TTA GGA AGT AAT AAT TTA ACA AAA GTA CCA TCA AAT GCC TTT GAA GTA  812

 L   K   S   L   R   R   L   S   L   S   H   N   P   I   E   A   I   Q   P   F   246
CTT AAA AGT CTT AGA AGA CTT TCT TTG TCT CAT AAT CCT ATT GAA GCA ATA CAG CCC TTT  872

 A   F   K   G   L   A   N   L   E   Y   L   L   L   K   N   S   R   I   R   N   266
GCA TTT AAA GGA CTT GCC AAT CTG GAA TAC CTC CTC CTG AAA AAT TCA AGA ATT AGG AAT  932

 V   T   R   D   G   F   S   G   I   N   N   L   K   H   L   I   L   S   H   N   286
GTT ACT AGG GAT GGG TTT AGT GGA ATT AAT AAT CTT AAA CAT TTG ATC TTA AGT CAT AAT  992
```

Fig. 5B

```
 D   L   E   N   L   N   S   D   T   F   S   L   L   K   N   L   I   Y   L   K    306
GAT TTA GAG AAT TTA AAT TCT GAC ACA TTC AGT TTG TTA AAG AAT TTA ATT TAC CTT AAG  1052

 L   D   R   N   R   I   I   S   I   D   N   D   T   F   E   N   M   G   A   S    326
TTA GAT AGA AAC AGA ATA ATT AGC ATT GAT AAT GAT ACA TTT GAA AAT ATG GGA GCA TCT  1112

 L   K   I   L   N   L   S   F   N   N   L   T   A   L   H   P   R   V   L   K    346
TTG AAG ATC CTT AAT CTG TCA TTT AAT AAT CTT ACA GCC TTG CAT CCA AGG GTC CTT AAG  1172

 P   L   S   S   L   I   H   L   Q   A   N   S   N   P   W   E   C   N   C   K    366
CCG TTG TCT TCA TTG ATT CAT CTT CAG GCA AAT TCT AAT CCT TGG GAA TGT AAC TGC AAA  1232

 L   L   G   L   R   D   W   L   A   S   S   A   I   T   L   N   I   Y   C   Q    386
CTT TTG GGC CTT CGA GAC TGG CTA GCA TCT TCA GCC ATT ACT CTA AAC ATC TAT TGT CAG  1292

 N   P   P   S   M   R   G   R   A   L   R   Y   I   N   I   T   N   C   V   T    406
AAT CCC CCA TCC ATG CGT GGC AGA GCA TTA CGT TAT ATT AAC ATT ACA AAT TGT GTT ACA  1352

 S   S   I   N   V   S   R   A   W   A   V   V   K   S   P   H   I   H   H   K    426
TCT TCA ATA AAT GTA TCC AGA GCT TGG GCT GTT GTA AAA TCT CCT CAT ATT CAT CAC AAG  1412

 T   T   A   L   M   M   A   W   H   K   V   T   T   N   G   S   P   L   E   N    446
ACT ACT GCG CTA ATG ATG GCC TGG CAT AAA GTA ACC ACA AAT GGC AGT CCT CTG GAA AAT  1472
```

Fig. 5C

```
 T   E   T   E   N   I   T   F   W   E   R   I   P   T   S   P   A   G   R   F     466
ACT GAG ACT GAG AAC ATT ACT TTC TGG GAA CGA ATT CCT ACT TCA CCT GCT GGT AGA TTT   1532

 F   Q   E   N   A   F   G   N   P   L   E   T   T   A   V   L   P   V   Q   I     486
TTT CAA GAG AAT GCC TTT GGT AAT CCA TTA GAG ACT ACA GCA GTG TTA CCT GTG CAA ATA   1592

 Q   L   T   T   S   V   T   L   N   L   E   K   N   S   A   L   P   N   D   A     506
CAA CTT ACT ACT TCT GTT ACC TTG AAC TTG GAA AAA AAC AGT GCT CTA CCG AAT GAT GCT   1652

 A   S   M   S   G   K   T   S   L   I   C   T   Q   E   V   E   K   L   N   E     526
GCT TCA ATG TCA GGG AAA ACA TCT CTA ATT TGT ACA CAA GAA GTT GAG AAG TTG AAT GAG   1712

 A   F   D   I   L   L   A   F   F   I   L   A   C   V   L   I   I   F   L   I     546
GCT TTT GAC ATT TTG CTA GCT TTT TTC ATC TTA GCT TGT GTT TTA ATC ATT TTT TTG ATC   1772

 Y   K   V   V   Q   F   K   Q   K   L   K   A   S   E   N   S   R   E   N   R     566
TAC AAA GTT GTT CAG TTT AAA CAA AAA CTA AAG GCA TCA GAA AAC TCA AGG GAA AAT AGA   1832

 L   E   Y   Y   S   F   Y   Q   S   A   R   Y   N   V   T   A   S   I   C   N     586
CTT GAA TAC TAC AGC TTT TAT CAG TCA GCA AGG TAT AAT GTA ACT GCC TCA ATT TGT AAC   1892

 T   S   P   N   S   L   E   S   P   G   L   E   Q   I   R   L   H   K   Q   I     606
ACT TCC CCA AAT TCT CTA GAA AGT CCT GGC TTG GAG CAG ATT CGA CTT CAT AAA CAA ATT   1952
```

Fig. 5D

```
 V   P   E   N   E   A   Q   V   I   L   F   E   H   S   A   L   *                  623
GTT CCT GAA AAT GAG GCA CAG GTC ATT CTT TTT GAA CAT TCT GCT TTA TAA                2003

CTCAACTAAATATTGTCTATAAGAAACTTCAGTGCCATGGACATGATTTAAACTGAAACCTCCTTATATAATTATATAC  2082

TTTAGTTGGAAATATAATGAATTATATGAGGTTAGCATTATTAAAATATGTTTTTAATAAAAAAAAAAAAAAAAAAAGG  2161

GCGGCCGC                                                                           2169
```

Fig. 5E

```
               10                  20            30             40            50            60
Slit MRGVGWQMLSLSLGLVLA-----ILNKVAPQACPAQCS-CSGSTVDCHGLALRSVPRNIPRNTERLDLNG
     : :.   .  : : ::..      .:.: .  .:.. :   :.:  ..:..:.: :.:.:.: .:  : :.:
 325 MCGLQFSLPCLRLFLVVTCYLLLLLHK-EILGCSSVCQLCTGRQINCRNLGLSSIPKNFPESTVFLYLTG
               10            20             30            40            50            60

          70            80             90            100           110           120           130
Slit NNITRITKTDFAGLRHLRVLQLMENKISTIERGAFQDLKELERLRLNRNHLQLFPELLFLGTAKLYRLDL
     :::. :. ....::. : .: : ...:  .   :: .:.                 .:.  .:::... . :::
 325 NNISYINESELTGLHSLVALYLDNSNILYVYPKAFVQLR------------HLY--FLFLNNNFIKRLD-
    70            80            90            100                           110             120

          140           150           160           170           180           190           200
Slit SENQIQAIPRKAFRGAVDIKNLQLDYNQISCIEDGAFRALRDLEVLTLNNNNITRLSVASFNHMPKLRTF
          ..:    :.: ....:: :.:::.: .  :.: .: ... :.:. : .: :. ..:
 325 -----PGI----FKGLLNLRNLYLQYNQVSFVPRGVFNDLVSVQYLNLQRNRLTVLGSGTF---------
                 130           140           150           160           170

          210           220           230           240           250           260           270
Slit RLHSNNLYCDCHLAWLSDWLRQRPRVGLYTQCMGPSHLRGHNVAEVQKREFVCSGHQSFMAPSCSVLHCP
                                ::.               ::
 325 --------------------------VGM--------------VA--------------------------
                                                       180
```

Fig. 5G

```
        280       290       300       310       320       330       340
Slit AACTCSNNIVDCRGKGLTEIPTNLPETITEIRLEQNTIKVIPPGAFSPYKKLRRIDLSNNQISELAPDAF
                                                        :: .:::::.:
325  ---------------------------------------------------LRILDLSNNNI--------
                                                              190

        350       360       370       380       390       400       410
Slit QGLRSLNSLVLYGNKITELPKSLFEGLFSLQLLLLNANKINCLRVDAFQDLHNLNLLSLYDNKLQTIAKG
       ::           :.:                           ..::.: ::. :
325  --LR-----------ISE---------------------------SGFQHLENLACL-------------
                                                  200

        420       430       440       450       460       470       480
Slit TFSPLRAIQTMHLAQNPFICDCHLKWLADYLHTNPIETSGARCTSPRRLANKRIGQIKSKKFRCSAKEQY
                                  :: .:
325  -----------------------------YLGSN------------------------------------
                                210

        490       500       510       520       530       540       550
Slit FIPGTEDYRSKLSGDCFADLACPEKCRCEGTTVDCSNQKLNKIPEHIPQYTAELRLNNNEFTVLEATGIF
                                           .:.:.:             .:.: :: .
325  --------------------------------------NLTKVP-------------SNAFEVLKS----
                                             220
```

Fig. 5H

```
           560       570       580       590       600       610       620
Slit KKLPQLRKINFSNNKITDIEEGAFEGASGVNEILLTSNRLENVQHKMFKGLESLKTLMLRSNRITCVGND
          ::....:.: : .:.  .:.                      ::::..:  :.:...::  :  :
325  -----LRRLSLSHNPIEAIQ--PFA----------------------FKGLANLEYLLLKNSRIRNVTRD
           230       240                            250       260       270

           630       640       650       660       670       680       690
Slit SFIGLSSVRLLSLYDNQITTVAPGAFDTLHSLSTLNLLANPFNCNCYLAWLGEWLRKKRIVTGNPRCQKP
     .: :..... : : .:.                    :.:
325  GFSGINNLKHLILSHND-------------------LEN------------------------------
               280                        290

           700       710       720       730       740       750       760
Slit YFLKEIPIQDVAIQDFTCDDGNDDNSCSPLSRCPTECTCLDTVVRCSNKGLKVLPKGIPRDVTELYLDGN
                                                                     :...
325  ------------------------------------------------------------------LNSD

           770       780       790       800        810       820       830
Slit QFTLVPKELSNYKHLTLIDLSNNRISTLSNQSFSNM-TQLLTLILSYNRLRCIPPRTFDGLKSLRLLSLH
      :.:.        :.:. . :. ::: ...:..: :: . : .: ::.: :   . ::.   ::.:
325  TFSLL-------KNLIYLKLDRNRIISIDNDTFENMGASLKILNLSFNNLTALHPRV---LKPL------
                 300       310       320       330       340
```

Fig. 5I

```
          840       850       860       870       880       890       900
Slit GNDISVVPEGAFNDLSALSHLAIGANPLYCDCNMQWLSDWVKSEYKEPGIARCAGPGEMADKLLLTTPSK
                    :.: ::  ..::  :.:..  : ::. :
325  ---------------SSLIHLQANSNPWECNCKLLGLRDWLAS---------------------------
                    350       360       370

          910       920       930       940       950       960       970
Slit KFTCQGPVDVNILAKCNPCLSNPCKNDGTCNSDPVDFYRCTCPYGFKGQDCDVPIHACISNPCKHGGTCH
          ...  .::                           :            :. :       : ..:
325  -----SAITLNI-------------------------Y------------CQNP-------PSMRG----
            380                                                   390

          980       990      1000      1010      1020      1030      1040
Slit LKEGEEDGFWCICADGFEGENCEVNVDDCEDNDCENNSTCVDGINNYTCLCPPEYTGELCEEKLDFCAQD
            ... :                      : ..::
325  ------RALRYI-----------------------NITNCV-----------------------------
                                     400

         1050      1060      1070      1080      1090      1100      1110
Slit LNPCQHDSKCILTPKGFKCDCTPGYVGEHCDIDFDDCQDNKCKNGAHCTDAVNGYTCICPEGYSGLFCEF
                                                    :...:
325  ------------------------------------------------TSSIN-----------------
                                                      410
```

Fig. 5J

```
          1120      1130      1140      1150      1160      1170      1180
Slit SPPMVLPRTSPCDNFDCQNGAQCIVRINEPICQCLPGYQGEKCEKLVSVNFINKESYLQIPSAKVRPQTN
          ..:. .          .:.                       : .. .: . : ..  ::
 325 -----VSRAWA------------VVK---------------------SPHIHHKTTALMMAWHKV-----
                                                  420       430

          1190      1200      1210      1220      1230      1240      1250
Slit ITLQIATDEDSGILLYKGDKDHIAVELYRGRVRASYDTGSHPASAIYSVETINDGNFHIVELLALDQSLS
          .:. ..   : . . ..:.   .. :. .:     ::. ..  .....  . ....:...  :.
 325 -----TTNGSP---LENTETENIT---FWERIPTS------PAGRFFQENAFGNP-LETTAVLPVQIQLT
           440         450          460             470        480

          1260      1270      1280      1290      1300      1310      1320
Slit LSVDGGNPKIITNLSKQSTLNFDSPLYVGGMPGKSNVASLRQAPGQNGTSFHGCIRNLYINSELQDFQKV
      ::      . :: :.:.:  :..   .:.::...                 :.         :. .:.
 325 TSV-------TLNLEKNSALPNDAA----SMSGKTSLI---------------CT---------QEVEKL
   490              500           510                               520

          1330      1340      1350      1360      1370      1380      1390
Slit PMQTGILPGCEPCHKKVCAHGTCQPSSQAGFTCECQEGWMGPLCDQRTNDPCLGNKCVHGTCLPINAFSY
        .:: .                    :                                    :
 325 NEAFDILLA--------------------F-------------------------------------FIL
        530
```

Fig. 5K

```
          1400      1410      1420      1430      1440      1450      1460
Slit SCKCLEGHGGVLCDEEEDLFNPCQAIKCKHGKCRLSGLGQPYCECSSGYTGDSCDREISCRGERIRDYYQ
     .:        ::      .:   .... :.   .: .              . .:      : .:. .::
325  AC--------VL-----IIFLIYKVVQFKQ---KLKA------------SENS-------RENRL-EYY-
                 540       550                         560              570

          1470       1480      1490      1500      1510      1520
Slit KQQGYAACQTTK-KVSRLECRGGCAGGQCCGPLRSKRRKYSFECTDGSSFVDEVEKVVKCGCTRCVS
       ..   :... .:.   :  . .. .  :  . . .:         .: : : :     . .
325  ---SF--YQSARYNVTASICNTSPNSLESPGLEQIRLHK---------QIVPENEAQVI-LFEHSAL
                 580       590       600                 610       620
```

Fig. 5L

```
             10        20        30        40        50        60        70
Slit CAGAGCAGGGTGGAGAGGGCGGTGGGAGGCGTGTGCCTGAGTGGGCTCTACTGCCTTGTTCCATATTATT

325  ----------------------------------------------------------------------

             80        90       100       110       120       130       140
Slit TTGTGCACATTTTCCCTGGCACTCTGGGTTGCTAGCCCCGCCGGGCACTGGGCCTCAGACACTGCGCGGT

325  ----------------------------------------------------------------------

            150       160       170       180       190       200       210
Slit TCCCTCGGAGCAGCAAGCTAAAGAAAGCCCCCAGTGCCGGCGAGGAAGGAGGCGGCGGGGAAAGATGCGC

325  ----------------------------------------------------------------------

            220       230       240       250       260       270       280
Slit GGCGTTGGCTGGCAGATGCTGTCCCTGTCGCTGGGGTTAGTGCTGGCGATCCTGAACAAGGTGGCACCGC
                               ::::                                   :::
325  --------------------------GTCG-----------------------------------ACC--
```

Fig. 5M-1

```
            290       300       310       320       330       340       350
Slit AGGCGTGCCCGGCGCAGTGCTCTTGCTCGGGCAGCACAGTGGACTGTCACGGGCTGGCGCTGCGCAGCGT
                                                    ::::                :::
325  -----------------------------------------------CACG----------------CGT
                                                      10

            360       370       380       390       400       410       420
Slit GCCCAGGAATATCCCCCGCAACACCGAGAGACTGGATTTAAATGGAAATAACATCACAAGAATTACGAAG
       ::.:.:::.::
325  --CCGGAAATGTC---------------------------------------------------------
            20

            430       440       450       460       470       480       490
Slit ACAGATTTTGCTGGTCTTAGACATCTAAGAGTTCTTCAGCTTATGGAGAATAAGATTAGCACCATTGAAA
                                   ::::::::: ::....:..:.::        ::.::.
325  ------------------------------GTTCTTCAGATTTAAAAAGAAAA--------CCTTTA---
                                      30        40                50

            500       510       520       530       540       550       560
Slit GAGGAGCATTCCAGGATCTTAAAGAACTAGAGAGACTGCGTTTAAACAGAAATCACCTTCAGCTGTTTCC
                :.:.:::      :.:: :::.:       ::::.   ::..:.        ..:::::
325  -----------CTGAATC------AGCT-GAGTG-------TTAAT---AATACG--------AATTTCC
                     60                70                  80
```

Fig. 5M-2

```
            570       580       590       600       610       620       630
Slit TGAGTTGCTGTTTCTTGGGACTGCGAAGCTATACAGGCTTGATCTCAGTGAAAACCAAATTCAGGCAATC
     :         :::::::   :  :.:. ::...:.:.       .:::. :::.::::...::::
 325 T---------TTTCTTG---C--CAATTCTGATCTGA-------ACAGA-AAATCCAAGAACAGG-----
              90            100       110               120       130

            640       650       660       670       680       690       700
Slit CCAAGGAAAGCTTTCCGTGGGGCAGTTGACATAAAAAATTTGCAACTGGATTACAACCAGATCAGCTGTA
                                       .:.:: ::    :::::::::            ::.
 325 ----------------------------------GATATGTG----TGGATTACA------------GTT
                                                 140                   150

            710       720       730       740       750       760       770
Slit TTGAAGATGGGGCATTCAGGGCTCTCCGGGACCTGGAAGTGCTCACTCTCAACAATAACAACATTACTAG
     ::                   ::::     .:::     :::       :.::.:
 325 TT-------------------CTCT-----GCCT-----TGC-------CTACGA---------------
                                   160                   170

            780       790       800       810       820       830       840
Slit ACTTTCTGTGGCAAGTTTCAACCATATGCCTAAACTTAGGACTTTTCGACTGCATTCAAACAACCTGTAT
          ::::  :..:::  .:::. .:.            .:::::                      ::
 325 -----CTGTTTCTGGTTGTTACCTGTTA------------TCTTTT----------------------AT
                 180       190                                         200
```

Fig. 5M-3

```
             850       860       870       880       890       900       910
Slit TGTGACTGCCACCTGGCCTGGCTCTCCGACTGGCTTCGCCAAAGGCCTCGGGTTGGTCTGTACACTCAGT
     :.: ::: :::: ..:                        ::: .:      ::::. :::.:. ::  :
 325 TATTACT-CCACAAAG------------------------AAATAC------TTGGA-TGTTCG-TC--T
            210                               220              230

             920       930       940       950       960       970       980
Slit GTATGGCCCCTCCCACCTGAGAGGCCATAATGTAGCCGAGGTTCAAAAACGAGAATTTGTCTGCAGTGG
     ::.::      ::                     :::                       :::::: :::
 325 GTTTG------TC---------------------AGC-----------------------TCTGCACTGG
      240                                                         250

             990      1000      1010      1020      1030      1040      1050
Slit TCACCAGTCATTTATGGCTCCTTCTTGTAGTGTTTTGCACTGCCCTGCCGCCTGTACCTGTAGCAACAAT
          ::.::..:..                       ::::::         ::: :: ..::
 325 G----AGACAAATTA-----------------------ACTGCC---------GTAACTTAGGC------
           260                             270                280

            1060      1070      1080      1090      1100      1110      1120
Slit ATCGTAGACTGTCGTGGGAAAGGTCTCACTGAGATCCCCACAAATCTTCCAGAGACCATCACAGAAATAC
            :: ::::.:    .. ::   ::.:::         :: ::::.::.:  .: ::::...:.:
 325 --------CTTTCGAG----TATTC---CTAAGA---------ATTTTCCTGAAA--GT-ACAGTTTTTC
                 290              300                310          320
```

Fig. 5M-4

```
            1130      1140      1150      1160      1170      1180      1190
Slit GTTTGGAACAGAACACAATCAAAGTCATCCCTCCTGGAGCTTTCTCACCATATAAAAAGCTTAGACGAAT
        :: :.:.::                     ::::.. :.. . : :.::::.:::  ..::. ::::
 325 ---TGTATCTGA---------------------CTGGGAATAATATATCTTATATAAATGAAAGT-GAAT
        330                          340       350       360         370

            1200      1210      1220      1230      1240      1250      1260
Slit TGACCTGAGCAATAATCAGATCTCTGAACTTGCACCAGATGCTTTCCAAGGACTACGCTCTCTGAATTCA
     :.::                                         ::::::.:        ::::.
 325 TAAC-----------------------------------------AGGACTTC---------ATTCT
                                                   380

            1270      1280      1290      1300      1310      1320      1330
Slit CTTGTCCTCTATGGAAATAAAATCACAGAACTCCCCAAAAGTTTATTTGAAGGACTGTTTTCCTTACAGC
     :::::                      :.:        : : :::::::.:      :..: ::.:::
 325 CTTGT----------------------AGC--------ATTGTATTTGGA------TAATTCTAACA--
    390                                   400             410       420

            1340      1350      1360      1370      1380      1390      1400
Slit TCCTATTATTGAATGCCAACAAGATAAACTGCCTTCGGGTAGATGCTTTTCAGGATCTCCACAACTTGAA
     : ::.:.. :..:: :::: :         ::::: :     : :..:: :::        ::.::. :.
     TTCTGTATGTATAT-CCAAAA---------GCCTTTG------TTCAATTGAGG-------CATCTATAT
            430        440                      450              460
```

Fig. 5M-5

```
             1410      1420      1430      1440      1450      1460      1470
Slit CCTTCTCTCCCTATATGACAACAAGCTTCAGACCATCGCCAAGGGGACCTTTTCACCTCTTCGGGCCATT
      :::: :  :::.:::.: ::                              :::::              :
 325 T-TTCTATTTCTAAATAATAA------------------------------TTTCA--------------T
      470       480                                         490

             1480      1490      1500      1510      1520      1530      1540
Slit CAAACTATGCATTTGGCCCAGAACCCCTTTATTTGTGACTGCCATCTCAAGTGGCTAGCGGATTATCTCC
     :::::   :: ::.:. ::.:.:     .:::::                 ::: :.::.    ...:::: :
 325 CAAAC---GC-TTAGATCCTGGA-----ATATTT--------------AAGGGACTTT---TAAATCTTC
            500       510                            520       530

             1550      1560      1570      1580      1590      1600      1610
Slit ATACCAACCCGATTGAGACCAGTGGTGCCCGTTGCACCAGCCCCCGCCGCCTGGCAAACAAAAGAATTGG
     .::                                                            :.. :..:
 325 GTA------------------------------------------------------------ATTTATATTT
     540                                                                  550

             1620      1630      1640      1650      1660      1670      1680
Slit ACAGATCAAAAGCAAGAAATTCCGTTGTTCAGCTAAAGAACAGTATTTCATTCCAGGTACAGAAGATTAT
     ::::.  :.:: ::.:.:  ::  ::::::  : :.::.  ::::::: ::
 325 ACAGT--ATAATCAGGTA--TCTTTTGTTC--CGAGAGG--AGTATTTAAT-------------------
               560       570       580       590
```

Fig. 5M-6

```
             1690      1700      1710      1720      1730      1740      1750
Slit CGATCAAAATTAAGTGGAGACTGCTTTGCGGATCTGGCTTGCCCTGAAAAGTGTCGCTGTGAAGGAACCA
      ::::.:..::              :.:.::.:
325  -GATCTAGTTT-------------CAGTTCAG-----------------------------
             600                   610

             1760      1770      1780      1790      1800      1810      1820
Slit CAGTAGATTGCTCTAATCAAAAGCTCAACAAAATCCCGGAGCACATTCCCCAGTACACTGCAGAGTTGCG
             :.:: .:::::.:        ::::     :::.     :: ::.   :::::
325  --------TACTTAAATCTA--------CAAA-----GGAA-----TCGCCT---CACTG----------
                    620                   630                 640

             1830      1840      1850      1860      1870      1880      1890
Slit TCTCAATAATAATGAATTTACCGTGTTGGAAGCCACAGGAATCTTTAAGAAACTTCCTCAATTACGTAAA
                        .::   ::::.::    .::              :.:::
325  -------------------TCC---TTGGGAG----TGG--------------TACCT------------
                                  650                      660

             1900      1910      1920      1930      1940      1950      1960
Slit ATAAACTTTAGCAACAATAAGATCACAGATATTGAGGAGGGAGCATTTGAAGGAGCATCTGGTGTAAATG
                                .:.:::. ..:: .::.          :.:: :
325  ----------------------------TTGTTGGTATGGTTGCT----------CTTCGG---------
                                         670               680
```

Fig. 5M-7

```
             1970      1980      1990      2000      2010      2020      2030
Slit AAATACTTCTTACGAGTAATCGTTTGGAAAATGTGCAGCATAAGATGTTCAAGGATTGGAAAGCCTCAA
       ::::::     :: :.:::                                                :
325  --ATACTT-----GATTTATC------------------------------------------------A
                690

             2040      2050      2060      2070      2080      2090      2100
Slit AACTTTGATGTTGAGAAGCAATCGAATAACCTGTGTGGGAATGACAGTTTCATAGGACTCAGTTCTGTG
     :::                     ::::::  .: : :.:.::..:::..:::
325  AAC---------------------AATAAC--ATTTTGAGGATATCAGAATCAG----------------
      700                              710       720

             2110      2120      2130      2140      2150      2160      2170
Slit CGTTTGCTTTCTTTGTATGATAATCAAATTACTACAGTTGCACCAGGGGCATTTGATACTCTCCATTCTT
          ::::::
325  -----GCTTTC-----------------------------------------------------------
         730

             2180      2190      2200      2210      2220      2230      2240
Slit TATCTACTCTAAACCTCTTGGCCAATCCTTTTAACTGTAACTGCTACCTGGCTTGGTTGGGAGAGTGGCT
                ::: :::::.  ::.::::                    ::::: :::  ..       :
325  -----------AACATCTTGA--AAACCTT--------------------GCTTGTTTGTAT-------T
                  740         750                            760
```

Fig. 5M-8

```
            2250      2260      2270      2280      2290      2300      2310
Slit GAGAAAGAAGAGAATTGTCACGGGAAATCCTAGATGTCAAAAACCATACTTCCTGAAAGAAATACCCATC
      ::.:::.:..:.::.  ::..:..::     .::::::.::.:.           :::.:::
325  TAGGAAGTAATAATTTA--ACAAAAGTACC-----ATCAAATGCCTTT----------GAAGTAC-----
       770       780        790            800                 810

            2320      2330      2340      2350      2360      2370      2380
Slit CAGGATGTGGCCATTCAGGACTTCACTTGTGATGACGGAAATGATGACAATAGTTGCTCCCCACTTTCTC
                 .:. :.:.:::                  .::.:::..:          :. : ::::
325  ------------TTAAAAGTCTT------------------AGAAGACTTT----------CTTTGTCTC
                    820                           830                 840

            2390      2400      2410      2420      2430      2440      2450
Slit GCTGTCCTACTGAATGTACTTGCTTGGATACAGTCGTCCGATGTAGCAACAAGGGTTTGAAGGTCTTGCC
     . ..::::: ::::          ::.   :::::: :  :: .::   ::       :::.::::.::::::
325  ATAATCCTATTGAA-------GCA---ATACAG-C--CCTTTG---CA-------TTTAAAGGACTTGCC
         850              860             870                 880       890

            2460      2470      2480      2490      2500      2510      2520
Slit GAAAGGTATTCCAAGAGATGTCACAGAGTTGTATCTGGATGGAAACCAATTTACACTGGTTCCCAAGGAA
      .:                            ::::::   :.:::            :::
325  AA------------------------------TCTGGA---ATACC-------------TCC-------
                                                 900
```

Fig. 5M-9

```
             2530      2540      2550      2560      2570      2580      2590
Slit CTCTCCAACTACAAACATTTAACACTTATAGACTTAAGTAACAACAGAATAAGCACGCTTTCTAATCAGA
        ::::.. .: :..::. .:     :...::   :.::.::.: .:.::..:        : ::.:  :.
 325 ---TCCTGAAAAATTCAAGAA-----TTAGGA---ATGTTACTA-GGGATGGG-------TTTAGT--GG
        910       920            930           940              950

             2600      2610      2620      2630      2640      2650      2660
Slit GCTTCAGCAACATGACCCAGCTCCTCACCTTAATTCTTAGTTACAACCGTCTGAGATGTATTCCTCCTCG
     . :: :  :.:.:.:           :: ::...:::::.       :::. ..:::.
 325 AATTAATAATCTTAA-----------ACATTTGATCTTAA--------GTCA-TAATGA-----------
       960       970                980                990

             2670      2680      2690      2700      2710      2720      2730
Slit CACCTTTGATGGATTAAAGTCTCTTCGATTACTTTCTCTACATGGAAATGACATTTCTGTTGTGCCTGAA
         :::...:.:::.::.:    :: .. ::.:::. :  .:: .::.:: :::  :..: :.::: ::
 325 ----TTTAGAGAATTTAAAT----TCTGACACATTCAGT--TTGTTAAAGA-ATT--TAATTTACCTTAA
             1000      1010           1020        1030          1040      1050

             2740      2750      2760      2770      2780      2790      2800
Slit GGTGCTTTCAATGATCTTTCTGCATTATCACATCTAGCAATTGGAGCCAACCCTCTTTACTGTGATTGTA
     :    ::. :..::.   .:.: ::.::      ::::::.:                   :. :.::..
 325 G----TTAGATAGAA---ACAGAATAAT------TAGCATT--------------------GATAATGAT
                1060          1070                                 1080
```

Fig. 5M-10

```
           2810      2820      2830      2840      2850      2860      2870
Slit ACATGCAGTGGTTATCCGACTGGGTGAAGTCGGAATATAAGGAGCCTGGAATTGCTCGTTGTGCTGGTCC
     ::::                         : :.::.....::::: :         : :::..  :.:::
 325 ACAT-------------------------TTGAAAATATGGAGCAT----------CTTTGAA--GATCC
   1090                               1100      1110                 1120

           2880      2890      2900      2910      2920      2930      2940
Slit TGGAGAAATGGCAGATAAACTTTTACTCACAACTCCCTCCAAAAAATTTACCTGTCAAGGTCCTGTGGAT
     :                                              :.: ::::::.
 325 T----------------------------------------------TAATCTGTCAT------------
                                                       1130

           2950      2960      2970      2980      2990      3000      3010
Slit GTCAATATTCTAGCTAAGTGTAACCCCTGCCTATCAAATCCGTGTAAAAATGATGGCACATGTAATAGTG
      : ::::.:::..:.             ::::. :  ::::..:                         :
 325 -TTAATAATCTTACA-------------GCCTTGC--ATCCAAG-------------------------G
        1140                   1150        1160

           3020      3030      3040      3050      3060      3070      3080
Slit ATCCAGTTGACTTTTACCGATGCACCTGTCCATATGGTTTCAAGGGGCAGGACTGTGATGTCCCAATTCA
     .:::       ::...:::.      ::::        ::::. :                    :::::
 325 GTCC-------TTAAGCCGT------TGTC--------TTCATTG--------------------ATTCA
               1170            1180                                  1190
```

Fig. 5M-11

```
                3090      3100      3110      3120      3130      3140      3150
Slit TGCCTGCATCAGTAACCCATGTAAACATGGAGGAACTTGCCACTTAAAGGAAGGAGAAGAAGATGGATTC
     :     :.::::    ::..:.           ::.. : :::       ::..:.:.:. :: :..:
 325 T-----CTTCAGG----CAAATT------------CTAATC-CTT-------GGGAATGTAACTGCAAAC
          1200                          1210              1220      1230

                3160      3170      3180      3190      3200      3210      3220
Slit TGGTGTATTTGTGCTGATGGATTTGAAGGAGAAAATTGTGAAGTCAACGTTGATGATTGTGAAGATAATG
     :      :::: ::                               :..::.                 :
 325 T------TTTGGGC--------------------------------CTTCGA-----------------G
          1240

                3230      3240      3250      3260      3270      3280      3290
Slit ACTGTGAAAATAATTCTACATGTGTCGATGGCATTAATAACTACACATGCCTTTGCCCACCTGAGTATAC
     ::::             .:         :.::::      ::.::   :::.::.:
 325 ACTG-------------GC---------TAGCAT------CTTCA---GCCATTAC--------------
   1250                             1260              1270

                3300      3310      3320      3330      3340      3350      3360
Slit AGGTGAGTTGTGTGAGGAGAAGCTGGACTTCTGTGCCCAGGACCTGAACCCCTGCCAGCACGATTCAAAG
                          ::..::.:::.:     :.:  .:.:::
 325 ---------------------TCTAAACATCTATT-----GTCAGAATCCCC------------------
                             1280          1290
```

Fig. 5M-12

```
           3370      3380      3390      3400      3410      3420      3430
Slit TGCATCCTAACTCCAAAGGGATTCAAATGTGACTGCACACCAGGGTACGTAGGTGAACACTGCGACATCG
       :::::...:                 :::.:.: .::      ::::::.
 325 --CATCCATGC-----------------GTGGCAGAGCA-----TTACGTT-------------------
    1300                       1310           1320

           3440      3450      3460      3470      3480      3490      3500
Slit ATTTTGACGACTGCCAAGACAACAAGTGTAAAAACGGAGCCCACTGCACAGATGCAGTGAACGGCTATAC
     ::.::.::       :. :::: ..:::::.:        : .:: ::                  :::
 325 ATATTAAC-------ATTACAAATTGTGTTA---------CATCTTCA------------------ATAA
     1330             1340      1350                                 1360

           3510      3520      3530      3540      3550      3560      3570
Slit GTGCATATGCCCCGAAGGTTACAGTGGCTTGTTCTGTGAGTTTTCTCCACCCATGGTCCTCCCTCGTACC
     .:: ::     ::..::    :.  :::: :::    :....:::::.:   ::. :: :: :. :.  :
 325 ATGTAT-----CCAGAG----CTTGGGCT-GTT----GTAAAATCTCCTC--ATATTCATCACAAGA--C
              1370          1380           1390        1400      1410

           3580      3590      3600      3610      3620      3630      3640
Slit AGCCCCTGTGATAATTTTGATTGTCAGAATGGAGCTCAGTGTATCGTCAGAATAAATGAGCCAATATGTC
     ..:   :: : ::::   ::: : :.:      ::. :..:::.:  ::            ::: ::: :
 325 TAC---TGCGCTAAT---GATGGCCTG------GCATAAAGTAAC--CA------------CAA-ATGGC
          1420         1430            1440                    1450
```

Fig. 5M-13

```
           3650      3660      3670      3680      3690      3700      3710
Slit AGTGTTTGCCTGGCTATCAGGGAGAAAAGTGTGAAAAATTGGTTAGTGTGAATTTTATAAACAAAGAGTC
     :::     :::  ::     :::.::.: ::.::            ::.::: .::: ...:...::.
 325 AGT-----CCT--CT-----GGAAAATACTGAGAC-----------TGAGAACATTACTTTCTGGGAA--
    1460                 1470      1480                 1490      1500

           3720      3730      3740      3750      3760      3770      3780
Slit TTATCTTCAGATTCCTTCAGCCAAGGTTCGGCCTCAGACGAACATAACACTTCAGATTGCCACAGATGAA
            :..::::::.:        :::. :  :.:. ..: .:.. .:.. :::.::::. .:.:.:
 325 -------CGAATTCCTAC--------TTCACCTGCTGGTAGA-TTTTTTCAAGAGAATGCCTTTGGTAA-
              1510                 1520      1530      1540      1550

           3790      3800      3810      3820      3830      3840      3850
Slit GACAGCGGAATCCTCCTGTATAAGGGTGACAAAGACCATATCGCGGTAGAACTCTATCGGGGGCGTGTTC
                 :::. ::     :.:::.:    ::    ::.::. .:: ::.:     ::...:.:
 325 -------------TCCATTA-----GAGACTA----CA----GCAGTGTTAC-CTGT-----GCAAATAC
                 1560                1570          1580            1590

           3860      3870      3880      3890      3900      3910      3920
Slit GTGCCAGCTATGACACCGGCTCTCATCCAGCTTCTGCCATTTACAGTGTGGAGACAATCAATGATGGAAA
     .. : ..:::                 :. ::  :.::.: .::.   ::::.: ::.::.:: :
 325 AA-CTTACTA-----------------CTTCTGTTACCTTGAACT---TGGAAAAAAACAGTGCT-----
          1600                       1610      1620         1630
```

Fig. 5M-14

```
           3930      3940      3950      3960      3970      3980      3990
Slit CTTCCACATTGTGGAACTACTTGCCTTGGATCAGAGTCTCTCTTTGTCCGTGGATGGTGGGAACCCCAAA
     ::.::.   ..::...::.:::                   :..::::         .:::::
 325 CTACCG---AATGATGCTGCTT-------------------CAATGTC---------AGGGAA-------
    1640         1650                            1660

           4000      4010      4020      4030      4040      4050      4060
Slit ATCATCACTAACTTGTCAAAGCAGTCCACTCTGAATTTTGACTCTCCACTCTATGTAGGAGGCATGCCAG
     :.::::.:::: ::::           ::.:...:. ::::
 325 AACATCTCTAATTTGT-----------ACACAAGAAGTTGA-----------------------------
  1670      1680                    1690

           4070      4080      4090      4100      4110      4120      4130
Slit GGAAGAGTAACGTGGCATCTCTGCGCCAGGCCCCTGGGCAGAACGGAACCAGCTTCCACGGCTGCATCCG
      ::::. :: :.::::.:                ": :.:: .. :   : :::::"
 325 -GAAGTTGAATGAGGCTT----------------TTGACATTTTG---CTAGCTT---------------
   1700      1710                         1720         1730

           4140      4150      4160      4170      4180      4190      4200
Slit GAACCTTTACATCAACAGTGAGCTGCAGGACTTCCAGAAGGTGCCGATGCAAACAGGCATTTTGCCTGGC
          :::.::::     : ::::                :::       ... :. ::::::
 325 -----TTTTCATC-----TTAGCTT---------------GTG-------TTTTAATCATTTT-------
            1740                          1750             1760
```

Fig. 5M-15

```
              4210      4220      4230      4240      4250      4260      4270
Slit TGTGAGCCATGCCACAAGAAGGTGTGTGCCCATGGCACATGCCAGCCCAGCAGCCAGGCAGGCTTCACCT
     : ::: :  :.:     .::: :::                                :::  :.    .
 325 TTTGATC--TAC-----AAAGTTGTT--------------------------------CAGTTTA----A
       1770             1780                                     1790

              4280      4290      4300      4310      4320      4330      4340
Slit GCGAGTGCCAGGAAGGATGGATGGGGCCCCTCTGTGACCAACGGACCAATGACCCTTGCCTTGGAAATAA
     .:.:...: :  ::::            : ::.:..: :.                  :..::.::.:.
 325 ACAAAAACTA--AAGG------------CATCAGAAAACT-------------------CAAGGGAAAAT
        1800                     1810                        1820

              4350      4360      4370      4380      4390      4400      4410
Slit ATGCGTACATGGCACCTGCTTGCCCATCAATGCGTTCTCCTACAGCTGTAAGTGCTTGGAGGGCCATGGA
     : .: :. ::. :. :.::::                  :: ::  .:::::.. ...:.          ::: :
 325 AGACTTGAATA-CTACAGCTT-------------TTATCAGTCAGCAAGGTATA-----------ATGTA
 1830      1840                     1850      1860                1870

              4420      4430      4440      4450      4460      4470      4480
Slit GGTGTCCTCTGTGATGAAGAGGAGGATCTGTTTAACCCATGCCAGGCGATCAAGTGCAAGCACGGGAAGT
     . :: :::::..: .::                :::: :.: ::       :::.: :.  :. .:.::::
 325 ACTG-CCTCAAT-TTG----------------TAACACTTCCC-------CAAATTCT--CT-AGAAAGT
        1880                        1890             1900         1910
```

Fig. 5M-16

```
                4490      4500      4510      4520      4530      4540      4550
Slit GCAGGCTTTCAGGTCTGGGGCAGCCCTACTGTGAATGCAGCAGTGGATACACGGGGACAGCTGTGATCG
      :.:::::        ::.::::                            ::.:      :::. :. :.:.:.
 325 CCTGGCTT--------GGAGCAG-----------------------ATTC------GACTTCA-TAAACA
     1920              1930                                      1940

                4560      4570      4580      4590      4600      4610      4620
Slit AGAAATCTCTTGTCGAGGGGAAAGGATAAGAGATTATTACCAAAAGCAGCAGGGCTATGCTGCTTGCCAA
     :....: ::    :        .:.:.:.:::            ::: :::: : :: ::  :::   :
 325 AATTGT-TC----C--------TGAAAATGAG-------------GCA-CAGGTC-ATTCTTTTG---A
    1950                   1960                   1970      1980

                4630      4640      4650      4660      4670      4680      4690
Slit ACAACCAAGAAGGTGTCCCGATTAGAGTGCAGAGGTGGGTGTGCAGGAGGGCAGTGCTGTGGACCGCTGA
     :::. :                                                :::: :. : : :
 325 ACATTC------------------------------------------------TGCTTTATAACTC---
     1990                                                      2000

                4700      4710      4720      4730      4740      4750      4760
Slit GGAGCAAGCGGCGGAAATACTCTTTCGAATGCACTGACGGCTCCTCCTTTGTGGACGAGGTTGAGAAAGT
       :.:.:.      :.::. :::.: ..:..:.   .:.:  ::.     :::::..:.:: :.:
 325 --AACTAA------ATATTGTCTATAAGAAACT---TCAGTGCCA------TGGACATGATTTAAA----
       2010            2020      2030         2040             2050
```

Fig. 5M-17

```
           4770      4780      4790      4800      4810      4820      4830
Slit GGTGAAGTGCGGCTGTACGAGGTGTGTGTCCTAAACACACTCCCGGCAGCTCTGTCTTTGGAAAAGGTTG
                 :::                 ::::   :::             :::   :.:...::.
 325 ------------CTG-----------------AAAC---CTC-------------CTT---ATATAATTA
                                    2060                       2070

           4840      4850      4860      4870      4880      4890      4900
Slit TATACTTCTTGACCATGTGGGACTAATGAATGCTTCATAGTGGAAATATTTGAAATATATTGTAAAATAC
     ::::::: :.:.   :: .... ::::::::  :. ...:: .. ::..::.::::::.:: :.::
 325 TATACTT-TAGT---TGGAAATATAATGAATTATATGAGGTTAGCATTATTAAAATATGTTTTTAA----
    2080          2090      2100      2110      2120      2130

           4910      4920      4930      4940      4950
Slit AGAACAGACTTATTTTTATTATGAGAATAAAGACTTTTTTTCTGCATTTG
               ::.....:..:..:.::.::.:.:       : ::
 325 ----------TAAAAAAAAAAAAAAAAAAAGGGCG-----GCCGC-----
              2140      2150      2160
```

Fig. 5M-18

```
ACGCGTCCGCACANGGCCGGCGCGGCTGGGAGCGGGTGGGCGGCCGGGAGGCCGGAGCAGCACGGCCGCAGGACCTGGA      79

                                   M   R   L   P   R   R   A   A   L   G   L        11
GCTCCGGCTGCGTCTTCCCGCAGCGCTACCCGCC ATG CGC CTG CCG CGC CGG GCC GCG CTG GGG CTC     146

 L   P   L   L   L   L   L   P   P   A   P   E   A   A   K   K   P   T   P   C      31
CTG CCG CTT CTG CTG CTG CTG CCG CCC GCG CCG GAG GCC GCC AAG AAG CCG ACG CCC TGC    206

 H   R   C   R   G   L   V   D   K   F   N   Q   G   M   V   D   T   A   K   K      51
CAC CGG TGC CGG GGG CTG GTG GAC AAG TTT AAC CAG GGG ATG GTG GAC ACC GCA AAG AAG    266

 N   F   G   G   G   N   T   A   W   E   E   K   T   L   S   K   Y   E   S   S      71
AAC TTT GGC GGC GGG AAC ACG GCT TGG GAG GAA AAG ACG CTG TCC AAG TAC GAG TCC AGC    326

 E   I   R   L   L   E   I   L   E   G   L   C   E   S   S   D   F   E   C   N      91
GAG ATT CGC CTG CTG GAG ATC CTG GAG GGG CTG TGC GAG AGC AGC GAC TTC GAA TGC AAT    386

 Q   M   L   E   A   Q   E   E   H   L   E   A   W   W   L   Q   L   K   S   E     111
CAG ATG CTA GAG GCG CAG GAG GAG CAC CTG GAG GCC TGG TGG CTG CAG CTG AAG AGC GAA    446

 Y   P   D   L   F   E   W   F   C   V   K   T   L   K   V   C   C   S   P   G     131
TAT CCT GAC TTA TTC GAG TGG TTT TGT GTG AAG ACA CTG AAA GTG TGC TGC TCT CCA GGA    506
```

Fig. 6A

```
T   Y   G   P   D   C   L   A   C   Q   G   G   S   Q   R   P   C   S   G   N     151
ACC TAC GGT CCC GAC TGT CTC GCA TGC CAG GGC GGA TCC CAG AGG CCC TGC AGC GGG AAT   566

G   H   C   S   G   D   G   S   R   Q   G   D   G   S   C   R   C   H   M   G     171
GGC CAC TGC AGC GGA GAT GGG AGC AGA CAG GGC GAC GGG TCC TGC CGG TGC CAC ATG GGG   626

Y   Q   G   P   L   C   T   D   C   M   D   G   Y   F   S   S   L   R   N   E     191
TAC CAG GGC CCG CTG TGC ACT GAC TGC ATG GAC GGC TAC TTC AGC TCG CTC CGG AAC GAG   686

T   H   S   I   C   T   A   C   D   E   S   C   K   T   C   S   G   L   T   N     211
ACC CAC AGC ATC TGC ACA GCC TGT GAC GAG TCC TGC AAG ACG TGC TCG GGC CTG ACC AAC   746

R   D   C   G   E   C   E   V   G   W   V   L   D   E   G   A   C   V   D   V     231
AGA GAC TGC GGC GAG TGT GAA GTG GGC TGG GTG CTG GAC GAG GGC GCC TGT GTG GAT GTG   806

D   E   C   A   A   E   P   P   P   C   S   A   A   Q   F   C   K   N   A   N     251
GAC GAG TGT GCG GCC GAG CCG CCT CCC TGC AGC GCT GCG CAG TTC TGT AAG AAC GCC AAC   866

G   S   Y   T   C   E   E   C   D   S   S   C   V   G   C   T   G   E   G   P     271
GGC TCC TAC ACG TGC GAA GAG TGT GAC TCC AGC TGT GTG GGC TGC ACA GGG GAA GGC CCA   926

G   N   C   K   E   C   I   S   G   Y   A   R   E   H   G   Q   C   A   D   V     291
GGA AAC TGT AAA GAG TGT ATC TCT GGC TAC GCG AGG GAG CAC GGA CAG TGT GCA GAT GTG   986
```

Fig. 6B

```
 D   E   C   S   L   A   E   K   T   C   V   R   K   N   E   N   C   Y   N   T     311
GAC GAG TGC TCA CTA GCA GAA AAA ACC TGT GTG AGG AAA AAC GAA AAC TGC TAC AAT ACT   1046

 P   G   S   Y   V   C   V   C   P   D   G   F   E   E   T   E   D   A   C   V     331
CCA GGG AGC TAC GTC TGT GTG TGT CCT GAC GGC TTC GAA GAA ACG GAA GAT GCC TGT GTG   1106

 P   P   A   E   A   E   A   T   E   G   E   S   P   T   Q   L   P   S   R   E     351
CCG CCG GCA GAG GCT GAA GCC ACA GAA GGA GAA AGC CCG ACA CAG CTG CCC TCC CGC GAA   1166

 D   L   *                                                                         354
GAC CTG TAA                                                                       1175

TGTGCCGGACTTACCCTTTAAATTATTCAGAAGGATGTCCCGTGGAAAATGTGGCCCTGAGGATGCCGTCTCCTGCAGT  1254

GGACAGCGGCGGGGAGAGGCTGCCTGCTCTCTAACGGTTGATTCTCATTTGTCCCTTAAACAGCTGCATTTCTTGGTTG  1335

TTCTTAAACAGACTTGTATATTTTGATACAGTTCTTTGTAATAAAATTGACCATTGTAGGTAATCAAAAAAAAAAAAAA  1412

AAAAAGGGCGGCCGCTAGAC                                                              1432
```

Fig. 6C

```
          10        20        30        40        50        60
C MHLPPAAAVGLL-LLLLPPPARVASRKPTMCQRCRALVDKFNQGMANTARKNFGGGNTAWEEKSLSKYEF
  :.::  ::.::: :::: :::  :..::: :.:::.:::::::::..::.:::::::::::::::.:::::
H MRLPRRAALGLLPLLLLLPPAPEAAKKPTPCHRCRGLVDKFNQGMVDTAKKNFGGGNTAWEEKTLSKYES
          10        20        30        40        50        60        70
 70       80        90       100       110       120       130
C SEIRLLEIMEGLCDSNDFECNQLLEQHEEQLEAWWQTLKKECPNLFEWFCVHTLKACCLPGTYGPDCQEC
  :::::::.::::.:.::::::.:: .::.:::::  :: : :.:::::::: :::.:: :::::::: .:
H SEIRLLEILEGLCESSDFECNQMLEAQEEHLEAWWLQLKSEYPDLFEWFCVKTLKVCCSPGTYGPDCLAC
          80        90       100       110       120       130       140
140      150       160       170       180       190       200
C QGGSQRPCSGNGHCDGDGSRQGDGSCQCHVGYKGPLCIDCMDGYFSLLRNETHSFCTACDESCKTCSGPT
  :::::::::::::.:::::::::::.::.::.:::.:::::::: :::::::.:::::::::::::: :
H QGGSQRPCSGNGHCSGDGSRQGDGSCRCHMGYQGPLCTDCMDGYFSSLRNETHSICTACDESCKTCSGLT
         150       160       170       180       190       200       210
210      220       230       240       250       260       270
C NKGCVECEVGWTRVEDACVDVDECAAETPPCSNVQYCENVNGSYTCEECDSTCVGCTGKGPANCKECISG
  :..: ::::::.    :.::::::::::: ::::..:.: :.:::::::::::.::::::: ::.:::::::
H NRDCGECEVGWVLDEGACVDVDECAAEPPPCSAAQFCKNANGSYTCEECDSSCVGCTGEGPGNCKECISG
         220       230       240       250       260       270       280
280      290       300       310       320       330       340
C YSKQKGECADIDECSLETKVCKKENENCYNTPGSFVCVCPEGFEE-DRRCLC-TDSRRRSGRGKSHTATL
  :... :.:::.::::. :.: . ::::::::::.::::.::::  .   :.   ...      :  . .. ..
H YAREHGQCADVDECSLAEKTCVRKNENCYNTPGSYVCVCPDGFEETEDACVPPAEAEATEGESPTQLPSR
         290       300       310       320       330       340       350
C P--

H EDL
```

Fig. 6E

```
             10          20                  30        40         50
C --GTAGCCGGG--GGAACGGC-CGGC-----GCGCTTG-----CCGGTGGGCGGAGGCGAGACT-CCACA
    : . ::: .  .:. :::: ::::     :::  ::     :::: .::: :..::.. ::  ::.::
H ACGCGTCCGCACANGGCCGGCGCGGCTGGGAGCGGGTGGGCGGCCGGGAGGCCGGAGCAGCACGGCCGCA
          10        20        30        40        50        60        70

         60           70          80          90       100        110
C G---CAGTT-CTC-TGCCG-GTCG-CCCGCGAGTGC-ACCCGCCATGCACCTGCCGC-CCGCTGCCGCAG
  :   :.: . :::  :: : :::  ::::: :: :: :::::::::::.:::::::: :::  :::::.
H GGACCTGGAGCTCCGGCTGCGTCTTCCCGC-AGCGCTACCCGCCATGCGCCTGCCGCGCCG-GGCCGCGC
          80        90       100        110       120       130

    120          130       140       150       160       170       180
C TCGGGCT---GCTACTGCTGCTGCTGCCGCCTCCCGCGCGCGTGGCCTCCCGGAAGCCGACAATGTGCCA
  : :::::   :: .:: :::::::::: ::: :::::::  :.:::: :: .:::::::::.   :::::
H TGGGGCTCCTGCCGCTTCTGCTGCTGCTGCCGCCCGCGCCGGAGGCCGCCAAGAAGCCGACGCCCTGCCA
 140       150       160       170       180       190       200

       190       200       210       220       230       240       250
C GAGGTGCCGGGCGCTGGTGGACAAGTTCAACCAGGGGATGGCCAACACGGCCAGGAAGAATTTCGGCGGC
    ::::::::: ::::::::::::::: :::::::::::::  .:::: :: :.:::::: :: ::::::
H CCGGTGCCGGGGGCTGGTGGACAAGTTTAACCAGGGGATGGTGGACACCGCAAAGAAGAACTTTGGCGGC
 210       220       230       240       250       260       270
```

Fig. 6F

```
           260       270       280       290       300       310       320
C GGCAACACGGCGTGGAGGAGAAGAGTCTGTCCAAGTACGAATTCAGTGAGATTCGGCTCCTGGAGATTA
  :: :::::::: ::::::::.::::  ::::::::::::::.: ::: :::::::: :: ::::::::
H GGGAACACGGCTTGGAGGAAAAGACGCTGTCCAAGTACGAGTCCAGCGAGATTCGCCTGCTGGAGATCC
   280       290       300       310       320       330       340

           330       340       350       360       370       380       390
C TGGAGGGCCTGTGTGACAGCAACGACTTTGAATGCAACCAACT-CTTGGAACAGCATGAGGAGCAGCTAG
  ::::::: ::::: :: ::::.:::::: :::::::: ::. : ::.:...: ::: :::::::: ::.:
H TGGAGGGGCTGTGCGAGAGCAGCGACTTCGAATGCAATCAGATGCTAGAGGC-GCAGGAGGAGCACCTGG
   350       360       370       380       390       400       410

            400       410       420       430       440       450       460
C AGGCCTGGTGGCAGACACTGAAGAAGGAGTGCCCTAACCTATTTGAGTGGTTCTGTGTACACACACTGAA
  ::::::::::::.:  .:::::::. ::.:. :::.:: :::: :::::::: :::::. : ::::::::
H AGGCCTGGTGGCTGCAGCTGAAGAGCGAATATCCTGACTTATTCGAGTGGTTTTGTGTGAAGACACTGAA
   420       430       440       450       460       470       480

            470       480       490       500       510       520       530
C AGCATGCTGTCTTCCAGGCACCTATGGGCCAGACTGTCAGGAATGCCAGGGTGGGTCTCAGAGGCCTTGT
  :: .:::::   :::::: ::::: :: :: :::::::. : ::::::::: ::.:: :::::::: ::
H AGTGTGCTGCTCTCCAGGAACCTACGGTCCCGACTGTCTCGCATGCCAGGGCGGATCCCAGAGGCCCTGC
   490       500       510       520       530       540       550
```

Fig. 6G

```
          540       550       560       570       580       590       600
C AGCGGGAATGGCCACTGCGACGGAGATGGCAGCAGACAGGGCGACGGGTCCTGCCAGTGTCACGTAGGAT
  ::::::::::::::::::..::::::::: :::::::::::::::::::::::::.::: :::.:.::.:
H AGCGGGAATGGCCACTGCAGCGGAGATGGGAGCAGACAGGGCGACGGGTCCTGCCGGTGCCACATGGGGT
  560       570       580       590       600       610       620

          610       620       630       640       650       660       670
C ACAAGGGGCCGCTGTGTATCGACTGCATGGATGGCTACTTCAGCTTGCTGAGGAACGAGACCCACAGCTT
  :: :::: :::::::: :  ::::::::::: ::::::::::::: :::  :::::::::::::::::.:
H ACCAGGGCCCGCTGTGCACTGACTGCATGGACGGCTACTTCAGCTCGCTCCGGAACGAGACCCACAGCAT
  630       640       650       660       670       680       690

          680       690       700       710       720       730       740
C CTGCACAGCCTGTGATGAGTCCTGCAAGACATGCTCAGGTCCAACCAACAAAGGCTGTGTGGAGTGCGAA
  ::::::::::::::: ::::::::::::::.:::::.:: : .:::::::.::.::: :  ::::: :::
H CTGCACAGCCTGTGACGAGTCCTGCAAGACGTGCTCGGGCCTGACCAACAGAGACTGCGGCGAGTGTGAA
  700       710       720       730       740       750       760

          750       760       770       780       790       800       810
C GTGGGCTGGACACGTGTGGAGGATGCCTGTGTGGATGTTGACGAGTGTGCAGCAGAGACCCCACCCTGCA
  :::::::::. .:  :. ::::. :::::::::::::: :::::::::::.:: ::: : ::.:::::::
H GTGGGCTGGGTGCTGGACGAGGGCGCCTGTGTGGATGTGGACGAGTGTGCGGCCGAGCCGCCTCCCTGCA
  770       780       790       800       810       820       830
```

Fig. 6H

```
          820       830       840       850       860       870       880
C  GCAATGTACAGTACTGTGAAAATGTCAACGGCTCCTACACATGTGAAGAGTGTGATTCTACCTGTGTGGG
   ::. :: .::::.::::.:.:: : ::::::::::::::.:: ::::::::::: :: : :::::::::
H  GCGCTGCGCAGTTCTGTAAGAACGCCAACGGCTCCTACACGTGCGAAGAGTGTGACTCCAGCTGTGTGGG
   840       850       860       870       880       890       900

          890       900       910       920       930       940       950
C  CTGCACAGGAAAAGGCCCAGCCAATTGTAAAGAGTGTATCTCTGGCTACAGCAAGCAGAAAGGAGAGTGT
   :::::::::..:::::::::  :: :::::::::::::::::::::::.   :.: :: : ::: :::::
H  CTGCACAGGGGAAGGCCCAGGAAACTGTAAAGAGTGTATCTCTGGCTACGCGAGGGAGCACGGACAGTGT
   910       920       930       940       950       960       970

          960       970       980       990      1000      1010      1020
C  GCAGATATAGATGAATGCTCATTAGAAACAAAGGTGTGTAAGAAGGAAAATGAGAACTGCTACAATACTC
   :::::::.:.:: ::.::::::: ::: :. :::..  :::..::.:.:::: ::.:::::::::::::::
H  GCAGATGTGGACGAGTGCTCACTAGCAGAAAAAACCTGTGTGAGGAAAAACGAAAACTGCTACAATACTC
   980       990      1000      1010      1020      1030      1040

         1030      1040      1050      1060      1070      1080      1090
C  CAGGGAGCTTTGTCTGCGTGTGTCCGGAAGGTTTCGAGGAAGACAGAAGATGCTTGTGTACAGACAGCAG
   :::::::::. ::::: :::::::: :: :: ::::::.::: ::.::::::::: :::::.: : :.::::
H  CAGGGAGCTACGTCTGTGTGTGTCCTGACGGCTTCGAAGAA-ACGGAAGATGCCTGTGTGCCGCCGGCAG
  1050      1060      1070      1080      1090      1100      1110
```

Fig. 6I

```
        1100      1110        1120      1130      1140      1150
C AAGGCGAAGTGGCAGAGGAAAGT--CCC-ACACAGCCACCCTCCCATGAGGATTTGTGACGGGCATCCAG
  :.:  ::::  .::::.:.:...  ::: ::::::: .:::::::. ::.::              ::.:
H AGGCTGAAGCCACAGAAGGAGAAAGCCCGACACAGCTGCCCTCCCGCGAAGA--------------CCTG
   1120      1130      1140      1150      1160                   1170
1160      1170      1180      1190      1200      1210      1220
C GTTCAGAAGCTGGACTCTCACCCTTTTAAGTTATTGAGAGGACATCCTATAGAAAATGTGGCCCATGGAC
    : : ..:: :::::   ::::::.:: :..: ..:::: .::: .:.:::::::::::. .:.
H --TAATGTGCCGGACTT--ACCCTTTAAATTATTCAGAAGGATGTCCCGTGGAAAATGTGGCCCTGAGGA
        1180        1190      1200      1210      1220      1230

1230      1240      1250       1260      1270      1280      1290
C ATCAACCCCATTTCTCCAGGAAGTTTTGG-AGGAAGAAGCTGCCTGCTTTGAAACAGTAGATACTCACTT
  . : . : :    :: ::: ... .  :: .::.:::.:::::::: : .:::.::.:::.:::: ::
H TGCCGTCTC----CTGCAGTGGACAGCGGCGGGGAGAGGCTGCCTGCTCTCTAACGGTTGATTCTCATTT
1240          1250      1260      1270      1280      1290      1300
 1300      1310      1320      1330      1340      1350      1360
C GGCCCTTTAAAACGCTGCATTTCTTGGTGGTTCTTAAACAGATTCGTATATTTTGATACTGTTCTTTATA
  : :::::.:: : ::::::::::::::: :::::::::::: : :::::::::::::.:::::::.::
H GTCCCTTAAACA-GCTGCATTTCTTGGTTGTTCTTAAACAGACTTGTATATTTTGATACAGTTCTTTGTA
    1310       1320      1330      1340      1350      1360      1370

 1370      1380      1390
C ATAAAATTGATCATTGAAGGTCACCAGGAA-----------------CA----------
  :::::::::: ::::::.:::: : ::..::                 :.
H ATAAAATTGACCATTGTAGGTAATCAAAAAAAAAAAAAAAAAAAAGGGCGGCCGCTAGAC
    1380      1390      1400      1410      1420      1430
```

Fig. 6J

```
GTCGACCCACGCGTCCGTCCTGCGGCCCCAGCCTCTCCTCACGCTCGCGCAGTCTCCGCCGCAGTCTCAGCTGCAGCTG    79

CAGGACTGAGCCGTGCACCCGGAGGAGACCCCCGGAGGAGGCGACAAACTTCGCAGTGCCGCGACCCAACCCCAGCCCT    158

                 M   A   Q   L   F   L   P   L   L   A   A   L   V   L   A   Q      16
GGGTAGCCTGCAGC ATG GCC CAG CTG TTC CTG CCC CTG CTG GCA GCC CTG GTC CTG GCC CAG     220

 A   P   A   A   L   A   D   V   L   E   G   D   S   S   E   D   R   A   F   R      36
GCT CCT GCA GCT TTA GCA GAT GTT CTG GAA GGA GAC AGC TCA GAG GAC CGC GCT TTT CGC     280

 V   R   I   A   G   D   A   P   L   Q   G   V   L   G   G   A   L   T   I   P      56
GTG CGC ATC GCG GGC GAC GCG CCA CTG CAG GGC GTG CTC GGC GGC GCC CTC ACC ATC CCT     340

 C   H   V   H   Y   L   R   P   P   P   S   R   R   A   V   L   G   S   P   R      76
TGC CAC GTC CAC TAC CTG CGG CCA CCG CCG AGC CGC CGG GCT GTG CTG GGC TCT CCG CGG     400

 V   K   W   T   F   L   S   R   G   R   E   A   E   V   L   V   A   R   G   V      96
GTC AAG TGG ACT TTC CTG TCC CGG GGC CGG GAG GCA GAG GTG CTG GTG GCG CGG GGA GTG     460

 R   V   K   V   N   E   A   Y   R   F   R   V   A   L   P   A   Y   P   A   S     116
CGC GTC AAG GTG AAC GAG GCC TAC CGG TTC CGC GTG GCA CTG CCT GCG TAC CCA GCG TCG     520

 L   T   D   V   S   L   A   L   S   E   L   R   P   N   D   S   G   I   Y   R     136
CTC ACC GAC GTC TCC CTG GCG CTG AGC GAG CTG CGC CCC AAC GAC TCA GGT ATC TAT CGC     580
```

Fig. 7A

```
 C   E   V   Q   H   G   I   D   D   S   S   D   A   V   E   V   K   V   K   G    156
TGT GAG GTC CAG CAC GGC ATC GAT GAC AGC AGC GAC GCT GTG GAG GTC AAG GTC AAA GGG   640

 V   V   F   L   Y   R   E   G   S   A   R   Y   A   F   S   F   S   G   A   Q    176
GTC GTC TTT CTC TAC CGA GAG GGC TCT GCC CGC TAT GCT TTC TCC TTT TCT GGG GCC CAG   700

 E   A   C   A   R   I   G   A   H   I   A   T   P   E   Q   L   Y   A   A   Y    196
GAG GCC TGT GCC CGC ATT GGA GCC CAC ATC GCC ACC CCG GAG CAG CTC TAT GCC GCC TAC   760

 L   G   G   Y   E   Q   C   D   A   G   W   L   S   D   Q   T   V   R   Y   P    216
CTT GGG GGC TAT GAG CAA TGT GAT GCT GGC TGG CTG TCG GAT CAG ACC GTG AGG TAT CCC   820

 I   Q   T   P   R   E   A   C   Y   G   D   M   D   G   F   P   G   V   R   N    236
ATC CAG ACC CCA CGA GAG GCC TGT TAC GGA GAC ATG GAT GGC TTC CCC GGG GTC CGG AAC   880

 Y   G   V   V   D   P   D   D   L   Y   D   V   Y   C   Y   A   E   D   L   N    256
TAT GGT GTG GTG GAC CCG GAT GAC CTC TAT GAT GTG TAC TGT TAT GCT GAA GAC CTA AAT   946

 G   E   L   F   L   G   D   P   P   E   K   L   T   L   E   E   A   R   A   Y    276
GGA GAA CTG TTC CTG GGT GAC CCT CCA GAG AAG CTG ACA TTG GAG GAA GCA CGG GCG TAC  1000

 C   Q   E   R   G   A   E   I   A   T   T   G   Q   L   Y   A   A   W   D   G    296
TGC CAG GAG CGG GGT GCA GAG ATT GCC ACC ACG GGC CAA CTG TAT GCA GCC TGG GAT GGT  1060
```

Fig. 7B

```
 G   L   D   H   C   S   P   G   W   L   A   D   G   S   V   R   Y   P   I   V    316
GGC CTG GAC CAC TGC AGC CCA GGG TGG CTA GCT GAT GGC AGT GTG CGC TAC CCC ATC GTC  1120

 T   P   S   Q   R   C   G   G   G   L   P   G   V   K   T   L   F   L   F   P    336
ACA CCC AGC CAG CGC TGT GGT GGG GGC TTG CCT GGT GTC AAG ACT CTC TTC CTC TTC CCC  1180

 N   Q   T   G   F   P   N   K   H   S   R   F   N   V   Y   C   F   R   D   S    356
AAC CAG ACT GGC TTC CCC AAT AAG CAC AGC CGC TTC AAC GTC TAC TGC TTC CGA GAC TCG  1240

 A   Q   P   S   A   I   P   E   A   S   N   P   A   S   N   P   A   S   D   G    376
GCC CAG CCT TCT GCC ATC CCT GAG GCC TCC AAC CCA GCC TCC AAC CCA GCC TCT GAT GGA  1300

 L   E   A   I   V   T   V   T   E   T   L   E   E   L   Q   L   P   Q   E   A    396
CTA GAG GCT ATC GTC ACA GTG ACA GAG ACC CTG GAG GAA CTG CAG CTG CCT CAG GAA GCC  1360

 T   E   S   E   S   R   G   A   I   Y   S   I   P   I   M   E   D   G   G   G    416
ACA GAG AGT GAA TCC CGT GGG GCC ATC TAC TCC ATC CCC ATC ATG GAG GAC GGA GGA GGT  1420

 G   S   S   T   P   E   D   P   A   E   A   P   R   T   L   L   E   F   E   T    436
GGA AGC TCC ACT CCA GAA GAC CCA GCA GAG GCC CCT AGG ACG CTC CTA GAA TTT GAA ACA  1480

 Q   S   M   V   P   P   T   G   F   S   E   E   E   G   K   A   L   E   E   E    456
CAA TCC ATG GTA CCG CCC ACG GGG TTC TCA GAA GAG GAA GGT AAG GCA TTG GAG GAA GAA  1540
```

Fig. 7C

```
E   K   Y   E   D   E   E   E   K   E   E   E   E   E   E   E   E   V   E   D    476
GAG AAA TAT GAA GAT GAA GAA GAG AAA GAG GAG GAA GAA GAA GAG GAG GAG GTG GAG GAT  1600

E   A   L   W   A   W   P   S   E   L   S   S   P   G   P   E   A   S   L   P    496
GAG GCT CTG TGG GCA TGG CCC AGC GAG CTC AGC AGC CCG GGC CCT GAG GCC TCT CTC CCC  1660

T   E   P   A   A   Q   E   K   S   L   S   Q   A   P   A   R   A   V   L   Q    516
ACT GAG CCA GCA GCC CAG GAG AAG TCA CTC TCC CAG GCG CCA GCA AGG GCA GTC CTG CAG  1720

P   G   A   S   P   L   P   D   G   E   S   E   A   S   R   P   P   R   V   H    536
CCT GGT GCA TCA CCA CTT CCT GAT GGA GAG TCA GAA GCT TCC AGG CCT CCA AGG GTC CAT  1780

G   P   P   T   E   T   L   P   T   P   R   E   R   N   L   A   S   P   S   P    556
GGA CCA CCT ACT GAG ACT CTG CCC ACT CCC AGG GAG AGG AAC CTA GCA TCC CCA TCA CCT  1840

S   T   L   V   E   A   R   E   V   G   E   A   T   G   G   P   E   L   S   G    576
TCC ACT CTG GTT GAG GCA AGA GAG GTG GGG GAG GCA ACT GGT GGT CCT GAG CTA TCT GGG  1900

V   P   R   G   E   S   E   E   T   G   S   S   E   G   A   P   S   L   L   P    596
GTC CCT CGA GGA GAG AGC GAG GAG ACA GGA AGC TCC GAG GGT GCC CCT TCC CTG CTT CCA  1960

A   T   R   A   P   E   G   T   R   E   L   E   A   P   S   E   D   N   S   G    616
GCC ACA CGG GCC CCT GAG GGT ACC AGG GAG CTG GAG GCC CCC TCT GAA GAT AAT TCT GGA  2020
```

Fig. 7D

```
 R   T   A   P   A   G   T   S   V   Q   A   Q   P   V   L   P   T   D   S   A    636
AGA ACT GCC CCA GCA GGG ACC TCA GTG CAG GCC CAG CCA GTG CTG CCC ACT GAC AGC GCC  2080

 S   R   G   G   V   A   V   V   P   A   S   G   N   S   A   Q   G   S   T   A    656
AGC CGA GGT GGA GTG GCC GTG GTC CCC GCA TCA GGT AAT TCT GCC CAA GGC TCA ACT GCC  2140

 L   S   I   L   L   L   F   F   P   L   Q   L   W   V   T   *                    672
CTC TCT ATC CTA CTC CTT TTC TTC CCC CTG CAG CTC TGG GTC ACC TGA                  2188

CCTGTAGTCCTTTAACCCACCATCATCCCAAACTCTCCTGTCCTTTGCCTTCATTCTCTTACCCACCTCTACCTATGGG  2267

TCTCCAATCTCGGATATCCACCTTGTGGGTATCTCAGCTCTCCGCGTCTTTACCCTGTGATCCCAGCCCCGCCACTGAC  2346

CATCTGTGACCCTTCCCTGCCATTGGGCCCTCCACCTGTGGCTCACATCTCGCCAGCCCCACAGAGCATCCTCAGGCCT  2425

CTCCAAGGGTCCTCATCACCTATTGCAGCCTTCAGGGCTCGGCCTATTTTCCACTACTCCCTTCATCCGCCTGTGTGCC  2504

GTCCCCTTTAGCTGCCTCCTATTGATCTCAGGGAAGCCTGGGAGTCCCTTCTCACCCCTCAACCTCCGGAGTCCAGGAG  2583

AACCCGTACCCCCACAGAGCCTTAAGCAACTACTTCTGTGAAGTATTTTTGACTGTTTCATGGAAAACAAGCCTTGGA  2662

AATAAATCTCTATTAAACCGCTTTGTAACCAAAAAAAAAAAAAAAAAAAAAAAAAAAAGGGCGGCCGC  2730
```

Fig. 7E

```
              10        20        30        40        50        60        70
332 MAQLFLPLLAALVLAQAPAALADVLEGDSSEDRAFRVRIAGDAPLQGVLGGALTIPCHVHYLRPPPSRRA
    ::::::::::::::::::::::::::::::::::::::::::::::::::::::::::::::::::::::
BEF MAQLFLPLLAALVLAQAPAALADVLEGDSSEDRAFRVRIAGDAPLQGVLGGALTIPCHVHYLRPPPSRRA
              10        20        30        40        50        60        70

              80        90       100       110       120       130       140
332 VLGSPRVKWTFLSRGREAEVLVARGVRVKVNEAYRFRVALPAYPASLTDVSLALSELRPNDSGIYRCEVQ
    ::::::::::::::::::::::::::::::::::::::::::::::::::::::::::::::::::::::
BEF VLGSPRVKWTFLSRGREAEVLVARGVRVKVNEAYRFRVALPAYPASLTDVSLALSELRPNDSGIYRCEVQ
              80        90       100       110       120       130       140

             150       160       170       180       190       200       210
332 HGIDDSSDAVEVKVKGVVFLYREGSARYAFSFSGAQEACARIGAHIATPEQLYAAYLGGYEQCDAGWLSD
    :::::::::::                                                         :.
BEF HGIDDSSDAVE---------------------------------------------------------SS
             150

             220       230       240       250       260       270       280
332 QTVRYPIQTPREACYGDMDGFPGVRNYGVVDPDDLYDVYCYAEDLNGELFLGDPPEKLTLEEARAYCQER
    :  :::::::::::::::::::::::::::::::::::::::::::::::::::::::::::::::::::
BEF Q--RYPIQTPREACYGDMDGFPGVRNYGVVDPDDLYDVYCYAEDLNGELFLGDPPEKLTLEEARAYCQER
            160       170       180       190       200       210       220

             290       300       310       320       330       340       350
332 GAEIATTGQLYAAWDGGLDHCSPGWLADGSVRYPIVTPSQRCGGGLPGVKTLFLFPNQTGFPNKHSRFNV
    ::::::::::::::::::::::::::::::::::::::::::::::::::::::::::::::::::::::
BEF GAEIATTGQLYAAWDGGLDHCSPGWLADGSVRYPIVTPSQRCGGGLPGVKTLFLFPNQTGFPNKHSRFNV
            230       240       250       260       270       280       290
```

Fig. 7G

```
               360       370       380       390       400       410
332 YCFRDSAQP-SAIPEASNPASNPASDGLEAIVTVTETLEELQLPQEATESESRGAIYSIPIMEDGGGGSS
    ::::::::  ...  ...:...  ::::::::::::::::::::::::::::::::::::::::::::::
BEF YCFRDSAQLLPSLRPPTQPPTQL--DGLEAIVTVTETLEELQLPQEATESESRGAIYSIPIMEDGGGGSS
              300       310         320       330       340       350

  420       430       440       450       460       470       480
332 TPEDPAEAPRTLLEFETQSMVPPTGFSEEEGKALEEEEKYEDEEEKEEEEEEEEVEDEALWAWPSELSSP
    ::::::::::::::::::::::::::::::::::::::::::::::::::::::::::::::::::::::
BEF TPEDPAEAPRTLLEFETQSMVPPTGFSEEEGKALEEEEKYEDEEEKEEEEEEEEVEDEALWAWPSELSSP
  360       370       380       390       400       410       420

  490       500       510       520       530       540       550
332 GPEASLPTEPAAQEKSLSQAPARAVLQPGASPLPDGESEASRPPRVHGPPTETLPTPRERNLASPSPSTL
    ::::::::::::: ::::::::::::::::::::::::::::::::::::::::::::::::::::::::
BEF GPEASLPTEPAAQEESLSQAPARAVLQPGASPLPDGESEASRPPRVHGPPTETLPTPRERNLASPSPSTL
  430       440       450       460       470       480       490

  560       570       580       590       600       610       620
332 VEAREVGEATGGPELSGVPRGESEETGSSEGAPSLLPATRAPEGTRELEAPSEDNSGRTAPAGTSVQAQP
    ::::::::::::::::::::                     :.:                     .:
BEF VEAREVGEATGGPELSGVPRG---------------------GAR---------------------TQ-
  500       510       520

  630       640       650       660       670
332 VLPTDSASRGGVAVVPASGNSAQGSTALSILLLFFPLQLWVT
                                      :.:
BEF ----------------------------------FAL-----
```

Fig. 7H

```
          10        20        30         40        50        60
M MIPLLLSLLAALVLTQAPAALADDLKEDSSEDRAFRVRI-GAAQLRGVLGGALAIPCHVHHLRPPRSRRA
  : .:.:.:::::::.:::::::: :  ::::::::::: :.:.:.:::::::.:::::: :::: ::::
H MAQLFLPLLAALVLAQAPAALADVLEGDSSEDRAFRVRIAGDAPLQGVLGGALTIPCHVHYLRPPPSRRA
          10        20        30        40        50        60        70

70        80        90        100       110       120       130
M APGFPRVKWTFLSGDREVEVLVARGLRVKVNEAYRFRVALPAYPASLTDVSLVLSELRPNDSGVYRCEVQ
  . : ::::::::: .::.::::::.:::::::::::::::::::::::::::.::::::::::.::::::
H VLGSPRVKWTFLSRGREAEVLVARGVRVKVNEAYRFRVALPAYPASLTDVSLALSELRPNDSGIYRCEVQ
          80        90        100       110       120       130       140

140       150       160       170       180       190       200
M HGIDDSSDAVEVKVKGVVFLYREGSARYAFSFAGAQEACARIGARIATPEQLYAAYLGGYEQCDAGWLSD
  ::::::::::::::::::::::::::::::.:::::::::::.:::::::::::::::::::::::::
H HGIDDSSDAVEVKVKGVVFLYREGSARYAFSFSGAQEACARIGAHIATPEQLYAAYLGGYEQCDAGWLSD
         150       160       170       180       190       200       210

210       220       230       240       250       260       270
M QTVRYPIQNPREACSGDMDGYPGVRNYGVVGPDDLYDVYCYAEDLNGELFLGAPPSKLTWEEARDYCLER
  :::::::.::::: ::::.::::::::.:::::::::::::::::::::.:: ::: ::::.:: ::
H QTVRYPIQTPREACYGDMDGFPGVRNYGVVDPDDLYDVYCYAEDLNGELFLGDPPEKLTLEEARAYCQER
         220       230       240       250       260       270       280

280       290       300       310       320       330       340
M GAQIASTGQLYAAWNGGLDRCSPGWLADGSVRYPIITPSQRCGGGLPGVKTLFLFPNQTGFPSKQNRFNV
  ::.::.::::::::.::::.:::::::::::::::.:::::::::::::::::::::::::::..::::
H GAEIATTGQLYAAWDGGLDHCSPGWLADGSVRYPIVTPSQRCGGGLPGVKTLFLFPNQTGFPNKHSRFNV
         290       300       310       320       330       340       350
```

Fig. 7I

```
350       360            370       380       390       400       410
M YCFRDSAHPSASSEASSPAS----DGLEAIVTVTEKLEELQLPQEAMESESRGAIYSIPISEDGGGGSST
  ::::::.::: .:::.:::    ::::::::::: :::::::::: ::::::::::::: :::::::::
H YCFRDSAQPSAIPEASNPASNPASDGLEAIVTVTETLEELQLPQEATESESRGAIYSIPIMEDGGGGSST
           360       370       380       390       400       410       420

    420       430       440       450       460            470
M PEDPAEAPRTPLESETQSIAPPTESSEEEGVALEEEERFKDLEALEEEKEQED-----LWVWPRELSSP-
  :::::::::: :: ::::..:::  ::::: :::::::.. : :. ::: :.:.      ::.:: :::::
H PEDPAEAPRTLLEFETQSMVPPTGFSEEEGKALEEEEKYEDEEEKEEEEEEEEVEDEALWAWPSELSSPG
           430       440       450       460       470       480       490

    480        490       500       510              520       530
M ----LPTGSET-EHSLSQVSPPAQAVLQLDASPSPG-------PPRFRGPPAETLLPPREWS-ATSTPGG
      ::: ... : ::::  .::.:::: .::: :.       ::: .:::.:::  :::.. :...:.
H PEASLPTEPAAQEKSLSQ--APARAVLQPGASPLPDGESEASRPPRVHGPPTETLPTPRERNLASPSPST
           500         510       520       530       540       550
     540       550        560       570       580       590       600
M ---AREVGGETGSPELSGVPR-ESEEAGSSSLEDGPSLLPATWAPVGPRELETPSEEKSGRTVLAGTSVQ
     ::::: .::.::::::::: ::::.:::   :..::::::::.:: : :::::::::..:::::. ::::::
H LVEAREVGEATGGPELSGVPRGESEETGSS--EGAPSLLPATRAPEGTRELEAPSEDNSGRTAPAGTSVQ
  560       570       580          590       600       610       620

      610       620       630       640       650       660       670
M AQPVLPTDSASHGGVAVAPSSGDCIPSPCHNGGTCLEEKEGFRCLCLPGYGGDLCDVGLHFCSPGWEAFQ
  ::::::::::.:::::.:.::.    .       :.: :
H AQPVLPTDSASRGGVAVVPASGNSAQ-----GSTAL----------------------------------
    630       640       650
```

Fig. 7J

```
         680       690       700       710       720       730       740
M GACYKHFSTRRSWEEAESQCRALGAHLTSICTPEEQDFVNDRYREYQWIGLNDRTIEGDFLWSDGAPLLY
                              ::                    :                ::.
H ----------------------------SI--------------------L----------------LLF
                                                   660

         750       760       770       780       790       800       810
M ENWNPGQPDSYFLSGENCVVMVWHDQGQWSDVPCNYHLSYTCKMGLVSCGPPPQLPLAQIFGRPRLRYAV
             :                                           ::
H -----------F-------------------------------------------PLQ------------

         820       830       840       850       860       870       880
M DTVLRYRCRDGLAQRNLPLIRCQENGLWEAPQISCVPRRPGRALRSMDAPEGPRGQLSRHRKAPLTPPSS
                            ::  .
H --------------------------LWVT----------------------------------------
                            670

M L

H -
```

```
           10                        20        30        40        50
H GTCG-ACCCA-CG------CGTCC--------GTCCTGCGGCCCCAGCCTCTCCTCACGCTCGCGCAGTC
  :. : .:::. ::      :: ::        :::: :::  :::.::: :: :::.::: :::::: ::
M GAGGCTCCCGGCGAGCTGGCGCCCCTGTCTGGGTCCCGCGCGCCCGGCC-CTGCTCGCGCCCGCGCA-TC
         10        20        30        40         50        60

      60        70        80        90       100       110       120
H TCCGCCGCAGTCTCAG-CTGCAGCTGCAGGACTGAGCCGTGCACCCGGAGGAGACCCCCGGAGGAGGCGA
   : :::::::::::.: ::::.:::::.::::  ..: : : .: ::::::.:::: :        ::.:
M GC-GCCGCAGTCTCGGTCTGCGGCTGCGGGACGTGACGGCGTGCGCGGAGGGGACCTC--------GCAA
  70         80        90       100       110       120

     130       140       150       160       170       180       190
H CAAACTTCGCAGTGCCGCGACCCAACCCCAGCCCTGGGTAGCCTGCAGCATGGCCCAGCTGTTCCTGCCC
   ...::::              ::.:          .::.   ::::: :::.  : .::: : ::: ::
M -GTTCTTC--------------CATC----------AGTG---TGCAGAATGATACCACTGCTTCTGTCC
 130                    140                     150       160       170

     200       210       220       230       240       250       260
H CTGCTGGCAGCCCTGGTCCTGGCCCAGGCTCCTGCAGCTTTAGCAGATGTTCTGGAAGGAGACAGCTCAG
  :::::::: :: :::::::::.::::.:: ::::: ::   : ::.::::. :::.:::.::::::::.:
M CTGCTGGCCGCTCTGGTCCTGACCCAAGCCCCTGCCGCCCTCGCTGATGACCTGAAAGAAGACAGCTCGG
        180       190       200       210       220       230       240

     270       280       290       300       310       320       330
H AGGACCGCGCTTTTCGCGTGCGCATCGCGGGCGACGCGCCACTGCAGGGCGTGCTCGGCGGCGCCCTCAC
  :::: :: :: :: ::::::::::::: : ::  ::::: .::::.:::::::::: ::::: ::::: .:
M AGGATCGAGCCTTCCGCGTGCGCATCG-GTGC--CGCGCAGCTGCGGGGCGTGCTGGGCGGTGCCCTGGC
        250       260        270        280       290       300
```

Fig. 7L

```
       340       350       360       370       380       390       400
H CATCCCTTGCCACGTCCACTACCTGCGGCCACCGCCGAGCCGCCGGGCTGTGCTGGGCTCTCCGCGGGTC
  ::::::.::::::::::::: ::::::::::.::::  :::::::::: : :: ::: : ::: ::::::
M CATCCCATGCCACGTCCACCACCTGCGGCCGCCGCGCAGCCGCCGGGCCGCGCCGGGTTTCCCCGGGTC
  310       320       330       340       350       360       370

       410       420       430       440       450       460       470
H AAGTGGACTTTCCTGTCCCGGGGCCGGGAGGCAGAGGTGCTGGTGGCGCGGGGAGTGCGCGTCAAGGTGA
  :::::::: ::::::::: :::.::::::::: :::::: :::::::: :: ::. ::::::::::::.:
M AAGTGGACCTTCCTGTCCGGGGACCGGGAGGTAGAGGTTCTGGTGGCTCGCGGGCTGCGCGTCAAGGTAA
  380       390       400       410       420       430       440

       480       490       500       510       520       530       540
H ACGAGGCCTACCGGTTCCGCGTGGCACTGCCTGCGTACCCAGCGTCGCTCACCGACGTCTCCCTGGCGCT
  ::::.:::::::::::::::::::::.:::::::: ::::: ::.:::::::: :: :: :: ::.: . :
M ACGAAGCCTACCGGTTCCGCGTGGCGCTGCCTGCCTACCCCGCATCGCTCACGGATGTGTCTCTAGTATT
  450       460       470       480       490       500       510
       550       560       570       580       590       600       610
H GAGCGAGCTGCGCCCCAACGACTCAGGTATCTATCGCTGTGAGGTCCAGCACGGCATCGATGACAGCAGC
  ::::::.::::: ::::: :: :: :: .:::::::::: ::::::::::::: ::::: ::::::::
M GAGCGAACTGCGGCCCAATGATTCCGGGGTCTATCGCTGCGAGGTCCAGCACGGTATCGACGACAGCAGT
  520       530       540       550       560       570       580

       620       630       640       650       660       670       680
H GACGCTGTGGAGGTCAAGGTCAAAGGGGTCGTCTTTCTCTACCGAGAGGGCTCTGCCCGCTATGCTTTCT
  :: ::::::::::::::::::::::::::::::: :::::: ::::::::::::: ::::::::::::
M GATGCTGTGGAGGTCAAGGTCAAAGGGGTCGTCTTCCTCTACAGAGAGGGCTCTGCGCGCTATGCTTTCT
  590       600       610       620       630       640       650
```

Fig. 7M

```
       690       700       710       720       730       740       750
H CCTTTTCTGGGGCCCAGGAGGCCTGTGCCCGCATTGGAGCCCACATCGCCACCCCGGAGCAGCTCTATGC
  ::::  ::::.::::::::.::::: :: :::::.:::::::. ::::::::::::::::::::::::::
M CCTTCGCTGGAGCCCAGGAAGCCTGCGCTCGCATAGGAGCCCGAATCGCCACCCCGGAGCAGCTCTATGC
   660       670       680       690       700       710       720

       760       770       780       790       800       810       820
H CGCCTACCTTGGGGGCTATGAGCAATGTGATGCTGGCTGGCTGTCGGATCAGACCGTGAGGTATCCCATC
   :::::::: :: :::::::::::.:::::::.:::::::::: :: ::.:: :::::::: ::::::
M TGCCTACCTCGGCGGCTATGAGCAGTGTGATGCAGGCTGGCTGTCCGACCAAACTGTGAGGTACCCCATC
   730       740       750       760       770       780       790

       830       840       850       860       870       880       890
H CAGACCCCACGAGAGGCCTGTTACGGAGACATGGATGGCTTCCCCGGGGTCCGGAACTATGGTGTGGTGG
  :::: ::::::::::::::: :  ::::::::::::::::. :: :: :: :::::::: ::.:::::::
M CAGAACCCACGAGAGGCCTGCTCTGGAGACATGGATGGCTATCCTGGCGTGCGGAACTACGGAGTGGTGG
   800       810       820       830       840       850       860

       900       910       920       930       940       950       960
H ACCCGGATGACCTCTATGATGTGTACTGTTATGCTGAAGACCTAAATGGAGAACTGTTCCTGGGTGACCC
   . :: ::::: ::::::::::: :::::::::: :::::::::::::::::::::::::.:: : :::
M GTCCTGATGATCTCTATGATGTCTACTGTTATGCCGAAGACCTAAATGGAGAACTGTTCCTAGGCGCCCC
   870       880       890       900       910       920       930

       970       980       990      1000      1010      1020      1030
H TCCAGAGAAGCTGACATTGGAGGAAGCACGGGCGTACTGCCAGGAGCGGGGTGCAGAGATTGCCACCACG
  ::: .. :::::::::: ::::::.::.::::  ::::: :.:::.:: :::::: :::: :: : :::.
M TCCCAGCAAGCTGACATGGGAGGAGGCTCGGGACTACTGTCTGGAACGTGGTGCACAGATCGCTAGCACA
   940       950       960       970       980       990      1000
```

Fig. 7N

```
    1040      1050      1060      1070      1080      1090      1100
H GGCCAACTGTATGCAGCCTGGGATGGTGGCCTGGACCACTGCAGCCCAGGGTGGCTAGCTGATGGCAGTG
  :::::.::::: ::::::::.:::::::::::::: . :: :::::.:: :::::.:::::::::: :
M GGCCAGCTGTACGCAGCCTGGAATGGTGGCCTGGACAGATGTAGCCCTGGCTGGCTGGCTGATGGCAGCG
1010      1020      1030      1040      1050      1060      1070

    1110      1120      1130      1140      1150      1160      1170
H TGCGCTACCCCATCGTCACACCCAGCCAGCGCTGTGGTGGGGGCTTGCCTGGTGTCAAGACTCTCTTCCT
  ::::::: ::::::.::::::::::::::.:::::::: :: ::: ::::.::.::::::::: ::::::::
M TGCGCTATCCCATCATCACACCCAGCCAACGCTGTGGGGGCGGCCTGCCAGGAGTCAAGACCCTCTTCCT
1080      1090      1100      1110      1120      1130      1140

    1180      1190      1200      1210      1220      1230      1240
H CTTCCCCAACCAGACTGGCTTCCCCAATAAGCACAGCCGCTTCAACGTCTACTGCTTCCGAGACTCGGCC
  ::: ::::::::::::::::::::::. ::::: :.::::::::: ::::::::::::::::::: :::
M CTTTCCCAACCAGACTGGCTTCCCCAGCAAGCAGAACCGCTTCAATGTCTACTGCTTCCGAGACTCTGCC
1150      1160      1170      1180      1190      1200      1210

    1250      1260      1270      1280      1290      1300      1310
H CAGCCTTCTGCCATCCCTGAGGCCTCCAACCCAGCCTCCAACCCAGCCTCTGATGGACTAGAGGCTATCG
  :: :: ::::: . : :::::::::: :.:::::::::            .::::::::.::::: :: :
M CATCCCTCTGCTTCCTCTGAGGCCTCTAGCCCAGCCTC------------AGATGGACTTGAGGCCATTG
1220      1230      1240      1250                    1260      1270

    1320      1330      1340      1350      1360      1370      1380
H TCACAGTGACAGAGACCCTGGAGGAACTGCAGCTGCCTCAGGAAGCCACAGAGAGTGAATCCCGTGGGGC
  :::::::::::::.:  :::::::::::::::::::::::::::: : .::::: ::.:: ::::::::
M TCACAGTGACAGAAAAGCTGGAGGAACTGCAGCTGCCTCAGGAAGCGATGGAGAGCGAGTCTCGTGGGGC
  1280      1290      1300      1310      1320      1330      1340
```

Fig. 7O

```
     1390      1400      1410      1420      1430      1440      1450
H CATCTACTCCATCCCCATCATGGAGGACGGAGGAGGTGGAAGCTCCACTCCAGAAGACCCAGCAGAGGCC
  ::::::::::::::::::. .::.:: ::.::::.:::::::::: ::::::::::::::::::::::
M CATCTACTCCATCCCCATCTCAGAAGATGGGGGAGGAGGAAGCTCCACCCCAGAAGACCCAGCAGAGGCC
  1350      1360      1370      1380      1390      1400      1410

     1460      1470      1480      1490      1500      1510      1520
H CCTAGGACGCTCCTAGAATTTGAAACACAATCCATGGTACCGCCCACGGGGTTCTCAGAAGAGGAAGGTA
  :: ::::: :  :::::::  ::::: :::::::: : :::.:: :: :.:: :::::::::::::: .
M CCCAGGACTCCGCTAGAATCGGAAACCCAATCCATTGCACCACCTACCGAGTCCTCAGAAGAGGAAGGCG
  1420      1430      1440      1450      1460      1470      1480

     1530      1540      1550      1560      1570      1580      1590
H AGGCATTGGAGGAAGAAGAGAAATATGAAGATGAAGAAGAGAAAGAGGAGGAAGAAGAAGAGGAGGAGGT
  ..::  :::::::::::::.:.::. .::::               ...::::   ..::.::::::.::::: .
M TAGCCCTGGAGGAAGAAGAAAGATTCAAAGAC---------TTGGAGGCTCTGGAGGAAGAGAAGGAGCA
  1490      1500      1510                1520      1530      1540

     1600      1610      1620      1630      1640      1650      1660
H GGAGGATGAGGCTCTGTGGGCATGGCCCAGCGAGCTCAGCAGCCCGGGCCCTGAGGCCTCTCTCCCCACT
  ::::::     : ::::::: .:::::::: :::::::::::::               :::::: :::
M GGAGGA-----C-CTGTGGGTGTGGCCCAGAGAGCTCAGCAGCCC---------------TCTCCCTACT
 1550                1560      1570      1580                     1590

     1670      1680      1690                1700      1710      1720
H GAGCCAGCAGCCCAGGAGAAGTCACTCTCCCAGG------CGCCAGCAAGGGCAGTCCTGCAGCCTGGTG
  :.  ::: :.:    .::: : :::::::::::::         :.:::::  .:::::: ::.::::  :.::
M GGCTCAGAAAC---AGAGCATTCACTCTCCCAGGTGTCCCCACCAGCCCAGGCAGTTCTACAGCTGGATG
  1600                1610      1620      1630      1640      1650      1660
```

Fig. 7P

```
  1730      1740      1750      1760      1770      1780      1790
H CATCACCACTTCCTGATGGAGAGTCAGAAGCTTCCAGGCCTCCAAGGGTCCATGGACCACCTACTGAGAC
  :.:::::.  :::::                     ::::::::::: :::.::::::.:::.:.:::::
M CGTCACCTTCTCCTG---------------------GGCCTCCAAGGTTCCGTGGACCGCCTGCAGAGAC
      1670                          1680      1690      1700      1710

  1800      1810      1820      1830      1840      1850      1860
H TCTGCCCACTCCCAGGGAGAGGAACCTAGCATCCCCATCACCTTCCACTCTGGTTGAGGCAAGAGAGGTG
  : ::: : : :: :::::.::::.:       :: ::::. :: ::    :::: :.:::::::::.::.
M TTTGCTCCCCCCGAGGGAGTGGAGC------GCCACATCTACT-CC----TGGT-GGGGCAAGAGAAGTA
       1720      1730            1740      1750           1760      1770

  1870      1880      1890      1900      1910      1920      1930
H GGGGAGGCAACTGGTGGTCCTGAGCTATCTGGGGTCCCTCGAGGAGAGAGCGAGGAGACAGGAAGCTCC-
  ::::.:: :::::: .: :::::::: :::::::: ::::::   ::::::::::::.::::.::::::
M GGGGGGGAAACTGGGAGCCCTGAGCTCTCTGGGGTTCCTCGA---GAGAGCGAGGAGGCAGGGAGCTCCA
          1780      1790      1800      1810         1820      1830

        1940      1950      1960      1970      1980      1990      2000
H -----GAGGGTGCCCCTTCCCTGCTTCCAGCCACACGGGCCCCTGAGGGTACCAGGGAGCTGGAGGCCCC
       ::::.:: :::::::::.::::::: ::: :::::::::.:::: :::::::::::::::.::::
M GCTTGGAGGATGGCCCTTCCCTACTTCCAGCTACATGGGCCCCTGTGGGTCCCAGGGAGCTGGAGACCCC
  1840      1850      1860      1870      1880      1890      1900

        2010      2020      2030      2040      2050      2060      2070
H CTCTGAAGATAATTCTGGAAGAACTGCCCCAGCAGGGACCTCAGTGCAGGCCCAGCCAGTGCTGCCCACT
  :::.::::: :: :::::::::::: :: .::::: :::::::::::::::::::::::::::::::
M CTCAGAAGAGAAGTCTGGAAGAACTGTCCTGGCAGGCACCTCAGTGCAGGCCCAGCCAGTGCTGCCCACC
  1910      1920      1930      1940      1950      1960      1970
```

Fig. 7Q

```
        2080      2090      2100      2110      2120             2130
H GACAGCGCCAGCCGAGGTGGAGTGGCCGTGGTCCCCGCATCAGGTAATT-------CTGCCCAAGGCTCA
  ::::: :::::::. ::::::::::: ::::  ::: :::::::::.: :       :.:::: .: :.::
M GACAGTGCCAGCCACGGTGGAGTGGCTGTGGCTCCCTCATCAGGTGACTGTATCCCCAGCCCCTGCCACA
   1980      1990      2000      2010      2020      2030      2040

                            2140             2150
H A--------C-TGC--------------------CCTCT--CTAT-----CCTA-CT----------CCT
  :        : :::                    :: ::  ::::     ::.. ::          :::
M ATGGTGGGACATGCTTGGAGGAGAAGGAGGGTTTCCGCTGCCTATGTTTGCCAGGCTATGGGGGGGACCT
   2050      2060      2070      2080      2090      2100      2110

   2160                 2170            2180           2190          2200
H TTTC-----TTCCC--C----CTGCAGCTCTGG------GTC--ACCTGA---CCTG----TAGTCCTTT
   : :      :  ::  :    ::::::: ::::       : :  .::.:.   ::::    .:: ::::
M GTGCGATGTTGGCCTTCATTTCTGCAGCCCTGGCTGGGAGGCCTTCCAGGGAGCCTGCTACAAGCACTTT
   2120      2130      2140      2150      2160      2170      2180

                             2210            2220                2230
H AACCCAC------------------CA-----TCA-TCCCAAACTCT-----C----CTGTCC----TTT
   . : :::                 ::     ::: : ::.:.: ::     :    :::.::    : :
M TCCACACGAAGGAGTTGGGAGGAGGCAGAAAGTCAGTGCCGAGCGCTAGGTGCTCATCTGACCAGCATCT
   2190      2200      2210      2220      2230      2240      2250

                      2240        2250            2260          2270
H GC----CT----------TCATTCTCT-TACCC---ACC---TCTACCTATGGGT----CTC--------
   ::    ::          .:.:: ::. :.  :   :::    . ::::..:::.:    :::
M GCACCCCTGAGGAGCAAGACTTTGTCAATGATCGATACCGGGAGTACCAGTGGATTGGGCTCAATGACAG
   2260      2270      2280      2290      2300      2310      2320
```

Fig. 7R

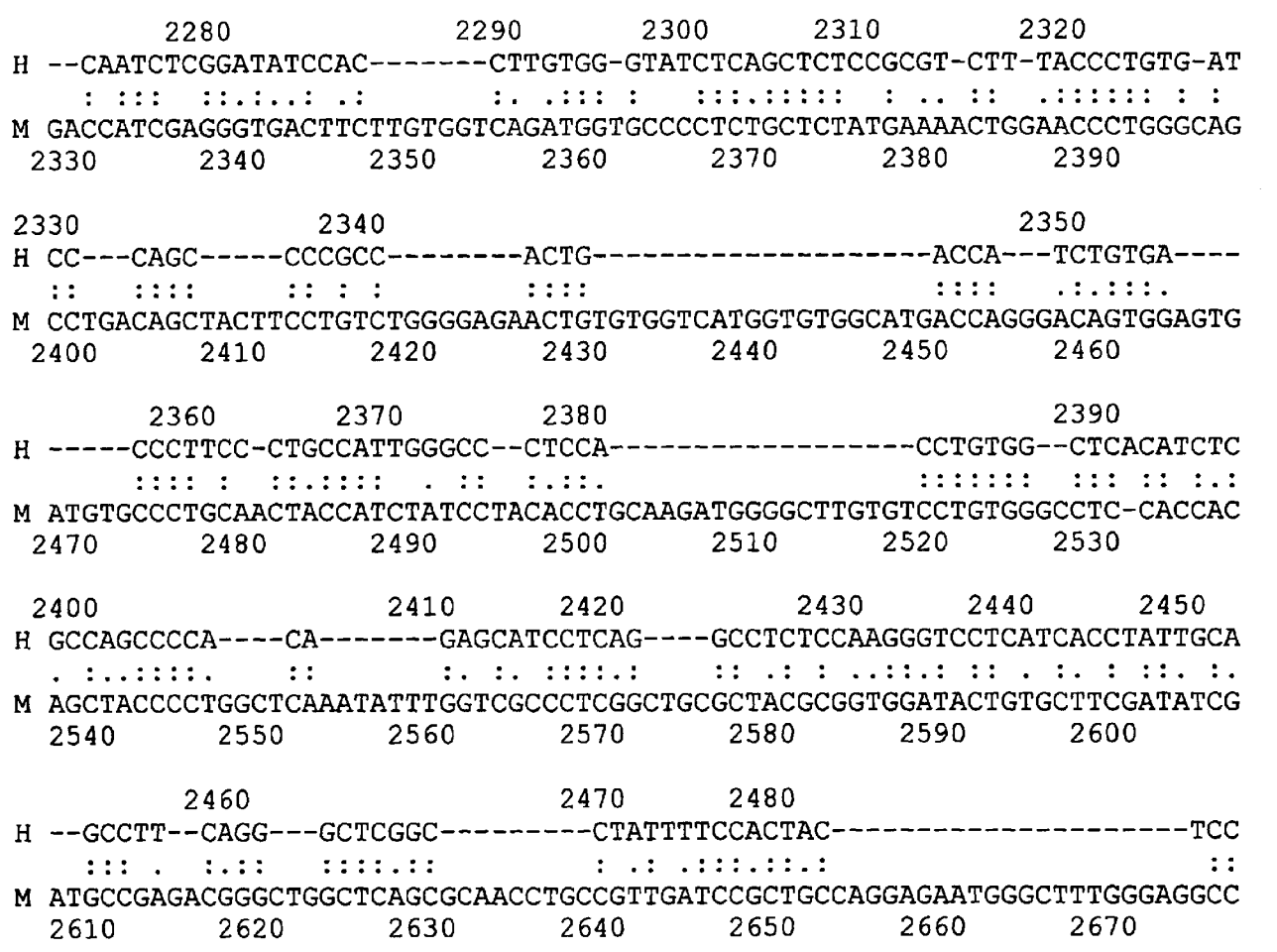

```
          2280            2290       2300      2310        2320
H --CAATCTCGGATATCCAC-------CTTGTGG-GTATCTCAGCTCTCCGCGT-CTT-TACCCTGTG-AT
     : :::  ::.:..: .:        :. .::: :   :::.:::::  : .. ::  .:::::: : :
M GACCATCGAGGGTGACTTCTTGTGGTCAGATGGTGCCCCTCTGCTCTATGAAAACTGGAACCCTGGGCAG
 2330      2340      2350      2360      2370      2380      2390

2330            2340                                        2350
H CC---CAGC-----CCCGCC--------ACTG--------------------ACCA---TCTGTGA----
  ::   ::::     :: : :        ::::                    ::::   .:.:::.
M CCTGACAGCTACTTCCTGTCTGGGGAGAACTGTGTGGTCATGGTGTGGCATGACCAGGGACAGTGGAGTG
 2400      2410      2420      2430      2440      2450      2460

        2360       2370        2380                          2390
H -----CCCTTCC-CTGCCATTGGGCC--CTCCA------------------CCTGTGG--CTCACATCTC
       :::: :  ::.::::  . ::  :.::.                  :::::::  ::: :: :.:
M ATGTGCCCTGCAACTACCATCTATCCTACACCTGCAAGATGGGGCTTGTGTCCTGTGGGCCTC-CACCAC
 2470      2480      2490      2500      2510      2520      2530

 2400                2410      2420          2430      2440      2450
H GCCAGCCCCA----CA-------GAGCATCCTCAG----GCCTCTCCAAGGGTCCTCATCACCTATTGCA
  . :..::::.    ::        :. :. ::::.:    :: .: : ..::.: :: . :. : ::. :.
M AGCTACCCCTGGCTCAAATATTTGGTCGCCCTCGGCTGCGCTACGCGGTGGATACTGTGCTTCGATATCG
  2540      2550      2560      2570      2580      2590      2600

         2460                  2470      2480
H --GCCTT--CAGG---GCTCGGC---------CTATTTTCCACTAC---------------------TCC
    ::: .  :.::   ::::.::         : .: .:::.::.:                      ::
M ATGCCGAGACGGGCTGGCTCAGCGCAACCTGCCGTTGATCCGCTGCCAGGAGAATGGGCTTTGGGAGGCC
  2610      2620      2630      2640      2650      2660      2670
```

Fig. 7S

```
   2490      2500            2510      2520                2530
H CTTCA-TCCGCCTGTGTGCC-----GTCC---CCTTTAGCTGC-CTCCT-----------ATTGATCTC
  : ::: .   ::::::::.::     : ::   :: :   :::: ::::.           :. :: :.:
M CCTCAGATTTCCTGTGTACCCCGGAGGCCTGGCCGTGCTCTGCGCTCCATGGACGCCCCAGAAGGACCAC
  2680      2690      2700      2710      2720      2730      2740

     2540                2550      2560        2570      2580
H AGGGA-AGC----------CTGGGAGTC-CC-TTCTCACC--CCTC-AACCTCCGGAGT-CCAGGAGAAC
  .:::: :::          :.::.:: : :: :: .::::  :::: :. ::: .:.:. ::.:::..::
M GGGGACAGCTCTCGAGGCACAGGAAGGCACCGTTGACACCGCCCTCCAGTCTCTAGGGAGCCTGGAAGAC
  2750      2760      2770      2780      2790      2800      2810

  2590      2600      2610            2620                       2630
H CCGTACCCCCA-CAGAGCCTTAA-GCAACTACT--------TCT--------------GTGAAGTATTT
     :.:::::: :::..:: : . .::.:.:::        :::              :::: ::.. .
M TGCTGCCCCCAGCAGGACCCTCTCACATCAACTGCCAGTGCTCTTCCCCATGATAGGGGGTGACGTGAGA
  2820      2830      2840      2850      2860      2870      2880

          2640                        2650
H ----TTTGACTGT--TTCA-----------------------TGGAAAACA-----------------
     :  :::::.  ::::                       :::.:::::
M GGGGTGGGACTGAAATTCAGAGGACAGCGCTCGAAGGGGTTTCTGGGAAACACTTGGGTGGCTCCGCCCC
  2890      2900      2910      2920      2930      2940      2950

              2660            2670                               2680
H ----------AGCCTTGGAAAT--------AAATCTCTATTAA-------------------------AC
           .:::: .:...:        ::.:: :::. ..                         .:
M CTCACACAAGGGCCTCAGGTTTTACCCGGTAAGTCCCTAAGTGCCTCAACTGCCCTCTCATGTCAGCTGC
  2960      2970      2980      2990      3000      3010      3020
```

Fig. 7T

```
                          2690                              2700
H CGCTTTGT------------------AAC------------------------CAAAAAAAAAAAAAAAAA
  : : ::::                  .::                        :.::.:.....:..:.
M CTCCTTGTCCCTCGATNTCGTNAGGGGACACTGTGCTATTCGATCTTGATTGTCGAAGAGTTTTTAGGAT
  3030      3040      3050      3060      3070      3080      3090

2710                    2720                      2730
H AAA--------------------AAAAAAAAAGGGCGG--CC-------------GC
  ..:                    :::.:::.. : : :  ::             .
M GGAGTACCAGCAAAACCAGGTGGAAATAAAGTTGTCTGAACCCAAAGAAAAAAAAAA
  3100      3110      3120      3130      3140      3150
```

Fig. 7U

SEQUENCE LISTING

<160> NUMBER OF SEQ ID NOS: 100

<210> SEQ ID NO 1
<211> LENGTH: 2895
<212> TYPE: DNA
<213> ORGANISM: Homo sapiens

<400> SEQUENCE: 1
gtcgacccac gcgtccgggg agcgcggcta agagtgccgc accgcctcac aacctgggaa 60
ccggagagta ggggccgtcg gctggcaaga acccgccgtg cctcctcggc aagggccatc 120
cggtgccacc catgtcgcac tagagcagaa gagggtgagt cctgaactgc aacctgcaca 180
gagctgctct gtactgtccc tggtggtcgc cgccatgacc tggttggtgc tgctggggac 240
actgctctgc atgctgcgcg ttgggttagg caccccggac tccgagggtt tcccgccccg 300
tgcgctccac aactgcccct acaaatgtat ctgcgctgcc gacctgctaa gctgcactgg 360

-continued

```
cctagggctg caggacgtgc cagccgagtt acctgccgct actgcggacc tcgacctgag     420
ccacaacgcg ctccagcgcc tgcgccccgg ctggttggcg cccctcttcc agctgcgcgc     480
cctgcaccta gaccacaacg aactagatgc gctgggtcgc ggcgtcttcg tcaacgccag     540
cggcctgagg ctgctcgatc tatcatctaa cacgttgcgg gcgcttggcc gccacgacct     600
cgacgggctg gggcgctgg agaagctgct tctgttcaat aaccgcttgg tgcacttgga      660
cgagcatgcc ttccacggcc tgcgcgcgct cagccatctc tacctgggct gcaacgaact     720
cgcctcgttc tccttcgacc acctgcacgg tctgagcgcc acccacctgc ttactctgga     780
cctctcctcc aaccggctgg gacacatctc cgtacctgag ctggccgcgc tgccggcctt     840
cctcaagaac ggcctctact tgcacaacaa ccctttgcct tgcgactgcc gcctctacca     900
cctgctacag cgctggcacc agcggggcct gagcgccgtg cgcgactttg cgcgcgagta     960
cgtatgcttg gccttcaagg tacccgcgtc ccgcgtgcgc ttcttccagc acagccgcgt    1020
ctttgagaac tgctcgtcgg ccccagctct tggcctaaag cggccggaag agcacctgta    1080
cgcgctggtg ggtcggtccc tgaggcttta ctgcaacacc agcgtcccgg ccatgcgcat    1140
tgcctgggtt tcgccgcagc aggagcttct cagggcgcca ggatcccgcg atggcagcat    1200
cgcggtgctg gccgacggca gcttggccat aggcaacgta caggagcagc atgcgggact    1260
cttcgtgtgc ctggccactg ggccccgcct gcaccacaac cagacgcacg agtacaacgt    1320
gagcgtgcac tttccgcgcc cagagcccga ggctttcaac acaggcttca ccacactgct    1380
gggctgtgcc gtgggccttg tgctcgtgct gctctacctg ttcgccccac cctgccgctg    1440
ctgccgccgt gcctgcccgc tgccgccgct ggccccaaac acccagcccg ctccaagagc    1500
tgagccgcac aagtcctcag tactcagcac cacaccgcca gacgcaccca gcccgcaagg    1560
ccaagcgtcc acaagcacgt agtctttctg gagccaggcc ggagggggcct caatggcccg    1620
cgtgcagctg gcagtagctg aggaattcga tctctacaac cctggaggcc tgcagctgaa    1680
ggctggctct gagtccgcca gctccatagg ctccgagggt cccatgacaa cctagactgc    1740
cagggctccc ccacccaggc ccccaccctc ttgctgctcg ccctgctccc tgcttcggtc    1800
cagagaactg gcagatactg gtgggaagca ctgtgcctgg ccccccagct tcctgtatgg    1860
gcctcgaaac acaatgggcc ttctcgctca ctggtagaga caggggttgt ggtccccaac    1920
ctgccttctg ctctgcccct gcacaggacc caaaggcccc aggccctgca aggtgtgcta    1980
gttcctgctt tcccgcggac ttcctagtgc ccaaatgccc tgtgaggctg agagacccag    2040
gcccctgtgg ctttcaacac agcacagctg tggaagtggc tgtgttcttc tacagcctgt    2100
ggaagaaccc ctgtagcaga gcctcccatc caccctcagg ggctgaggca gctctcgagg    2160
agtggtgctc aagagctgac gcagggccac ctccccttcc caagggggtg ggagggagtg    2220
ggcccacagg gaaaagaagg cggctctgaa ggaagatctc gcccacaccc caggacagaa    2280
agaggaaaca agcccgccct ctggtgaaat gggactccct ccatccacca acacccaacc    2340
tcctgaaagc ttcacaactt cacgcagagt ccggtggcag gcaccaggca ggaaaggctc    2400
ctcaagaggt tcctggtggt ctggcctaag ccccagccag aggccctgct ctctctggcc    2460
tggggcatcc acccgttgtt ctgaaggcag agcccattct gtgggctcac aagacacagt    2520
gaaggggatc atggcctgca cccctgcttt tcagcagtaa aaagcccgaa aagcctggcg    2580
agcatggccg agctgggagg gccgagccgg aactccacgt ccctcgagag caggagcctc    2640
ttaagggctg gcactggtct cagcctaatg gctgaggcgg taccctggct tcatatgcat    2700
ctcactgctc ccactgcagg ggggcaggga agggggggtct gggagccctt catgtgtggg    2760
```

-continued

```
ggccgagctg ggggccccca tggccatcct ggacctcgct gctccagagt ttaataaagg   2820

tagcacatgc ttattgctag aaaaaaaaaa aaaaaaaaaa aaaaaaaaaa aaaaaaaaaa   2880

aaaaagggcg gccgc                                                    2895
```

<210> SEQ ID NO 2
<211> LENGTH: 1365
<212> TYPE: DNA
<213> ORGANISM: Homo sapiens

<400> SEQUENCE: 2

```
atgacctggt tggtgctgct ggggacactg ctctgcatgc tgcgcgttgg gttaggcacc     60

ccggactccg agggtttccc gccccgtgcg ctccacaact gcccctacaa atgtatctgc    120

gctgccgacc tgctaagctg cactggccta gggctgcagg acgtgccagc cgagttacct    180

gccgctactg cggacctcga cctgagccac aacgcgctcc agcgcctgcg ccccggctgg    240

ttggcgcccc tcttccagct gcgcgccctg cacctagacc acaacgaact agatgcgctg    300

ggtcgcggcg tcttcgtcaa cgccagcggc ctgaggctgc tcgatctatc atctaacacg    360

ttgcgggcgc ttggccgcca cgacctcgac gggctggggg cgctggagaa gctgcttctg    420

ttcaataacc gcttggtgca cttggacgag catgccttcc acggcctgcg cgcgctcagc    480

catctctacc tgggctgcaa cgaactcgcc tcgttctcct tcgaccacct gcacggtctg    540

agcgccaccc acctgcttac tctggacctc tcctccaacc ggctgggaca catctccgta    600

cctgagctgg ccgcgctgcc ggccttcctc aagaacggcc tctacttgca caacaaccct    660

ttgccttgcg actgccgcct ctaccacctg ctacagcgct ggcaccagcg gggcctgagc    720

gccgtgcgcg actttgcgcg cgagtacgta tgcttggcct tcaaggtacc cgcgtcccgc    780

gtgcgcttct tccagcacag ccgcgtcttt gagaactgct cgtcggcccc agctcttggc    840

ctaaagcggc cggaagagca cctgtacgcg ctggtgggtc ggtccctgag gctttactgc    900

aacaccagcg tcccggccat gcgcattgcc tgggtttcgc cgcagcagga gcttctcagg    960

gcgccaggat cccgcgatgg cagcatcgcg gtgctggccg acggcagctt ggccataggc   1020

aacgtacagg agcagcatgc gggactcttc gtgtgcctgg ccactgggcc ccgcctgcac   1080

cacaaccaga cgcacgagta caacgtgagc gtgcactttc cgcgcccaga gcccgaggct   1140

ttcaacacag gcttcaccac actgctgggc tgtgccgtgg gccttgtgct cgtgctgctc   1200

tacctgttcg ccccaccctg ccgctgctgc cgccgtgcct gcccgctgcc gccgctggcc   1260

ccaaacaccc agcccgctcc aagagctgag ccgcacaagt cctcagtact cagcaccaca   1320

ccgccagacg cacccagccc gcaaggccaa gcgtccacaa gcacg                   1365
```

<210> SEQ ID NO 3
<211> LENGTH: 455
<212> TYPE: PRT
<213> ORGANISM: Homo sapiens

<400> SEQUENCE: 3

```
Met Thr Trp Leu Val Leu Leu Gly Thr Leu Leu Cys Met Leu Arg Val
1               5                   10                  15

Gly Leu Gly Thr Pro Asp Ser Glu Gly Phe Pro Pro Arg Ala Leu His
            20                  25                  30

Asn Cys Pro Tyr Lys Cys Ile Cys Ala Ala Asp Leu Leu Ser Cys Thr
        35                  40                  45

Gly Leu Gly Leu Gln Asp Val Pro Ala Glu Leu Pro Ala Ala Thr Ala
```

-continued

```
    50                  55                  60

Asp Leu Asp Leu Ser His Asn Ala Leu Gln Arg Leu Arg Pro Gly Trp
65                  70                  75                  80

Leu Ala Pro Leu Phe Gln Leu Arg Ala Leu His Leu Asp His Asn Glu
                85                  90                  95

Leu Asp Ala Leu Gly Arg Gly Val Phe Val Asn Ala Ser Gly Leu Arg
            100                 105                 110

Leu Leu Asp Leu Ser Ser Asn Thr Leu Arg Ala Leu Gly Arg His Asp
        115                 120                 125

Leu Asp Gly Leu Gly Ala Leu Glu Lys Leu Leu Leu Phe Asn Asn Arg
    130                 135                 140

Leu Val His Leu Asp Glu His Ala Phe His Gly Leu Arg Ala Leu Ser
145                 150                 155                 160

His Leu Tyr Leu Gly Cys Asn Glu Leu Ala Ser Phe Ser Phe Asp His
                165                 170                 175

Leu His Gly Leu Ser Ala Thr His Leu Leu Thr Leu Asp Leu Ser Ser
            180                 185                 190

Asn Arg Leu Gly His Ile Ser Val Pro Glu Leu Ala Ala Leu Pro Ala
        195                 200                 205

Phe Leu Lys Asn Gly Leu Tyr Leu His Asn Asn Pro Leu Pro Cys Asp
    210                 215                 220

Cys Arg Leu Tyr His Leu Leu Gln Arg Trp His Gln Arg Gly Leu Ser
225                 230                 235                 240

Ala Val Arg Asp Phe Ala Arg Glu Tyr Val Cys Leu Ala Phe Lys Val
                245                 250                 255

Pro Ala Ser Arg Val Arg Phe Phe Gln His Ser Arg Val Phe Glu Asn
            260                 265                 270

Cys Ser Ser Ala Pro Ala Leu Gly Leu Lys Arg Pro Glu Glu His Leu
        275                 280                 285

Tyr Ala Leu Val Gly Arg Ser Leu Arg Leu Tyr Cys Asn Thr Ser Val
    290                 295                 300

Pro Ala Met Arg Ile Ala Trp Val Ser Pro Gln Gln Glu Leu Leu Arg
305                 310                 315                 320

Ala Pro Gly Ser Arg Asp Gly Ser Ile Ala Val Leu Ala Asp Gly Ser
                325                 330                 335

Leu Ala Ile Gly Asn Val Gln Glu Gln His Ala Gly Leu Phe Val Cys
            340                 345                 350

Leu Ala Thr Gly Pro Arg Leu His His Asn Gln Thr His Glu Tyr Asn
        355                 360                 365

Val Ser Val His Phe Pro Arg Pro Glu Pro Glu Ala Phe Asn Thr Gly
    370                 375                 380

Phe Thr Thr Leu Leu Gly Cys Ala Val Gly Leu Val Leu Val Leu Leu
385                 390                 395                 400

Tyr Leu Phe Ala Pro Pro Cys Arg Cys Cys Arg Arg Ala Cys Pro Leu
                405                 410                 415

Pro Pro Leu Ala Pro Asn Thr Gln Pro Ala Pro Arg Ala Glu Pro His
            420                 425                 430

Lys Ser Ser Val Leu Ser Thr Thr Pro Pro Asp Ala Pro Ser Pro Gln
        435                 440                 445

Gly Gln Ala Ser Thr Ser Thr
    450                 455
```

<210> SEQ ID NO 4

-continued

```
<211> LENGTH: 20
<212> TYPE: PRT
<213> ORGANISM: Homo sapiens

<400> SEQUENCE: 4

Met Thr Trp Leu Val Leu Leu Gly Thr Leu Leu Cys Met Leu Arg Val
1               5                   10                  15

Gly Leu Gly Thr
            20


<210> SEQ ID NO 5
<211> LENGTH: 435
<212> TYPE: PRT
<213> ORGANISM: Homo sapiens

<400> SEQUENCE: 5

Pro Asp Ser Glu Gly Phe Pro Pro Arg Ala Leu His Asn Cys Pro Tyr
1               5                   10                  15

Lys Cys Ile Cys Ala Ala Asp Leu Leu Ser Cys Thr Gly Leu Gly Leu
            20                  25                  30

Gln Asp Val Pro Ala Glu Leu Pro Ala Ala Thr Ala Asp Leu Asp Leu
        35                  40                  45

Ser His Asn Ala Leu Gln Arg Leu Arg Pro Gly Trp Leu Ala Pro Leu
    50                  55                  60

Phe Gln Leu Arg Ala Leu His Leu Asp His Asn Glu Leu Asp Ala Leu
65                  70                  75                  80

Gly Arg Gly Val Phe Val Asn Ala Ser Gly Leu Arg Leu Leu Asp Leu
                85                  90                  95

Ser Ser Asn Thr Leu Arg Ala Leu Gly Arg His Asp Leu Asp Gly Leu
            100                 105                 110

Gly Ala Leu Glu Lys Leu Leu Leu Phe Asn Asn Arg Leu Val His Leu
        115                 120                 125

Asp Glu His Ala Phe His Gly Leu Arg Ala Leu Ser His Leu Tyr Leu
    130                 135                 140

Gly Cys Asn Glu Leu Ala Ser Phe Ser Phe Asp His Leu His Gly Leu
145                 150                 155                 160

Ser Ala Thr His Leu Leu Thr Leu Asp Leu Ser Ser Asn Arg Leu Gly
                165                 170                 175

His Ile Ser Val Pro Glu Leu Ala Ala Leu Pro Ala Phe Leu Lys Asn
            180                 185                 190

Gly Leu Tyr Leu His Asn Asn Pro Leu Pro Cys Asp Cys Arg Leu Tyr
        195                 200                 205

His Leu Leu Gln Arg Trp His Gln Arg Gly Leu Ser Ala Val Arg Asp
    210                 215                 220

Phe Ala Arg Glu Tyr Val Cys Leu Ala Phe Lys Val Pro Ala Ser Arg
225                 230                 235                 240

Val Arg Phe Phe Gln His Ser Arg Val Phe Glu Asn Cys Ser Ser Ala
                245                 250                 255

Pro Ala Leu Gly Leu Lys Arg Pro Glu Glu His Leu Tyr Ala Leu Val
            260                 265                 270

Gly Arg Ser Leu Arg Leu Tyr Cys Asn Thr Ser Val Pro Ala Met Arg
        275                 280                 285

Ile Ala Trp Val Ser Pro Gln Gln Glu Leu Leu Arg Ala Pro Gly Ser
    290                 295                 300

Arg Asp Gly Ser Ile Ala Val Leu Ala Asp Gly Ser Leu Ala Ile Gly
305                 310                 315                 320
```

-continued

```
Asn Val Gln Glu Gln His Ala Gly Leu Phe Val Cys Leu Ala Thr Gly
                325                 330                 335

Pro Arg Leu His His Asn Gln Thr His Glu Tyr Asn Val Ser Val His
            340                 345                 350

Phe Pro Arg Pro Glu Pro Glu Ala Phe Asn Thr Gly Phe Thr Thr Leu
        355                 360                 365

Leu Gly Cys Ala Val Gly Leu Val Leu Val Leu Leu Tyr Leu Phe Ala
    370                 375                 380

Pro Pro Cys Arg Cys Cys Arg Arg Ala Cys Pro Leu Pro Pro Leu Ala
385                 390                 395                 400

Pro Asn Thr Gln Pro Ala Pro Arg Ala Glu Pro His Lys Ser Ser Val
                405                 410                 415

Leu Ser Thr Thr Pro Pro Asp Ala Pro Ser Pro Gln Gly Gln Ala Ser
            420                 425                 430

Thr Ser Thr
        435


<210> SEQ ID NO 6
<211> LENGTH: 363
<212> TYPE: PRT
<213> ORGANISM: Homo sapiens

<400> SEQUENCE: 6

Pro Asp Ser Glu Gly Phe Pro Pro Arg Ala Leu His Asn Cys Pro Tyr
1               5                   10                  15

Lys Cys Ile Cys Ala Ala Asp Leu Leu Ser Cys Thr Gly Leu Gly Leu
            20                  25                  30

Gln Asp Val Pro Ala Glu Leu Pro Ala Ala Thr Ala Asp Leu Asp Leu
        35                  40                  45

Ser His Asn Ala Leu Gln Arg Leu Arg Pro Gly Trp Leu Ala Pro Leu
    50                  55                  60

Phe Gln Leu Arg Ala Leu His Leu Asp His Asn Glu Leu Asp Ala Leu
65                  70                  75                  80

Gly Arg Gly Val Phe Val Asn Ala Ser Gly Leu Arg Leu Leu Asp Leu
                85                  90                  95

Ser Ser Asn Thr Leu Arg Ala Leu Gly Arg His Asp Leu Asp Gly Leu
            100                 105                 110

Gly Ala Leu Glu Lys Leu Leu Leu Phe Asn Asn Arg Leu Val His Leu
        115                 120                 125

Asp Glu His Ala Phe His Gly Leu Arg Ala Leu Ser His Leu Tyr Leu
    130                 135                 140

Gly Cys Asn Glu Leu Ala Ser Phe Ser Phe Asp His Leu His Gly Leu
145                 150                 155                 160

Ser Ala Thr His Leu Leu Thr Leu Asp Leu Ser Ser Asn Arg Leu Gly
                165                 170                 175

His Ile Ser Val Pro Glu Leu Ala Ala Leu Pro Ala Phe Leu Lys Asn
            180                 185                 190

Gly Leu Tyr Leu His Asn Asn Pro Leu Pro Cys Asp Cys Arg Leu Tyr
        195                 200                 205

His Leu Leu Gln Arg Trp His Gln Arg Gly Leu Ser Ala Val Arg Asp
    210                 215                 220

Phe Ala Arg Glu Tyr Val Cys Leu Ala Phe Lys Val Pro Ala Ser Arg
225                 230                 235                 240

Val Arg Phe Phe Gln His Ser Arg Val Phe Glu Asn Cys Ser Ser Ala
```

-continued 245 250 255

Pro Ala Leu Gly Leu Lys Arg Pro Glu Glu His Leu Tyr Ala Leu Val
260 265 270

Gly Arg Ser Leu Arg Leu Tyr Cys Asn Thr Ser Val Pro Ala Met Arg
275 280 285

Ile Ala Trp Val Ser Pro Gln Gln Glu Leu Leu Arg Ala Pro Gly Ser
290 295 300

Arg Asp Gly Ser Ile Ala Val Leu Ala Asp Gly Ser Leu Ala Ile Gly
305 310 315 320

Asn Val Gln Glu Gln His Ala Gly Leu Phe Val Cys Leu Ala Thr Gly
325 330 335

Pro Arg Leu His His Asn Gln Thr His Glu Tyr Asn Val Ser Val His
340 345 350

Phe Pro Arg Pro Glu Pro Glu Ala Phe Asn Thr
355 360

<210> SEQ ID NO 7
<211> LENGTH: 20
<212> TYPE: PRT
<213> ORGANISM: Homo sapiens

<400> SEQUENCE: 7

Gly Phe Thr Thr Leu Leu Gly Cys Ala Val Gly Leu Val Leu Val Leu
1 5 10 15

Leu Tyr Leu Phe
20

<210> SEQ ID NO 8
<211> LENGTH: 52
<212> TYPE: PRT
<213> ORGANISM: Homo sapiens

<400> SEQUENCE: 8

Ala Pro Pro Cys Arg Cys Cys Arg Arg Ala Cys Pro Leu Pro Pro Leu
1 5 10 15

Ala Pro Asn Thr Gln Pro Ala Pro Arg Ala Glu Pro His Lys Ser Ser
20 25 30

Val Leu Ser Thr Thr Pro Pro Asp Ala Pro Ser Pro Gln Gly Gln Ala
35 40 45

Ser Thr Ser Thr
50

<210> SEQ ID NO 9
<211> LENGTH: 1518
<212> TYPE: DNA
<213> ORGANISM: Homo sapiens

<400> SEQUENCE: 9
gtcgacccac gcgtccggcg aaccccagcg tccgccgaca tggcctggac caagtaccag 60
ctgttcctgg ccgggctcat gcttgttacc ggctccatca acacgctctc ggcaaaatgg 120
gcggacaatt tcatggccga gggctgtgga gggagcaagg agcacagctt ccagcatccc 180
ttcctccagg cagtgggcat gttcctggga gaattctcct gcctggctgc cttctacctc 240
ctccgatgca gagctgcagg gcaatcagac tccagcgtag acccccagca gcccttcaac 300
cctcttcttt tcctgccccc agcgctctgt gacatgacag ggaccagcct catgtatgtg 360
gctctgaaca tgaccagtgc ctccagcttc cagatgctgc ggggtgcagt gatcatattc 420

-continued

```
actggcctgt tctcggtggc cttcctgggc cggaggctgg tgctgagcca gtggctgggc    480

atcctagcca ccatcgcggg gctggtggtc gtgggcctgg ctgacctcct gagcaagcac    540

gacagtcagc acaagctcag cgaagtgatc acaggggacc tgttgatcat catggcccag    600

atcatcgttg ccatccagat ggtgctagag gagaagttcg tctacaaaca caatgtgcac    660

ccactgcggg cagttggcac tgagggcctc tttggctttg tgatcctctc cctgctgctg    720

gtgcccatgt actacatccc cgccggctcc ttcagcggaa accctcgtgg gacactggag    780

gatgcattgg acgccttctg ccaggtgggc cagcagccgc tcattgccgt ggcactgctg    840

ggcaacatca gcagcattgc cttcttcaac ttcgcaggca tcagcgtcac caaggaactg    900

agcgccacca cccgcatggt gttggacagc ttgcgcaccg ttgtcatctg ggcactgagc    960

ctggcactgg gctgggaggc cttccatgca ctgcagatcc ttggcttcct catactcctt   1020

ataggcactg ccctctacaa tgggctacac cgtccgctgc tgggccgcct gtccaggggc   1080

cggcccctgg cagaggagag cgagcaggag agactgctgg gtggcacccg cactcccatc   1140

aatgatgcca gctgaggttc cctggaggct tctactgcca cccgggtgct ccttctccct   1200

gagactgagg ccacacaggc tggtgggccc cgaatgccct atccccaagg cctcaccctg   1260

tcccctccct gcagaacccc cagggcagct gctgccacag aagataacaa cacccaagtc   1320

ctctttttct cactaccacc tgcagggtgg tgttacccag cccccacaag cctgagtgca   1380

gtggcagacc tcagctctct ggacccctcc tacagcacta gagctaaatc atgaagttga   1440

attgtaggaa tttaccaccg tagtgtatct gaatcataaa ctagattatc ataaaaaaaa   1500

aaaaaaaagg gcggccgc                                                  1518
```

<210> SEQ ID NO 10
<211> LENGTH: 1113
<212> TYPE: DNA
<213> ORGANISM: Homo sapiens

<400> SEQUENCE: 10

```
atggcctgga ccaagtacca gctgttcctg gccgggctca tgcttgttac cggctccatc     60

aacacgctct cggcaaaatg ggcggacaat ttcatggccg agggctgtgg agggagcaag    120

gagcacagct tccagcatcc cttcctccag gcagtgggca tgttcctggg agaattctcc    180

tgcctggctg ccttctacct cctccgatgc agagctgcag ggcaatcaga ctccagcgta    240

gacccccagc agcccttcaa ccctcttctt ttcctgcccc cagcgctctg tgacatgaca    300

gggaccagcc tcatgtatgt ggctctgaac atgaccagtg cctccagctt ccagatgctg    360

cggggtgcag tgatcatatt cactggcctg ttctcggtgg ccttcctggg ccggaggctg    420

gtgctgagcc agtggctggg catcctagcc accatcgcgg ggctggtggt cgtgggcctg    480

gctgacctcc tgagcaagca cgacagtcag cacaagctca gcgaagtgat cacaggggac    540

ctgttgatca tcatggccca gatcatcgtt gccatccaga tggtgctaga ggagaagttc    600

gtctacaaac acaatgtgca cccactgcgg gcagttggca ctgagggcct ctttggcttt    660

gtgatcctct ccctgctgct ggtgcccatg tactacatcc ccgccggctc cttcagcgga    720

aaccctcgtg ggacactgga ggatgcattg gacgccttct gccaggtggg ccagcagccg    780

ctcattgccg tggcactgct gggcaacatc agcagcattg ccttcttcaa cttcgcaggc    840

atcagcgtca ccaaggaact gagcgccacc acccgcatgg tgttggacag cttgcgcacc    900

gttgtcatct gggcactgag cctggcactg ggctgggagg ccttccatgc actgcagatc    960

cttggcttcc tcatactcct tataggcact gccctctaca atgggctaca ccgtccgctg   1020
```

-continued

```
ctgggccgcc tgtccagggg ccggcccctg gcagaggaga gcgagcagga gagactgctg   1080

ggtggcaccc gcactcccat caatgatgcc agc                                1113


<210> SEQ ID NO 11
<211> LENGTH: 371
<212> TYPE: PRT
<213> ORGANISM: Homo sapiens

<400> SEQUENCE: 11

Met Ala Trp Thr Lys Tyr Gln Leu Phe Leu Ala Gly Leu Met Leu Val
1               5                   10                  15

Thr Gly Ser Ile Asn Thr Leu Ser Ala Lys Trp Ala Asp Asn Phe Met
            20                  25                  30

Ala Glu Gly Cys Gly Gly Ser Lys Glu His Ser Phe Gln His Pro Phe
        35                  40                  45

Leu Gln Ala Val Gly Met Phe Leu Gly Glu Phe Ser Cys Leu Ala Ala
    50                  55                  60

Phe Tyr Leu Leu Arg Cys Arg Ala Ala Gly Gln Ser Asp Ser Ser Val
65                  70                  75                  80

Asp Pro Gln Gln Pro Phe Asn Pro Leu Leu Phe Leu Pro Pro Ala Leu
                85                  90                  95

Cys Asp Met Thr Gly Thr Ser Leu Met Tyr Val Ala Leu Asn Met Thr
            100                 105                 110

Ser Ala Ser Ser Phe Gln Met Leu Arg Gly Ala Val Ile Ile Phe Thr
        115                 120                 125

Gly Leu Phe Ser Val Ala Phe Leu Gly Arg Arg Leu Val Leu Ser Gln
    130                 135                 140

Trp Leu Gly Ile Leu Ala Thr Ile Ala Gly Leu Val Val Val Gly Leu
145                 150                 155                 160

Ala Asp Leu Leu Ser Lys His Asp Ser Gln His Lys Leu Ser Glu Val
                165                 170                 175

Ile Thr Gly Asp Leu Leu Ile Ile Met Ala Gln Ile Ile Val Ala Ile
            180                 185                 190

Gln Met Val Leu Glu Glu Lys Phe Val Tyr Lys His Asn Val His Pro
        195                 200                 205

Leu Arg Ala Val Gly Thr Glu Gly Leu Phe Gly Phe Val Ile Leu Ser
    210                 215                 220

Leu Leu Leu Val Pro Met Tyr Tyr Ile Pro Ala Gly Ser Phe Ser Gly
225                 230                 235                 240

Asn Pro Arg Gly Thr Leu Glu Asp Ala Leu Asp Ala Phe Cys Gln Val
                245                 250                 255

Gly Gln Gln Pro Leu Ile Ala Val Ala Leu Leu Gly Asn Ile Ser Ser
            260                 265                 270

Ile Ala Phe Phe Asn Phe Ala Gly Ile Ser Val Thr Lys Glu Leu Ser
        275                 280                 285

Ala Thr Thr Arg Met Val Leu Asp Ser Leu Arg Thr Val Val Ile Trp
    290                 295                 300

Ala Leu Ser Leu Ala Leu Gly Trp Glu Ala Phe His Ala Leu Gln Ile
305                 310                 315                 320

Leu Gly Phe Leu Ile Leu Leu Ile Gly Thr Ala Leu Tyr Asn Gly Leu
                325                 330                 335

His Arg Pro Leu Leu Gly Arg Leu Ser Arg Gly Arg Pro Leu Ala Glu
            340                 345                 350
```

-continued

```
Glu Ser Glu Gln Glu Arg Leu Leu Gly Gly Thr Arg Thr Pro Ile Asn
        355                 360                 365

Asp Ala Ser
    370


<210> SEQ ID NO 12
<211> LENGTH: 18
<212> TYPE: PRT
<213> ORGANISM: Homo sapiens

<400> SEQUENCE: 12

Met Ala Trp Thr Lys Tyr Gln Leu Phe Leu Ala Gly Leu Met Leu Val
1               5                   10                  15

Thr Gly


<210> SEQ ID NO 13
<211> LENGTH: 353
<212> TYPE: PRT
<213> ORGANISM: Homo sapiens

<400> SEQUENCE: 13

Ser Ile Asn Thr Leu Ser Ala Lys Trp Ala Asp Asn Phe Met Ala Glu
1               5                   10                  15

Gly Cys Gly Gly Ser Lys Glu His Ser Phe Gln His Pro Phe Leu Gln
            20                  25                  30

Ala Val Gly Met Phe Leu Gly Glu Phe Ser Cys Leu Ala Ala Phe Tyr
        35                  40                  45

Leu Leu Arg Cys Arg Ala Ala Gly Gln Ser Asp Ser Ser Val Asp Pro
    50                  55                  60

Gln Gln Pro Phe Asn Pro Leu Leu Phe Leu Pro Pro Ala Leu Cys Asp
65                  70                  75                  80

Met Thr Gly Thr Ser Leu Met Tyr Val Ala Leu Asn Met Thr Ser Ala
                85                  90                  95

Ser Ser Phe Gln Met Leu Arg Gly Ala Val Ile Ile Phe Thr Gly Leu
            100                 105                 110

Phe Ser Val Ala Phe Leu Gly Arg Arg Leu Val Leu Ser Gln Trp Leu
        115                 120                 125

Gly Ile Leu Ala Thr Ile Ala Gly Leu Val Val Val Gly Leu Ala Asp
    130                 135                 140

Leu Leu Ser Lys His Asp Ser Gln His Lys Leu Ser Glu Val Ile Thr
145                 150                 155                 160

Gly Asp Leu Leu Ile Ile Met Ala Gln Ile Ile Val Ala Ile Gln Met
                165                 170                 175

Val Leu Glu Glu Lys Phe Val Tyr Lys His Asn Val His Pro Leu Arg
            180                 185                 190

Ala Val Gly Thr Glu Gly Leu Phe Gly Phe Val Ile Leu Ser Leu Leu
        195                 200                 205

Leu Val Pro Met Tyr Tyr Ile Pro Ala Gly Ser Phe Ser Gly Asn Pro
    210                 215                 220

Arg Gly Thr Leu Glu Asp Ala Leu Asp Ala Phe Cys Gln Val Gly Gln
225                 230                 235                 240

Gln Pro Leu Ile Ala Val Ala Leu Leu Gly Asn Ile Ser Ser Ile Ala
                245                 250                 255

Phe Phe Asn Phe Ala Gly Ile Ser Val Thr Lys Glu Leu Ser Ala Thr
            260                 265                 270

Thr Arg Met Val Leu Asp Ser Leu Arg Thr Val Val Ile Trp Ala Leu
```

-continued

```
        275                 280                 285

Ser Leu Ala Leu Gly Trp Glu Ala Phe His Ala Leu Gln Ile Leu Gly
    290                 295                 300

Phe Leu Ile Leu Leu Ile Gly Thr Ala Leu Tyr Asn Gly Leu His Arg
305                 310                 315                 320

Pro Leu Leu Gly Arg Leu Ser Arg Gly Arg Pro Leu Ala Glu Glu Ser
                325                 330                 335

Glu Gln Glu Arg Leu Leu Gly Gly Thr Arg Thr Pro Ile Asn Asp Ala
            340                 345                 350

Ser


<210> SEQ ID NO 14
<211> LENGTH: 29
<212> TYPE: PRT
<213> ORGANISM: Homo sapiens

<400> SEQUENCE: 14

Ser Ile Asn Thr Leu Ser Ala Lys Trp Ala Asp Asn Phe Met Ala Glu
1               5                   10                  15

Gly Cys Gly Gly Ser Lys Glu His Ser Phe Gln His Pro
            20                  25


<210> SEQ ID NO 15
<211> LENGTH: 9
<212> TYPE: PRT
<213> ORGANISM: Homo sapiens

<400> SEQUENCE: 15

Asn Met Thr Ser Ala Ser Ser Phe Gln
1               5


<210> SEQ ID NO 16
<211> LENGTH: 14
<212> TYPE: PRT
<213> ORGANISM: Homo sapiens

<400> SEQUENCE: 16

Asp Leu Leu Ser Lys His Asp Ser Gln His Lys Leu Ser Glu
1               5                   10


<210> SEQ ID NO 17
<211> LENGTH: 27
<212> TYPE: PRT
<213> ORGANISM: Homo sapiens

<400> SEQUENCE: 17

Pro Ala Gly Ser Phe Ser Gly Asn Pro Arg Gly Thr Leu Glu Asp Ala
1               5                   10                  15

Leu Asp Ala Phe Cys Gln Val Gly Gln Gln Pro
            20                  25


<210> SEQ ID NO 18
<211> LENGTH: 7
<212> TYPE: PRT
<213> ORGANISM: Homo sapiens

<400> SEQUENCE: 18

Glu Ala Phe His Ala Leu Gln
1               5


<210> SEQ ID NO 19
```

-continued

<211> LENGTH: 21
<212> TYPE: PRT
<213> ORGANISM: Homo sapiens

<400> SEQUENCE: 19

Phe Leu Gln Ala Val Gly Met Phe Leu Gly Glu Phe Ser Cys Leu Ala
1 5 10 15

Ala Phe Tyr Leu Leu
20

<210> SEQ ID NO 20
<211> LENGTH: 21
<212> TYPE: PRT
<213> ORGANISM: Homo sapiens

<400> SEQUENCE: 20

Leu Leu Phe Leu Pro Pro Ala Leu Cys Asp Met Thr Gly Thr Ser Leu
1 5 10 15

Met Tyr Val Ala Leu
20

<210> SEQ ID NO 21
<211> LENGTH: 19
<212> TYPE: PRT
<213> ORGANISM: Homo sapiens

<400> SEQUENCE: 21

Met Leu Arg Gly Ala Val Ile Ile Phe Thr Gly Leu Phe Ser Val Ala
1 5 10 15

Phe Leu Gly

<210> SEQ ID NO 22
<211> LENGTH: 17
<212> TYPE: PRT
<213> ORGANISM: Homo sapiens

<400> SEQUENCE: 22

Trp Leu Gly Ile Leu Ala Thr Ile Ala Gly Leu Val Val Val Gly Leu
1 5 10 15

Ala

<210> SEQ ID NO 23
<211> LENGTH: 17
<212> TYPE: PRT
<213> ORGANISM: Homo sapiens

<400> SEQUENCE: 23

Val Ile Thr Gly Asp Leu Leu Ile Ile Met Ala Gln Ile Ile Val Ala
1 5 10 15

Ile

<210> SEQ ID NO 24
<211> LENGTH: 18
<212> TYPE: PRT
<213> ORGANISM: Homo sapiens

<400> SEQUENCE: 24

Gly Leu Phe Gly Phe Val Ile Leu Ser Leu Leu Leu Val Pro Met Tyr
1 5 10 15

Tyr Ile

-continued

<210> SEQ ID NO 25
<211> LENGTH: 23
<212> TYPE: PRT
<213> ORGANISM: Homo sapiens

<400> SEQUENCE: 25

```
Leu Ile Ala Val Ala Leu Leu Gly Asn Ile Ser Ser Ile Ala Phe Phe
1               5                   10                  15

Asn Phe Ala Gly Ile Ser Val
            20
```

<210> SEQ ID NO 26
<211> LENGTH: 20
<212> TYPE: PRT
<213> ORGANISM: Homo sapiens

<400> SEQUENCE: 26

```
Met Val Leu Asp Ser Leu Arg Thr Val Val Ile Trp Ala Leu Ser Leu
1               5                   10                  15

Ala Leu Gly Trp
            20
```

<210> SEQ ID NO 27
<211> LENGTH: 17
<212> TYPE: PRT
<213> ORGANISM: Homo sapiens

<400> SEQUENCE: 27

```
Ile Leu Gly Phe Leu Ile Leu Leu Ile Gly Thr Ala Leu Tyr Asn Gly
1               5                   10                  15

Leu
```

<210> SEQ ID NO 28
<211> LENGTH: 20
<212> TYPE: PRT
<213> ORGANISM: Homo sapiens

<400> SEQUENCE: 28

```
Arg Cys Arg Ala Ala Gly Gln Ser Asp Ser Ser Val Asp Pro Gln Gln
1               5                   10                  15

Pro Phe Asn Pro
            20
```

<210> SEQ ID NO 29
<211> LENGTH: 7
<212> TYPE: PRT
<213> ORGANISM: Homo sapiens

<400> SEQUENCE: 29

```
Arg Arg Leu Val Leu Ser Gln
1               5
```

<210> SEQ ID NO 30
<211> LENGTH: 23
<212> TYPE: PRT
<213> ORGANISM: Homo sapiens

<400> SEQUENCE: 30

```
Gln Met Val Leu Glu Glu Lys Phe Val Tyr Lys His Asn Val His Pro
1               5                   10                  15

Leu Arg Ala Val Gly Thr Glu
            20
```

-continued

<210> SEQ ID NO 31
<211> LENGTH: 9
<212> TYPE: PRT
<213> ORGANISM: Homo sapiens

<400> SEQUENCE: 31

Thr Lys Glu Leu Ser Ala Thr Thr Arg
1               5

<210> SEQ ID NO 32
<211> LENGTH: 35
<212> TYPE: PRT
<213> ORGANISM: Homo sapiens

<400> SEQUENCE: 32

His Arg Pro Leu Leu Gly Arg Leu Ser Arg Gly Arg Pro Leu Ala Glu
1               5                   10                  15

Glu Ser Glu Gln Glu Arg Leu Leu Gly Gly Thr Arg Thr Pro Ile Asn
            20                  25                  30

Asp Ala Ser
        35

<210> SEQ ID NO 33
<211> LENGTH: 2811
<212> TYPE: DNA
<213> ORGANISM: Homo sapiens

<400> SEQUENCE: 33
gtcgacccac gcgtccgcgg gacagctggc ctgaagctca gagccggggc gtgcgccatg 60
gccccacact gggctgtctg gctgctggca gcaaggctgt ggggcctggg cattggggct 120
gaggtgtggt ggaaccttgt gccgcgtaag acagtgtctt ctggggagct ggccacggta 180
gtacggcggt tctcccagac cggcatccag gacttcctga cactgacgct gacggagccc 240
actgggcttc tgtacgtggg cgcccgagag gccctgtttg ccttcagcat ggaggccctg 300
gagctgcaag gagcgatctc ctgggaggcc cccgtggaga agaagactga gtgtatccag 360
aaagggaaga acaaccagac cgagtgcttc aacttcatcc gcttcctgca gccctacaat 420
gcctcccacc tgtacgtctg tggcacctac gccttccagc ccaagtgcac ctacgtcgtg 480
agtgctgccc tcctacctcg gtgtccccag cccccgccc tcctcaccct tctctggact 540
cgtggatgtg gcccacagag ccctgccctt aagcatctcc tcatcacctc tctctctgtc 600
cttagaacat gctcaccttc actttggagc atggagagtt tgaagatggg aagggcaagt 660
gtccctatga cccagctaag ggccatgctg gccttcttgt ggatggtgag ctgtactcgg 720
ccacactcaa caacttcctg ggcacggaac ccattatcct gcgtaacatg ggccccacc 780 actccatgaa gacagagtac ctggcctttt ggctcaacga acctcacttt gtaggctctg 840
cctatgtacc tgagagtgtg ggcagcttca cgggggacga cgacaaggtc tacttcttct 900
tcagggagcg ggcagtggag tccgactgct atgccgagca ggtggtggct cgtgtggccc 960
gtgtctgcaa gggcgatatg gggggcgcac ggaccctgca gaggaagtgg accacgttcc 1020
tgaaggcgcg gctggcatgc tctgccccga actggcagct ctacttcaac cagctgcagg 1080
cgatgcacac cctgcaggac acctcctggc acaacaccac cttctttggg gtttttcaag 1140
cacagtgggg tgacatgtac ctgtcggcca tctgtgagta ccagttggaa gagatccagc 1200
gggtgtttga gggcccctat aaggagtacc atgaggaagc ccagaagtgg gaccgctaca 1260
ctgaccctgt acccaggccc tggttgtgat ggctgcccag ccccgccatg ccggggccta 1320

-continued ccactgcttt tcagaggagc agggggcgcg gctggctgct gaaggctacc ttgtggctgt 1380
cgtggcaggc ccgtcggtga ccttggaggc ccgggccccc ctggaaaacc tggggctggt 1440
gtggctggcg gtggtggccc tgggggctgt gtgcctggtg ctgctgctgc tggtgctgtc 1500
attgcgccgg cggctgcggg aagagctgga gaaaggggcc aaggctactg agaggacctt 1560
ggtgtacccc ctggagctgc ccaaggagcc caccagtccc cccttccggc cctgtcctga 1620
accagatgag aaactttggg atcctgtcgg ttactactat tcagatggct cccttaagat 1680
agtacctggg catgcccggt gccagcccgg tggggggccc ccttcgccac ctccaggcat 1740
cccaggccag cctctgcctt ctccaactcg gcttcacctg gggggtgggc ggaactcaaa 1800
tgccaatggt tacgtgcgct tacaactagg aggggaggac cggggagggc tcgggcaccc 1860
cctgcctgag ctcgcggatg aactgagacg caaactgcag caacgccagc cactgcccga 1920
ctccaacccc gaggagtcat cagtatgagg ggaaccccca ccgcgtcggc gggaagcgtg 1980
ggaggtgtag ctcctacttt tgcacaggca ccagctacct cagggacatg gcacgggcac 2040
ctgctctgtc tgggacagat actgcccagc acccacccgg ccatgaggac ctgctctgct 2100
cagcacgggc actgccactt ggtgtggctc accagggcac cagcctcgca gaaggcatct 2160
tcctcctctc tgtgaatcac agacacgcgg gaccccagcc gccaaaactt ttcaaggcag 2220
aagtttcaag atgtgtgttt gtctgtattt gcacatgtgt ttgtgtgtgt gtgtatgtgt 2280
gtgtgcacgc gcgtgcgcgc ttgtggcata gccttcctgt ttctgtcaag tcttcccttg 2340
gcctgggtcc tcctggtgag tcattggagc tatgaagggg aaggggtcgt atcactttgt 2400
ctctcctacc cccactgccc cgagtgtcgg gcagcgatgt acatatggag gtggggtgga 2460
cagggtgctg tgccccttca gagggagtgc agggcttggg gtgggcctag tcctgctcct 2520
agggctgtga atgttttcag ggtgggggga gggagatgga gcctcctgtg tgtttggggg 2580
gaagggtggg tggggcctcc cacttggccc cggggttcag tggtatttta tacttgcctt 2640
cttcctgtac agggctggga aaggctgtgt gaggggagag aagggagagg gtgggcctgc 2700
tgtggacaat ggcatactct cttccagccc taggaggagg gctcctaaca gtgtaactta 2760
ttgtgtcccc gcgtatttat ttgttgtaaa tatttgagat ttttatattg a 2811

<210> SEQ ID NO 34
<211> LENGTH: 729
<212> TYPE: DNA
<213> ORGANISM: Homo sapiens

<400> SEQUENCE: 34
atggccccac actgggctgt ctggctgctg gcagcaaggc tgtggggcct gggcattggg 60
gctgaggtgt ggtggaacct tgtgccgcgt aagacagtgt cttctgggga gctggccacg 120
gtagtacggc ggttctccca gaccggcatc caggacttcc tgacactgac gctgacggag 180
cccactgggc ttctgtacgt gggcgcccga gaggccctgt ttgccttcag catggaggcc 240
ctggagctgc aaggagcgat ctcctgggag gcccccgtgg agaagaagac tgagtgtatc 300
cagaaaggga agaacaacca gaccgagtgc ttcaacttca tccgcttcct gcagccctac 360
aatgcctccc acctgtacgt ctgtggcacc tacgccttcc agcccaagtg cacctacgtc 420
gtgagtgctg ccctcctacc tcggtgtccc cagccccccg ccctcctcac ccttctctgg 480
actcgtggat gtggcccaca gagccctgcc cttaagcatc tcctcatcac ctctctctct 540
gtccttagaa catgctcacc ttcactttgg agcatggaga gtttgaagat gggaagggca 600

-continued agtgtcccta tgacccagct aagggccatg ctggccttct tgtggatggt gagctgtact 660
cggccacact caacaacttc ctgggcacgg aacccattat cctgcgtaac atggggcccc 720
accactcca 729

<210> SEQ ID NO 35
<211> LENGTH: 243
<212> TYPE: PRT
<213> ORGANISM: Homo sapiens

<400> SEQUENCE: 35

Met Ala Pro His Trp Ala Val Trp Leu Leu Ala Ala Arg Leu Trp Gly
1 5 10 15

Leu Gly Ile Gly Ala Glu Val Trp Trp Asn Leu Val Pro Arg Lys Thr
20 25 30

Val Ser Ser Gly Glu Leu Ala Thr Val Val Arg Arg Phe Ser Gln Thr
35 40 45

Gly Ile Gln Asp Phe Leu Thr Leu Thr Leu Thr Glu Pro Thr Gly Leu
50 55 60

Leu Tyr Val Gly Ala Arg Glu Ala Leu Phe Ala Phe Ser Met Glu Ala
65 70 75 80

Leu Glu Leu Gln Gly Ala Ile Ser Trp Glu Ala Pro Val Glu Lys Lys
85 90 95

Thr Glu Cys Ile Gln Lys Gly Lys Asn Asn Gln Thr Glu Cys Phe Asn
100 105 110

Phe Ile Arg Phe Leu Gln Pro Tyr Asn Ala Ser His Leu Tyr Val Cys
115 120 125

Gly Thr Tyr Ala Phe Gln Pro Lys Cys Thr Tyr Val Val Ser Ala Ala
130 135 140

Leu Leu Pro Arg Cys Pro Gln Pro Pro Ala Leu Leu Thr Leu Leu Trp
145 150 155 160

Thr Arg Gly Cys Gly Pro Gln Ser Pro Ala Leu Lys His Leu Leu Ile
165 170 175

Thr Ser Leu Ser Val Leu Arg Thr Cys Ser Pro Ser Leu Trp Ser Met
180 185 190

Glu Ser Leu Lys Met Gly Arg Ala Ser Val Pro Met Thr Gln Leu Arg
195 200 205

Ala Met Leu Ala Phe Leu Trp Met Val Ser Cys Thr Arg Pro His Ser
210 215 220

Thr Thr Ser Trp Ala Arg Asn Pro Leu Ser Cys Val Thr Trp Gly Pro
225 230 235 240

Thr Thr Pro

<210> SEQ ID NO 36
<211> LENGTH: 20
<212> TYPE: PRT
<213> ORGANISM: Homo sapiens

<400> SEQUENCE: 36

Met Ala Pro His Trp Ala Val Trp Leu Leu Ala Ala Arg Leu Trp Gly
1 5 10 15

Leu Gly Ile Gly
20

<210> SEQ ID NO 37
<211> LENGTH: 223
<212> TYPE: PRT

-continued

<213> ORGANISM: Homo sapiens

<400> SEQUENCE: 37

```
Ala Glu Val Trp Trp Asn Leu Val Pro Arg Lys Thr Val Ser Ser Gly
1               5                   10                  15

Glu Leu Ala Thr Val Val Arg Arg Phe Ser Gln Thr Gly Ile Gln Asp
            20                  25                  30

Phe Leu Thr Leu Thr Leu Thr Glu Pro Thr Gly Leu Leu Tyr Val Gly
        35                  40                  45

Ala Arg Glu Ala Leu Phe Ala Phe Ser Met Glu Ala Leu Glu Leu Gln
    50                  55                  60

Gly Ala Ile Ser Trp Glu Ala Pro Val Glu Lys Lys Thr Glu Cys Ile
65                  70                  75                  80

Gln Lys Gly Lys Asn Asn Gln Thr Glu Cys Phe Asn Phe Ile Arg Phe
                85                  90                  95

Leu Gln Pro Tyr Asn Ala Ser His Leu Tyr Val Cys Gly Thr Tyr Ala
            100                 105                 110

Phe Gln Pro Lys Cys Thr Tyr Val Val Ser Ala Ala Leu Leu Pro Arg
        115                 120                 125

Cys Pro Gln Pro Pro Ala Leu Leu Thr Leu Leu Trp Thr Arg Gly Cys
    130                 135                 140

Gly Pro Gln Ser Pro Ala Leu Lys His Leu Leu Ile Thr Ser Leu Ser
145                 150                 155                 160

Val Leu Arg Thr Cys Ser Pro Ser Leu Trp Ser Met Glu Ser Leu Lys
                165                 170                 175

Met Gly Arg Ala Ser Val Pro Met Thr Gln Leu Arg Ala Met Leu Ala
            180                 185                 190

Phe Leu Trp Met Val Ser Cys Thr Arg Pro His Ser Thr Thr Ser Trp
        195                 200                 205

Ala Arg Asn Pro Leu Ser Cys Val Thr Trp Gly Pro Thr Thr Pro
    210                 215                 220
```

<210> SEQ ID NO 38
<211> LENGTH: 2498
<212> TYPE: DNA
<213> ORGANISM: Homo sapiens

<400> SEQUENCE: 38

```
gtcgacccac gcgtccgcgg acgcgtgggc gcgcgggggc catccagacc ctgcggagag     60

cgaggcccgg agcgtcgccg aggtttgagg gcgccggaga ccgagggcct ggcggccgaa    120

ggaaccgccc caagaagagc ctctggcccg ggggctgctg gaacatgtgc ggggggacac    180

agtttgtttg acagttgcca gactatgttt acgcttctgg ttctactcag ccaactgccc    240

acagttaccc tggggtttcc tcattgcgca agaggtccaa aggcttctaa gcatgcggga    300

gaagaagtgt ttacatcaaa agaagaagca aactttttca tacatagacg ccttctgtat    360

aatagatttg atctggagct cttcactccc ggcaacctag aaagagagtg caatgaagaa    420

ctttgcaatt atgaggaagc cagagagatt tttgtggatg aagataaaac gattgcattt    480

tggcaggaat attcagctaa aggaccaacc acaaaatcag atggcaacag agagaaaata    540

gatgttatgg gccttctgac tggattaatt gctgctggag tatttttggt tatttttgga    600

ttacttggct actatctttg tatcactaag tgtaataggc tacaacatcc atgctcttca    660

gccgtctatg aaagggggag gcacactccc tccatcattt tcagaagacc tgaggaggct    720

gccttgtctc cattgccgcc ttctgtggag gatgcaggat taccttctta tgaacaggca    780
```

-continued

```
gtggcgctga ccagaaaaca cagtgtttca ccaccaccac catatcctgg gcacacaaaa    840
ggatttaggg tatttaaaaa atctatgtct ctcccatctc actgactacc ttgtcatttt    900
ggtataagaa atttgtgtta tttgataggc cgggcatggt ggctcatgcc tgtaatccca    960
gcactttggg aggccaggag ttcgagacca gcctggccaa catggtgaaa cccggtctct   1020
actaaaaatt caaaaattac ctaggcgtca tggggcatgc ctgtagtccc acctacttgg   1080
gaggctgaag caggagaatt gctcgaacct gggaggcaga ggttgcagta agctgagatc   1140
acgccactgc attccagcct gggcgacaga gcaagactcc atctcaaaaa taaaataaaa   1200
aaagaaagaa agaaaagaag aagaaaagag aagaaggaga aggagatgaa ggaggaggag   1260
gaggagaagg agaagaagaa gaagaagaag accacaaaag acatgactat ccaacttttt   1320
atgacaaact gcaaggaata aaggaagaat aagtccatgt actgtaccac agaagttctg   1380
tctgcatctt ggacctgaac ttgatcatta tcagcttgat aagagacttt ttgactctat   1440
atccttgcag ttaagaagaa agcacttttt tgtaatgttt gttttaatgg ttcaaaaaaa   1500
atctttctta taaagagcat aggtagaatt agtgaactct ttggatcctt tgtacagata   1560
aaggttatag atttcttgtg ttgaatatta aaaaagcaag gatgtctaac cattaagatt   1620
atccaaagtc aggctgggcg cagtggctca cgcctgtaat cccagcactt tgggagggat   1680
aggtgggcgg atcacctgag gtcaggagtt tgagaccagc ctggccaaca tggcaaaacc   1740
ccgtctctac aaaaatacaa aagaaattag ccagacatga tggcgggtgc ctctaatccc   1800
agctactggg gaggctgagg tgggagaatc gcttgaactc gggaggtgga ggttgtagtg   1860
aggcgagatt gtgccattgc actccaacct gggcgacaga gtgagactcc atctcaaaaa   1920
aaaaaaaaaa aaaaagatta tccaaaaaga tattggacct actctttctt aggatttttt   1980
tggcgggggg ttagaaatac ttcacagaat ttgacatttc agtataaatc tgtgacctta   2040
atataatcac ttggttttat atgttaaatt attgcacagc agtcatcata ttttgcagag   2100
tttagttctt aactcttgct gtcagtcatg ttttattata ggtagtgggg tcagtagttt   2160
tcttcttcta aaaaatacta tttgctatga agttagttct tcagaagata caagtttgca   2220
atgaaaagga tttgcaaggg ttgttatgct atcaaataaa cagacctaaa atctaggaga   2280
cactagaact taatgaagtt gcccctgtta ctgattagta aatactccca tcttcgttgc   2340
aaaattatct ctctgtataa ctacatatga ttattttgaa atttgttaaa cttcataagt   2400
aatagtttga gaatgtggaa aaagtaattt gcttttctgc tcttaaaata atattgatta   2460
atgttaccag aaaaaaaaaa aaaaaaaagg gcggccgc                            2498
```

<210> SEQ ID NO 39
<211> LENGTH: 678
<212> TYPE: DNA
<213> ORGANISM: Homo sapiens

<400> SEQUENCE: 39

```
atgtttacgc ttctggttct actcagccaa ctgcccacag ttaccctggg gtttcctcat     60
tgcgcaagag gtccaaaggc ttctaagcat gcgggagaag aagtgtttac atcaaaagaa    120
gaagcaaact ttttcataca tagacgcctt ctgtataata gatttgatct ggagctcttc    180
actcccggca acctagaaag agagtgcaat gaagaacttt gcaattatga ggaagccaga    240
gagatttttg tggatgaaga taaaacgatt gcattttggc aggaatattc agctaaagga    300
ccaaccacaa aatcagatgg caacagagag aaaatagatg ttatgggcct tctgactgga    360
```

-continued

```
ttaattgctg ctggagtatt tttggttatt tttggattac ttggctacta tctttgtatc    420

actaagtgta ataggctaca acatccatgc tcttcagccg tctatgaaag ggggaggcac    480

actccctcca tcattttcag aagacctgag gaggctgcct tgtctccatt gccgccttct    540

gtggaggatg caggattacc ttcttatgaa caggcagtgg cgctgaccag aaaacacagt    600

gtttcaccac caccaccata tcctgggcac acaaaaggat ttagggtatt taaaaaatct    660

atgtctctcc catctcac                                                   678


<210> SEQ ID NO 40
<211> LENGTH: 226
<212> TYPE: PRT
<213> ORGANISM: Homo sapiens

<400> SEQUENCE: 40

Met Phe Thr Leu Leu Val Leu Leu Ser Gln Leu Pro Thr Val Thr Leu
1               5                   10                  15

Gly Phe Pro His Cys Ala Arg Gly Pro Lys Ala Ser Lys His Ala Gly
            20                  25                  30

Glu Glu Val Phe Thr Ser Lys Glu Glu Ala Asn Phe Phe Ile His Arg
        35                  40                  45

Arg Leu Leu Tyr Asn Arg Phe Asp Leu Glu Leu Phe Thr Pro Gly Asn
    50                  55                  60

Leu Glu Arg Glu Cys Asn Glu Glu Leu Cys Asn Tyr Glu Glu Ala Arg
65                  70                  75                  80

Glu Ile Phe Val Asp Glu Asp Lys Thr Ile Ala Phe Trp Gln Glu Tyr
                85                  90                  95

Ser Ala Lys Gly Pro Thr Thr Lys Ser Asp Gly Asn Arg Glu Lys Ile
            100                 105                 110

Asp Val Met Gly Leu Leu Thr Gly Leu Ile Ala Ala Gly Val Phe Leu
        115                 120                 125

Val Ile Phe Gly Leu Leu Gly Tyr Tyr Leu Cys Ile Thr Lys Cys Asn
    130                 135                 140

Arg Leu Gln His Pro Cys Ser Ser Ala Val Tyr Glu Arg Gly Arg His
145                 150                 155                 160

Thr Pro Ser Ile Ile Phe Arg Arg Pro Glu Glu Ala Ala Leu Ser Pro
                165                 170                 175

Leu Pro Pro Ser Val Glu Asp Ala Gly Leu Pro Ser Tyr Glu Gln Ala
            180                 185                 190

Val Ala Leu Thr Arg Lys His Ser Val Ser Pro Pro Pro Pro Tyr Pro
        195                 200                 205

Gly His Thr Lys Gly Phe Arg Val Phe Lys Lys Ser Met Ser Leu Pro
    210                 215                 220

Ser His
225


<210> SEQ ID NO 41
<211> LENGTH: 17
<212> TYPE: PRT
<213> ORGANISM: Homo sapiens

<400> SEQUENCE: 41

Met Phe Thr Leu Leu Val Leu Leu Ser Gln Leu Pro Thr Val Thr Leu
1               5                   10                  15

Gly
```

-continued

<210> SEQ ID NO 42
<211> LENGTH: 209
<212> TYPE: PRT
<213> ORGANISM: Homo sapiens

<400> SEQUENCE: 42

```
Phe Pro His Cys Ala Arg Gly Pro Lys Ala Ser Lys His Ala Gly Glu
1               5                   10                  15

Glu Val Phe Thr Ser Lys Glu Glu Ala Asn Phe Phe Ile His Arg Arg
            20                  25                  30

Leu Leu Tyr Asn Arg Phe Asp Leu Glu Leu Phe Thr Pro Gly Asn Leu
        35                  40                  45

Glu Arg Glu Cys Asn Glu Glu Leu Cys Asn Tyr Glu Glu Ala Arg Glu
    50                  55                  60

Ile Phe Val Asp Glu Asp Lys Thr Ile Ala Phe Trp Gln Glu Tyr Ser
65                  70                  75                  80

Ala Lys Gly Pro Thr Thr Lys Ser Asp Gly Asn Arg Glu Lys Ile Asp
                85                  90                  95

Val Met Gly Leu Leu Thr Gly Leu Ile Ala Ala Gly Val Phe Leu Val
            100                 105                 110

Ile Phe Gly Leu Leu Gly Tyr Tyr Leu Cys Ile Thr Lys Cys Asn Arg
        115                 120                 125

Leu Gln His Pro Cys Ser Ser Ala Val Tyr Glu Arg Gly Arg His Thr
    130                 135                 140

Pro Ser Ile Ile Phe Arg Arg Pro Glu Glu Ala Ala Leu Ser Pro Leu
145                 150                 155                 160

Pro Pro Ser Val Glu Asp Ala Gly Leu Pro Ser Tyr Glu Gln Ala Val
                165                 170                 175

Ala Leu Thr Arg Lys His Ser Val Ser Pro Pro Pro Pro Tyr Pro Gly
            180                 185                 190

His Thr Lys Gly Phe Arg Val Phe Lys Lys Ser Met Ser Leu Pro Ser
        195                 200                 205

His
```

<210> SEQ ID NO 43
<211> LENGTH: 96
<212> TYPE: PRT
<213> ORGANISM: Homo sapiens

<400> SEQUENCE: 43

```
Phe Pro His Cys Ala Arg Gly Pro Lys Ala Ser Lys His Ala Gly Glu
1               5                   10                  15

Glu Val Phe Thr Ser Lys Glu Glu Ala Asn Phe Phe Ile His Arg Arg
            20                  25                  30

Leu Leu Tyr Asn Arg Phe Asp Leu Glu Leu Phe Thr Pro Gly Asn Leu
        35                  40                  45

Glu Arg Glu Cys Asn Glu Glu Leu Cys Asn Tyr Glu Glu Ala Arg Glu
    50                  55                  60

Ile Phe Val Asp Glu Asp Lys Thr Ile Ala Phe Trp Gln Glu Tyr Ser
65                  70                  75                  80

Ala Lys Gly Pro Thr Thr Lys Ser Asp Gly Asn Arg Glu Lys Ile Asp
                85                  90                  95
```

<210> SEQ ID NO 44
<211> LENGTH: 25
<212> TYPE: PRT
<213> ORGANISM: Homo sapiens -continued

<400> SEQUENCE: 44

```
Val Met Gly Leu Leu Thr Gly Leu Ile Ala Ala Gly Val Phe Leu Val
1               5                   10                  15

Ile Phe Gly Leu Leu Gly Tyr Tyr Leu
            20                  25
```

<210> SEQ ID NO 45
<211> LENGTH: 88
<212> TYPE: PRT
<213> ORGANISM: Homo sapiens

<400> SEQUENCE: 45

```
Cys Ile Thr Lys Cys Asn Arg Leu Gln His Pro Cys Ser Ser Ala Val
1               5                   10                  15

Tyr Glu Arg Gly Arg His Thr Pro Ser Ile Ile Phe Arg Arg Pro Glu
            20                  25                  30

Glu Ala Ala Leu Ser Pro Leu Pro Pro Ser Val Glu Asp Ala Gly Leu
        35                  40                  45

Pro Ser Tyr Glu Gln Ala Val Ala Leu Thr Arg Lys His Ser Val Ser
    50                  55                  60

Pro Pro Pro Pro Tyr Pro Gly His Thr Lys Gly Phe Arg Val Phe Lys
65                  70                  75                  80

Lys Ser Met Ser Leu Pro Ser His
                85
```

<210> SEQ ID NO 46
<211> LENGTH: 2169
<212> TYPE: DNA
<213> ORGANISM: Homo sapiens

<400> SEQUENCE: 46

```
gtcgacccac gcgtccggaa atgtcgttct tcagatttaa aaagaaaacc tttactgaat     60

cagctgagtg ttaataatac gaatttcctt ttcttgccaa ttctgatctg aacagaaaat    120

ccaagaacag ggatatgtgt ggattacagt tttctctgcc ttgcctacga ctgtttctgg    180

ttgttacctg ttatctttta ttattactcc acaaagaaat acttggatgt tcgtctgttt    240

gtcagctctg cactgggaga caaattaact gccgtaactt aggcctttcg agtattccta    300

agaattttcc tgaaagtaca gtttttctgt atctgactgg gaataatata tcttatataa    360

atgaaagtga attaacagga cttcattctc ttgtagcatt gtatttggat aattctaaca    420

ttctgtatgt atatccaaaa gcctttgttc aattgaggca tctatatttt ctatttctaa    480

ataataattt catcaaacgc ttagatcctg gaatatttaa gggactttta aatcttcgta    540

atttatattt acagtataat caggtatctt ttgttccgag aggagtattt aatgatctag    600

tttcagttca gtacttaaat ctacaaagga atcgcctcac tgtccttggg agtggtacct    660

ttgttggtat ggttgctctt cggatacttg atttatcaaa caataacatt ttgaggatat    720

cagaatcagg ctttcaacat cttgaaaacc ttgcttgttt gtatttagga agtaataatt    780

taacaaaagt accatcaaat gcctttgaag tacttaaaag tcttagaaga ctttctttgt    840

ctcataatcc tattgaagca atacagccct ttgcatttaa aggacttgcc aatctggaat    900

acctcctcct gaaaaattca agaattagga atgttactag ggatgggttt agtggaatta    960

ataatcttaa acatttgatc ttaagtcata atgatttaga gaatttaaat tctgacacat   1020

tcagtttgtt aaagaattta atttacctta agttagatag aaacagaata attagcattg   1080
```

-continued

```
ataatgatac atttgaaaat atgggagcat ctttgaagat ccttaatctg tcatttaata   1140

atcttacagc cttgcatcca agggtcctta agccgttgtc ttcattgatt catcttcagg   1200

caaattctaa tccttgggaa tgtaactgca aacttttggg ccttcgagac tggctagcat   1260

cttcagccat tactctaaac atctattgtc agaatccccc atccatgcgt ggcagagcat   1320

tacgttatat taacattaca aattgtgtta catcttcaat aaatgtatcc agagcttggg   1380

ctgttgtaaa atctcctcat attcatcaca agactactgc gctaatgatg gcctggcata   1440

aagtaaccac aaatggcagt cctctggaaa atactgagac tgagaacatt actttctggg   1500

aacgaattcc tacttcacct gctggtagat tttttcaaga gaatgccttt ggtaatccat   1560

tagagactac agcagtgtta cctgtgcaaa tacaacttac tacttctgtt accttgaact   1620

tggaaaaaaa cagtgctcta ccgaatgatg ctgcttcaat gtcagggaaa acatctctaa   1680

tttgtacaca agaagttgag aagttgaatg aggcttttga cattttgcta gcttttttca   1740

tcttagcttg tgttttaatc attttttga tctacaaagt tgttcagttt aaacaaaaac   1800

taaaggcatc agaaaactca agggaaaata gacttgaata ctacagcttt tatcagtcag   1860

caaggtataa tgtaactgcc tcaatttgta acacttcccc aaattctcta gaaagtcctg   1920

gcttggagca gattcgactt cataaacaaa ttgttcctga aaatgaggca caggtcattc   1980

tttttgaaca ttctgcttta taactcaact aaatattgtc tataagaaac ttcagtgcca   2040

tggacatgat ttaaactgaa acctccttat ataattatat actttagttg gaaatataat   2100

gaattatatg aggttagcat tattaaaata tgtttttaat aaaaaaaaaa aaaaaaaaag   2160

ggcggccgc                                                            2169
```

<210> SEQ ID NO 47
<211> LENGTH: 1866
<212> TYPE: DNA
<213> ORGANISM: Homo sapiens

<400> SEQUENCE: 47

```
atgtgtggat tacagttttc tctgccttgc ctacgactgt ttctggttgt tacctgttat     60

cttttattat tactccacaa agaaatactt ggatgttcgt ctgtttgtca gctctgcact    120

gggagacaaa ttaactgccg taacttaggc ctttcgagta ttcctaagaa ttttcctgaa    180

agtacagttt ttctgtatct gactgggaat aatatatctt atataaatga aagtgaatta    240

acaggacttc attctcttgt agcattgtat ttggataatt ctaacattct gtatgtatat    300

ccaaaagcct ttgttcaatt gaggcatcta tattttctat ttctaaataa taatttcatc    360

aaacgcttag atcctggaat atttaaggga cttttaaatc ttcgtaattt atatttacag    420

tataatcagg tatcttttgt tccgagagga gtatttaatg atctagtttc agttcagtac    480

ttaaatctac aaaggaatcg cctcactgtc cttgggagtg gtacctttgt tggtatggtt    540

gctcttcgga tacttgattt atcaaacaat aacattttga ggatatcaga atcaggcttt    600

caacatcttg aaaaccttgc ttgtttgtat ttaggaagta ataatttaac aaaagtacca    660

tcaaatgcct ttgaagtact taaaagtctt agaagacttt ctttgtctca taatcctatt    720

gaagcaatac agccctttgc atttaaagga cttgccaatc tggaatacct cctcctgaaa    780

aattcaagaa ttaggaatgt tactagggat gggtttagtg gaattaataa tcttaaacat    840

ttgatcttaa gtcataatga tttagagaat ttaaattctg acacattcag tttgttaaag    900

aatttaattt accttaagtt agatagaaac agaataatta gcattgataa tgatacattt    960

gaaaatatgg gagcatcttt gaagatcctt aatctgtcat ttaataatct tacagccttg   1020
```

-continued

```
catccaaggg tccttaagcc gttgtcttca ttgattcatc ttcaggcaaa ttctaatcct   1080
tgggaatgta actgcaaact tttgggcctt cgagactggc tagcatcttc agccattact   1140
ctaaacatct attgtcagaa tcccccatcc atgcgtggca gagcattacg ttatattaac   1200
attacaaatt gtgttacatc ttcaataaat gtatccagag cttgggctgt tgtaaaatct   1260
cctcatattc atcacaagac tactgcgcta atgatggcct ggcataaagt aaccacaaat   1320
ggcagtcctc tggaaaatac tgagactgag aacattactt tctgggaacg aattcctact   1380
tcacctgctg gtagattttt tcaagagaat gcctttggta atccattaga gactacagca   1440
gtgttacctg tgcaaataca acttactact tctgttacct tgaacttgga aaaaaacagt   1500
gctctaccga atgatgctgc ttcaatgtca gggaaaacat ctctaatttg tacacaagaa   1560
gttgagaagt tgaatgaggc ttttgacatt ttgctagctt ttttcatctt agcttgtgtt   1620
ttaatcattt ttttgatcta caaagttgtt cagtttaaac aaaaactaaa ggcatcagaa   1680
aactcaaggg aaaatagact tgaatactac agcttttatc agtcagcaag gtataatgta   1740
actgcctcaa tttgtaacac ttccccaaat tctctagaaa gtcctggctt ggagcagatt   1800
cgacttcata aacaaattgt tcctgaaaat gaggcacagg tcattctttt tgaacattct   1860
gcttta                                                              1866
```

<210> SEQ ID NO 48
<211> LENGTH: 622
<212> TYPE: PRT
<213> ORGANISM: Homo sapiens

<400> SEQUENCE: 48

```
Met Cys Gly Leu Gln Phe Ser Leu Pro Cys Leu Arg Leu Phe Leu Val
1               5                   10                  15

Val Thr Cys Tyr Leu Leu Leu Leu Leu His Lys Glu Ile Leu Gly Cys
            20                  25                  30

Ser Ser Val Cys Gln Leu Cys Thr Gly Arg Gln Ile Asn Cys Arg Asn
        35                  40                  45

Leu Gly Leu Ser Ser Ile Pro Lys Asn Phe Pro Glu Ser Thr Val Phe
    50                  55                  60

Leu Tyr Leu Thr Gly Asn Asn Ile Ser Tyr Ile Asn Glu Ser Glu Leu
65                  70                  75                  80

Thr Gly Leu His Ser Leu Val Ala Leu Tyr Leu Asp Asn Ser Asn Ile
                85                  90                  95

Leu Tyr Val Tyr Pro Lys Ala Phe Val Gln Leu Arg His Leu Tyr Phe
            100                 105                 110

Leu Phe Leu Asn Asn Asn Phe Ile Lys Arg Leu Asp Pro Gly Ile Phe
        115                 120                 125

Lys Gly Leu Leu Asn Leu Arg Asn Leu Tyr Leu Gln Tyr Asn Gln Val
    130                 135                 140

Ser Phe Val Pro Arg Gly Val Phe Asn Asp Leu Val Ser Val Gln Tyr
145                 150                 155                 160

Leu Asn Leu Gln Arg Asn Arg Leu Thr Val Leu Gly Ser Gly Thr Phe
                165                 170                 175

Val Gly Met Val Ala Leu Arg Ile Leu Asp Leu Ser Asn Asn Asn Ile
            180                 185                 190

Leu Arg Ile Ser Glu Ser Gly Phe Gln His Leu Glu Asn Leu Ala Cys
        195                 200                 205

Leu Tyr Leu Gly Ser Asn Asn Leu Thr Lys Val Pro Ser Asn Ala Phe
```

-continued

```
    210                 215                 220

Glu Val Leu Lys Ser Leu Arg Arg Leu Ser Leu Ser His Asn Pro Ile
225                 230                 235                 240

Glu Ala Ile Gln Pro Phe Ala Phe Lys Gly Leu Ala Asn Leu Glu Tyr
                245                 250                 255

Leu Leu Leu Lys Asn Ser Arg Ile Arg Asn Val Thr Arg Asp Gly Phe
            260                 265                 270

Ser Gly Ile Asn Asn Leu Lys His Leu Ile Leu Ser His Asn Asp Leu
        275                 280                 285

Glu Asn Leu Asn Ser Asp Thr Phe Ser Leu Leu Lys Asn Leu Ile Tyr
    290                 295                 300

Leu Lys Leu Asp Arg Asn Arg Ile Ile Ser Ile Asp Asn Asp Thr Phe
305                 310                 315                 320

Glu Asn Met Gly Ala Ser Leu Lys Ile Leu Asn Leu Ser Phe Asn Asn
                325                 330                 335

Leu Thr Ala Leu His Pro Arg Val Leu Lys Pro Leu Ser Ser Leu Ile
            340                 345                 350

His Leu Gln Ala Asn Ser Asn Pro Trp Glu Cys Asn Cys Lys Leu Leu
        355                 360                 365

Gly Leu Arg Asp Trp Leu Ala Ser Ser Ala Ile Thr Leu Asn Ile Tyr
    370                 375                 380

Cys Gln Asn Pro Pro Ser Met Arg Gly Arg Ala Leu Arg Tyr Ile Asn
385                 390                 395                 400

Ile Thr Asn Cys Val Thr Ser Ser Ile Asn Val Ser Arg Ala Trp Ala
                405                 410                 415

Val Val Lys Ser Pro His Ile His His Lys Thr Thr Ala Leu Met Met
            420                 425                 430

Ala Trp His Lys Val Thr Thr Asn Gly Ser Pro Leu Glu Asn Thr Glu
        435                 440                 445

Thr Glu Asn Ile Thr Phe Trp Glu Arg Ile Pro Thr Ser Pro Ala Gly
    450                 455                 460

Arg Phe Phe Gln Glu Asn Ala Phe Gly Asn Pro Leu Glu Thr Thr Ala
465                 470                 475                 480

Val Leu Pro Val Gln Ile Gln Leu Thr Thr Ser Val Thr Leu Asn Leu
                485                 490                 495

Glu Lys Asn Ser Ala Leu Pro Asn Asp Ala Ala Ser Met Ser Gly Lys
            500                 505                 510

Thr Ser Leu Ile Cys Thr Gln Glu Val Glu Lys Leu Asn Glu Ala Phe
        515                 520                 525

Asp Ile Leu Leu Ala Phe Phe Ile Leu Ala Cys Val Leu Ile Ile Phe
    530                 535                 540

Leu Ile Tyr Lys Val Val Gln Phe Lys Gln Lys Leu Lys Ala Ser Glu
545                 550                 555                 560

Asn Ser Arg Glu Asn Arg Leu Glu Tyr Tyr Ser Phe Tyr Gln Ser Ala
                565                 570                 575

Arg Tyr Asn Val Thr Ala Ser Ile Cys Asn Thr Ser Pro Asn Ser Leu
            580                 585                 590

Glu Ser Pro Gly Leu Glu Gln Ile Arg Leu His Lys Gln Ile Val Pro
        595                 600                 605

Glu Asn Glu Ala Gln Val Ile Leu Phe Glu His Ser Ala Leu
    610                 615                 620
```

<210> SEQ ID NO 49

-continued

<211> LENGTH: 31
<212> TYPE: PRT
<213> ORGANISM: Homo sapiens

<400> SEQUENCE: 49

```
Met Cys Gly Leu Gln Phe Ser Leu Pro Cys Leu Arg Leu Phe Leu Val
1               5                   10                  15

Val Thr Cys Tyr Leu Leu Leu Leu Leu His Lys Glu Ile Leu Gly
            20                  25                  30
```

<210> SEQ ID NO 50
<211> LENGTH: 591
<212> TYPE: PRT
<213> ORGANISM: Homo sapiens

<400> SEQUENCE: 50

```
Cys Ser Ser Val Cys Gln Leu Cys Thr Gly Arg Gln Ile Asn Cys Arg
1               5                   10                  15

Asn Leu Gly Leu Ser Ser Ile Pro Lys Asn Phe Pro Glu Ser Thr Val
            20                  25                  30

Phe Leu Tyr Leu Thr Gly Asn Asn Ile Ser Tyr Ile Asn Glu Ser Glu
        35                  40                  45

Leu Thr Gly Leu His Ser Leu Val Ala Leu Tyr Leu Asp Asn Ser Asn
    50                  55                  60

Ile Leu Tyr Val Tyr Pro Lys Ala Phe Val Gln Leu Arg His Leu Tyr
65                  70                  75                  80

Phe Leu Phe Leu Asn Asn Asn Phe Ile Lys Arg Leu Asp Pro Gly Ile
                85                  90                  95

Phe Lys Gly Leu Leu Asn Leu Arg Asn Leu Tyr Leu Gln Tyr Asn Gln
            100                 105                 110

Val Ser Phe Val Pro Arg Gly Val Phe Asn Asp Leu Val Ser Val Gln
        115                 120                 125

Tyr Leu Asn Leu Gln Arg Asn Arg Leu Thr Val Leu Gly Ser Gly Thr
    130                 135                 140

Phe Val Gly Met Val Ala Leu Arg Ile Leu Asp Leu Ser Asn Asn Asn
145                 150                 155                 160

Ile Leu Arg Ile Ser Glu Ser Gly Phe Gln His Leu Glu Asn Leu Ala
                165                 170                 175

Cys Leu Tyr Leu Gly Ser Asn Asn Leu Thr Lys Val Pro Ser Asn Ala
            180                 185                 190

Phe Glu Val Leu Lys Ser Leu Arg Arg Leu Ser Leu Ser His Asn Pro
        195                 200                 205

Ile Glu Ala Ile Gln Pro Phe Ala Phe Lys Gly Leu Ala Asn Leu Glu
    210                 215                 220

Tyr Leu Leu Leu Lys Asn Ser Arg Ile Arg Asn Val Thr Arg Asp Gly
225                 230                 235                 240

Phe Ser Gly Ile Asn Asn Leu Lys His Leu Ile Leu Ser His Asn Asp
                245                 250                 255

Leu Glu Asn Leu Asn Ser Asp Thr Phe Ser Leu Leu Lys Asn Leu Ile
            260                 265                 270

Tyr Leu Lys Leu Asp Arg Asn Arg Ile Ile Ser Ile Asp Asn Asp Thr
        275                 280                 285

Phe Glu Asn Met Gly Ala Ser Leu Lys Ile Leu Asn Leu Ser Phe Asn
    290                 295                 300

Asn Leu Thr Ala Leu His Pro Arg Val Leu Lys Pro Leu Ser Ser Leu
305                 310                 315                 320
```

Ile His Leu Gln Ala Asn Ser Asn Pro Trp Glu Cys Asn Cys Lys Leu
325 330 335

Leu Gly Leu Arg Asp Trp Leu Ala Ser Ser Ala Ile Thr Leu Asn Ile
340 345 350

Tyr Cys Gln Asn Pro Pro Ser Met Arg Gly Arg Ala Leu Arg Tyr Ile
355 360 365

Asn Ile Thr Asn Cys Val Thr Ser Ser Ile Asn Val Ser Arg Ala Trp
370 375 380

Ala Val Val Lys Ser Pro His Ile His His Lys Thr Thr Ala Leu Met
385 390 395 400

Met Ala Trp His Lys Val Thr Thr Asn Gly Ser Pro Leu Glu Asn Thr
405 410 415

Glu Thr Glu Asn Ile Thr Phe Trp Glu Arg Ile Pro Thr Ser Pro Ala
420 425 430

Gly Arg Phe Phe Gln Glu Asn Ala Phe Gly Asn Pro Leu Glu Thr Thr
435 440 445

Ala Val Leu Pro Val Gln Ile Gln Leu Thr Thr Ser Val Thr Leu Asn
450 455 460

Leu Glu Lys Asn Ser Ala Leu Pro Asn Asp Ala Ala Ser Met Ser Gly
465 470 475 480

Lys Thr Ser Leu Ile Cys Thr Gln Glu Val Glu Lys Leu Asn Glu Ala
485 490 495

Phe Asp Ile Leu Leu Ala Phe Phe Ile Leu Ala Cys Val Leu Ile Ile
500 505 510

Phe Leu Ile Tyr Lys Val Val Gln Phe Lys Gln Lys Leu Lys Ala Ser
515 520 525

Glu Asn Ser Arg Glu Asn Arg Leu Glu Tyr Tyr Ser Phe Tyr Gln Ser
530 535 540

Ala Arg Tyr Asn Val Thr Ala Ser Ile Cys Asn Thr Ser Pro Asn Ser
545 550 555 560

Leu Glu Ser Pro Gly Leu Glu Gln Ile Arg Leu His Lys Gln Ile Val
565 570 575

Pro Glu Asn Glu Ala Gln Val Ile Leu Phe Glu His Ser Ala Leu
580 585 590

<210> SEQ ID NO 51
<211> LENGTH: 498
<212> TYPE: PRT
<213> ORGANISM: Homo sapiens

<400> SEQUENCE: 51

Cys Ser Ser Val Cys Gln Leu Cys Thr Gly Arg Gln Ile Asn Cys Arg
1 5 10 15

Asn Leu Gly Leu Ser Ser Ile Pro Lys Asn Phe Pro Glu Ser Thr Val
20 25 30

Phe Leu Tyr Leu Thr Gly Asn Asn Ile Ser Tyr Ile Asn Glu Ser Glu
35 40 45

Leu Thr Gly Leu His Ser Leu Val Ala Leu Tyr Leu Asp Asn Ser Asn
50 55 60

Ile Leu Tyr Val Tyr Pro Lys Ala Phe Val Gln Leu Arg His Leu Tyr
65 70 75 80

Phe Leu Phe Leu Asn Asn Asn Phe Ile Lys Arg Leu Asp Pro Gly Ile
85 90 95

Phe Lys Gly Leu Leu Asn Leu Arg Asn Leu Tyr Leu Gln Tyr Asn Gln

-continued

```
            100                 105                 110

Val Ser Phe Val Pro Arg Gly Val Phe Asn Asp Leu Val Ser Val Gln
        115                 120                 125

Tyr Leu Asn Leu Gln Arg Asn Arg Leu Thr Val Leu Gly Ser Gly Thr
    130                 135                 140

Phe Val Gly Met Val Ala Leu Arg Ile Leu Asp Leu Ser Asn Asn Asn
145                 150                 155                 160

Ile Leu Arg Ile Ser Glu Ser Gly Phe Gln His Leu Glu Asn Leu Ala
                165                 170                 175

Cys Leu Tyr Leu Gly Ser Asn Asn Leu Thr Lys Val Pro Ser Asn Ala
            180                 185                 190

Phe Glu Val Leu Lys Ser Leu Arg Arg Leu Ser Leu Ser His Asn Pro
        195                 200                 205

Ile Glu Ala Ile Gln Pro Phe Ala Phe Lys Gly Leu Ala Asn Leu Glu
    210                 215                 220

Tyr Leu Leu Leu Lys Asn Ser Arg Ile Arg Asn Val Thr Arg Asp Gly
225                 230                 235                 240

Phe Ser Gly Ile Asn Asn Leu Lys His Leu Ile Leu Ser His Asn Asp
                245                 250                 255

Leu Glu Asn Leu Asn Ser Asp Thr Phe Ser Leu Leu Lys Asn Leu Ile
            260                 265                 270

Tyr Leu Lys Leu Asp Arg Asn Arg Ile Ile Ser Ile Asp Asn Asp Thr
        275                 280                 285

Phe Glu Asn Met Gly Ala Ser Leu Lys Ile Leu Asn Leu Ser Phe Asn
    290                 295                 300

Asn Leu Thr Ala Leu His Pro Arg Val Leu Lys Pro Leu Ser Ser Leu
305                 310                 315                 320

Ile His Leu Gln Ala Asn Ser Asn Pro Trp Glu Cys Asn Cys Lys Leu
                325                 330                 335

Leu Gly Leu Arg Asp Trp Leu Ala Ser Ser Ala Ile Thr Leu Asn Ile
            340                 345                 350

Tyr Cys Gln Asn Pro Pro Ser Met Arg Gly Arg Ala Leu Arg Tyr Ile
        355                 360                 365

Asn Ile Thr Asn Cys Val Thr Ser Ser Ile Asn Val Ser Arg Ala Trp
    370                 375                 380

Ala Val Val Lys Ser Pro His Ile His His Lys Thr Thr Ala Leu Met
385                 390                 395                 400

Met Ala Trp His Lys Val Thr Thr Asn Gly Ser Pro Leu Glu Asn Thr
                405                 410                 415

Glu Thr Glu Asn Ile Thr Phe Trp Glu Arg Ile Pro Thr Ser Pro Ala
            420                 425                 430

Gly Arg Phe Phe Gln Glu Asn Ala Phe Gly Asn Pro Leu Glu Thr Thr
        435                 440                 445

Ala Val Leu Pro Val Gln Ile Gln Leu Thr Thr Ser Val Thr Leu Asn
    450                 455                 460

Leu Glu Lys Asn Ser Ala Leu Pro Asn Asp Ala Ala Ser Met Ser Gly
465                 470                 475                 480

Lys Thr Ser Leu Ile Cys Thr Gln Glu Val Glu Lys Leu Asn Glu Ala
                485                 490                 495

Phe Asp

<210> SEQ ID NO 52
<211> LENGTH: 18
```

<212> TYPE: PRT
<213> ORGANISM: Homo sapiens

<400> SEQUENCE: 52

Ile Leu Leu Ala Phe Phe Ile Leu Ala Cys Val Leu Ile Ile Phe Leu
1 5 10 15

Ile Tyr

<210> SEQ ID NO 53
<211> LENGTH: 75
<212> TYPE: PRT
<213> ORGANISM: Homo sapiens

<400> SEQUENCE: 53

Lys Val Val Gln Phe Lys Gln Lys Leu Lys Ala Ser Glu Asn Ser Arg
1 5 10 15

Glu Asn Arg Leu Glu Tyr Tyr Ser Phe Tyr Gln Ser Ala Arg Tyr Asn
20 25 30

Val Thr Ala Ser Ile Cys Asn Thr Ser Pro Asn Ser Leu Glu Ser Pro
35 40 45

Gly Leu Glu Gln Ile Arg Leu His Lys Gln Ile Val Pro Glu Asn Glu
50 55 60

Ala Gln Val Ile Leu Phe Glu His Ser Ala Leu
65 70 75

<210> SEQ ID NO 54
<211> LENGTH: 1432
<212> TYPE: DNA
<213> ORGANISM: Homo sapiens
<220> FEATURE:
<221> NAME/KEY: misc_feature
<222> LOCATION: (14)..(14)
<223> OTHER INFORMATION: unknown

<400> SEQUENCE: 54
acgcgtccgc acanggccgg cgcggctggg agcgggtggg cggccgggag gccggagcag 60
cacggccgca ggacctggag ctccggctgc gtcttcccgc agcgctaccc gccatgcgcc 120
tgccgcgccg ggccgcgctg gggctcctgc cgcttctgct gctgctgccg cccgcgccgg 180
aggccgccaa gaagccgacg ccctgccacc ggtgccgggg gctggtggac aagtttaacc 240
aggggatggt ggacaccgca aagaagaact ttggcggcgg gaacacggct tgggaggaaa 300
agacgctgtc caagtacgag tccagcgaga ttcgcctgct ggagatcctg gaggggctgt 360
gcgagagcag cgacttcgaa tgcaatcaga tgctagaggc gcaggaggag cacctggagg 420
cctggtggct gcagctgaag agcgaatatc ctgacttatt cgagtggttt tgtgtgaaga 480
cactgaaagt gtgctgctct ccaggaacct acggtcccga ctgtctcgca tgccagggcg 540
gatcccagag gccctgcagc gggaatggcc actgcagcgg agatgggagc agacagggcg 600
acgggtcctg ccggtgccac atggggtacc agggcccgct gtgcactgac tgcatggacg 660
gctacttcag ctcgctccgg aacgagaccc acagcatctg cacagcctgt gacgagtcct 720
gcaagacgtg ctcgggcctg accaacagag actgcggcga gtgtgaagtg ggctgggtgc 780
tggacgaggg cgcctgtgtg gatgtggacg agtgtgcggc cgagccgcct ccctgcagcg 840
ctgcgcagtt ctgtaagaac gccaacggct cctacacgtg cgaagagtgt gactccagct 900
gtgtgggctg cacaggggaa ggcccaggaa actgtaaaga gtgtatctct ggctacgcga 960
gggagcacgg acagtgtgca gatgtggacg agtgctcact agcagaaaaa acctgtgtga 1020

-continued

```
ggaaaaacga aaactgctac aatactccag ggagctacgt ctgtgtgtgt cctgacggct   1080

tcgaagaaac ggaagatgcc tgtgtgccgc cggcagaggc tgaagccaca gaaggagaaa   1140

gcccgacaca gctgccctcc cgcgaagacc tgtaatgtgc cggacttacc ctttaaatta   1200

ttcagaagga tgtcccgtgg aaaatgtggc cctgaggatg ccgtctcctg cagtggacag   1260

cggcggggag aggctgcctg ctctctaacg gttgattctc atttgtccct taaacagctg   1320

catttcttgg ttgttcttaa acagacttgt atattttgat acagttcttt gtaataaaat   1380

tgaccattgt aggtaatcaa aaaaaaaaaa aaaaaaaggg cggccgctag ac           1432
```

<210> SEQ ID NO 55
<211> LENGTH: 1059
<212> TYPE: DNA
<213> ORGANISM: Homo sapiens

<400> SEQUENCE: 55

```
atgcgcctgc cgcgccgggc cgcgctgggg ctcctgccgc ttctgctgct gctgccgccc     60

gcgccggagg ccgccaagaa gccgacgccc tgccaccggt gccgggggct ggtggacaag    120

tttaaccagg ggatggtgga caccgcaaag aagaactttg gcggcgggaa cacggcttgg    180

gaggaaaaga cgctgtccaa gtacgagtcc agcgagattc gcctgctgga gatcctggag    240

gggctgtgcg agagcagcga cttcgaatgc aatcagatgc tagaggcgca ggaggagcac    300

ctggaggcct ggtggctgca gctgaagagc gaatatcctg acttattcga gtggtttttgt    360

gtgaagacac tgaaagtgtg ctgctctcca ggaacctacg gtcccgactg tctcgcatgc    420

cagggcggat cccagaggcc ctgcagcggg aatggccact gcagcggaga tgggagcaga    480

cagggcgacg ggtcctgccg gtgccacatg ggtaccagg gcccgctgtg cactgactgc    540

atggacggct acttcagctc gctccggaac gagacccaca gcatctgcac agcctgtgac    600

gagtcctgca agacgtgctc gggcctgacc aacagagact gcggcgagtg tgaagtgggc    660

tgggtgctgg acgagggcgc ctgtgtggat gtggacgagt gtgcggccga gccgcctccc    720

tgcagcgctg cgcagttctg taagaacgcc aacggctcct acacgtgcga agagtgtgac    780

tccagctgtg tgggctgcac aggggaaggc ccaggaaact gtaaagagtg tatctctggc    840

tacgcgaggg agcacggaca gtgtgcagat gtggacgagt gctcactagc agaaaaaacc    900

tgtgtgagga aaaacgaaaa ctgctacaat actccaggga gctacgtctg tgtgtgtcct    960

gacggcttcg aagaaacgga agatgcctgt gtgccgccgg cagaggctga agccacagaa   1020

ggagaaagcc cgacacagct gccctcccgc gaagacctg                          1059
```

<210> SEQ ID NO 56
<211> LENGTH: 353
<212> TYPE: PRT
<213> ORGANISM: Homo sapiens

<400> SEQUENCE: 56

```
Met Arg Leu Pro Arg Arg Ala Ala Leu Gly Leu Leu Pro Leu Leu Leu
1               5                   10                  15

Leu Leu Pro Pro Ala Pro Glu Ala Ala Lys Lys Pro Thr Pro Cys His
            20                  25                  30

Arg Cys Arg Gly Leu Val Asp Lys Phe Asn Gln Gly Met Val Asp Thr
        35                  40                  45

Ala Lys Lys Asn Phe Gly Gly Gly Asn Thr Ala Trp Glu Glu Lys Thr
    50                  55                  60

Leu Ser Lys Tyr Glu Ser Ser Glu Ile Arg Leu Leu Glu Ile Leu Glu
```

-continued

```
65                  70                  75                  80

Gly Leu Cys Glu Ser Ser Asp Phe Glu Cys Asn Gln Met Leu Glu Ala
                85                  90                  95

Gln Glu Glu His Leu Glu Ala Trp Trp Leu Gln Leu Lys Ser Glu Tyr
            100                 105                 110

Pro Asp Leu Phe Glu Trp Phe Cys Val Lys Thr Leu Lys Val Cys Cys
        115                 120                 125

Ser Pro Gly Thr Tyr Gly Pro Asp Cys Leu Ala Cys Gln Gly Gly Ser
    130                 135                 140

Gln Arg Pro Cys Ser Gly Asn Gly His Cys Ser Gly Asp Gly Ser Arg
145                 150                 155                 160

Gln Gly Asp Gly Ser Cys Arg Cys His Met Gly Tyr Gln Gly Pro Leu
                165                 170                 175

Cys Thr Asp Cys Met Asp Gly Tyr Phe Ser Ser Leu Arg Asn Glu Thr
            180                 185                 190

His Ser Ile Cys Thr Ala Cys Asp Glu Ser Cys Lys Thr Cys Ser Gly
        195                 200                 205

Leu Thr Asn Arg Asp Cys Gly Glu Cys Glu Val Gly Trp Val Leu Asp
    210                 215                 220

Glu Gly Ala Cys Val Asp Val Asp Glu Cys Ala Ala Glu Pro Pro Pro
225                 230                 235                 240

Cys Ser Ala Ala Gln Phe Cys Lys Asn Ala Asn Gly Ser Tyr Thr Cys
                245                 250                 255

Glu Glu Cys Asp Ser Ser Cys Val Gly Cys Thr Gly Glu Gly Pro Gly
            260                 265                 270

Asn Cys Lys Glu Cys Ile Ser Gly Tyr Ala Arg Glu His Gly Gln Cys
        275                 280                 285

Ala Asp Val Asp Glu Cys Ser Leu Ala Glu Lys Thr Cys Val Arg Lys
    290                 295                 300

Asn Glu Asn Cys Tyr Asn Thr Pro Gly Ser Tyr Val Cys Val Cys Pro
305                 310                 315                 320

Asp Gly Phe Glu Glu Thr Glu Asp Ala Cys Val Pro Pro Ala Glu Ala
                325                 330                 335

Glu Ala Thr Glu Gly Glu Ser Pro Thr Gln Leu Pro Ser Arg Glu Asp
            340                 345                 350

Leu


<210> SEQ ID NO 57
<211> LENGTH: 24
<212> TYPE: PRT
<213> ORGANISM: Homo sapiens

<400> SEQUENCE: 57

Met Arg Leu Pro Arg Arg Ala Ala Leu Gly Leu Leu Pro Leu Leu Leu
1               5                   10                  15

Leu Leu Pro Pro Ala Pro Glu Ala
            20


<210> SEQ ID NO 58
<211> LENGTH: 329
<212> TYPE: PRT
<213> ORGANISM: Homo sapiens

<400> SEQUENCE: 58

Ala Lys Lys Pro Thr Pro Cys His Arg Cys Arg Gly Leu Val Asp Lys
1               5                   10                  15
```

-continued

```
Phe Asn Gln Gly Met Val Asp Thr Ala Lys Lys Asn Phe Gly Gly Gly
            20                  25                  30

Asn Thr Ala Trp Glu Glu Lys Thr Leu Ser Lys Tyr Glu Ser Ser Glu
        35                  40                  45

Ile Arg Leu Leu Glu Ile Leu Glu Gly Leu Cys Glu Ser Ser Asp Phe
    50                  55                  60

Glu Cys Asn Gln Met Leu Glu Ala Gln Glu Glu His Leu Glu Ala Trp
65                  70                  75                  80

Trp Leu Gln Leu Lys Ser Glu Tyr Pro Asp Leu Phe Glu Trp Phe Cys
                85                  90                  95

Val Lys Thr Leu Lys Val Cys Cys Ser Pro Gly Thr Tyr Gly Pro Asp
            100                 105                 110

Cys Leu Ala Cys Gln Gly Gly Ser Gln Arg Pro Cys Ser Gly Asn Gly
        115                 120                 125

His Cys Ser Gly Asp Gly Ser Arg Gln Gly Asp Gly Ser Cys Arg Cys
    130                 135                 140

His Met Gly Tyr Gln Gly Pro Leu Cys Thr Asp Cys Met Asp Gly Tyr
145                 150                 155                 160

Phe Ser Ser Leu Arg Asn Glu Thr His Ser Ile Cys Thr Ala Cys Asp
                165                 170                 175

Glu Ser Cys Lys Thr Cys Ser Gly Leu Thr Asn Arg Asp Cys Gly Glu
            180                 185                 190

Cys Glu Val Gly Trp Val Leu Asp Glu Gly Ala Cys Val Asp Val Asp
        195                 200                 205

Glu Cys Ala Ala Glu Pro Pro Pro Cys Ser Ala Ala Gln Phe Cys Lys
    210                 215                 220

Asn Ala Asn Gly Ser Tyr Thr Cys Glu Glu Cys Asp Ser Ser Cys Val
225                 230                 235                 240

Gly Cys Thr Gly Glu Gly Pro Gly Asn Cys Lys Glu Cys Ile Ser Gly
                245                 250                 255

Tyr Ala Arg Glu His Gly Gln Cys Ala Asp Val Asp Glu Cys Ser Leu
            260                 265                 270

Ala Glu Lys Thr Cys Val Arg Lys Asn Glu Asn Cys Tyr Asn Thr Pro
        275                 280                 285

Gly Ser Tyr Val Cys Val Cys Pro Asp Gly Phe Glu Glu Thr Glu Asp
    290                 295                 300

Ala Cys Val Pro Pro Ala Glu Ala Glu Ala Thr Glu Gly Glu Ser Pro
305                 310                 315                 320

Thr Gln Leu Pro Ser Arg Glu Asp Leu
                325
```

<210> SEQ ID NO 59
<211> LENGTH: 2730
<212> TYPE: DNA
<213> ORGANISM: Homo sapiens

<400> SEQUENCE: 59

```
gtcgacccac gcgtccgtcc tgcggcccca gcctctcctc acgctcgcgc agtctccgcc     60

gcagtctcag ctgcagctgc aggactgagc cgtgcacccg gaggagaccc ccggaggagg    120

cgacaaactt cgcagtgccg cgacccaacc ccagccctgg gtagcctgca gcatggccca    180

gctgttcctg cccctgctgg cagccctggt cctggcccag gctcctgcag ctttagcaga    240

tgttctggaa ggagacagct cagaggaccg cgcttttcgc gtgcgcatcg cgggcgacgc    300
```

-continued

```
gccactgcag ggcgtgctcg gcggcgccct caccatccct tgccacgtcc actacctgcg    360
gccaccgccg agccgccggg ctgtgctggg ctctccgcgg gtcaagtgga ctttcctgtc    420
ccggggccgg gaggcagagg tgctggtggc gcggggagtg cgcgtcaagg tgaacgaggc    480
ctaccggttc cgcgtggcac tgcctgcgta cccagcgtcg ctcaccgacg tctccctggc    540
gctgagcgag ctgcgcccca acgactcagg tatctatcgc tgtgaggtcc agcacggcat    600
cgatgacagc agcgacgctg tggaggtcaa ggtcaaaggg gtcgtctttc tctaccgaga    660
gggctctgcc cgctatgctt tctccttttc tggggcccag gaggcctgtg cccgcattgg    720
agcccacatc gccaccccgg agcagctcta tgccgcctac cttgggggct atgagcaatg    780
tgatgctggc tggctgtcgg atcagaccgt gaggtatccc atccagaccc cacgagaggc    840
ctgttacgga gacatggatg gcttccccgg ggtccggaac tatggtgtgg tggacccgga    900
tgacctctat gatgtgtact gttatgctga agacctaaat ggagaactgt tcctgggtga    960
ccctccagag aagctgacat tggaggaagc acgggcgtac tgccaggagc ggggtgcaga   1020
gattgccacc acgggccaac tgtatgcagc ctgggatggt ggcctggacc actgcagccc   1080
agggtggcta gctgatggca gtgtgcgcta ccccatcgtc acacccagcc agcgctgtgg   1140
tgggggcttg cctggtgtca agactctctt cctcttcccc aaccagactg gcttccccaa   1200
taagcacagc cgcttcaacg tctactgctt ccgagactcg gcccagcctt ctgccatccc   1260
tgaggcctcc aacccagcct ccaacccagc ctctgatgga ctagaggcta tcgtcacagt   1320
gacagagacc ctggaggaac tgcagctgcc tcaggaagcc acagagagtg aatcccgtgg   1380
ggccatctac tccatcccca tcatggagga cggaggaggt ggaagctcca ctccagaaga   1440
cccagcagag gcccctagga cgctcctaga atttgaaaca caatccatgg taccgcccac   1500
ggggttctca gaagaggaag gtaaggcatt ggaggaagaa gagaaatatg aagatgaaga   1560
agagaaagag gaggaagaag aagaggagga ggtggaggat gaggctctgt gggcatggcc   1620
cagcgagctc agcagcccgg gccctgaggc ctctctcccc actgagccag cagcccagga   1680
gaagtcactc tcccaggcgc cagcaagggc agtcctgcag cctggtgcat caccacttcc   1740
tgatggagag tcagaagctt ccaggcctcc aagggtccat ggaccaccta ctgagactct   1800
gcccactccc agggagagga acctagcatc ccccatcacct tccactctgg ttgaggcaag   1860
agaggtgggg gaggcaactg gtggtcctga gctatctggg gtccctcgag gagagagcga   1920
ggagacagga agctccgagg gtgccccttc cctgcttcca gccacacggg cccctgaggg   1980
taccagggag ctggaggccc cctctgaaga taattctgga agaactgccc cagcagggac   2040
ctcagtgcag gcccagccag tgctgcccac tgacagcgcc agccgaggtg gagtggccgt   2100
ggtccccgca tcaggtaatt ctgcccaagg ctcaactgcc ctctctatcc tactcctttt   2160
cttcccccctg cagctctggg tcacctgacc tgtagtcctt taacccacca tcatcccaaa   2220
ctctcctgtc ctttgccttc attctcttac ccacctctac ctatgggtct ccaatctcgg   2280
atatccacct tgtgggtatc tcagctctcc gcgtctttac cctgtgatcc cagccccgcc   2340
actgaccatc tgtgaccctt ccctgccatt gggccctcca cctgtggctc acatctcgcc   2400
agccccacag agcatcctca ggcctctcca agggtcctca tcacctattg cagccttcag   2460
ggctcggcct attttccact actcccttca tccgcctgtg tgccgtcccc tttagctgcc   2520
tcctattgat ctcagggaag cctgggagtc ccttctcacc cctcaacctc cggagtccag   2580
gagaacccgt acccccacag agccttaagc aactacttct gtgaagtatt ttttgactgt   2640
ttcatggaaa acaagccttg gaaataaatc tctattaaac cgctttgtaa ccaaaaaaaa   2700
```

-continued aaaaaaaaaa aaaaaaaaaa gggcggccgc 2730

<210> SEQ ID NO 60
<211> LENGTH: 2013
<212> TYPE: DNA
<213> ORGANISM: Homo sapiens

<400> SEQUENCE: 60
atggcccagc tgttcctgcc cctgctggca gccctggtcc tggcccaggc tcctgcagct 60
ttagcagatg ttctggaagg agacagctca gaggaccgcg cttttcgcgt gcgcatcgcg 120
ggcgacgcgc cactgcaggg cgtgctcggc ggcgccctca ccatcccttg ccacgtccac 180
tacctgcggc caccgccgag ccgccgggct gtgctgggct ctccgcgggt caagtggact 240
ttcctgtccc ggggccggga ggcagaggtg ctggtggcgc ggggagtgcg cgtcaaggtg 300
aacgaggcct accggttccg cgtggcactg cctgcgtacc cagcgtcgct caccgacgtc 360
tccctggcgc tgagcgagct gcgccccaac gactcaggta tctatcgctg tgaggtccag 420
cacggcatcg atgacagcag cgacgctgtg gaggtcaagg tcaaaggggt cgtctttctc 480
taccgagagg gctctgcccg ctatgctttc tccttttctg ggcccagga ggcctgtgcc 540 cgcattggag cccacatcgc caccccggag cagctctatg ccgcctacct tgggggctat 600
gagcaatgtg atgctggctg gctgtcggat cagaccgtga ggtatcccat ccagacccca 660
cgagaggcct gttacggaga catggatggc ttccccgggg tccggaacta tggtgtggtg 720
gacccggatg acctctatga tgtgtactgt tatgctgaag acctaaatgg agaactgttc 780
ctgggtgacc ctccagagaa gctgacattg gaggaagcac gggcgtactg ccaggagcgg 840
ggtgcagaga ttgccaccac gggccaactg tatgcagcct gggatggtgg cctggaccac 900
tgcagcccag ggtggctagc tgatggcagt gtgcgctacc ccatcgtcac acccagccag 960
cgctgtggtg gggcttgcc tggtgtcaag actctcttcc tcttccccaa ccagactggc 1020
ttccccaata agcacagccg cttcaacgtc tactgcttcc gagactcggc ccagccttct 1080
gccatccctg aggcctccaa cccagcctcc aacccagcct ctgatggact agaggctatc 1140
gtcacagtga cagagaccct ggaggaactg cagctgcctc aggaagccac agagagtgaa 1200
tcccgtgggg ccatctactc catccccatc atggaggacg gaggaggtgg aagctccact 1260
ccagaagacc cagcagaggc ccctaggacg ctcctagaat ttgaaacaca atccatggta 1320
ccgcccacgg ggttctcaga agaggaaggt aaggcattgg aggaagaaga gaaatatgaa 1380
gatgaagaag agaaagagga ggaagaagaa gaggaggagg tggaggatga ggctctgtgg 1440
gcatggccca gcgagctcag cagcccgggc cctgaggcct ctctccccac tgagccagca 1500
gcccaggaga agtcactctc ccaggcgcca gcaagggcag tcctgcagcc tggtgcatca 1560
ccacttcctg atggagagtc agaagcttcc aggcctccaa gggtccatgg accacctact 1620
gagactctgc ccactcccag ggagaggaac ctagcatccc catcaccttc cactctggtt 1680
gaggcaagag aggtggggga ggcaactggt ggtcctgagc tatctggggt ccctcgagga 1740
gagagcgagg agacaggaag ctccgagggt gccccttccc tgcttccagc cacacgggcc 1800
cctgagggta ccagggagct ggaggccccc tctgaagata attctggaag aactgcccca 1860
gcagggacct cagtgcaggc ccagccagtg ctgcccactg acagcgccag ccgaggtgga 1920
gtggccgtgg tccccgcatc aggtaattct gcccaaggct caactgccct ctctatccta 1980
ctccttttct tcccctgca gctctgggtc acc 2013

-continued

<210> SEQ ID NO 61
<211> LENGTH: 671
<212> TYPE: PRT
<213> ORGANISM: Homo sapiens

<400> SEQUENCE: 61

```
Met Ala Gln Leu Phe Leu Pro Leu Leu Ala Ala Leu Val Leu Ala Gln
1               5                   10                  15

Ala Pro Ala Ala Leu Ala Asp Val Leu Glu Gly Asp Ser Ser Glu Asp
            20                  25                  30

Arg Ala Phe Arg Val Arg Ile Ala Gly Asp Ala Pro Leu Gln Gly Val
        35                  40                  45

Leu Gly Gly Ala Leu Thr Ile Pro Cys His Val His Tyr Leu Arg Pro
    50                  55                  60

Pro Pro Ser Arg Arg Ala Val Leu Gly Ser Pro Arg Val Lys Trp Thr
65                  70                  75                  80

Phe Leu Ser Arg Gly Arg Glu Ala Glu Val Leu Val Ala Arg Gly Val
                85                  90                  95

Arg Val Lys Val Asn Glu Ala Tyr Arg Phe Arg Val Ala Leu Pro Ala
            100                 105                 110

Tyr Pro Ala Ser Leu Thr Asp Val Ser Leu Ala Leu Ser Glu Leu Arg
        115                 120                 125

Pro Asn Asp Ser Gly Ile Tyr Arg Cys Glu Val Gln His Gly Ile Asp
    130                 135                 140

Asp Ser Ser Asp Ala Val Glu Val Lys Val Lys Gly Val Val Phe Leu
145                 150                 155                 160

Tyr Arg Glu Gly Ser Ala Arg Tyr Ala Phe Ser Phe Ser Gly Ala Gln
                165                 170                 175

Glu Ala Cys Ala Arg Ile Gly Ala His Ile Ala Thr Pro Glu Gln Leu
            180                 185                 190

Tyr Ala Ala Tyr Leu Gly Gly Tyr Glu Gln Cys Asp Ala Gly Trp Leu
        195                 200                 205

Ser Asp Gln Thr Val Arg Tyr Pro Ile Gln Thr Pro Arg Glu Ala Cys
    210                 215                 220

Tyr Gly Asp Met Asp Gly Phe Pro Gly Val Arg Asn Tyr Gly Val Val
225                 230                 235                 240

Asp Pro Asp Asp Leu Tyr Asp Val Tyr Cys Tyr Ala Glu Asp Leu Asn
                245                 250                 255

Gly Glu Leu Phe Leu Gly Asp Pro Pro Glu Lys Leu Thr Leu Glu Glu
            260                 265                 270

Ala Arg Ala Tyr Cys Gln Glu Arg Gly Ala Glu Ile Ala Thr Thr Gly
        275                 280                 285

Gln Leu Tyr Ala Ala Trp Asp Gly Gly Leu Asp His Cys Ser Pro Gly
    290                 295                 300

Trp Leu Ala Asp Gly Ser Val Arg Tyr Pro Ile Val Thr Pro Ser Gln
305                 310                 315                 320

Arg Cys Gly Gly Gly Leu Pro Gly Val Lys Thr Leu Phe Leu Phe Pro
                325                 330                 335

Asn Gln Thr Gly Phe Pro Asn Lys His Ser Arg Phe Asn Val Tyr Cys
            340                 345                 350

Phe Arg Asp Ser Ala Gln Pro Ser Ala Ile Pro Glu Ala Ser Asn Pro
        355                 360                 365

Ala Ser Asn Pro Ala Ser Asp Gly Leu Glu Ala Ile Val Thr Val Thr
    370                 375                 380
```

-continued

```
Glu Thr Leu Glu Glu Leu Gln Leu Pro Gln Glu Ala Thr Glu Ser Glu
385                 390                 395                 400

Ser Arg Gly Ala Ile Tyr Ser Ile Pro Ile Met Glu Asp Gly Gly Gly
                405                 410                 415

Gly Ser Ser Thr Pro Glu Asp Pro Ala Glu Ala Pro Arg Thr Leu Leu
            420                 425                 430

Glu Phe Glu Thr Gln Ser Met Val Pro Pro Thr Gly Phe Ser Glu Glu
        435                 440                 445

Glu Gly Lys Ala Leu Glu Glu Glu Glu Lys Tyr Glu Asp Glu Glu Glu
    450                 455                 460

Lys Glu Glu Glu Glu Glu Glu Glu Glu Val Glu Asp Glu Ala Leu Trp
465                 470                 475                 480

Ala Trp Pro Ser Glu Leu Ser Ser Pro Gly Pro Glu Ala Ser Leu Pro
                485                 490                 495

Thr Glu Pro Ala Ala Gln Glu Lys Ser Leu Ser Gln Ala Pro Ala Arg
            500                 505                 510

Ala Val Leu Gln Pro Gly Ala Ser Pro Leu Pro Asp Gly Glu Ser Glu
        515                 520                 525

Ala Ser Arg Pro Pro Arg Val His Gly Pro Pro Thr Glu Thr Leu Pro
    530                 535                 540

Thr Pro Arg Glu Arg Asn Leu Ala Ser Pro Ser Pro Ser Thr Leu Val
545                 550                 555                 560

Glu Ala Arg Glu Val Gly Glu Ala Thr Gly Gly Pro Glu Leu Ser Gly
                565                 570                 575

Val Pro Arg Gly Glu Ser Glu Glu Thr Gly Ser Ser Glu Gly Ala Pro
            580                 585                 590

Ser Leu Leu Pro Ala Thr Arg Ala Pro Glu Gly Thr Arg Glu Leu Glu
        595                 600                 605

Ala Pro Ser Glu Asp Asn Ser Gly Arg Thr Ala Pro Ala Gly Thr Ser
    610                 615                 620

Val Gln Ala Gln Pro Val Leu Pro Thr Asp Ser Ala Ser Arg Gly Gly
625                 630                 635                 640

Val Ala Val Val Pro Ala Ser Gly Asn Ser Ala Gln Gly Ser Thr Ala
                645                 650                 655

Leu Ser Ile Leu Leu Leu Phe Phe Pro Leu Gln Leu Trp Val Thr
            660                 665                 670


<210> SEQ ID NO 62
<211> LENGTH: 22
<212> TYPE: PRT
<213> ORGANISM: Homo sapiens

<400> SEQUENCE: 62

Met Ala Gln Leu Phe Leu Pro Leu Leu Ala Ala Leu Val Leu Ala Gln
1               5                   10                  15

Ala Pro Ala Ala Leu Ala
            20


<210> SEQ ID NO 63
<211> LENGTH: 649
<212> TYPE: PRT
<213> ORGANISM: Homo sapiens

<400> SEQUENCE: 63

Asp Val Leu Glu Gly Asp Ser Ser Glu Asp Arg Ala Phe Arg Val Arg
1               5                   10                  15
```

-continued

```
Ile Ala Gly Asp Ala Pro Leu Gln Gly Val Leu Gly Gly Ala Leu Thr
            20                  25                  30

Ile Pro Cys His Val His Tyr Leu Arg Pro Pro Pro Ser Arg Arg Ala
        35                  40                  45

Val Leu Gly Ser Pro Arg Val Lys Trp Thr Phe Leu Ser Arg Gly Arg
    50                  55                  60

Glu Ala Glu Val Leu Val Ala Arg Gly Val Arg Val Lys Val Asn Glu
65                  70                  75                  80

Ala Tyr Arg Phe Arg Val Ala Leu Pro Ala Tyr Pro Ala Ser Leu Thr
                85                  90                  95

Asp Val Ser Leu Ala Leu Ser Glu Leu Arg Pro Asn Asp Ser Gly Ile
            100                 105                 110

Tyr Arg Cys Glu Val Gln His Gly Ile Asp Asp Ser Ser Asp Ala Val
        115                 120                 125

Glu Val Lys Val Lys Gly Val Val Phe Leu Tyr Arg Glu Gly Ser Ala
    130                 135                 140

Arg Tyr Ala Phe Ser Phe Ser Gly Ala Gln Glu Ala Cys Ala Arg Ile
145                 150                 155                 160

Gly Ala His Ile Ala Thr Pro Glu Gln Leu Tyr Ala Ala Tyr Leu Gly
                165                 170                 175

Gly Tyr Glu Gln Cys Asp Ala Gly Trp Leu Ser Asp Gln Thr Val Arg
            180                 185                 190

Tyr Pro Ile Gln Thr Pro Arg Glu Ala Cys Tyr Gly Asp Met Asp Gly
        195                 200                 205

Phe Pro Gly Val Arg Asn Tyr Gly Val Val Asp Pro Asp Asp Leu Tyr
    210                 215                 220

Asp Val Tyr Cys Tyr Ala Glu Asp Leu Asn Gly Glu Leu Phe Leu Gly
225                 230                 235                 240

Asp Pro Pro Glu Lys Leu Thr Leu Glu Glu Ala Arg Ala Tyr Cys Gln
                245                 250                 255

Glu Arg Gly Ala Glu Ile Ala Thr Thr Gly Gln Leu Tyr Ala Ala Trp
            260                 265                 270

Asp Gly Gly Leu Asp His Cys Ser Pro Gly Trp Leu Ala Asp Gly Ser
        275                 280                 285

Val Arg Tyr Pro Ile Val Thr Pro Ser Gln Arg Cys Gly Gly Gly Leu
    290                 295                 300

Pro Gly Val Lys Thr Leu Phe Leu Phe Pro Asn Gln Thr Gly Phe Pro
305                 310                 315                 320

Asn Lys His Ser Arg Phe Asn Val Tyr Cys Phe Arg Asp Ser Ala Gln
                325                 330                 335

Pro Ser Ala Ile Pro Glu Ala Ser Asn Pro Ala Ser Asn Pro Ala Ser
            340                 345                 350

Asp Gly Leu Glu Ala Ile Val Thr Val Thr Glu Thr Leu Glu Glu Leu
        355                 360                 365

Gln Leu Pro Gln Glu Ala Thr Glu Ser Glu Ser Arg Gly Ala Ile Tyr
    370                 375                 380

Ser Ile Pro Ile Met Glu Asp Gly Gly Gly Gly Ser Ser Thr Pro Glu
385                 390                 395                 400

Asp Pro Ala Glu Ala Pro Arg Thr Leu Leu Glu Phe Glu Thr Gln Ser
                405                 410                 415

Met Val Pro Pro Thr Gly Phe Ser Glu Glu Glu Gly Lys Ala Leu Glu
            420                 425                 430
```

-continued

```
Glu Glu Glu Lys Tyr Glu Asp Glu Glu Glu Lys Glu Glu Glu Glu Glu
        435                 440                 445

Glu Glu Glu Val Glu Asp Glu Ala Leu Trp Ala Trp Pro Ser Glu Leu
    450                 455                 460

Ser Ser Pro Gly Pro Glu Ala Ser Leu Pro Thr Glu Pro Ala Ala Gln
465                 470                 475                 480

Glu Lys Ser Leu Ser Gln Ala Pro Ala Arg Ala Val Leu Gln Pro Gly
                485                 490                 495

Ala Ser Pro Leu Pro Asp Gly Glu Ser Glu Ala Ser Arg Pro Pro Arg
            500                 505                 510

Val His Gly Pro Pro Thr Glu Thr Leu Pro Thr Pro Arg Glu Arg Asn
        515                 520                 525

Leu Ala Ser Pro Ser Pro Ser Thr Leu Val Glu Ala Arg Glu Val Gly
    530                 535                 540

Glu Ala Thr Gly Gly Pro Glu Leu Ser Gly Val Pro Arg Gly Glu Ser
545                 550                 555                 560

Glu Glu Thr Gly Ser Ser Glu Gly Ala Pro Ser Leu Leu Pro Ala Thr
                565                 570                 575

Arg Ala Pro Glu Gly Thr Arg Glu Leu Glu Ala Pro Ser Glu Asp Asn
            580                 585                 590

Ser Gly Arg Thr Ala Pro Ala Gly Thr Ser Val Gln Ala Gln Pro Val
        595                 600                 605

Leu Pro Thr Asp Ser Ala Ser Arg Gly Gly Val Ala Val Val Pro Ala
    610                 615                 620

Ser Gly Asn Ser Ala Gln Gly Ser Thr Ala Leu Ser Ile Leu Leu Leu
625                 630                 635                 640

Phe Phe Pro Leu Gln Leu Trp Val Thr
                645


<210> SEQ ID NO 64
<211> LENGTH: 456
<212> TYPE: PRT
<213> ORGANISM: Sus scrofa

<400> SEQUENCE: 64

Met Asn Leu Asp Ile His Cys Glu Gln Leu Ser Asp Ala Arg Trp Thr
1               5                   10                  15

Glu Leu Leu Pro Leu Leu Gln Gln Tyr Glu Val Val Arg Leu Asp Asp
            20                  25                  30

Cys Gly Leu Thr Glu Glu His Cys Lys Asp Ile Gly Ser Ala Leu Arg
        35                  40                  45

Ala Asn Pro Ser Leu Thr Glu Leu Cys Leu Arg Thr Asn Glu Leu Gly
    50                  55                  60

Asp Ala Gly Val His Leu Val Leu Gln Gly Leu Gln Ser Pro Thr Cys
65                  70                  75                  80

Lys Ile Gln Lys Leu Ser Leu Gln Asn Cys Ser Leu Thr Glu Ala Gly
                85                  90                  95

Cys Gly Val Leu Pro Ser Thr Leu Arg Ser Leu Pro Thr Leu Arg Glu
            100                 105                 110

Leu His Leu Ser Asp Asn Pro Leu Gly Asp Ala Gly Leu Arg Leu Leu
        115                 120                 125

Cys Glu Gly Leu Leu Asp Pro Gln Cys His Leu Glu Lys Leu Gln Leu
    130                 135                 140

Glu Tyr Cys Arg Leu Thr Ala Ala Ser Cys Glu Pro Leu Ala Ser Val
145                 150                 155                 160
```

-continued

Leu Arg Ala Thr Arg Ala Leu Lys Glu Leu Thr Val Ser Asn Asn Asp
165 170 175

Ile Gly Glu Ala Gly Ala Arg Val Leu Gly Gln Gly Leu Ala Asp Ser
180 185 190

Ala Cys Gln Leu Glu Thr Leu Arg Leu Glu Asn Cys Gly Leu Thr Pro
195 200 205

Ala Asn Cys Lys Asp Leu Cys Gly Ile Val Ala Ser Gln Ala Ser Leu
210 215 220

Arg Glu Leu Asp Leu Gly Ser Asn Gly Leu Gly Asp Ala Gly Ile Ala
225 230 235 240

Glu Leu Cys Pro Gly Leu Leu Ser Pro Ala Ser Arg Leu Lys Thr Leu
245 250 255

Trp Leu Trp Glu Cys Asp Ile Thr Ala Ser Gly Cys Arg Asp Leu Cys
260 265 270

Arg Val Leu Gln Ala Lys Glu Thr Leu Lys Glu Leu Ser Leu Ala Gly
275 280 285

Asn Lys Leu Gly Asp Glu Gly Ala Arg Leu Leu Cys Glu Ser Leu Leu
290 295 300

Gln Pro Gly Cys Gln Leu Glu Ser Leu Trp Val Lys Ser Cys Ser Leu
305 310 315 320

Thr Ala Ala Cys Cys Gln His Val Ser Leu Met Leu Thr Gln Asn Lys
325 330 335

His Leu Leu Glu Leu Gln Leu Ser Ser Asn Lys Leu Gly Asp Ser Gly
340 345 350

Ile Gln Glu Leu Cys Gln Ala Leu Ser Gln Pro Gly Thr Thr Leu Arg
355 360 365

Val Leu Cys Leu Gly Asp Cys Glu Val Thr Asn Ser Gly Cys Ser Ser
370 375 380

Leu Ala Ser Leu Leu Leu Ala Asn Arg Ser Leu Arg Glu Leu Asp Leu
385 390 395 400

Ser Asn Asn Cys Val Gly Asp Pro Gly Val Leu Gln Leu Leu Gly Ser
405 410 415

Leu Glu Gln Pro Gly Cys Ala Leu Glu Gln Leu Val Leu Tyr Asp Thr
420 425 430

Tyr Trp Thr Glu Glu Val Glu Asp Arg Leu Gln Ala Leu Glu Gly Ser
435 440 445

Lys Pro Gly Leu Arg Val Ile Ser
450 455

<210> SEQ ID NO 65
<211> LENGTH: 834
<212> TYPE: PRT
<213> ORGANISM: Mus sp.

<400> SEQUENCE: 65

Met Ala Pro His Trp Ala Val Trp Leu Leu Ala Ala Gly Leu Trp Gly
1 5 10 15

Leu Gly Ile Gly Ala Glu Met Trp Trp Asn Leu Val Pro Arg Lys Thr
20 25 30

Val Ser Ser Gly Glu Leu Val Thr Val Val Arg Arg Phe Ser Gln Thr
35 40 45

Gly Ile Gln Asp Phe Leu Thr Leu Thr Leu Thr Glu His Ser Gly Leu
50 55 60

Leu Tyr Val Gly Ala Arg Glu Ala Leu Phe Ala Phe Ser Val Glu Ala

-continued

```
65                  70                  75                  80

Leu Glu Leu Gln Gly Ala Ile Ser Trp Glu Ala Pro Ala Glu Lys Lys
                85                  90                  95

Ile Glu Cys Thr Gln Lys Gly Lys Ser Asn Gln Thr Glu Cys Phe Asn
            100                 105                 110

Phe Ile Arg Phe Leu Gln Pro Tyr Asn Ser Ser His Leu Tyr Val Cys
        115                 120                 125

Gly Thr Tyr Ala Phe Gln Pro Lys Cys Thr Tyr Ile Asn Met Leu Thr
    130                 135                 140

Phe Thr Leu Asp Arg Ala Glu Phe Glu Asp Gly Lys Gly Lys Cys Pro
145                 150                 155                 160

Tyr Asp Pro Ala Lys Gly His Thr Gly Leu Leu Val Asp Gly Glu Leu
                165                 170                 175

Tyr Ser Ala Thr Leu Asn Asn Phe Leu Gly Thr Glu Pro Val Ile Leu
            180                 185                 190

Arg Tyr Met Gly Thr His His Ser Ile Lys Thr Glu Tyr Leu Ala Phe
        195                 200                 205

Trp Leu Asn Glu Pro His Phe Val Gly Ser Ala Phe Val Pro Glu Ser
    210                 215                 220

Val Gly Ser Phe Thr Gly Asp Asp Asp Lys Ile Tyr Phe Phe Phe Ser
225                 230                 235                 240

Glu Arg Ala Val Glu Tyr Asp Cys Tyr Ser Glu Gln Val Val Ala Arg
                245                 250                 255

Val Ala Arg Val Cys Lys Gly Asp Met Gly Gly Ala Arg Thr Leu Gln
            260                 265                 270

Lys Lys Trp Thr Thr Phe Leu Lys Ala Arg Leu Val Cys Ser Ala Pro
        275                 280                 285

Asp Trp Lys Val Tyr Phe Asn Gln Leu Lys Ala Val His Thr Leu Arg
    290                 295                 300

Gly Ala Ser Trp His Asn Thr Thr Phe Phe Gly Val Phe Gln Ala Arg
305                 310                 315                 320

Trp Gly Asp Met Asp Leu Ser Ala Val Cys Glu Tyr Gln Leu Glu Gln
                325                 330                 335

Ile Gln Gln Val Phe Glu Gly Pro Tyr Lys Glu Tyr Ser Glu Gln Ala
            340                 345                 350

Gln Lys Trp Ala Arg Tyr Thr Asp Pro Val Pro Ser Pro Arg Pro Gly
        355                 360                 365

Ser Cys Ile Asn Asn Trp His Arg Asp Asn Gly Tyr Thr Ser Ser Leu
    370                 375                 380

Glu Leu Pro Asp Asn Thr Leu Asn Phe Ile Lys Lys His Pro Leu Met
385                 390                 395                 400

Glu Asp Gln Val Lys Pro Arg Leu Gly Arg Pro Leu Leu Val Lys Lys
                405                 410                 415

Asn Thr Asn Phe Thr His Val Val Ala Asp Arg Val Pro Gly Leu Asp
            420                 425                 430

Gly Ala Thr Tyr Thr Val Leu Phe Ile Gly Thr Gly Asp Gly Trp Leu
        435                 440                 445

Leu Lys Ala Val Ser Leu Gly Pro Trp Ile His Met Val Glu Glu Leu
    450                 455                 460

Gln Val Phe Asp Gln Glu Pro Val Glu Ser Leu Val Leu Ser Gln Ser
465                 470                 475                 480

Lys Lys Val Leu Phe Ala Gly Ser Arg Ser Gln Leu Val Gln Leu Ser
                485                 490                 495
```

-continued

```
Leu Ala Asp Cys Thr Lys Tyr Arg Phe Cys Val Asp Cys Val Leu Ala
            500                 505                 510

Arg Asp Pro Tyr Cys Ala Trp Asn Val Asn Thr Ser Arg Cys Val Ala
        515                 520                 525

Thr Thr Ser Gly Arg Ser Gly Ser Phe Leu Val Gln His Val Ala Asn
    530                 535                 540

Leu Asp Thr Ser Lys Met Cys Asn Gln Tyr Gly Ile Lys Lys Val Arg
545                 550                 555                 560

Ser Ile Pro Lys Asn Ile Thr Val Val Ser Gly Thr Asp Leu Val Leu
                565                 570                 575

Pro Cys His Leu Ser Ser Asn Leu Ala His Ala His Trp Thr Phe Gly
            580                 585                 590

Ser Gln Asp Leu Pro Ala Glu Gln Pro Gly Ser Phe Leu Tyr Asp Thr
        595                 600                 605

Gly Leu Gln Ala Leu Val Val Met Ala Ala Gln Ser Arg His Ser Gly
    610                 615                 620

Pro Tyr Arg Cys Tyr Ser Glu Glu Gln Gly Thr Arg Leu Ala Ala Glu
625                 630                 635                 640

Ser Tyr Leu Val Ala Val Val Ala Gly Ser Ser Val Thr Leu Glu Ala
                645                 650                 655

Arg Ala Pro Leu Glu Asn Leu Gly Leu Val Trp Leu Ala Val Val Ala
            660                 665                 670

Leu Gly Ala Val Cys Leu Val Leu Leu Leu Leu Val Leu Ser Leu Arg
        675                 680                 685

Arg Arg Leu Arg Glu Glu Leu Glu Lys Gly Ala Lys Ala Ser Glu Arg
    690                 695                 700

Thr Leu Val Tyr Pro Leu Glu Leu Pro Lys Glu Pro Ala Ser Pro Pro
705                 710                 715                 720

Phe Arg Pro Gly Pro Glu Thr Asp Glu Lys Leu Trp Asp Pro Val Gly
                725                 730                 735

Tyr Tyr Tyr Ser Asp Gly Ser Leu Lys Ile Val Pro Gly His Ala Arg
            740                 745                 750

Cys Gln Pro Gly Gly Gly Pro Pro Ser Pro Pro Pro Gly Ile Pro Gly
        755                 760                 765

Gln Pro Leu Pro Ser Pro Thr Arg Leu His Leu Gly Gly Gly Arg Asn
    770                 775                 780

Ser Asn Ala Asn Gly Tyr Val Arg Leu Gln Leu Gly Gly Glu Asp Arg
785                 790                 795                 800

Gly Gly Ser Gly His Pro Leu Pro Glu Leu Ala Asp Glu Leu Arg Arg
                805                 810                 815

Lys Leu Gln Gln Arg Gln Pro Leu Pro Asp Ser Asn Pro Glu Glu Ser
            820                 825                 830

Ser Val
```

<210> SEQ ID NO 66
<211> LENGTH: 3503
<212> TYPE: DNA
<213> ORGANISM: Mus sp.

<400> SEQUENCE: 66

```
ggcacgaggt ggccggagtc aaacgcgagg gcagcgccag ggattggagc tgcacgaaag     60

agggctgctg gactgaagtt tagaccctgg gtgtctgcca tggccccaca ctgggctgtc    120

tggctgctgg cagcagggct gtggggcctg ggcatcgggg ctgagatgtg gtggaacctt    180
```

-continued

```
gtgccccgga agacagtatc ttctggggag ctggtcacag tagtgaggcg gttctcccag    240
acaggcatcc aggacttcct gacactgacc ctgacagaac attctggcct tttatatgtg    300
ggggcccgag aggcgctgtt tgccttcagt gtagaggctc tggagctgca aggagcgatc    360
tcttgggagg ctccagctga gaagaaaatt gaatgtaccc agaaagggaa gagcaaccag    420
accgaatgct tcaacttcat ccgcttcctt cagccataca attcctccca tctgtatgtc    480
tgcggcacct atgccttcca gcccaagtgc acctacatca acatgctcac gttcaccttg    540
gaccgtgcag aatttgagga tgggaagggt aaatgcccat atgacccagc taagggtcac    600
accggactcc ttgtggacgg tgagctgtac tcagccacac tcaataactt cctgggcaca    660
gagccggtta tccttcgata catggggacc caccactcca tcaagacaga gtacctggct    720
ttttggctga atgaacccca ctttgtaggc tctgcctttg tccctgagag tgtgggaagc    780
ttcacgggag acgatgacaa gatctacttc ttcttcagtg agcgggcagt ggagtatgac    840
tgctattccg agcaggtggt ggctcgtgtg gcgagagtct gtaagggtga catgggggga    900
gcacggacgc tgcagaagaa atggacgacg ttcctgaagg ctcggttggt gtgctcagcc    960
cctgactgga aggtctactt caaccagctg aaggcggtgc acaccctgcg gggcgcctct   1020
tggcacaaca ccaccttctt cggggttttt caagcgcgat ggggcgatat ggacctgtct   1080
gcagtttgtg agtaccagtt ggaacagatc cagcaagtgt ttgagggtcc ctacaaggag   1140
tacagtgagc aagcccagaa gtgggcccgc tatactgacc cggtacccag ccctcggcct   1200
ggttcgtgta tcaacaactg gcaccgagac aatggctaca ccagttccct ggaactgccg   1260
gacaacaccc tcaacttcat caagaagcac cccctgatgg aggaccaggt gaagcctcgg   1320
ttgggccgcc ccctacttgt gaagaagaac actaacttca cacacgtggt ggccgacagg   1380
gtcccagggc ttgatggtgc cacctataca gtgttgttca ttggtacagg agatggctgg   1440
ctgctgaagg ctgtgagcct ggggccctgg atccacatgg tggaggaact gcaggtgttt   1500
gaccaggagc cagtggaaag tctggtgctg tctcagagca agaaggtgct ctttgctggc   1560
tcccgctctc agctggttca gctgtctctg gccgactgca caaagtaccg tttctgtgta   1620
gactgtgtcc tggccaggga cccttactgt gcctggaatg tcaacaccag ccgctgtgtg   1680
gccaccacca gtggtcgctc ggggtccttt ctggtccaac atgtggcgaa cttggacact   1740
tcaaagatgt gtaaccagta tggcattaaa aaagtcagat ctattcccaa gaacatcacc   1800
gttgtgtcag gcacagacct ggtcctaccc tgccacctct cgtccaattt ggcccatgcc   1860
cactggacct tcggaagcca ggacctgcct gcagaacaac ctggctcctt tctttatgac   1920
acgggactcc aggcgctggt ggtgatggcc gcacagtccc gtcactctgg accctatcgt   1980
tgctattcag aggagcaggg gacaagactg gctgcagaaa gctaccttgt tgctgtcgtg   2040
gccggctcgt cggtgacact ggaggcacgg gctcccttgg aaaacctggg gctcgtgtgg   2100
ctcgctgtgg tggccctggg ggctgtgtgc ctggtgctgc tgctgctggt cctatcgctc   2160
cgccggcgac ttcgagaaga gctagaaaag ggtgccaagg catctgagag gacactggtg   2220
taccccttgg aactgcccaa ggagcctgcc agtccccccct tccgtcctgg ccccgaaact   2280
gatgagaaac tttgggatcc tgtcgggtac tactattcgg atggctctct caagattgtg   2340
cctggtcacg cccggtgcca gcctggggggt gggccccctt ccccacctcc tggcatacct   2400
ggccagcctc tgccttctcc aactcggctc cacctaggag gtggtcggaa ctcaaatgcc   2460
aatggttatg tgcgtttaca gttgggcgga gaggaccgag gaggatctgg gcacccactg   2520
```

-continued

```
cctgagctcg cggatgaatt acgacggaaa ctacaacagc gccagccgct gcctgactcc   2580

aacccagagg agtcttcagt atgaggggac cccccacct cattggcggg gggggtctc     2640

atgggaggtg cactcttaac ttttgcacag gcaccagcta cctcagggac atggcagggg   2700

cacttgctct gcctgggaca gacactgccc atcatttgcc cggccgtgag gacctgctca   2760

gcatgggcac tgccacttgg tgtggctcac caggacttca gcctcacagg agacacaccc   2820

tcctctgtga atttgagaca tgtgggaccc cagcagccaa aactttgcaa ggaagaggtt   2880

tcaagatgtg ggcgtgtttg tgcatatatg tgttggtatg catgtggaag aatgtgtgtg   2940

tgtgtgtgtg tgtgttgtaa ctttcctgtc tctatcacgt cttcccttgg cctggggtcc   3000

tcctggttga gtctttggag ctatgaaggg gaagggggtc atagcacttt gcttctccta   3060

cccccagctg tcccaagctt tggggcagtg atgtacatac ggggaaggga aggacagggt   3120

gttgtacccc ttttggggga gtgcgggact cgggggtggg cctagccctg ctcctagggc   3180

tgtgaatgtt ttcagggcgg gggttggggg tggagatgga acctcctgct tcagggggag   3240

gggtgggcag ggcctcccac ttgccctccg ggttcggtgg tattttatat ttgcgctctt   3300

ctgacagggc tgggaagggt tgttggggga gggaagggag gaggtgggca tgctatggat   3360

actggcctat cctctccctg ctctgggaaa agggctaaca gtgtaactta ttgtgtcccc   3420

acatatttat ttgttgtaaa tatttgagta tttttatatt gacaaataaa atggagaaaa   3480

tgaaatttaa aaaaaaaaaa aaa                                           3503
```

<210> SEQ ID NO 67
<211> LENGTH: 1529
<212> TYPE: PRT
<213> ORGANISM: Homo sapiens

<400> SEQUENCE: 67

```
Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
```

-continued

```
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Thr Ile Lys Val Ile Pro Pro Gly Ala Phe
305                 310                 315                 320

Ser Pro Tyr Lys Lys Leu Arg Arg Ile Asp Leu Ser Asn Asn Gln Ile
                325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
        355                 360                 365

Glu Gly Leu Phe Ser Leu Gln Leu Leu Leu Leu Asn Ala Asn Lys Ile
    370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Ile Ala Lys Gly Thr Phe
                405                 410                 415

Ser Pro Leu Arg Ala Ile Gln Thr Met His Leu Ala Gln Asn Pro Phe
            420                 425                 430

Ile Cys Asp Cys His Leu Lys Trp Leu Ala Asp Tyr Leu His Thr Asn
        435                 440                 445

Pro Ile Glu Thr Ser Gly Ala Arg Cys Thr Ser Pro Arg Arg Leu Ala
    450                 455                 460

Asn Lys Arg Ile Gly Gln Ile Lys Ser Lys Lys Phe Arg Cys Ser Ala
465                 470                 475                 480

Lys Glu Gln Tyr Phe Ile Pro Gly Thr Glu Asp Tyr Arg Ser Lys Leu
                485                 490                 495

Ser Gly Asp Cys Phe Ala Asp Leu Ala Cys Pro Glu Lys Cys Arg Cys
            500                 505                 510

Glu Gly Thr Thr Val Asp Cys Ser Asn Gln Lys Leu Asn Lys Ile Pro
        515                 520                 525

Glu His Ile Pro Gln Tyr Thr Ala Glu Leu Arg Leu Asn Asn Asn Glu
    530                 535                 540

Phe Thr Val Leu Glu Ala Thr Gly Ile Phe Lys Lys Leu Pro Gln Leu
545                 550                 555                 560

Arg Lys Ile Asn Phe Ser Asn Asn Lys Ile Thr Asp Ile Glu Glu Gly
                565                 570                 575

Ala Phe Glu Gly Ala Ser Gly Val Asn Glu Ile Leu Leu Thr Ser Asn
            580                 585                 590

Arg Leu Glu Asn Val Gln His Lys Met Phe Lys Gly Leu Glu Ser Leu
        595                 600                 605

Lys Thr Leu Met Leu Arg Ser Asn Arg Ile Thr Cys Val Gly Asn Asp
    610                 615                 620
```

-continued

Ser Phe Ile Gly Leu Ser Ser Val Arg Leu Leu Ser Leu Tyr Asp Asn
625 630 635 640

Gln Ile Thr Thr Val Ala Pro Gly Ala Phe Asp Thr Leu His Ser Leu
645 650 655

Ser Thr Leu Asn Leu Leu Ala Asn Pro Phe Asn Cys Asn Cys Tyr Leu
660 665 670

Ala Trp Leu Gly Glu Trp Leu Arg Lys Lys Arg Ile Val Thr Gly Asn
675 680 685

Pro Arg Cys Gln Lys Pro Tyr Phe Leu Lys Glu Ile Pro Ile Gln Asp
690 695 700

Val Ala Ile Gln Asp Phe Thr Cys Asp Asp Gly Asn Asp Asp Asn Ser
705 710 715 720

Cys Ser Pro Leu Ser Arg Cys Pro Thr Glu Cys Thr Cys Leu Asp Thr
725 730 735

Val Val Arg Cys Ser Asn Lys Gly Leu Lys Val Leu Pro Lys Gly Ile
740 745 750

Pro Arg Asp Val Thr Glu Leu Tyr Leu Asp Gly Asn Gln Phe Thr Leu
755 760 765

Val Pro Lys Glu Leu Ser Asn Tyr Lys His Leu Thr Leu Ile Asp Leu
770 775 780

Ser Asn Asn Arg Ile Ser Thr Leu Ser Asn Gln Ser Phe Ser Asn Met
785 790 795 800

Thr Gln Leu Leu Thr Leu Ile Leu Ser Tyr Asn Arg Leu Arg Cys Ile
805 810 815

Pro Pro Arg Thr Phe Asp Gly Leu Lys Ser Leu Arg Leu Leu Ser Leu
820 825 830

His Gly Asn Asp Ile Ser Val Val Pro Glu Gly Ala Phe Asn Asp Leu
835 840 845

Ser Ala Leu Ser His Leu Ala Ile Gly Ala Asn Pro Leu Tyr Cys Asp
850 855 860

Cys Asn Met Gln Trp Leu Ser Asp Trp Val Lys Ser Glu Tyr Lys Glu
865 870 875 880

Pro Gly Ile Ala Arg Cys Ala Gly Pro Gly Glu Met Ala Asp Lys Leu
885 890 895

Leu Leu Thr Thr Pro Ser Lys Lys Phe Thr Cys Gln Gly Pro Val Asp
900 905 910

Val Asn Ile Leu Ala Lys Cys Asn Pro Cys Leu Ser Asn Pro Cys Lys
915 920 925

Asn Asp Gly Thr Cys Asn Ser Asp Pro Val Asp Phe Tyr Arg Cys Thr
930 935 940

Cys Pro Tyr Gly Phe Lys Gly Gln Asp Cys Asp Val Pro Ile His Ala
945 950 955 960

Cys Ile Ser Asn Pro Cys Lys His Gly Gly Thr Cys His Leu Lys Glu
965 970 975

Gly Glu Glu Asp Gly Phe Trp Cys Ile Cys Ala Asp Gly Phe Glu Gly
980 985 990

Glu Asn Cys Glu Val Asn Val Asp Asp Cys Glu Asp Asn Asp Cys Glu
995 1000 1005

Asn Asn Ser Thr Cys Val Asp Gly Ile Asn Asn Tyr Thr Cys Leu
1010 1015 1020

Cys Pro Pro Glu Tyr Thr Gly Glu Leu Cys Glu Glu Lys Leu Asp
1025 1030 1035

-continued

```
Phe Cys  Ala Gln Asp Leu Asn  Pro Cys Gln His Asp  Ser Lys Cys
    1040                 1045                 1050

Ile Leu  Thr Pro Lys Gly Phe  Lys Cys Asp Cys Thr  Pro Gly Tyr
    1055                 1060                 1065

Val Gly  Glu His Cys Asp Ile  Asp Phe Asp Asp Cys  Gln Asp Asn
    1070                 1075                 1080

Lys Cys  Lys Asn Gly Ala His  Cys Thr Asp Ala Val  Asn Gly Tyr
    1085                 1090                 1095

Thr Cys  Ile Cys Pro Glu Gly  Tyr Ser Gly Leu Phe  Cys Glu Phe
    1100                 1105                 1110

Ser Pro  Pro Met Val Leu Pro  Arg Thr Ser Pro Cys  Asp Asn Phe
    1115                 1120                 1125

Asp Cys  Gln Asn Gly Ala Gln  Cys Ile Val Arg Ile  Asn Glu Pro
    1130                 1135                 1140

Ile Cys  Gln Cys Leu Pro Gly  Tyr Gln Gly Glu Lys  Cys Glu Lys
    1145                 1150                 1155

Leu Val  Ser Val Asn Phe Ile  Asn Lys Glu Ser Tyr  Leu Gln Ile
    1160                 1165                 1170

Pro Ser  Ala Lys Val Arg Pro  Gln Thr Asn Ile Thr  Leu Gln Ile
    1175                 1180                 1185

Ala Thr  Asp Glu Asp Ser Gly  Ile Leu Leu Tyr Lys  Gly Asp Lys
    1190                 1195                 1200

Asp His  Ile Ala Val Glu Leu  Tyr Arg Gly Arg Val  Arg Ala Ser
    1205                 1210                 1215

Tyr Asp  Thr Gly Ser His Pro  Ala Ser Ala Ile Tyr  Ser Val Glu
    1220                 1225                 1230

Thr Ile  Asn Asp Gly Asn Phe  His Ile Val Glu Leu  Leu Ala Leu
    1235                 1240                 1245

Asp Gln  Ser Leu Ser Leu Ser  Val Asp Gly Gly Asn  Pro Lys Ile
    1250                 1255                 1260

Ile Thr  Asn Leu Ser Lys Gln  Ser Thr Leu Asn Phe  Asp Ser Pro
    1265                 1270                 1275

Leu Tyr  Val Gly Gly Met Pro  Gly Lys Ser Asn Val  Ala Ser Leu
    1280                 1285                 1290

Arg Gln  Ala Pro Gly Gln Asn  Gly Thr Ser Phe His  Gly Cys Ile
    1295                 1300                 1305

Arg Asn  Leu Tyr Ile Asn Ser  Glu Leu Gln Asp Phe  Gln Lys Val
    1310                 1315                 1320

Pro Met  Gln Thr Gly Ile Leu  Pro Gly Cys Glu Pro  Cys His Lys
    1325                 1330                 1335

Lys Val  Cys Ala His Gly Thr  Cys Gln Pro Ser Ser  Gln Ala Gly
    1340                 1345                 1350

Phe Thr  Cys Glu Cys Gln Glu  Gly Trp Met Gly Pro  Leu Cys Asp
    1355                 1360                 1365

Gln Arg  Thr Asn Asp Pro Cys  Leu Gly Asn Lys Cys  Val His Gly
    1370                 1375                 1380

Thr Cys  Leu Pro Ile Asn Ala  Phe Ser Tyr Ser Cys  Lys Cys Leu
    1385                 1390                 1395

Glu Gly  His Gly Gly Val Leu  Cys Asp Glu Glu Glu  Asp Leu Phe
    1400                 1405                 1410

Asn Pro  Cys Gln Ala Ile Lys  Cys Lys His Gly Lys  Cys Arg Leu
    1415                 1420                 1425

Ser Gly  Leu Gly Gln Pro Tyr  Cys Glu Cys Ser Ser  Gly Tyr Thr
```

-continued

```
    1430                1435                1440

Gly Asp  Ser Cys Asp Arg Glu  Ile Ser Cys Arg Gly  Glu Arg Ile
    1445                1450                1455

Arg Asp  Tyr Tyr Gln Lys Gln  Gln Gly Tyr Ala Ala  Cys Gln Thr
    1460                1465                1470

Thr Lys  Lys Val Ser Arg Leu  Glu Cys Arg Gly Gly  Cys Ala Gly
    1475                1480                1485

Gly Gln  Cys Cys Gly Pro Leu  Arg Ser Lys Arg Arg  Lys Tyr Ser
    1490                1495                1500

Phe Glu  Cys Thr Asp Gly Ser  Ser Phe Val Asp Glu  Val Glu Lys
    1505                1510                1515

Val Val  Lys Cys Gly Cys Thr  Arg Cys Val Ser
    1520                1525
```

<210> SEQ ID NO 68
<211> LENGTH: 4900
<212> TYPE: DNA
<213> ORGANISM: Homo sapiens

<400> SEQUENCE: 68

```
cagagcaggg tggagagggc ggtgggaggc gtgtgcctga gtgggctcta ctgccttgtt     60
ccatattatt ttgtgcacat tttccctggc actctgggtt gctagccccg ccgggcactg    120
ggcctcagac actgcgcggt tccctcggag cagcaagcta aagaaagccc ccagtgccgg    180
cgaggaagga ggcggcgggg aaagatgcgc ggcgttggct ggcagatgct gtccctgtcg    240
ctggggttag tgctggcgat cctgaacaag gtggcaccgc aggcgtgccc ggcgcagtgc    300
tcttgctcgg gcagcacagt ggactgtcac gggctggcgc tgcgcagcgt gcccaggaat    360
atcccccgca acaccgagag actggattta aatggaaata acatcacaag aattacgaag    420
acagattttg ctggtcttag acatctaaga gttcttcagc ttatggagaa taagattagc    480
accattgaaa gaggagcatt ccaggatctt aaagaactag agagactgcg tttaaacaga    540
aatcaccttc agctgtttcc tgagttgctg tttcttggga ctgcgaagct atacaggctt    600
gatctcagtg aaaaccaaat tcaggcaatc ccaaggaaag ctttccgtgg ggcagttgac    660
ataaaaaatt tgcaactgga ttacaaccag atcagctgta ttgaagatgg ggcattcagg    720
gctctccggg acctggaagt gctcactctc aacaataaca acattactag actttctgtg    780
gcaagtttca accatatgcc taaacttagg acttttcgac tgcattcaaa caacctgtat    840
tgtgactgcc acctggcctg gctctccgac tggcttcgcc aaaggcctcg ggttggtctg    900
tacactcagt gtatgggccc ctcccacctg agaggccata atgtagccga ggttcaaaaa    960
cgagaatttg tctgcagtgg tcaccagtca tttatggctc cttcttgtag tgttttgcac   1020
tgccctgccg cctgtacctg tagcaacaat atcgtagact gtcgtgggaa aggtctcact   1080
gagatcccca caaatcttcc agagaccatc acagaaatac gtttggaaca gaacacaatc   1140
aaagtcatcc ctcctggagc tttctcacca tataaaaagc ttagacgaat tgacctgagc   1200
aataatcaga tctctgaact tgcaccagat gctttccaag gactacgctc tctgaattca   1260
cttgtcctct atggaaataa aatcacagaa ctccccaaaa gtttatttga aggactgttt   1320
tccttacagc tcctattatt gaatgccaac aagataaact gccttcgggt agatgctttt   1380
caggatctcc acaacttgaa ccttctctcc ctatatgaca acaagcttca gaccatcgcc   1440
aaggggacct tttcacctct tcgggccatt caaactatgc atttggccca gaacccettt   1500
atttgtgact gccatctcaa gtggctagcg gattatctcc ataccaaccc gattgagacc   1560
```

-continued

```
agtggtgccc gttgcaccag cccccgccgc ctggcaaaca aaagaattgg acagatcaaa   1620
agcaagaaat tccgttgttc agctaaagaa cagtatttca ttccaggtac agaagattat   1680
cgatcaaaat taagtggaga ctgctttgcg gatctggctt gccctgaaaa gtgtcgctgt   1740
gaaggaacca cagtagattg ctctaatcaa aagctcaaca aaatcccgga gcacattccc   1800
cagtacactg cagagttgcg tctcaataat aatgaattta ccgtgttgga agccacagga   1860
atctttaaga aacttcctca attacgtaaa ataaacttta gcaacaataa gatcacagat   1920
attgaggagg gagcatttga aggagcatct ggtgtaaatg aaatacttct tacgagtaat   1980
cgtttggaaa atgtgcagca taagatgttc aagggattgg aaagcctcaa aactttgatg   2040
ttgagaagca atcgaataac ctgtgtgggg aatgacagtt tcataggact cagttctgtg   2100
cgtttgcttt ctttgtatga taatcaaatt actacagttg caccaggggc atttgatact   2160
ctccattctt tatctactct aaacctcttg gccaatcctt ttaactgtaa ctgctacctg   2220
gcttggttgg gagagtggct gagaaagaag agaattgtca cgggaaatcc tagatgtcaa   2280
aaaccatact tcctgaaaga aatacccatc caggatgtgg ccattcagga cttcacttgt   2340
gatgacggaa atgatgacaa tagttgctcc ccactttctc gctgtcctac tgaatgtact   2400
tgcttggata cagtcgtccg atgtagcaac aagggtttga aggtcttgcc gaaaggtatt   2460
ccaagagatg tcacagagtt gtatctggat ggaaaccaat ttacactggt tcccaaggaa   2520
ctctccaact acaaacattt aacacttata gacttaagta acaacagaat aagcacgctt   2580
tctaatcaga gcttcagcaa catgacccag ctcctcacct taattcttag ttacaaccgt   2640
ctgagatgta ttcctcctcg cacctttgat ggattaaagt ctcttcgatt actttctcta   2700
catggaaatg acatttctgt tgtgcctgaa ggtgctttca atgatctttc tgcattatca   2760
catctagcaa ttggagccaa ccctctttac tgtgattgta acatgcagtg gttatccgac   2820
tgggtgaagt cggaatataa ggagcctgga attgctcgtt gtgctggtcc tggagaaatg   2880
gcagataaac ttttactcac aactccctcc aaaaaattta cctgtcaagg tcctgtggat   2940
gtcaatattc tagctaagtg taacccctgc ctatcaaatc cgtgtaaaaa tgatggcaca   3000
tgtaatagtg atccagttga cttttaccga tgcacctgtc catatggttt caaggggcag   3060
gactgtgatg tcccaattca tgcctgcatc agtaacccat gtaaacatgg aggaacttgc   3120
cacttaaagg aaggagaaga agatggattc tggtgtattt gtgctgatgg atttgaagga   3180
gaaaattgtg aagtcaacgt tgatgattgt gaagataatg actgtgaaaa taattctaca   3240
tgtgtcgatg gcattaataa ctacacatgc ctttgcccac ctgagtatac aggtgagttg   3300
tgtgaggaga agctggactt ctgtgcccag gacctgaacc cctgccagca cgattcaaag   3360
tgcatcctaa ctccaaaggg attcaaatgt gactgcacac cagggtacgt aggtgaacac   3420
tgcgacatcg attttgacga ctgccaagac aacaagtgta aaaacggagc ccactgcaca   3480
gatgcagtga acggctatac gtgcatatgc cccgaaggtt acagtggctt gttctgtgag   3540
ttttctccac ccatggtcct ccctcgtacc agcccctgtg ataattttga ttgtcagaat   3600
ggagctcagt gtatcgtcag aataaatgag ccaatatgtc agtgtttgcc tggctatcag   3660
ggagaaaagt gtgaaaaatt ggttagtgtg aattttataa acaaagagtc ttatcttcag   3720
attccttcag ccaaggttcg gcctcagacg aacataacac ttcagattgc cacagatgaa   3780
gacagcggaa tcctcctgta taagggtgac aaagaccata tcgcggtaga actctatcgg   3840
gggcgtgttc gtgccagcta tgacaccggc tctcatccag cttctgccat ttacagtgtg   3900
```

-continued

```
gagacaatca atgatggaaa cttccacatt gtggaactac ttgccttgga tcagagtctc   3960

tctttgtccg tggatggtgg gaaccccaaa atcatcacta acttgtcaaa gcagtccact   4020

ctgaattttg actctccact ctatgtagga ggcatgccag ggaagagtaa cgtggcatct   4080

ctgcgccagg cccctgggca gaacggaacc agcttccacg gctgcatccg gaacctttac   4140

atcaacagtg agctgcagga cttccagaag gtgccgatgc aaacaggcat tttgcctggc   4200

tgtgagccat gccacaagaa ggtgtgtgcc catggcacat gccagcccag cagccaggca   4260

ggcttcacct gcgagtgcca ggaaggatgg atggggcccc tctgtgacca acggaccaat   4320

gacccttgcc ttggaaataa atgcgtacat ggcacctgct tgcccatcaa tgcgttctcc   4380

tacagctgta agtgcttgga gggccatgga ggtgtcctct gtgatgaaga ggaggatctg   4440

tttaacccat gccaggcgat caagtgcaag cacgggaagt gcaggctttc aggtctgggg   4500

cagccctact gtgaatgcag cagtggatac acgggggaca gctgtgatcg agaaatctct   4560

tgtcgagggg aaaggataag agattattac caaaagcagc agggctatgc tgcttgccaa   4620

acaaccaaga aggtgtcccg attagagtgc agaggtgggt gtgcaggagg gcagtgctgt   4680

ggaccgctga ggagcaagcg gcggaaatac tctttcgaat gcactgacgg ctcctccttt   4740

gtggacgagg ttgagaaagt ggtgaagtgc ggctgtacga ggtgtgtgtc ctaaacacac   4800

tcccggcagc tctgtctttg gaaaaggttg tatacttctt gaccatgtgg gactaatgaa   4860

tgcttcatag tggaaatatt tgaaatatat tgtaaaatac                        4900
```

<210> SEQ ID NO 69
<211> LENGTH: 348
<212> TYPE: PRT
<213> ORGANISM: Cricetulus griseus

<400> SEQUENCE: 69

```
Met His Leu Pro Pro Ala Ala Ala Val Gly Leu Leu Leu Leu Leu Leu
1               5                   10                  15

Pro Pro Pro Ala Arg Val Ala Ser Arg Lys Pro Thr Met Cys Gln Arg
            20                  25                  30

Cys Arg Ala Leu Val Asp Lys Phe Asn Gln Gly Met Ala Asn Thr Ala
        35                  40                  45

Arg Lys Asn Phe Gly Gly Gly Asn Thr Ala Trp Glu Glu Lys Ser Leu
    50                  55                  60

Ser Lys Tyr Glu Phe Ser Glu Ile Arg Leu Leu Glu Ile Met Glu Gly
65                  70                  75                  80

Leu Cys Asp Ser Asn Asp Phe Glu Cys Asn Gln Leu Leu Glu Gln His
                85                  90                  95

Glu Glu Gln Leu Glu Ala Trp Trp Gln Thr Leu Lys Lys Glu Cys Pro
            100                 105                 110

Asn Leu Phe Glu Trp Phe Cys Val His Thr Leu Lys Ala Cys Cys Leu
        115                 120                 125

Pro Gly Thr Tyr Gly Pro Asp Cys Gln Glu Cys Gln Gly Gly Ser Gln
    130                 135                 140

Arg Pro Cys Ser Gly Asn Gly His Cys Asp Gly Asp Gly Ser Arg Gln
145                 150                 155                 160

Gly Asp Gly Ser Cys Gln Cys His Val Gly Tyr Lys Gly Pro Leu Cys
                165                 170                 175

Ile Asp Cys Met Asp Gly Tyr Phe Ser Leu Leu Arg Asn Glu Thr His
            180                 185                 190

Ser Phe Cys Thr Ala Cys Asp Glu Ser Cys Lys Thr Cys Ser Gly Pro
```

-continued

```
        195                 200                 205

Thr Asn Lys Gly Cys Val Glu Cys Glu Val Gly Trp Thr Arg Val Glu
    210                 215                 220

Asp Ala Cys Val Asp Val Asp Glu Cys Ala Ala Glu Thr Pro Pro Cys
225                 230                 235                 240

Ser Asn Val Gln Tyr Cys Glu Asn Val Asn Gly Ser Tyr Thr Cys Glu
                245                 250                 255

Glu Cys Asp Ser Thr Cys Val Gly Cys Thr Gly Lys Gly Pro Ala Asn
            260                 265                 270

Cys Lys Glu Cys Ile Ser Gly Tyr Ser Lys Gln Lys Gly Glu Cys Ala
        275                 280                 285

Asp Ile Asp Glu Cys Ser Leu Glu Thr Lys Val Cys Lys Lys Glu Asn
    290                 295                 300

Glu Asn Cys Tyr Asn Thr Pro Gly Ser Phe Val Cys Val Cys Pro Glu
305                 310                 315                 320

Gly Phe Glu Glu Asp Arg Arg Cys Leu Cys Thr Asp Ser Arg Arg Arg
                325                 330                 335

Ser Gly Arg Gly Lys Ser His Thr Ala Thr Leu Pro
            340                 345
```

<210> SEQ ID NO 70
<211> LENGTH: 1399
<212> TYPE: DNA
<213> ORGANISM: Cricetulus griseus

<400> SEQUENCE: 70

```
gtagccgggg gaacggccgg cgcgcttgcc ggtgggcgga ggcgagactc cacagcagtt     60

ctctgccggt cgcccgcgag tgcacccgcc atgcacctgc cgcccgctgc cgcagtcggg    120

ctgctactgc tgctgctgcc gcctcccgcg cgcgtggcct cccggaagcc gacaatgtgc    180

cagaggtgcc gggcgctggt ggacaagttc aaccagggga tggccaacac ggccaggaag    240

aatttcggcg gcggcaacac ggcgtgggag gagaagagtc tgtccaagta cgaattcagt    300

gagattcggc tcctggagat tatggagggc ctgtgtgaca gcaacgactt tgaatgcaac    360

caactcttgg aacagcatga ggagcagcta gaggcctggt ggcagacact gaagaaggag    420

tgccctaacc tatttgagtg gttctgtgta cacacactga aagcatgctg tcttccaggc    480

acctatgggc cagactgtca ggaatgccag ggtgggtctc agaggccttg tagcgggaat    540

ggccactgcg acggagatgg cagcagacag ggcgacgggt cctgccagtg tcacgtagga    600

tacaaggggc cgctgtgtat cgactgcatg gatggctact tcagcttgct gaggaacgag    660

acccacagct tctgcacagc ctgtgatgag tcctgcaaga catgctcagg tccaaccaac    720

aaaggctgtg tggagtgcga agtgggctgg acacgtgtgg aggatgcctg tgtggatgtt    780

gacgagtgtg cagcagagac ccccaccctgc agcaatgtac agtactgtga aaatgtcaac    840

ggctcctaca catgtgaaga gtgtgattct acctgtgtgg gctgcacagg aaaaggccca    900

gccaattgta aagagtgtat ctctggctac agcaagcaga aaggagagtg tgcagatata    960

gatgaatgct cattagaaac aaaggtgtgt aagaaggaaa atgagaactg ctacaatact   1020

ccagggagct ttgtctgcgt gtgtccggaa ggtttcgagg aagacagaag atgcttgtgt   1080

acagacagca gaaggcgaag tggcagagga aagtcccaca cagccaccct cccatgagga   1140

tttgtgacgg gcatccaggt tcagaagctg gactctcacc cttttaagtt attgagagga   1200

catcctatag aaaatgtggc ccatggacat caaccccatt tctccaggaa gttttggagg   1260
```

-continued

```
aagaagctgc ctgctttgaa acagtagata ctcacttggc cctttaaaac gctgcatttc   1320

ttggtggttc ttaaacagat tcgtatattt tgatactgtt ctttataata aaattgatca   1380

ttgaaggtca ccaggaaca                                                1399


<210> SEQ ID NO 71
<211> LENGTH: 528
<212> TYPE: PRT
<213> ORGANISM: Homo sapiens

<400> SEQUENCE: 71

Met Ala Gln Leu Phe Leu Pro Leu Leu Ala Ala Leu Val Leu Ala Gln
1               5                   10                  15

Ala Pro Ala Ala Leu Ala Asp Val Leu Glu Gly Asp Ser Ser Glu Asp
            20                  25                  30

Arg Ala Phe Arg Val Arg Ile Ala Gly Asp Ala Pro Leu Gln Gly Val
        35                  40                  45

Leu Gly Gly Ala Leu Thr Ile Pro Cys His Val His Tyr Leu Arg Pro
    50                  55                  60

Pro Pro Ser Arg Arg Ala Val Leu Gly Ser Pro Arg Val Lys Trp Thr
65                  70                  75                  80

Phe Leu Ser Arg Gly Arg Glu Ala Glu Val Leu Val Ala Arg Gly Val
                85                  90                  95

Arg Val Lys Val Asn Glu Ala Tyr Arg Phe Arg Val Ala Leu Pro Ala
            100                 105                 110

Tyr Pro Ala Ser Leu Thr Asp Val Ser Leu Ala Leu Ser Glu Leu Arg
        115                 120                 125

Pro Asn Asp Ser Gly Ile Tyr Arg Cys Glu Val Gln His Gly Ile Asp
    130                 135                 140

Asp Ser Ser Asp Ala Val Glu Ser Ser Gln Arg Tyr Pro Ile Gln Thr
145                 150                 155                 160

Pro Arg Glu Ala Cys Tyr Gly Asp Met Asp Gly Phe Pro Gly Val Arg
                165                 170                 175

Asn Tyr Gly Val Val Asp Pro Asp Asp Leu Tyr Asp Val Tyr Cys Tyr
            180                 185                 190

Ala Glu Asp Leu Asn Gly Glu Leu Phe Leu Gly Asp Pro Pro Glu Lys
        195                 200                 205

Leu Thr Leu Glu Glu Ala Arg Ala Tyr Cys Gln Glu Arg Gly Ala Glu
    210                 215                 220

Ile Ala Thr Thr Gly Gln Leu Tyr Ala Ala Trp Asp Gly Gly Leu Asp
225                 230                 235                 240

His Cys Ser Pro Gly Trp Leu Ala Asp Gly Ser Val Arg Tyr Pro Ile
                245                 250                 255

Val Thr Pro Ser Gln Arg Cys Gly Gly Gly Leu Pro Gly Val Lys Thr
            260                 265                 270

Leu Phe Leu Phe Pro Asn Gln Thr Gly Phe Pro Asn Lys His Ser Arg
        275                 280                 285

Phe Asn Val Tyr Cys Phe Arg Asp Ser Ala Gln Leu Leu Pro Ser Leu
    290                 295                 300

Arg Pro Pro Thr Gln Pro Pro Thr Gln Leu Asp Gly Leu Glu Ala Ile
305                 310                 315                 320

Val Thr Val Thr Glu Thr Leu Glu Glu Leu Gln Leu Pro Gln Glu Ala
                325                 330                 335

Thr Glu Ser Glu Ser Arg Gly Ala Ile Tyr Ser Ile Pro Ile Met Glu
            340                 345                 350
```

-continued

```
Asp Gly Gly Gly Gly Ser Ser Thr Pro Glu Asp Pro Ala Glu Ala Pro
        355                 360                 365

Arg Thr Leu Leu Glu Phe Glu Thr Gln Ser Met Val Pro Pro Thr Gly
    370                 375                 380

Phe Ser Glu Glu Glu Gly Lys Ala Leu Glu Glu Glu Glu Lys Tyr Glu
385                 390                 395                 400

Asp Glu Glu Glu Lys Glu Glu Glu Glu Glu Glu Glu Glu Val Glu Asp
                405                 410                 415

Glu Ala Leu Trp Ala Trp Pro Ser Glu Leu Ser Ser Pro Gly Pro Glu
            420                 425                 430

Ala Ser Leu Pro Thr Glu Pro Ala Ala Gln Glu Glu Ser Leu Ser Gln
        435                 440                 445

Ala Pro Ala Arg Ala Val Leu Gln Pro Gly Ala Ser Pro Leu Pro Asp
    450                 455                 460

Gly Glu Ser Glu Ala Ser Arg Pro Pro Arg Val His Gly Pro Pro Thr
465                 470                 475                 480

Glu Thr Leu Pro Thr Pro Arg Glu Arg Asn Leu Ala Ser Pro Ser Pro
                485                 490                 495

Ser Thr Leu Val Glu Ala Arg Glu Val Gly Glu Ala Thr Gly Gly Pro
            500                 505                 510

Glu Leu Ser Gly Val Pro Arg Gly Gly Ala Arg Thr Gln Phe Ala Leu
        515                 520                 525


<210> SEQ ID NO 72
<211> LENGTH: 883
<212> TYPE: PRT
<213> ORGANISM: Mus sp.

<400> SEQUENCE: 72

Met Ile Pro Leu Leu Leu Ser Leu Leu Ala Ala Leu Val Leu Thr Gln
1               5                   10                  15

Ala Pro Ala Ala Leu Ala Asp Asp Leu Lys Glu Asp Ser Ser Glu Asp
            20                  25                  30

Arg Ala Phe Arg Val Arg Ile Gly Ala Ala Gln Leu Arg Gly Val Leu
        35                  40                  45

Gly Gly Ala Leu Ala Ile Pro Cys His Val His His Leu Arg Pro Pro
    50                  55                  60

Arg Ser Arg Arg Ala Ala Pro Gly Phe Pro Arg Val Lys Trp Thr Phe
65                  70                  75                  80

Leu Ser Gly Asp Arg Glu Val Glu Val Leu Val Ala Arg Gly Leu Arg
                85                  90                  95

Val Lys Val Asn Glu Ala Tyr Arg Phe Arg Val Ala Leu Pro Ala Tyr
            100                 105                 110

Pro Ala Ser Leu Thr Asp Val Ser Leu Val Leu Ser Glu Leu Arg Pro
        115                 120                 125

Asn Asp Ser Gly Val Tyr Arg Cys Glu Val Gln His Gly Ile Asp Asp
    130                 135                 140

Ser Ser Asp Ala Val Glu Val Lys Val Lys Gly Val Val Phe Leu Tyr
145                 150                 155                 160

Arg Glu Gly Ser Ala Arg Tyr Ala Phe Ser Phe Ala Gly Ala Gln Glu
                165                 170                 175

Ala Cys Ala Arg Ile Gly Ala Arg Ile Ala Thr Pro Glu Gln Leu Tyr
            180                 185                 190

Ala Ala Tyr Leu Gly Gly Tyr Glu Gln Cys Asp Ala Gly Trp Leu Ser
```

-continued

```
        195                 200                 205

Asp Gln Thr Val Arg Tyr Pro Ile Gln Asn Pro Arg Glu Ala Cys Ser
    210                 215                 220

Gly Asp Met Asp Gly Tyr Pro Gly Val Arg Asn Tyr Gly Val Val Gly
225                 230                 235                 240

Pro Asp Asp Leu Tyr Asp Val Tyr Cys Tyr Ala Glu Asp Leu Asn Gly
                245                 250                 255

Glu Leu Phe Leu Gly Ala Pro Pro Ser Lys Leu Thr Trp Glu Glu Ala
            260                 265                 270

Arg Asp Tyr Cys Leu Glu Arg Gly Ala Gln Ile Ala Ser Thr Gly Gln
        275                 280                 285

Leu Tyr Ala Ala Trp Asn Gly Gly Leu Asp Arg Cys Ser Pro Gly Trp
    290                 295                 300

Leu Ala Asp Gly Ser Val Arg Tyr Pro Ile Ile Thr Pro Ser Gln Arg
305                 310                 315                 320

Cys Gly Gly Gly Leu Pro Gly Val Lys Thr Leu Phe Leu Phe Pro Asn
                325                 330                 335

Gln Thr Gly Phe Pro Ser Lys Gln Asn Arg Phe Asn Val Tyr Cys Phe
            340                 345                 350

Arg Asp Ser Ala His Pro Ser Ala Ser Ser Glu Ala Ser Ser Pro Ala
        355                 360                 365

Ser Asp Gly Leu Glu Ala Ile Val Thr Val Thr Glu Lys Leu Glu Glu
    370                 375                 380

Leu Gln Leu Pro Gln Glu Ala Met Glu Ser Glu Ser Arg Gly Ala Ile
385                 390                 395                 400

Tyr Ser Ile Pro Ile Ser Glu Asp Gly Gly Gly Gly Ser Ser Thr Pro
                405                 410                 415

Glu Asp Pro Ala Glu Ala Pro Arg Thr Pro Leu Glu Ser Glu Thr Gln
            420                 425                 430

Ser Ile Ala Pro Pro Thr Glu Ser Ser Glu Glu Glu Gly Val Ala Leu
        435                 440                 445

Glu Glu Glu Glu Arg Phe Lys Asp Leu Glu Ala Leu Glu Glu Glu Lys
    450                 455                 460

Glu Gln Glu Asp Leu Trp Val Trp Pro Arg Glu Leu Ser Ser Pro Leu
465                 470                 475                 480

Pro Thr Gly Ser Glu Thr Glu His Ser Leu Ser Gln Val Ser Pro Pro
                485                 490                 495

Ala Gln Ala Val Leu Gln Leu Asp Ala Ser Pro Ser Pro Gly Pro Pro
            500                 505                 510

Arg Phe Arg Gly Pro Pro Ala Glu Thr Leu Leu Pro Pro Arg Glu Trp
        515                 520                 525

Ser Ala Thr Ser Thr Pro Gly Gly Ala Arg Glu Val Gly Gly Glu Thr
    530                 535                 540

Gly Ser Pro Glu Leu Ser Gly Val Pro Arg Glu Ser Glu Glu Ala Gly
545                 550                 555                 560

Ser Ser Ser Leu Glu Asp Gly Pro Ser Leu Leu Pro Ala Thr Trp Ala
                565                 570                 575

Pro Val Gly Pro Arg Glu Leu Glu Thr Pro Ser Glu Glu Lys Ser Gly
            580                 585                 590

Arg Thr Val Leu Ala Gly Thr Ser Val Gln Ala Gln Pro Val Leu Pro
        595                 600                 605

Thr Asp Ser Ala Ser His Gly Gly Val Ala Val Ala Pro Ser Ser Gly
    610                 615                 620
```

-continued

```
Asp Cys Ile Pro Ser Pro Cys His Asn Gly Gly Thr Cys Leu Glu Glu
625                 630                 635                 640

Lys Glu Gly Phe Arg Cys Leu Cys Leu Pro Gly Tyr Gly Gly Asp Leu
                645                 650                 655

Cys Asp Val Gly Leu His Phe Cys Ser Pro Gly Trp Glu Ala Phe Gln
            660                 665                 670

Gly Ala Cys Tyr Lys His Phe Ser Thr Arg Arg Ser Trp Glu Glu Ala
        675                 680                 685

Glu Ser Gln Cys Arg Ala Leu Gly Ala His Leu Thr Ser Ile Cys Thr
    690                 695                 700

Pro Glu Glu Gln Asp Phe Val Asn Asp Arg Tyr Arg Glu Tyr Gln Trp
705                 710                 715                 720

Ile Gly Leu Asn Asp Arg Thr Ile Glu Gly Asp Phe Leu Trp Ser Asp
                725                 730                 735

Gly Ala Pro Leu Leu Tyr Glu Asn Trp Asn Pro Gly Gln Pro Asp Ser
            740                 745                 750

Tyr Phe Leu Ser Gly Glu Asn Cys Val Val Met Val Trp His Asp Gln
        755                 760                 765

Gly Gln Trp Ser Asp Val Pro Cys Asn Tyr His Leu Ser Tyr Thr Cys
    770                 775                 780

Lys Met Gly Leu Val Ser Cys Gly Pro Pro Pro Gln Leu Pro Leu Ala
785                 790                 795                 800

Gln Ile Phe Gly Arg Pro Arg Leu Arg Tyr Ala Val Asp Thr Val Leu
                805                 810                 815

Arg Tyr Arg Cys Arg Asp Gly Leu Ala Gln Arg Asn Leu Pro Leu Ile
            820                 825                 830

Arg Cys Gln Glu Asn Gly Leu Trp Glu Ala Pro Gln Ile Ser Cys Val
        835                 840                 845

Pro Arg Arg Pro Gly Arg Ala Leu Arg Ser Met Asp Ala Pro Glu Gly
    850                 855                 860

Pro Arg Gly Gln Leu Ser Arg His Arg Lys Ala Pro Leu Thr Pro Pro
865                 870                 875                 880

Ser Ser Leu
```

<210> SEQ ID NO 73
<211> LENGTH: 3153
<212> TYPE: DNA
<213> ORGANISM: Mus sp.
<220> FEATURE:
<221> NAME/KEY: misc_feature
<222> LOCATION: (3043)..(3043)
<223> OTHER INFORMATION: unknown
<220> FEATURE:
<221> NAME/KEY: misc_feature
<222> LOCATION: (3048)..(3048)
<223> OTHER INFORMATION: unknown

<400> SEQUENCE: 73

```
gaggctcccg gcgagctggc gcccctgtct gggtcccgcg cgcccggccc tgctcgcgcc      60

cgcgcatcgc gccgcagtct cggtctgcgg ctgcgggacg tgacggcgtg cgcggagggg     120

acctcgcaag ttcttccatc agtgtgcaga atgataccac tgcttctgtc cctgctggcc     180

gctctggtcc tgacccaagc ccctgccgcc ctcgctgatg acctgaaaga agacagctcg     240

gaggatcgag ccttccgcgt gcgcatcggt gccgcgcagc tgcggggcgt gctgggcggt     300

gccctggcca tcccatgcca cgtccaccac ctgcggccgc cgcgcagccg ccgggccgcg     360
```

-continued

```
ccgggttttc cccgggtcaa gtggaccttc ctgtccgggg accgggaggt agaggttctg    420
gtggctcgcg ggctgcgcgt caaggtaaac gaagcctacc ggttccgcgt ggcgctgcct    480
gcctaccccg catcgctcac ggatgtgtct ctagtattga gcgaactgcg gcccaatgat    540
tccggggtct atcgctgcga ggtccagcac ggtatcgacg acagcagtga tgctgtggag    600
gtcaaggtca aaggggtcgt cttcctctac agagagggct ctgcgcgcta tgctttctcc    660
ttcgctggag cccaggaagc ctgcgctcgc ataggagccc gaatcgccac cccggagcag    720
ctctatgctg cctacctcgg cggctatgag cagtgtgatg caggctggct gtccgaccaa    780
actgtgaggt accccatcca gaacccacga gaggcctgct ctggagacat ggatggctat    840
cctggcgtgc ggaactacgg agtggtgggt cctgatgatc tctatgatgt ctactgttat    900
gccgaagacc taaatggaga actgttccta ggcgcccctc ccagcaagct gacatgggag    960
gaggctcggg actactgtct ggaacgtggt gcacagatcg ctagcacagg ccagctgtac   1020
gcagcctgga atggtggcct ggacagatgt agccctggct ggctggctga tggcagcgtg   1080
cgctatccca tcatcacacc cagccaacgc tgtgggggcg gcctgccagg agtcaagacc   1140
ctcttcctct ttcccaacca gactggcttc cccagcaagc agaaccgctt caatgtctac   1200
tgcttccgag actctgccca tccctctgct tcctctgagg cctctagccc agcctcagat   1260
ggacttgagg ccattgtcac agtgacagaa aagctggagg aactgcagct gcctcaggaa   1320
gcgatggaga gcgagtctcg tggggccatc tactccatcc ccatctcaga agatgggga    1380
ggaggaagct ccaccccaga agacccagca gaggccccca ggactccgct agaatcggaa   1440
acccaatcca ttgcaccacc taccgagtcc tcagaagagg aaggcgtagc cctggaggaa   1500
gaagaaagat tcaaagactt ggaggctctg gaggaagaga aggagcagga ggacctgtgg   1560
gtgtggccca gagagctcag cagccctctc cctactggct cagaaacaga gcattcactc   1620
tcccaggtgt ccccaccagc ccaggcagtt ctacagctgg atgcgtcacc ttctcctggg   1680
cctccaaggt tccgtggacc gcctgcagag actttgctcc ccccgaggga gtggagcgcc   1740
acatctactc ctggtggggc aagagaagta ggggggggaaa ctgggagccc tgagctctct   1800
ggggttcctc gagagagcga ggaggcaggg agctccagct tggaggatgg cccttcccta   1860
cttccagcta catgggcccc tgtgggtccc agggagctgg agaccccctc agaagagaag   1920
tctggaagaa ctgtcctggc aggcacctca gtgcaggccc agccagtgct gcccaccgac   1980
agtgccagcc acggtggagt ggctgtggct ccctcatcag gtgactgtat ccccagcccc   2040
tgccacaatg gtgggacatg cttggaggag aaggagggtt tccgctgcct atgtttgcca   2100
ggctatgggg gggacctgtg cgatgttggc cttcatttct gcagccctgg ctgggaggcc   2160
ttccagggag cctgctacaa gcacttttcc acacgaagga gttgggagga ggcagaaagt   2220
cagtgccgag cgctaggtgc tcatctgacc agcatctgca cccctgagga gcaagacttt   2280
gtcaatgatc gataccggga gtaccagtgg attgggctca atgacaggac catcgagggt   2340
gacttcttgt ggtcagatgg tgcccctctg ctctatgaaa actggaaccc tgggcagcct   2400
gacagctact tcctgtctgg ggagaactgt gtggtcatgg tgtggcatga ccagggacag   2460
tggagtgatg tgccctgcaa ctaccatcta tcctacacct gcaagatggg gcttgtgtcc   2520
tgtgggcctc caccacagct accccctggct caaatatttg gtcgccctcg gctgcgctac   2580
gcggtggata ctgtgcttcg atatcgatgc cgagacgggc tggctcagcg caacctgccg   2640
ttgatccgct gccaggagaa tgggctttgg gaggcccctc agatttcctg tgtaccccgg   2700
aggcctggcc gtgctctgcg ctccatggac gccccagaag gaccacgggg acagctctcg   2760
```

-continued

```
aggcacagga aggcaccgtt gacaccgccc tccagtctct agggagcctg gaagactgct   2820

gcccccagca ggaccctctc acatcaactg ccagtgctct tccccatgat agggggtgac   2880

gtgagagggg tgggactgaa attcagagga cagcgctcga aggggtttct gggaaacact   2940

tgggtggctc cgccccctca cacaagggcc tcaggtttta cccggtaagt ccctaagtgc   3000

ctcaactgcc ctctcatgtc agctgcctcc ttgtccctcg atntcgtnag gggacactgt   3060

gctattcgat cttgattgtc gaagagtttt taggatggag taccagcaaa accaggtgga   3120

aataaagttg tctgaaccca aagaaaaaaa aaa                                3153
```

<210> SEQ ID NO 74
<211> LENGTH:
<212> TYPE:
<213> ORGANISM:

<400> SEQUENCE: 74

000

<210> SEQ ID NO 75
<211> LENGTH:
<212> TYPE:
<213> ORGANISM:

<400> SEQUENCE: 75

000

<210> SEQ ID NO 76
<211> LENGTH:
<212> TYPE:
<213> ORGANISM:

<400> SEQUENCE: 76

000

<210> SEQ ID NO 77
<211> LENGTH:
<212> TYPE:
<213> ORGANISM:

<400> SEQUENCE: 77

000

<210> SEQ ID NO 78
<211> LENGTH:
<212> TYPE:
<213> ORGANISM:

<400> SEQUENCE: 78

000

<210> SEQ ID NO 79
<211> LENGTH:
<212> TYPE:
<213> ORGANISM:

<400> SEQUENCE: 79

000

<210> SEQ ID NO 80
<211> LENGTH:
<212> TYPE:

-continued

<213> ORGANISM:

<400> SEQUENCE: 80

000

<210> SEQ ID NO 81
<211> LENGTH: 2002
<212> TYPE: DNA
<213> ORGANISM: gerbil

<400> SEQUENCE: 81
gtcgacccac gcgtccgctg cgttctcacc cctggaccac cctgggagaa cagttgaccg 60
aagtttgttt ggcagttgct gctggactat gtttctgctt ctggtggtac tcagccagct 120
gcccagactt accctcgcgg ttcctcatac aagaagccta aagaattctg aacatgcccc 180
agaaggagtc tttgcatcaa aaaaagcagc aagcatcttt atgcaccgtc gcctcctata 240
caatagattt gatttagaac tcttcactcc cgggaacctg gagagagagt gctatgagga 300
gttctgtagt tatgaagaag ccagagagat cctcggggac aacgaagaaa tgatcacatt 360
ctggcgggaa tattcagtca aggaccaac cacaagatca gatgtcaaca aagagaaaat 420
tgatgttatg ggccttctga ctggcttaat tgcggctgga gtattcttgg ttgtttttgg 480
cttacttggt tactatctgt gtatcaccaa gtgtaatagg cagccatatc aaggttcttc 540
agctgtctac acaagaagga ccaggcacac accgtccatc attttcagaa cccatgagga 600
agctgtcttg tctccatcgt catcctcaga ggacgcggga ctaccttcct atgaacaggc 660
agtagctctg accagaaaac acagtgtctc accaccacct ccatatcctg ggccagcaaa 720
aggatttagg gtatttaaaa agtcaatgtc actcccatct cactaagccc accttgccgc 780
cttgctgtgg tctgaataat atgttcttcc tgaaacaaca acaacaaaaa aatttgcctg 840
ttcagctttt tatgacaaag cacaaggaat aaaggaacac tatatacaga acagaattca 900
ccacagcccc gctttcagct ctgcccccaa ctggattgct gtcttggtaa gagacttcta 960
ccgtgcttcc tcgaagttaa gaagaaagtg cctttttgca atgtaaactg tactggttca 1020
aacattcttg ctacagctag gtacctataa tccccacctt caggagactt aggcgggagg 1080
gatgagagtt caaggccagc ctgggccctg tcaggacgct gtctcaaaac aaagtttgtt 1140
atcaatagaa taattagaat taacaaacta ggattttcag tcttaagtca tgatattgga 1200
tcttctcttc agtaaggttt ctttttggct agaaatactt catagaattt gacattttgg 1260
tatacatctg tggccttgat acaatgactt gattttctgt tttaattagt gcagaggatt 1320
cagcaaattt gcaggtcttc attttgttcc ctcgctatcc atcgatcatg tttcagtgta 1380
ttaagaggag tcagccaggc gtggtggccc acacctgtga tcccagcact tagggggca 1440 taggcaggca gatctctgtg agctgaagga cagcctggcc tacaaagtcc aggacaaccg 1500
agaccacaca gagaaacctt gtcttgaaaa acaaaacaaa aacaagagag agagagagag 1560
agagagaaaa gagatgtcaa gaggtttttg tttttttttt tttaaattac tatttatggg 1620
cctcacttgg aaaagtgctt gccatgcaaa tagaaggaca ggagttcaat cctcattacc 1680
cacatttgaa acaaataaca agaaaaacaa accaaaaaac caaaacaaac aaaatcttga 1740
gaacttgagt gaataccggt aacctcaggg ctaggcactg taactgaatc aggagcctcc 1800
agatccaggg aaacgctgtc tcaacaaata aataaataag taagtcagtg aggtggtctt 1860
taaacccagc acttgagagc caaaggcagg cagagctcag tgagttggag accagcctgg 1920
tctacaaagc aagttctaag ggagccaggg cacagagaaa ccctgtctga aggaaaaaaa 1980

-continued

```
aaaaaaaaaa aagggcggcc gc                                             2002

<210> SEQ ID NO 82
<211> LENGTH: 675
<212> TYPE: DNA
<213> ORGANISM: gerbil

<400> SEQUENCE: 82

atgtttctgc ttctggtggt actcagccag ctgcccagac ttaccctcgc ggttcctcat     60

acaagaagcc taaagaattc tgaacatgcc ccagaaggag tctttgcatc aaaaaaagca    120

gcaagcatct ttatgcaccg tcgcctccta tacaatagat ttgatttaga actcttcact    180

cccgggaacc tggagagaga gtgctatgag gagttctgta gttatgaaga agccagagag    240

atcctcgggg acaacgaaga aatgatcaca ttctggcggg aatattcagt caaaggacca    300

accacaagat cagatgtcaa caaagagaaa attgatgtta tgggccttct gactggctta    360

attgcggctg gagtattctt ggttgttttt ggcttacttg gttactatct gtgtatcacc    420

aagtgtaata ggcagccata tcaaggttct tcagctgtct acacaagaag gaccaggcac    480

acaccgtcca tcattttcag aacccatgag gaagctgtct tgtctccatc gtcatcctca    540

gaggacgcgg gactaccttc ctatgaacag gcagtagctc tgaccagaaa acacagtgtc    600

tcaccaccac ctccatatcc tgggccagca aaaggattta gggtatttaa aaagtcaatg    660

tcactcccat ctcac                                                     675

<210> SEQ ID NO 83
<211> LENGTH: 225
<212> TYPE: PRT
<213> ORGANISM: gerbil

<400> SEQUENCE: 83

Met Phe Leu Leu Leu Val Val Leu Ser Gln Leu Pro Arg Leu Thr Leu
1               5                   10                  15

Ala Val Pro His Thr Arg Ser Leu Lys Asn Ser Glu His Ala Pro Glu
            20                  25                  30

Gly Val Phe Ala Ser Lys Lys Ala Ala Ser Ile Phe Met His Arg Arg
        35                  40                  45

Leu Leu Tyr Asn Arg Phe Asp Leu Glu Leu Phe Thr Pro Gly Asn Leu
    50                  55                  60

Glu Arg Glu Cys Tyr Glu Glu Phe Cys Ser Tyr Glu Glu Ala Arg Glu
65                  70                  75                  80

Ile Leu Gly Asp Asn Glu Glu Met Ile Thr Phe Trp Arg Glu Tyr Ser
                85                  90                  95

Val Lys Gly Pro Thr Thr Arg Ser Asp Val Asn Lys Glu Lys Ile Asp
            100                 105                 110

Val Met Gly Leu Leu Thr Gly Leu Ile Ala Ala Gly Val Phe Leu Val
        115                 120                 125

Val Phe Gly Leu Leu Gly Tyr Tyr Leu Cys Ile Thr Lys Cys Asn Arg
    130                 135                 140

Gln Pro Tyr Gln Gly Ser Ser Ala Val Tyr Thr Arg Arg Thr Arg His
145                 150                 155                 160

Thr Pro Ser Ile Ile Phe Arg Thr His Glu Glu Ala Val Leu Ser Pro
                165                 170                 175

Ser Ser Ser Ser Glu Asp Ala Gly Leu Pro Ser Tyr Glu Gln Ala Val
            180                 185                 190
```

-continued

```
Ala Leu Thr Arg Lys His Ser Val Ser Pro Pro Pro Pro Tyr Pro Gly
        195                 200                 205

Pro Ala Lys Gly Phe Arg Val Phe Lys Lys Ser Met Ser Leu Pro Ser
    210                 215                 220

His
225


<210> SEQ ID NO 84
<211> LENGTH: 17
<212> TYPE: PRT
<213> ORGANISM: gerbil

<400> SEQUENCE: 84

Met Phe Leu Leu Leu Val Val Leu Ser Gln Leu Pro Arg Leu Thr Leu
1               5                   10                  15

Ala


<210> SEQ ID NO 85
<211> LENGTH: 208
<212> TYPE: PRT
<213> ORGANISM: gerbil

<400> SEQUENCE: 85

Val Pro His Thr Arg Ser Leu Lys Asn Ser Glu His Ala Pro Glu Gly
1               5                   10                  15

Val Phe Ala Ser Lys Lys Ala Ala Ser Ile Phe Met His Arg Arg Leu
            20                  25                  30

Leu Tyr Asn Arg Phe Asp Leu Glu Leu Phe Thr Pro Gly Asn Leu Glu
        35                  40                  45

Arg Glu Cys Tyr Glu Glu Phe Cys Ser Tyr Glu Glu Ala Arg Glu Ile
    50                  55                  60

Leu Gly Asp Asn Glu Glu Met Ile Thr Phe Trp Arg Glu Tyr Ser Val
65                  70                  75                  80

Lys Gly Pro Thr Thr Arg Ser Asp Val Asn Lys Glu Lys Ile Asp Val
                85                  90                  95

Met Gly Leu Leu Thr Gly Leu Ile Ala Ala Gly Val Phe Leu Val Val
            100                 105                 110

Phe Gly Leu Leu Gly Tyr Tyr Leu Cys Ile Thr Lys Cys Asn Arg Gln
        115                 120                 125

Pro Tyr Gln Gly Ser Ser Ala Val Tyr Thr Arg Arg Thr Arg His Thr
    130                 135                 140

Pro Ser Ile Ile Phe Arg Thr His Glu Glu Ala Val Leu Ser Pro Ser
145                 150                 155                 160

Ser Ser Ser Glu Asp Ala Gly Leu Pro Ser Tyr Glu Gln Ala Val Ala
                165                 170                 175

Leu Thr Arg Lys His Ser Val Ser Pro Pro Pro Pro Tyr Pro Gly Pro
            180                 185                 190

Ala Lys Gly Phe Arg Val Phe Lys Lys Ser Met Ser Leu Pro Ser His
        195                 200                 205


<210> SEQ ID NO 86
<211> LENGTH: 95
<212> TYPE: PRT
<213> ORGANISM: gerbil

<400> SEQUENCE: 86

Val Pro His Thr Arg Ser Leu Lys Asn Ser Glu His Ala Pro Glu Gly
1               5                   10                  15
```

-continued

Val Phe Ala Ser Lys Lys Ala Ala Ser Ile Phe Met His Arg Arg Leu
            20                  25                  30

Leu Tyr Asn Arg Phe Asp Leu Glu Leu Phe Thr Pro Gly Asn Leu Glu
        35                  40                  45

Arg Glu Cys Tyr Glu Glu Phe Cys Ser Tyr Glu Glu Ala Arg Glu Ile
    50                  55                  60

Leu Gly Asp Asn Glu Glu Met Ile Thr Phe Trp Arg Glu Tyr Ser Val
65                  70                  75                  80

Lys Gly Pro Thr Thr Arg Ser Asp Val Asn Lys Glu Lys Ile Asp
                85                  90                  95

<210> SEQ ID NO 87
<211> LENGTH: 25
<212> TYPE: PRT
<213> ORGANISM: gerbil

<400> SEQUENCE: 87

Val Met Gly Leu Leu Thr Gly Leu Ile Ala Ala Gly Val Phe Leu Val
1               5                   10                  15

Val Phe Gly Leu Leu Gly Tyr Tyr Leu
            20                  25

<210> SEQ ID NO 88
<211> LENGTH: 88
<212> TYPE: PRT
<213> ORGANISM: gerbil

<400> SEQUENCE: 88

Cys Ile Thr Lys Cys Asn Arg Gln Pro Tyr Gln Gly Ser Ser Ala Val
1               5                   10                  15

Tyr Thr Arg Arg Thr Arg His Thr Pro Ser Ile Ile Phe Arg Thr His
            20                  25                  30

Glu Glu Ala Val Leu Ser Pro Ser Ser Ser Ser Glu Asp Ala Gly Leu
        35                  40                  45

Pro Ser Tyr Glu Gln Ala Val Ala Leu Thr Arg Lys His Ser Val Ser
    50                  55                  60

Pro Pro Pro Pro Tyr Pro Gly Pro Ala Lys Gly Phe Arg Val Phe Lys
65                  70                  75                  80

Lys Ser Met Ser Leu Pro Ser His
                85

<210> SEQ ID NO 89
<211> LENGTH:
<212> TYPE:
<213> ORGANISM:

<400> SEQUENCE: 89

000

<210> SEQ ID NO 90
<211> LENGTH:
<212> TYPE:
<213> ORGANISM:

<400> SEQUENCE: 90

000

<210> SEQ ID NO 91
<211> LENGTH:

-continued

<212> TYPE:
<213> ORGANISM:

<400> SEQUENCE: 91

000

<210> SEQ ID NO 92
<211> LENGTH: 962
<212> TYPE: DNA
<213> ORGANISM: Mus sp.

<400> SEQUENCE: 92

```
ccgtttctct ttaaccactt gcacggtctg ggttaaccc gcctgcggac tctggacctc     60

tcctccaact ggctgaaaca tatctccatc cctgagttgg ctgcactgcc aacttatctc    120

aagaacaggc tctacctgca caacaacccg ctgccctgtg actgcagcct ctaccacctg    180

ctccggcgct ggcaccagcg gggcctgagt gccctgcatg attttgaacg cgagtacaca    240

tgcttggtct ttaaggtgtc agagtcccga gtgcgctttt ttgagcacag ccgggtcttc    300

aagaactgct ctgtggctgc agctccaggc ttagagctgc ctgaagagca gctgcacgcg    360

caggtgggcc agtccctgag gctcttctgc aacaccagtg tgcctgccac tcgggtggcc    420

tgggtctccc cgaagaatga gctgcttgtg gcgccagcct ctcaggatgg tagcatcgct    480

gtgttggctg atggcagctt agccataggc agggtgcaag agcagcacgc aggcgtcttt    540

gtgtgcctgg ccagtgggcc ccgcctgcac cacaaccaga cacttgagta caatgtgagt    600

gtgcaaaagg ctcgccccga gccagagact ttcaacacag gctttaccac cctgctgggc    660

tgtattgtgg gcctggtgct ggtgttgctc tacttgtttg caccaccctg tcgtggctgc    720

tgtcactgct gtcagcgggc ctgccgcaac cgttgctggc cccgggcatc cagtccactc    780

caggagctga gcgcacagtc ctccatgctt agcactacgc caccagatgc acccagccgc    840

aaggccagtg tccacaagca tgtggtcttc ctggagccgg gcaagaaggg cctcaatggc    900

cgtgtgcagc tcgcagtacc tccagactcc gatctgtgca accccatggg cttgcaactc    960

aa                                                                   962
```

<210> SEQ ID NO 93
<211> LENGTH: 320
<212> TYPE: PRT
<213> ORGANISM: Mus sp.

<400> SEQUENCE: 93

```
Pro Phe Leu Phe Asn His Leu His Gly Leu Gly Leu Thr Arg Leu Arg
1               5                   10                  15

Thr Leu Asp Leu Ser Ser Asn Trp Leu Lys His Ile Ser Ile Pro Glu
            20                  25                  30

Leu Ala Ala Leu Pro Thr Tyr Leu Lys Asn Arg Leu Tyr Leu His Asn
        35                  40                  45

Asn Pro Leu Pro Cys Asp Cys Ser Leu Tyr His Leu Leu Arg Arg Trp
    50                  55                  60

His Gln Arg Gly Leu Ser Ala Leu His Asp Phe Glu Arg Glu Tyr Thr
65                  70                  75                  80

Cys Leu Val Phe Lys Val Ser Glu Ser Arg Val Arg Phe Phe Glu His
                85                  90                  95

Ser Arg Val Phe Lys Asn Cys Ser Val Ala Ala Ala Pro Gly Leu Glu
            100                 105                 110

Leu Pro Glu Glu Gln Leu His Ala Gln Val Gly Gln Ser Leu Arg Leu
```

-continued

```
        115                 120                 125

Phe Cys Asn Thr Ser Val Pro Ala Thr Arg Val Ala Trp Val Ser Pro
    130                 135                 140

Lys Asn Glu Leu Leu Val Ala Pro Ala Ser Gln Asp Gly Ser Ile Ala
145                 150                 155                 160

Val Leu Ala Asp Gly Ser Leu Ala Ile Gly Arg Val Gln Glu Gln His
                165                 170                 175

Ala Gly Val Phe Val Cys Leu Ala Ser Gly Pro Arg Leu His His Asn
            180                 185                 190

Gln Thr Leu Glu Tyr Asn Val Ser Val Gln Lys Ala Arg Pro Glu Pro
        195                 200                 205

Glu Thr Phe Asn Thr Gly Phe Thr Thr Leu Leu Gly Cys Ile Val Gly
    210                 215                 220

Leu Val Leu Val Leu Leu Tyr Leu Phe Ala Pro Pro Cys Arg Gly Cys
225                 230                 235                 240

Cys His Cys Cys Gln Arg Ala Cys Arg Asn Arg Cys Trp Pro Arg Ala
                245                 250                 255

Ser Ser Pro Leu Gln Glu Leu Ser Ala Gln Ser Ser Met Leu Ser Thr
            260                 265                 270

Thr Pro Pro Asp Ala Pro Ser Arg Lys Ala Ser Val His Lys His Val
        275                 280                 285

Val Phe Leu Glu Pro Gly Lys Lys Gly Leu Asn Gly Arg Val Gln Leu
    290                 295                 300

Ala Val Pro Pro Asp Ser Asp Leu Cys Asn Pro Met Gly Leu Gln Leu
305                 310                 315                 320


<210> SEQ ID NO 94
<211> LENGTH: 16
<212> TYPE: PRT
<213> ORGANISM: Mus sp.

<400> SEQUENCE: 94

Pro Phe Leu Phe Asn His Leu His Gly Leu Gly Leu Thr Arg Leu Arg
1               5                   10                  15


<210> SEQ ID NO 95
<211> LENGTH: 304
<212> TYPE: PRT
<213> ORGANISM: Mus sp.

<400> SEQUENCE: 95

Thr Leu Asp Leu Ser Ser Asn Trp Leu Lys His Ile Ser Ile Pro Glu
1               5                   10                  15

Leu Ala Ala Leu Pro Thr Tyr Leu Lys Asn Arg Leu Tyr Leu His Asn
            20                  25                  30

Asn Pro Leu Pro Cys Asp Cys Ser Leu Tyr His Leu Leu Arg Arg Trp
        35                  40                  45

His Gln Arg Gly Leu Ser Ala Leu His Asp Phe Glu Arg Glu Tyr Thr
    50                  55                  60

Cys Leu Val Phe Lys Val Ser Glu Ser Arg Val Arg Phe Phe Glu His
65                  70                  75                  80

Ser Arg Val Phe Lys Asn Cys Ser Val Ala Ala Ala Pro Gly Leu Glu
                85                  90                  95

Leu Pro Glu Glu Gln Leu His Ala Gln Val Gly Gln Ser Leu Arg Leu
            100                 105                 110

Phe Cys Asn Thr Ser Val Pro Ala Thr Arg Val Ala Trp Val Ser Pro
```

-continued

```
        115                 120                 125

Lys Asn Glu Leu Leu Val Ala Pro Ala Ser Gln Asp Gly Ser Ile Ala
    130                 135                 140

Val Leu Ala Asp Gly Ser Leu Ala Ile Gly Arg Val Gln Glu Gln His
145                 150                 155                 160

Ala Gly Val Phe Val Cys Leu Ala Ser Gly Pro Arg Leu His His Asn
                165                 170                 175

Gln Thr Leu Glu Tyr Asn Val Ser Val Gln Lys Ala Arg Pro Glu Pro
            180                 185                 190

Glu Thr Phe Asn Thr Gly Phe Thr Thr Leu Leu Gly Cys Ile Val Gly
        195                 200                 205

Leu Val Leu Val Leu Leu Tyr Leu Phe Ala Pro Pro Cys Arg Gly Cys
    210                 215                 220

Cys His Cys Cys Gln Arg Ala Cys Arg Asn Arg Cys Trp Pro Arg Ala
225                 230                 235                 240

Ser Ser Pro Leu Gln Glu Leu Ser Ala Gln Ser Ser Met Leu Ser Thr
                245                 250                 255

Thr Pro Pro Asp Ala Pro Ser Arg Lys Ala Ser Val His Lys His Val
            260                 265                 270

Val Phe Leu Glu Pro Gly Lys Lys Gly Leu Asn Gly Arg Val Gln Leu
        275                 280                 285

Ala Val Pro Pro Asp Ser Asp Leu Cys Asn Pro Met Gly Leu Gln Leu
    290                 295                 300


<210> SEQ ID NO 96
<211> LENGTH: 197
<212> TYPE: PRT
<213> ORGANISM: Mus sp.

<400> SEQUENCE: 96

Thr Leu Asp Leu Ser Ser Asn Trp Leu Lys His Ile Ser Ile Pro Glu
1               5                   10                  15

Leu Ala Ala Leu Pro Thr Tyr Leu Lys Asn Arg Leu Tyr Leu His Asn
            20                  25                  30

Asn Pro Leu Pro Cys Asp Cys Ser Leu Tyr His Leu Leu Arg Arg Trp
        35                  40                  45

His Gln Arg Gly Leu Ser Ala Leu His Asp Phe Glu Arg Glu Tyr Thr
    50                  55                  60

Cys Leu Val Phe Lys Val Ser Glu Ser Arg Val Arg Phe Phe Glu His
65                  70                  75                  80

Ser Arg Val Phe Lys Asn Cys Ser Val Ala Ala Ala Pro Gly Leu Glu
                85                  90                  95

Leu Pro Glu Glu Gln Leu His Ala Gln Val Gly Gln Ser Leu Arg Leu
            100                 105                 110

Phe Cys Asn Thr Ser Val Pro Ala Thr Arg Val Ala Trp Val Ser Pro
        115                 120                 125

Lys Asn Glu Leu Leu Val Ala Pro Ala Ser Gln Asp Gly Ser Ile Ala
    130                 135                 140

Val Leu Ala Asp Gly Ser Leu Ala Ile Gly Arg Val Gln Glu Gln His
145                 150                 155                 160

Ala Gly Val Phe Val Cys Leu Ala Ser Gly Pro Arg Leu His His Asn
                165                 170                 175

Gln Thr Leu Glu Tyr Asn Val Ser Val Gln Lys Ala Arg Pro Glu Pro
            180                 185                 190
```

-continued

```
Glu Thr Phe Asn Thr
        195


<210> SEQ ID NO 97
<211> LENGTH: 20
<212> TYPE: PRT
<213> ORGANISM: Mus sp.

<400> SEQUENCE: 97

Gly Phe Thr Thr Leu Leu Gly Cys Ile Val Gly Leu Val Leu Val Leu
1               5                   10                  15

Leu Tyr Leu Phe
            20


<210> SEQ ID NO 98
<211> LENGTH: 87
<212> TYPE: PRT
<213> ORGANISM: Mus sp.

<400> SEQUENCE: 98

Ala Pro Pro Cys Arg Gly Cys Cys His Cys Cys Gln Arg Ala Cys Arg
1               5                   10                  15

Asn Arg Cys Trp Pro Arg Ala Ser Ser Pro Leu Gln Glu Leu Ser Ala
            20                  25                  30

Gln Ser Ser Met Leu Ser Thr Thr Pro Pro Asp Ala Pro Ser Arg Lys
        35                  40                  45

Ala Ser Val His Lys His Val Val Phe Leu Glu Pro Gly Lys Lys Gly
    50                  55                  60

Leu Asn Gly Arg Val Gln Leu Ala Val Pro Pro Asp Ser Asp Leu Cys
65                  70                  75                  80

Asn Pro Met Gly Leu Gln Leu
                85


<210> SEQ ID NO 99
<211> LENGTH: 24
<212> TYPE: DNA
<213> ORGANISM: artificial sequence
<220> FEATURE:
<223> OTHER INFORMATION: TANGO 331 human radiation panel forward primer

<400> SEQUENCE: 99

attattcaga aggatgtccc gtgg                                            24


<210> SEQ ID NO 100
<211> LENGTH: 23
<212> TYPE: DNA
<213> ORGANISM: artificial sequence
<220> FEATURE:
<223> OTHER INFORMATION: TANGO 331 human radiation panel reverse primer

<400> SEQUENCE: 100

cctcctgatt acctacaatg gtc                                             23
```

TANGO 332 POLYPEPTIDES

CROSS REFERENCE TO RELATED APPLICATIONS

This application is a divisional of U.S. patent application Ser. No. 09/596,194, filed Jun. 16, 2000, now abandoned, which is a continuation-in-part of U.S. patent application Ser. No. 09/342,364, filed Jun. 29, 1999, now abandoned.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

The molecular bases underlying many human and animal physiological states (e.g., diseased and homeostatic states of various tissues) remain unknown. Nonetheless, it is well understood that these states result from interactions among the proteins and nucleic acids present in the cells of the relevant tissues. In the past, the complexity of biological systems overwhelmed the ability of practitioners to understand the molecular interactions giving rise to normal and abnormal physiological states. More recently, though, the techniques of molecular biology, transgenic and null mutant animal production, computational biology, pharmacogenomics, and the like have enabled practitioners to discern the role and importance of individual genes and proteins in particular physiological states.

Knowledge of the sequences and other properties of genes (particularly including the portions of genes encoding proteins) and the proteins encoded thereby enables the practitioner to design and screen agents which will affect, prospectively or retrospectively, the physiological state of an animal tissue in a favorable way. Such knowledge also enables the practitioner, by detecting the levels of gene expression and protein production, to diagnose the current physiological state of a tissue or animal and to predict such physiological states in the future. This knowledge furthermore enables the practitioner to identify and design molecules which bind with the polynucleotides and proteins, in vitro, in vivo, or both.

The present invention provides sequence information for polynucleotides derived from human genes and for proteins encoded thereby, and thus enables the practitioner to assess, predict, and affect the physiological state of various human tissues.

BRIEF SUMMARY OF THE INVENTION

The present invention is based, at least in part, on the discovery of a variety of human cDNA molecules which encode proteins which are herein designated INTERCEPT 217, INTERCEPT 297, TANGO 276, TANGO 292, TANGO 325, TANGO 331, and TANGO 332. These seven proteins, fragments thereof, derivatives thereof, and variants thereof are collectively referred to herein as the polypeptides of the invention or the proteins of the invention. Nucleic acid molecules encoding polypeptides of the invention are collectively referred to as nucleic acids of the invention.

The nucleic acids and polypeptides of the present invention are useful as modulating agents in regulating a variety of cellular processes. Accordingly, in one aspect, the present invention provides isolated nucleic acid molecules encoding a polypeptide of the invention or a biologically active portion thereof. The present invention also provides nucleic acid molecules which are suitable as primers or hybridization probes for the detection of nucleic acids encoding a polypeptide of the invention.

The nucleic acids and polypeptides of the present invention are useful as modulating agents in regulating a variety of cellular processes. Accordingly, in one aspect, the present invention provides isolated nucleic acid molecules encoding a polypeptide of the invention or a biologically active portion thereof. The present invention also provides nucleic acid molecules which are suitable as primers or hybridization probes for the detection of nucleic acids encoding a polypeptide of the invention.

The invention also features nucleic acid molecules which are at least 40% (or 50%, 60%, 70%, 80%, 90%, 95%, or 98%) identical to the nucleotide sequence of any of SEQ ID NOs: 1, 2, 9, 10, 33, 34, 38, 39, 46, 47, 54, 55, 59, 60, 81, 82, and 92, or the nucleotide sequence of a cDNA clone deposited with ATCC® as one of Accession numbers PTA-147, PTA-150, 207230, and PTA-151 ("a cDNA of a clone deposited as ATCC® PTA-147, PTA-150, 207230, or PTA-151"), or a complement thereof.

The invention features nucleic acid molecules which include a fragment of at least 15 (25, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or 4928) consecutive nucleotide residues of any of SEQ ID NOs: 1, 2, 9, 10, 33, 34, 38, 39, 46, 47, 54, 55, 59, 60, 81, 82, and 92, or a cDNA of a clone deposited as ATCC® PTA-147, PTA-150, 207230, or PTA-151, or a complement thereof.

The invention also features nucleic acid molecules which include a nucleotide sequence encoding a protein having an amino acid sequence that is at least 50% (or 60%, 70%, 80%, 90%, 95%, or 98%) identical to the amino acid sequence of any of SEQ ID NOs: 3–8, 11–32, 35–37, 40–45, 48–53, 56–58, 61–63, 83–88, and 93–98, or the amino acid sequence encoded by a cDNA of a clone deposited as ATCC® PTA-147, PTA-150, 207230, or PTA-151, or a complement thereof.

In preferred embodiments, the nucleic acid molecules have the nucleotide sequence of any of SEQ ID NOs: 1, 2, 9, 10, 33, 34, 38, 39, 46, 47, 54, 55, 59, 60, 81, 82, and 92, or a cDNA of a clone deposited as ATCC® PTA-147, PTA-150, 207230, or PTA-151.

Also within the invention are nucleic acid molecules which encode a fragment of a polypeptide having the amino acid sequence of any of SEQ ID NOs. 3–8, 11–32, 35–37, 40–45, 48–53, 56–58, 61–63, 83–88, and 93–98, or the amino acid sequence encoded by a cDNA of a clone deposited as ATCC® PTA-147, PTA-150, 207230, or PTA-151, the fragment including at least 8 (10, 15, 20, 25, 30, 40, 50, 75, 100, 125, 150, or 200) consecutive amino acids of any of SEQ ID NOs: 3–8, 11–32, 35–37, 40–45, 48–53, 56–58, 61–63, 83–88, and 93–98, acid sequence encoded by a cDNA of a clone deposited as ATCC® PTA-147, PTA-150, 207230, or PTA-151.

The invention includes nucleic acid molecules which encode a naturally occurring allelic variant of a polypeptide comprising the amino acid sequence of any of SEQ ID NOs: 3–8, 11–32, 35–37, 40–45, 48–53, 56–58, 61–63, 83–88, and 93–98, or the amino acid sequence encoded by a cDNA of a clone deposited as one of ATCC® PTA-147, PTA-150, 207230, and PTA-151, wherein the nucleic acid molecule hybridizes under stringent conditions to a nucleic acid molecule having a nucleic acid sequence encoding any of SEQ ID NOs: 1, 2, 9, 10, 33, 34, 38, 39, 46, 47, 54, 55, 59, 60, 81, 82, and 92, or a cDNA of a clone deposited as ATCC® PTA-147, PTA-150, 207230, or PTA-151, or a complement thereof.

Also within the invention are isolated polypeptides or proteins having an amino acid sequence that is at least about 50%, preferably 60%, 75%, 90%, 95%, or 98% identical to the amino acid sequence of any of SEQ ID NOs: 3–8, 11–32, 35–37, 40–45, 48–53, 56–58, 61–63, 83-88, and 93–98.

Also within the invention are isolated polypeptides or proteins which are encoded by a nucleic acid molecule having a nucleotide sequence that is at least about 40%, preferably 50%, 75%, 85%, or 95% identical the nucleic acid sequence encoding any of SEQ ID NOs: 3–8, 11–32, 35–37, 40–45, 48–53, 56–58, 61–63, 83–88, and 93–98, and isolated polypeptides proteins which are encoded by a nucleic acid molecule consisting of the nucleotide sequence which hybridizes under stringent hybridization conditions to a nucleic acid molecule having the nucleotide sequence of any of SEQ ID NOs: 1, 2, 9, 10, 33, 34, 38, 39, 46, 47, 54, 55, 59, 60, 81, 82, and 92.

Also within the invention are polypeptides which are naturally occurring allelic variants of a polypeptide that includes the amino acid sequence of any of SEQ ID NOs: 3–8, 11–32, 35–37, 40–45, 48–53, 56–58, 61–63, 83–88, and 93–98, or the amino acid sequence encoded by a cDNA of a clone deposited as ATCC® PTA-147, PTA-150, 207230, or PTA-151, wherein the polypeptide is encoded by a nucleic acid molecule which hybridizes under stringent conditions to a nucleic acid molecule having the nucleotide sequence of any of SEQ ID NOs: 1, 2, 9, 10, 33, 34, 38, 39, 46, 47, 54, 55, 59, 60, 81, 82, and 92, or a complement thereof.

The invention also features nucleic acid molecules that hybridize under stringent conditions to a nucleic acid molecule having the nucleotide sequence of any of SEQ ID NOs: 1, 2, 9, 10, 33, 34, 38, 39, 46, 47, 54, 55, 59, 60, 81, 82, and 92, or a cDNA of a clone deposited as ATCC® PTA-147, PTA-150, 207230, or PTA-151, or a complement thereof. In other embodiments, the nucleic acid molecules are at least 15 (25, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or 4928) nucleotides in length and hybridize under stringent conditions to a nucleic acid molecule having the nucleotide sequence of any of SEQ ID NOs: 1, 2, 9, 10, 33, 34, 38, 39, 46, 47, 54, 55, 59, 60, 81, 82, and 92, or a cDNA of a clone deposited as ATCC® PTA-147, PTA-150, 207230, or PTA-151, or a complement thereof. In some embodiments, the isolated nucleic acid molecules encode a cytoplasmic, transmembrane, extracellular, or other domain of a polypeptide of the invention. In other embodiments, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. In another embodiment, the invention provides isolated host cells, e.g., mammalian and non-mammalian cells, containing such a vector or a nucleic acid of the invention. The invention also provides methods for producing a polypeptide of the invention by culturing, in a suitable medium, a host cell of the invention containing a recombinant expression vector encoding a polypeptide of the invention such that the polypeptide of the invention is produced.

Another aspect of this invention features isolated or recombinant proteins and polypeptides of the invention. Preferred proteins and polypeptides possess at least one biological activity possessed by the corresponding naturally-occurring human polypeptide. An activity, a biological activity, and a functional activity of a polypeptide of the invention refers to an activity exerted by a protein or polypeptide of the invention on a responsive cell as determined in vivo, or in vitro, according to standard techniques. Such activities can be a direct activity, such as an association with or an enzymatic activity on a second protein or an indirect activity, such as a cellular processes mediated by interaction of the protein with a second protein.

By way of example, INTERCEPT 217 polypeptides, nucleic acids, and modulators thereof exhibit the ability to affect growth, proliferation, survival, differentiation, and activity of human pancreas, skeletal muscle, heart, brain, placenta, lung, liver, and kidney cells. INTERCEPT 217 modulates cellular binding to one or more mediators, modulates activity and release of one or more pancreatically secreted digestive enzymes, and protects tissue from endogenous digestive enzymes. Thus, INTERCEPT 217 polypeptides, nucleic acids, and modulators thereof can be used to prevent, diagnose, or treat disorders relating to aberrant endogenous digestive enzyme activity, inappropriate interaction (or non-interaction) of cells with mediators, inappropriate cellular development and proliferation, inappropriate inflammation, and inappropriate immune responses. Exemplary disorders for which INTERCEPT 217 polypeptides, nucleic acids, and modulators thereof are useful include immune disorders (e.g., insufficient immune responses and auto-immune disorders), infectious diseases, auto-immune disorders, pancreatic disorders (e.g., pancreatitis and pancreatic carcinoma), disorders related to malexpression of growth factors, cancers, inflammatory disorders, acute and chronic traumas, and the like.

Further by way of example, INTERCEPT 297 polypeptides, nucleic acids, and modulators thereof exhibit the ability to affect growth, proliferation, survival, differentiation, and activity of human fetal cells and spleen cells and of (e.g., bacterial or fungal) cells and viruses which infect humans. Furthermore, INTERCEPT 297 modulates organization, structure, and function of biological membranes. Thus, INTERCEPT 297 polypeptides, nucleic acids, and modulators thereof can be used to affect development and persistence of atherogenesis and arteriosclerosis, for example, or to modulate transmembrane transport processes such as ion transport across neuronal and muscle cell membranes (e.g., ion transport relating to nerve impulse conduction and muscle contraction). INTERCEPT 297 polypeptides, nucleic acids, and modulators thereof can be used to prevent, diagnose, or treat transmembrane transport disorders such as cystic fibrosis, pain, seizure, epilepsy, mental disorders, and the like. Other exemplary disorders for which INTERCEPT 297 polypeptides, nucleic acids, and modulators thereof are useful include disorders involving generation and persistence of an immune response to bacterial, fungal, and viral infections.

Still further by way of example, TANGO 276 polypeptides, nucleic acids, and modulators thereof modulate growth, proliferation, survival, differentiation, and activity of human heart, placenta, brain, lung, liver, skin, kidney, pancreas, spleen, and fetal tissues. TANGO 276 guides neuronal growth and development and modulates growth, homeostasis, and regeneration of other epithelial tissues. TANGO 276 is a secreted protein which mediates cellular interaction with cells, molecules, and structures (e.g., extracellular matrix) in the extracellular environment. TANGO 276 is therefore involved in growth, organization, migration, and adhesion of tissues and the cells which constitute those tissues. Furthermore, TANGO 276 modulates growth, proliferation, survival, differentiation, and activity of neuronal cells and immune system cells. Thus, TANGO 276 polypeptides, nucleic acids, and modulators thereof can be used, for example, to prevent, diagnose, or treat disorders characterized by aberrant organization or development of a tissue or organ, for modulating migration and adhesion of cells (e.g., in disorders such as cancer metastasis, autoimmune disorders, and graft-versus-host disease or in normal or aberrant processes involving angiogenesis, such as tumor growth and persistence), for guiding neural axon development and regeneration, for modulating differentiation of cells of the immune system (e.g., to treat bacterial, fungal, or viral infection or to prevent, diagnose, or treat autoimmune disorders), for modulating cytokine production by cells of the immune system (e.g., to prevent, detect, or treat inflammation and pain), for modulating reactivity of cells of the immune system toward cytokines, for modulating initiation and persistence of an inflammatory response, and for modulating proliferation of epithelial cells.

Yet further by way of example, TANGO 292 polypeptides, nucleic acids, and modulators thereof modulate growth, proliferation, survival, differentiation, and activity of human keratinocytes, including embryonic keratinocytes. TANGO 292, a transmembrane protein, is also involved in binding and uptake of calcium and other metal ions, and in responses of cells which express it to the presence and uptake of such ions. TANGO 292 polypeptides, nucleic acids, and modulators thereof can therefore be used to prevent, diagnose, and treat disorders involving one or more physiological activities mediated by TANGO 292 protein. These activities include, for example, bone uptake, maintenance, and deposition, formation, maintenance, and repair of cartilage and skin, formation and maintenance of extracellular matrices, movement of cells through extracellular matrices, coagulation and dissolution of blood components, and deposition of materials in and on arterial walls. TANGO 292 is also related to a variety of disorders which involve these activities. Such disorders include, for example, various bone-related disorders such as osteoporosis, skeletal development disorders, bone fragility, traumatic bone injuries, rickets, osteomalacia, Paget's disease, and other bone disorders, osteoarthritis, rheumatoid arthritis, ankylosing spondylitis, and other disorders of the joints and cartilage, skin disorders such as psoriasis, eczema, scleroderma, and skin tumors (e.g., keratoses, squamous cell carcinomas, malignant melanomas, and Kaposi's sarcomas), iron deficiency anemia, hemophilia, inappropriate blood coagulation, stroke, arteriosclerosis, atherosclerosis, aneurysm, and other disorders related to blood and blood vessels, metastasis and other disorders related to inappropriate movement of cells through extracellular matrices, and the like. TANGO 292 polypeptides, nucleic acids, and modulators thereof can thus be used to prevent, diagnose, and treat one or more of these disorders. TANGO 292 is also involved in skin disorders such as psoriasis, eczema, scleroderma, skin tumors (e.g., keratoses, squamous cell carcinomas, malignant melanomas, and Kaposi's sarcomas), in placental disorders such as placenta previa and abruptio placentae, in liver disorders such as cirrhosis of the liver, liver fibrosis, hepatitis, and hepatic cancers, in kidney disorders such as urolithiasis, glomerulonephritis, nephrosis, renal cell carcinomas, and renal failure (both acute and chronic), in lung disorders such as cystic fibrosis, chronic obstructive pulmonary diseases (e.g., emphysema, bronchitis, and bronchiectasis), lung cancers, and asthma, in pancreatic disorders such as diabetes, pancreatitis, pancreatic cancers, and pancreatic insufficiency, in cardiac disorders such as coronary artery disease (and other ischemic heart diseases), arrhythmia, congestive heart failure, endocarditis, and pericarditis, and the like. Thus, TANGO 292 polypeptides, nucleic acids, and modulators thereof can thus be used to prevent, diagnose, and treat one or more of these disorders.

As an additional example, TANGO 325 polypeptides, nucleic acids, and modulators thereof modulate growth, proliferation, survival, differentiation, and activity of human tissues such as vascular endothelium, including aortic endothelium, other heart tissues, placenta, liver, kidney, and pancreas tissues. Thus, TANGO 325 polypeptides, nucleic acids, and modulators thereof can therefore be used to prevent, diagnose, and treat disorders involving one or more physiological activities mediated by TANGO 325 protein in tissues in which it is expressed. Such activities include, for example, modulation of cardiac contractility and vasomotor tone, modulation of leukocyte extravasation, sensing physiological signals by the endocrine system, modulating growth, development, maintenance, and regeneration of neurons, and the like. Disorders related to these activities include, by way of example and not limitation, cardiovascular disorders such as arteriosclerosis, atherosclerosis, coronary artery disease (and other ischemic heart diseases), angina, myocardial infarction, restenotic disorders, hypertension, Buerger's disease, aneurysm, stroke, arrythmia, congestive heart failure, endocarditis, and pericarditis, placental disorders such as placenta previa and abruptio placentae, liver disorders such as cirrhosis of the liver, liver fibrosis, hepatitis, and hepatic cancers, kidney disorders such as urolithiasis, glomerulonephritis, nephrosis, renal cell carcinomas, and renal failure (both acute and chronic), pancreatic disorders such as diabetes, pancreatitis, pancreatic cancers, and pancreatic insufficiency, neurological system disorders, immune and auto-immune disorders, hyperthyroidism, hypothyroidism, diabetes, goiter, growth and developmental disorders, and the like.

Further by way of example, TANGO 331 polypeptides, nucleic acids, and modulators thereof modulate growth, proliferation, survival, differentiation; and activity of human fetal, lung, spleen, and thymus cells and tissues. As described herein, TANGO 331 is involved in physiological activities such as maintenance of epithelia, carcinogenesis, modulation and storage of protein factors and metals, lactation, and infant nutrition. TANGO 331 also modulates cellular binding and uptake of cytokines, growth factors, and metal ions. Thus, TANGO 331 polypeptides, nucleic acids, and modulators thereof can be used to prevent, diagnose, and treat disorders such as breast cancer, insufficient lactation, infant nutritional and growth disorders, malnutrition and mineral deficiency disorders, hemochromatosis, inappropriate calcification of body tissues, bone disorders such as osteoporosis, autoimmune disorders, insufficient or inappropriate host responses to infection, acquired immune deficiency syndrome, and the like.

As another example, TANGO 332 polypeptides, nucleic acids, and modulators thereof modulate growth, proliferation, survival, differentiation, and activity of human brain and other tissues. As described herein, TANGO 332 is involved in modulating establishment and maintenance of neural connections, cell-to-cell adhesion, tissue and extracellular matrix invasivity, and the like. Thus, TANGO 332 polypeptides, nucleic acids, and modulators thereof can be used to prevent, diagnose, and treat disorders such as brain cancers (e.g., gliomas, astrocytomas, medulloblastomas, ependymomas, Schwannomas, pituitary adenomas, teratomas, and the like), disorders of neural connection establishment or maintenance, impaired cognitive function, dementia, senility, Alzheimer's disease, mental retardation, inflammation, immune and autoimmune responses, and the like.

In one embodiment, a polypeptide of the invention has an amino acid sequence sufficiently identical to an identified domain of a polypeptide of the invention. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

In one embodiment, the isolated polypeptide of the invention lacks both a transmembrane and a cytoplasmic domain. In another embodiment, the polypeptide lacks both a transmembrane domain and a cytoplasmic domain and is soluble under physiological conditions.

The polypeptides of the present invention, or biologically active portions thereof, can be operably linked to a heterologous amino acid sequence to form fusion proteins. The invention further features antibody substances that specifically bind a polypeptide of the invention such as monoclonal or polyclonal antibodies, antibody fragments, single-chain antibodies, and the like. In addition, the polypeptides of the invention or biologically active portions thereof can be incorporated into pharmaceutical compositions, which optionally include pharmaceutically acceptable carriers. These antibody substances can be made, for example, by providing the polypeptide of the invention to an immunocompetent vertebrate and thereafter harvesting blood or serum from the vertebrate.

In another aspect, the present invention provides methods for detecting the presence of the activity or expression of a polypeptide of the invention in a biological sample by contacting the biological sample with an agent capable of detecting an indicator of activity such that the presence of activity is detected in the biological sample.

In another aspect, the invention provides methods for modulating activity of a polypeptide of the invention comprising contacting a cell with an agent that modulates (inhibits or enhances) the activity or expression of a polypeptide of the invention such that activity or expression in the cell is modulated. In one embodiment, the agent is an antibody that specifically binds to a polypeptide of the invention.

In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense with respect to the coding strand of an mRNA encoding a polypeptide of the invention.

The present invention also provides methods to treat a subject having a disorder characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, the modulator is a protein of the invention. In another embodiment, the modulator is a nucleic acid of the invention. In other embodiments, the modulator is a peptide, peptidomimetic, or other small molecule.

The present invention also provides diagnostic assays for identifying the presence or absence of a genetic lesion or mutation characterized by at least one of: (i) aberrant modification or mutation of a gene encoding a polypeptide of the invention, (ii) mis-regulation of a gene encoding a polypeptide of the invention, and (iii) aberrant post-translational modification of a polypeptide of the invention wherein a wild-type form of the gene encodes a polypeptide having the activity of the polypeptide of the invention.

In another aspect, the invention provides a method for identifying a compound that binds to or modulates the activity of a polypeptide of the invention. In general, such methods entail measuring a biological activity of the polypeptide in the presence and absence of a test compound and identifying those compounds which alter the activity of the polypeptide.

The invention also features methods for identifying a compound which modulates the expression of a polypeptide or nucleic acid of the invention by measuring the expression of the polypeptide or nucleic acid in the presence and absence of the compound.

In yet a further aspect, the invention provides substantially purified antibodies or fragments thereof, including non-human antibodies or fragments thereof, which antibodies or fragments specifically bind to a polypeptide having an amino acid sequence comprising a sequence selected from the group consisting of (i) SEQ ID NOs: 3–8, 11–32, 35–37, 40–45, 48–53, 56–58, 61–63, 83–88, and 93–

(ii) the amino acid sequence encoded by a cDNA of a clone deposited as ATCC® PTA-147, PTA-150, 207230, or PTA-151;

(iii) a fragment of at least 15 amino acid residues of the amino acid sequence of SEQ ID NO: 3–8, 11–32, 35–37, 40–45, 48–53, 56–58, 61–63, 83–88, or 93–98;

(iv) an amino acid sequence which is at least 95% identical to the amino acid sequence of SEQ ID NO: 3–8, 11–32, 35–37, 40–45, 48–53, 56–58, 61–63, 83–88, or 93–98, percent identity is determined using the ALIGN program of the GCG software package with a PAM120 weight residue table, a gap length penalty of 12, and a gap penalty of 4; and (v) an amino acid sequence which is encoded by a nucleic acid molecule, the complement of which hybridizes with a nucleic acid molecule having the sequence of SEQ ID NO: 1, 2, 9, 10, 33, 34, 38, 39, 46, 47, 54, 55, 59, 60, 81, 82, or 92, or with a cDNA of a clone deposited as ATCC® PTA-147, PTA-150, 207230, or PTA-151, under conditions of hybridization of 6×SSC (standard saline citrate buffer) at 45° C. and washing in 0.2×SSC, 0.1% SDS at 65° C.

In various embodiments, the substantially purified antibodies of the invention, or fragments thereof, can be human, non-human, chimeric and/or humanized antibodies.

In another aspect, the invention provides non-human antibodies or fragments thereof, which antibodies or fragments specifically bind with a polypeptide having an amino acid sequence comprising a sequence selected from the group consisting of (i) SEQ ID NOs: 3–8, 11–32, 35–37, 40–45, 48–53, 56–58, 61–63, 83–88, and 93-

(ii) the amino acid sequence encoded by a cDNA of a clone deposited as ATCC® PTA-147, PTA-150, 207230, or PTA-151;

(iii) a fragment of at least 15 amino acid residues of the amino acid sequence of SEQ ID NO: 3–8, 11–32, 35–37, 40–45, 48–53, 56–58, 61–63, 83–88, or 93–98;

(iv) an amino acid sequence which is at least 95% identical to the amino acid sequence of SEQ ID NO: 3–8, 11–32, 35–37, 40–45, 48–53, 56–58, 61–63, 83–88, or 93–98, wherein the percent identity is determined using the ALIGN program of the GCG software package with a PAM120 weight residue table, a gap length penalty of 12, and a gap penalty of 4; and (v) an amino acid sequence which is encoded by a nucleic acid molecule, the complement of which hybridizes with a nucleic acid molecule having the sequence of SEQ ID NO: 1, 2, 9, 10, 33, 34, 38, 39, 46, 47, 54, 55, 59, 60, 81, 82, or 92, or with a cDNA of a clone deposited as ATCC® PTA-147, PTA-150, 207230, or PTA-151, under conditions of hybridization of 6×SSC (standard saline citrate buffer) at 45° C. and washing in 0.2×SSC, 0.1% SDS at 65° C.

Such non-human antibodies can be goat, mouse, sheep, horse, chicken, rabbit, or rat antibodies. Alternatively, the non-human antibodies of the inventions can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind to a polypeptide having an amino acid sequence comprising a sequence selected from the group consisting of (i) SEQ ID NOs: 3–8, 11–32, 35–37, 40–45, 48–53, 56–58, 61–63, 83–88, and 93–98;

(ii) the amino acid sequence encoded by a cDNA of a clone deposited as ATCC® PTA-147, PTA-150, 207230, or PTA-151;

(iii) a fragment of at least 15 amino acid residues of the amino acid sequence of SEQ ID NO: 3–8, 11–32, 35–37, 40–45, 48–53, 56–58, 61–63, 83–88, or 93–98;

(iv) an amino acid sequence which is at least 95% identical to the amino acid sequence of SEQ ID NO: 3–8, 11–32, 35–37, 40–45, 48–53, 56–58, 61–63, 83–88, or 93–98, wherein the percent identity is determined using the ALIGN program of the GCG software package with a PAM120 weight residue table, a gap length penalty of 12, and a gap penalty of 4; and (v) an amino acid sequence which is encoded by a nucleic acid molecule, the complement of which hybridizes with a nucleic acid molecule having the sequence of SEQ ID NO: 1, 2, 9, 10, 33, 34, 38, 39, 46, 47, 54, 55, 59, 60, 81, 82, or 92, or with a cDNA of a clone deposited as ATCC® PTA-147, PTA-150, 207230, or PTA-151, under conditions of hybridization of 6×SSC (standard saline citrate buffer) at 45° C. and washing in 0.2×SSC, 0.1% SDS at 65° C.

The monoclonal antibodies can be human, humanized, chimeric and/or non-human antibodies.

In a particularly preferred embodiment, the antibody substance of the invention specifically binds with an extracellular domain of one of INTERCEPT 217, INTERCEPT 297, TANGO 276, TANGO 292, TANGO 325, TANGO 331, and TANGO 332. Preferably, the extracellular domain with which the antibody substance binds has an amino acid sequence selected from the group consisting of SEQ ID NOs: 6, 14–18, 37, 43, 51, 58, 63, 83, and 93.

Any of the antibodies of the invention can be conjugated with a therapeutic moiety or with a detectable substance. Non-limiting examples of detectable substances that can be conjugated with the antibodies of the invention include an enzyme, a prosthetic group, a fluorescent material, a luminescent material, a bioluminescent material, and a radioactive material.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Other features and advantages of the invention will be apparent from the following detailed description and claims.

BRIEF DESCRIPTION OF THE SEVERAL VIEWS OF THE DRAWINGS

FIG. 1 comprises FIGS. 1A through 1M. The nucleotide sequence (SEQ ID NO: 1) of a cDNA encoding the human INTERCEPT 217 protein described herein is listed in FIGS. 1A through 1E. The open reading frame (ORF; residues 215 to 1579; SEQ ID NO: 2) of the cDNA is indicated by nucleotide triplets, above which the amino acid sequence (SEQ ID NO: 3) of human INTERCEPT 217 is listed.

FIG. 2 comprises FIGS. 2A through 2D. The nucleotide sequence (SEQ ID NO: 9) of a cDNA encoding the human INTERCEPT 297 protein described herein is listed in FIGS. 2A, 2B, and 2C. The open reading frame (ORF; residues 40 to 1152; SEQ ID NO: 10) of the cDNA is indicated by nucleotide triplets, above which the amino acid sequence (SEQ ID NO: 11) of human INTERCEPT 297 is listed.

FIG. 3 comprises FIGS. 3A through 3R. The nucleotide sequence (SEQ ID NO: 33) of a cDNA encoding the human TANGO 276 protein described herein is listed in FIGS. 3A to 3D. The ORF (residues 58 to 786; SEQ ID NO: 34) of the cDNA is indicated by nucleotide triplets, above which the amino acid sequence (SEQ ID NO: 35) of human TANGO 276 is listed. In FIGS. 3I through 3R, an alignment of the nucleotide sequences of the cDNA encoding human TANGO 276 protein ("H"; SEQ ID NO: 33) and the nucleotide sequences of the cDNA encoding murine protein M-Sema-F ("M"; SEQ ID NO: 66) is shown. These alignments were made using the ALIGN software {Myers and Miller (1989) CABIOS, ver. 2.0}; pam120.mat scoring matrix; gap opening penalty=12, gap extension penalty=4).

FIG. 4 comprises FIGS. 4A through 4M. The nucleotide sequence (SEQ ID NO: 38) of a cDNA encoding the human TANGO 292 protein described herein is listed in FIGS. 4A to 4C. The ORF (residues 205 to 882; SEQ ID NO: 39) of the cDNA is indicated by nucleotide triplets, beneath which the amino acid sequence (SEQ ID NO: 40) of human TANGO 292 is listed. FIGS. 4I to 4K are an alignment of the nucleotide sequences of the ORF encoding human TANGO 292 protein ("H"; SEQ ID NO: 38) and the nucleotide sequence of the ORF encoding gerbil TANGO 292 protein ("G"; SEQ ID NO: 81), made using the ALIGN software {Myers and Miller (1989) CABIOS, ver. 2.0}; pam120.mat scoring matrix; gap opening penalty 12, gap extension penalty=4), wherein identical nucleotide residues are indicated by "|". FIG. 4L is an alignment of the human (H) and gerbil (G) TANGO 292 amino acid sequences, made using the same software and parameters, wherein identical amino acid residues are indicated by "|" and similar amino acid residues are indicated by ".".

FIG. 5 comprises FIGS. 5A through 5M-18. The nucleotide sequence (SEQ ID NO: 46) of a cDNA encoding the human TANGO 325 protein described herein is listed in FIGS. 5A through 5E. The ORF (residues 135 to 2000; SEQ ID NO: 47) of the cDNA is indicated by nucleotide triplets, above which the amino acid sequence (SEQ ID NO: 48) of human TANGO 325 is listed. In FIGS. 5M-1 to 5M-18, an alignment of the nucleotide sequences of the cDNA encoding human TANGO 325 protein ("325"; SEQ ID NO: 33) and the nucleotide sequence of the cDNA encoding Slit-1 protein ("Slit"; SEQ ID NO: 68) is shown. This alignment was made using the ALIGN software {Myers and Miller (1989) CABIOS, ver. 2.0}; pam120. mat scoring matrix; gap opening penalty=12, gap extension penalty=4).

FIG. 6 comprises FIGS. 6A through 6J. The nucleotide sequence (SEQ ID NO: 54) of a cDNA encoding the human TANGO 331 protein described herein is listed in FIGS. 6A, 6B, and 6C. The ORF (residues 114 to 1172; SEQ ID NO: 55) of the cDNA is indicated by nucleotide triplets, above which the amino acid sequence (SEQ ID NO: 56) of human TANGO 331 is listed. In FIGS. 6F through 6J, an alignment of the nucleotide sequences of the cDNA encoding human TANGO 331 protein ("H"; SEQ ID NO: 54) and the nucleotide sequence of the cDNA encoding Chinese hamster protein HT ("C"; SEQ ID NO: 70) is shown. These alignments were made using the ALIGN software {Myers and Miller (1989) CABIOS, ver. 2.0}; pam120.mat scoring matrix; gap opening penalty=12, gap extension penalty=4).

FIG. 7 comprises FIGS. 7A through 7U. The nucleotide sequence (SEQ ID NO: 59) of a cDNA encoding the human TANGO 332 protein described herein is listed in FIGS. 7A through 7E. The ORF (residues 173 to 2185; SEQ ID NO: 60) of the cDNA is indicated by nucleotide triplets, above which the amino acid sequence (SEQ ID NO: 61) of human TANGO 332 protein is listed. In FIGS. 7L through 7U, an alignment of the nucleotide sequences of the cDNA encoding human TANGO 332 protein ("H"; SEQ ID NO: 60) and the nucleotide sequence of the cDNA encoding murine brevidin protein ("M"; SEQ ID NO: 73) is shown. These alignments were made using the ALIGN software {Myers and Miller (1989) CABIOS, ver. 2.0}; pam120.mat scoring matrix; gap opening penalty=12, gap extension penalty=4).

DETAILED DESCRIPTION OF THE INVENTION

Figure 1F:
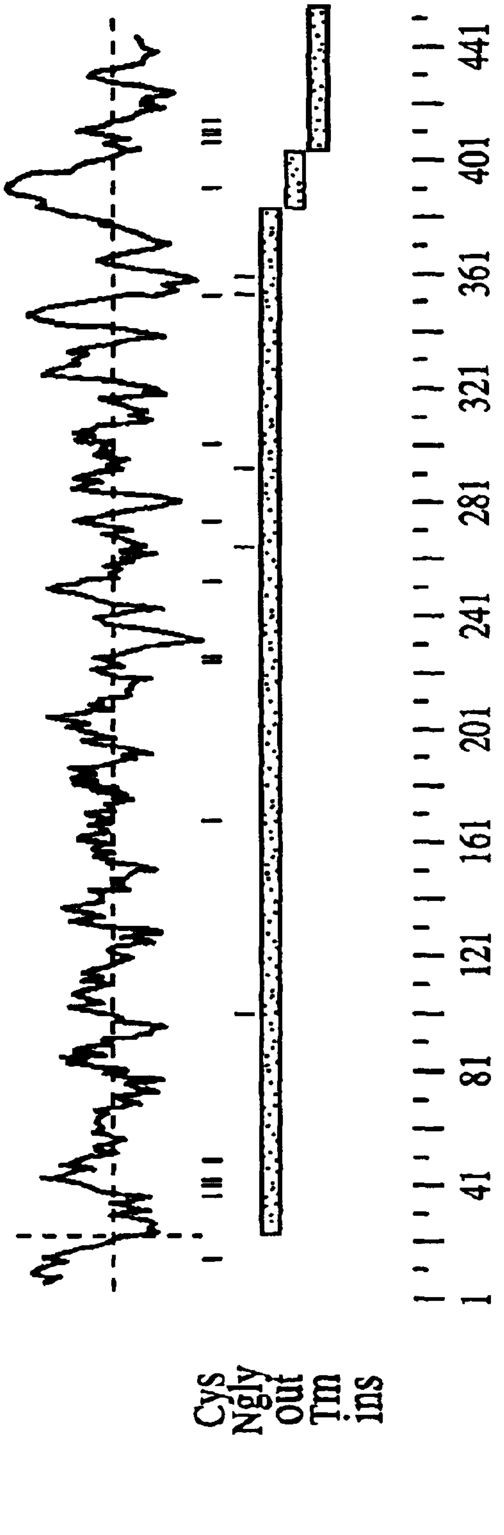
FIG. 1F is a hydrophilicity plot of human INTERCEPT 217 protein, in which the locations of cysteine residues ("Cys") and potential N-glycosylation sites ("Ngly") are indicated by vertical bars and the predicted extracellular ("out"), intracellular ("ins"), or transmembrane ("TM") locations of the protein backbone is indicated by a horizontal bar. An alignment of the amino acid sequences of human INTERCEPT 217 protein ("H"; SEQ ID NO: 3) and porcine ribonuclease inhibitor protein ("P"; SwissProt Accession number P10775; SEQ ID NO: 64) is shown in FIGS. 1G and 1H, wherein identical amino acid residues are indicated by ":" and similar amino acid residues are indicated by ".". These alignments were made using the ALIGN software {Myers and Miller (1989) CABIOS, ver. 2.0}; pam120.mat scoring matrix; gap opening penalty=12, gap extension penalty=4). The nucleotide sequence (SEQ ID NO: 92) of an ORF encoding the murine INTERCEPT 217 protein described herein is listed in FIGS. 1I through 1K. The ORF is indicated by nucleotide triplets, beneath which the amino acid sequence, (SEQ ID NO: 93) of murine INTERCEPT 217 is listed.

The present invention is based, at least in part, on the discovery of a variety of human cDNA molecules which encode proteins which are herein designated INTERCEPT 217, INTERCEPT 297, TANGO 276, TANGO 292, TANGO 325, TANGO 331, and TANGO 332. These proteins exhibit a variety of physiological activities, and are included in a single application for the sake of convenience. It is understood that the allowability or non-allowability of claims directed to one of these proteins has no bearing on the allowability of claims directed to the others. The characteristics of each of these proteins and the cDNAs encoding them are now described separately.

INTERCEPT 217

A cDNA clone (designated jthqc035f08) encoding at least a portion of human INTERCEPT 217 protein was isolated from a human prostate cDNA library. The human INTERCEPT 217 protein is predicted by structural analysis to be a transmembrane protein. In addition, cDNA clones (including those designated jtmca047g07, jTmob373b05, and jambd078d12) encoding at least a portion of murine INTERCEPT 217 protein were isolated from murine cDNA libraries.

The full length of the cDNA encoding human INTERCEPT 217 protein (FIG. 1; SEQ ID NO: 1) is 2895 nucleotide residues. The ORF of this cDNA, nucleotide residues 215 to 1579 of SEQ ID NO: 1 (i.e., SEQ ID NO: 2), encodes a 455-amino acid transmembrane protein (FIG. 1; SEQ ID NO: 3). The murine ORF (FIG. 1; SEQ ID NO: 92) comprises at least 962 nucleotide residues. The protein encoded by the murine ORF comprises at least 320 amino acid residues (i.e., SEQ ID NO: 93), and is also a transmembrane protein.

The invention also includes purified human INTERCEPT 217 protein, both in the form of the immature 455 amino acid residue protein (SEQ ID NO: 3) and in the form of the mature, approximately 435 amino acid residue protein (SEQ ID NO: 5). Mature human INTERCEPT 217 protein can be synthesized without the signal sequence polypeptide at the amino terminus thereof, or it can be synthesized by generating immature INTERCEPT 217 protein and cleaving the signal sequence therefrom.

The invention thus includes purified murine INTERCEPT 217 protein, both in the immature form comprising the 320 amino acid residues of SEQ ID NO: 93 and in the mature form comprising the approximately 305 carboxyl terminal amino acid residues of SEQ ID NO: 93 (i.e., comprising SEQ ID NO: 95). Mature murine INTERCEPT 217 protein can be synthesized without the signal sequence polypeptide at the amino terminus thereof, or it can be synthesized by generating immature INTERCEPT 217 protein and cleaving the signal sequence therefrom.

In addition to full length mature and immature human and murine INTERCEPT 217 proteins, the invention includes fragments, derivatives, and variants of these INTERCEPT 217 proteins, as described herein. These proteins, fragments, derivatives, and variants are collectively referred to herein as INTERCEPT 217 polypeptides of the invention or INTERCEPT 217 proteins of the invention.

The invention also includes nucleic acid molecules which encode an INTERCEPT 217 polypeptide of the invention. Such nucleic acids include, for example, a DNA molecule having the nucleotide sequence listed in SEQ ID NO: 1, in SEQ ID NO: 92 (i.e., the murine ORF), or in some portion of either of these, such as the portion which encodes mature human INTERCEPT 217 protein, immature human INTERCEPT 217 protein, or a domain of human INTERCEPT 217 protein. These nucleic acids are collectively referred to as INTERCEPT 217 nucleic acids of the invention.

INTERCEPT 217 proteins and nucleic acid molecules encoding them comprise a family of molecules having certain conserved structural and functional features. Each of these molecules is included in the invention. As used herein, the term "family" is intended to mean two or more proteins or nucleic acid molecules having a common or similar domain structure and having sufficient amino acid or nucleotide sequence identity as defined herein. Family members can be from either the same or different species. For example, a family can comprise two or more proteins of human origin, or can comprise one or more proteins of human origin and one or more of non-human origin (e.g., the human and murine INTERCEPT 217 proteins described herein).

A common domain present in INTERCEPT 217 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a INTERCEPT 217 protein contains a signal sequence corresponding to about amino acid residues 1 to 20 of SEQ ID NO: 3 (SEQ ID NO: 4). The signal sequence is cleaved during processing of the mature protein.

INTERCEPT 217 proteins can include an extracellular domain. As used herein, an "extracellular domain" refers to a portion of a protein which is localized to the non-cytoplasmic side of a lipid bilayer of a cell when a nucleic acid encoding the protein is expressed in the cell. The human INTERCEPT 217 protein extracellular domain is located from about amino acid residue 21 to about amino acid residue 383 of SEQ ID NO: 3 (SEQ ID NO: 6). The murine INTERCEPT 217 protein extracellular domain is located from about amino acid residue 17 to about amino acid residue 213 of SEQ ID NO: 93 (SEQ ID NO: 96).

In addition, INTERCEPT 217 includes a transmembrane domain. As used herein, a "transmembrane domain" refers to an amino acid sequence which is at least about 20 to 25 amino acid residues in length and which contains at least about 65–70% hydrophobic amino acid residues such as alanine, leucine, phenylalanine, protein, tyrosine, tryptophan, or valine. In a preferred embodiment, a transmembrane domain contains at least about 15 to 30 amino acid residues, preferably about 20–25 amino acid residues, and has at least about 60–80%, more preferably 65–75%, and more preferably at least about 70% hydrophobic residues. Thus, in one embodiment, an INTERCEPT 217 protein of the invention contains a transmembrane domain corresponding to about amino acid residues 384 to 403 of SEQ ID NO: 3 (SEQ ID NO: 7) or to about amino acid residues 214 to 233 of SEQ ID NO: 93 (SEQ ID NO: 97).

The present invention includes INTERCEPT 217 proteins having a cytoplasmic domain, particularly including proteins having a carboxyl-terminal cytoplasmic domain. As used herein, a "cytoplasmic domain" refers to a portion of a protein which is localized to the cytoplasmic side of a lipid bilayer of a cell when a nucleic acid encoding the protein is expressed in the cell. The human INTERCEPT 217 cytoplasmic domain is located from about amino acid residue 404 to amino acid residue 455 of SEQ ID NO: 3 (SEQ ID NO: 8). The murine INTERCEPT 217 cytoplasmic domain is located from about amino acid residue 234 to amino acid residue 320 of SEQ ID NO: 93 (SEQ ID NO: 98).

In one embodiment, the amino acid residues of human INTERCEPT 217 corresponding to SEQ ID NO: 8 are part of an extracellular domain, and the amino acid residues corresponding to SEQ ID NO: 6 are part of a cytoplasmic domain. In another embodiment, the amino acid residues of murine INTERCEPT 217 corresponding to SEQ ID NO: 98 are part of an extracellular domain, and the amino acid residues corresponding to SEQ ID NO: 96 are part of a cytoplasmic domain.

INTERCEPT 217 proteins typically comprise a variety of potential post-translational modification sites (often within an extracellular domain), such as those described herein in Tables IA (for human INTERCEPT 217) and IB (for murine INTERCEPT 217), as predicted by computerized sequence analysis of INTERCEPT 217 proteins using amino acid sequence comparison software (comparing the amino acid sequence of INTERCEPT 217 with the information in the PROSITE database {rel. 12.2; February, 1995} and the Hidden Markov Models database {Rel. PFAM 3.3 }). In certain embodiments, a protein of the invention has at least 1, 2, 4, 6, or 10 or more of the post-translational modification sites listed in Tables IA and IB.

TABLE IA

| Type of Potential Modification Site or Domain | Amino Acid Residues of SEQ ID NO: 3 | Amino Acid Sequence |
|---|---|---|
| N-glycosylation site | 107 to 110 | NASG |
| | 272 to 275 | NCSS |
| | 301 to 304 | NTSV |
| | 362 to 365 | NQTH |
| | 368 to 371 | NVSV |
| Protein kinase C phosphorylation site | 120 to 122 | TLR |
| | 192 to 194 | SNR |
| | 295 to 297 | SLR |
| Casein kinase II phosphorylation site | 199 to 202 | SVPE |
| | 440 to 443 | TPPD |
| Tyrosine Kinase Phosphorylation Site | 282 to 289 | KRPEEHLY |
| N-myristoylation site | 8 to 13 | GTLLCM |
| | 19 to 24 | GTPDSE |
| | 103 to 108 | GVFVNA |
| | 179 to 184 | GLSATH |
| | 323 to 328 | GSRDGS |
| | 348 to 353 | GLFVCL |
| | 390 to 395 | GCAVGL |
| | 449 to 454 | GQASTS |
| Leucine zipper pattern | 45 to 66 | See FIG. 1 |
| Leucine rich repeat amino terminal domain (LLRNT) | 33 to 61 | See FIG. 1 |
| Leucine rich repeat (LRR) Domain | 62 to 85 | See FIG. 1 |
| | 86 to 109 | See FIG. 1 |
| | 110 to 133 | See FIG. 1 |
| | 134 to 157 | See FIG. 1 |
| | 158 to 181 | See FIG. 1 |
| | 184 to 207 | See FIG. 1 |
| Leucine rich repeat carboxyl terminal (LLRCT) domain | 219 to 274 | See FIG. 1 |

TABLE IB

| Type of Potential Modification Site or Domain | Amino Acid Residues of SEQ ID NO: 93 | Amino Acid Sequence |
|---|---|---|
| N-glycosylation site | 102 to 105 | NCSV |
| | 131 to 134 | NTSV |
| | 192 to 195 | NQTL |
| | 198 to 201 | NVSV |
| cAMP- and cGMP-dependent protein kinase site | 280 to 283 | RKAS |
| Protein kinase C phosphorylation site | 125 to 127 | SLR |
| | 143 to 145 | SPK |
| | 279 to 281 | SRK |
| Casein kinase II phosphorylation site | 29 to 32 | SIPE |
| | 273 to 276 | TPPD |
| N-myristoylation site | 9 to 14 | GLGLTR |
| | 178 to 183 | GVFVCL |
| | 220 to 225 | GCIVGL |
| | 239 to 244 | GCCHCC |
| Amidation Site | 293 to 296 | PGKK |
| Immunoglobulin Domain | 14 to 37 | See FIG. 1 |
| Leucine rich repeat (LRR) Domain | 49 to 104 | See FIG. 1 |
| Leucine rich repeat carboxyl terminal (LLRCT) domain | 123 to 184 | See FIG. 1 |

Among the domains that occur in INTERCEPT 217 proteins are LRR domains, LRRNT domains, LRRCT domains, and immunoglobulin domains. In one embodiment, the protein of the invention has at least one domain that is at least 55%, preferably at least about 65%, more preferably at least about 75%, yet more preferably at least about 85%, and most preferably at least about 95% identical to one of these domains. In other embodiments, the protein has at least one of each of the LRR, LRRNT, and LRRCT domains described herein in Tables IA and IB. In other embodiments, the protein has at least one LRRNT domain, at least one LRRCT domain, and a plurality of (e.g., 2, 3, 4, or more) LRR domains.

One or more LRR domains are present in a variety of proteins involved in protein-protein interactions. Such proteins include, for example, proteins involved in signal transduction, cell-to-cell adhesion, cell-to-extracellular matrix adhesion, cell development, DNA repair, RNA processing, and cellular molecular recognition processes. Specialized LRR domains, designated LRR amino terminal (LRRNT) domains and LRR carboxyl terminal (LRRCT) domains often occur near the amino and carboxyl, respectively, ends of a series of LRR domains. Human INTERCEPT 217 protein has eight clustered LRR domains, including (from the amino terminus toward the carboxyl terminus of INTERCEPT 217) an LRRNT domain, six LRR domains, and an LRRCT domain.

The organization of LRR domains in human INTERCEPT 217 protein closely mirrors the organization of LRR domains in human platelet glycoprotein IB alpha chain precursor (GP-IB-alpha), which also has eight clustered LRR domains from about amino acid residue 19 to about amino acid residue 281 thereof. The eight LRR domains of GP-IB-alpha include an LRRNT domain at the end of the cluster nearest the amino terminus of GP-IB-alpha and an LRRCT domain at the end of the cluster nearest the carboxyl terminus of GP-IB-alpha. GP-IB-alpha is a membrane-bound protein of human platelets that is involved in binding of von Willebrand's factor and in aggregation of platelets during thrombus formation. Thus, INTERCEPT 217 is involved in both normal and aberrant physiological activities involving blood clotting and thrombus formation. Examples of disorders involving such activities include, for example, stroke, embolism (e.g., cerebral, renal, and pulmonary emboli), hemophilia, restenotic injury, prosthesis-associated thrombogenesis, atherosclerosis, and arteriosclerosis.

INTERCEPT 217 is involved in one or more physiological processes in which these other LRR domain-containing proteins are involved, namely binding of cells with extracellular proteins such as soluble extracellular proteins and cell surface proteins of other cells.

Human INTERCEPT 217 comprises a leucine zipper region at about amino acid residue 45 to about amino acid residue 66 (i.e., 45 LsctglgLqdvpaeLpaa tadL 66). Leucine zipper regions are known to be involved in dimerization of proteins. Leucine zipper regions interact with one another, leading to formation of homo- or hetero-dimers between proteins, depending on their identity. The presence in INTERCEPT 217 of a leucine zipper region is a further indication that this protein is involved in protein-protein interactions.

The amino acid sequence of human INTERCEPT 217 protein includes multiple potential proline-rich Src homology 3 (SH3) domain binding sites in the cytoplasmic portion of the protein. SH3 domains mediate specific assembly of protein complexes, presumably by interacting with proline-rich protein domains (Morton and Campbell (1994) Curr. Biol. 4:615–617). SH3 domains also mediate interactions between proteins involved in transmembrane signal transduction. Coupling of proteins mediated by SH3 domains has been implicated in a variety of physiological systems, including those involving regulation of cell growth and proliferation, endocytosis, and activation of respiratory burst.

SH3 domains have been described in the art (e.g., Mayer et al. (1988) Nature 332:272–275; Musacchio et al. (1992) FEBS Lett. 307:55–61; Pawson and Schlessinger (1993) Curr. Biol. 3:434–442; Mayer and Baltimore (1993) Trends Cell Biol. 3:8–13; Pawson (1993) Nature 373:573–580), and occur in a variety of cytoplasmic proteins, including several (e.g., protein tyrosine kinases) involved in transmembrane signal transduction. Among the proteins in which one or more SH3 domains occur are protein tyrosine kinases such as those of the Src, Abl, Bkt, Csk and ZAP70 families, mammalian phosphatidylinositol-specific phospholipases C-gamma-1 and -2, mammalian phosphatidylinositol 3-kinase regulatory p85 subunit, mammalian Ras GTPase-activating protein (GAP), proteins which mediate binding of guanine nucleotide exchange factors and growth factor receptors (e.g., vertebrate GRB2, *Caenorhabditis elegans* sem-5, and Drosophila DRK proteins), mammalian Vav oncoprotein, guanidine nucleotide releasing factors of the CDC 25 family (e.g., yeast CDC25, yeast SCD25, and fission yeast ste6 proteins), MAGUK proteins (e.g., mammalian tight junction protein ZO-1, vertebrate erythrocyte membrane protein p55, *C. elegans* protein lin-2, rat protein CASK, and mammalian synaptic proteins SAP90/PSD-95, CHAPSYN-110/PSD-93, SAP97/DLG1, and SAP102), proteins which interact with vertebrate receptor protein tyrosine kinases (e.g., mammalian cytoplasmic protein Nck and oncoprotein Crk), chicken Src substrate p80/85 protein (cortactin), human hemopoietic lineage cell specific protein Hs1, mammalian dihydrouridine-sensitive L-type calcium channel beta subunit, human myasthenic syndrome antigen B (MSYB), mammalian neutrophil cytosolic activators of NADPH oxidase (e.g., p47 {NCF-1}, p67 {NCF-2}, and *C. elegans* protein B0303.7), myosin heavy chains (MYO3) from amoebae, from slime molds, and from yeast, vertebrate and Drosophila spectrin and fodrin alpha chain proteins, human amphiphysin, yeast actin-binding proteins ABP1 and SLA3, yeast protein BEM1, fission yeast protein scd2 (ral3), yeast BEM1-binding proteins BOI2 (BEB1) and BOB1 (BOI1), yeast fusion protein FUS 1, yeast protein RSV167, yeast protein SSU81, yeast hypothetical proteins YAR014c, YFR024c, YHL002w, YHR016c, YJL020C, and YHR114w, hypothetical fission yeast protein SpAC12C2.05c, and *C. elegans* hypothetical protein F42H10.3. Of these proteins, multiple SH3 domains occur in vertebrate GRB2 protein, *C. elegans* sem-5 protein, Drosophila DRK protein, oncoprotein Crk, mammalian neutrophil cytosolic activators of NADPH oxidase p47 and p67, yeast protein BEM 1, fission yeast protein scd2, yeast hypothetical protein YHR114w, mammalian cytoplasmic protein Nck, *C. elegans* neutrophil cytosolic activator of NADPH oxidase B0303.7, and yeast actin-binding protein SLA1. Of these proteins, three or more SH3 domains occur in mammalian cytoplasmic protein Nck, *C. elegans* neutrophil cytosolic activator of NADPH oxidase B0303.7, and yeast actin-binding protein SLA1. The presence of SH3 domain binding sites in INTERCEPT 217 indicates that INTERCEPT 217 interacts with one or more of these and other SH3 domain-containing proteins and is thus involved in physiological processes in which one or more of these or other SH3 domain-containing proteins are involved.

Human INTERCEPT 217 exhibits amino acid sequence similarity to porcine ribonuclease inhibitor, a protein which binds with high affinity to pancreatic ribonucleases and inhibits their activity. INTERCEPT 217 thus is involved with similar physiological processes in humans. An alignment of the amino acid sequences of human INTERCEPT 217 and porcine ribonuclease inhibitor protein (SwissProt Accession number P10775) is shown in FIG. 1G. In this alignment (made using the ALIGN software {Myers and Miller (1989) CABIOS, ver. 2.0}; pam120. mat scoring matrix; gap opening penalty=12, gap extension penalty=4), the proteins are 20.5% identical. An alignment of human (SEQ ID NO: 3) and murine INTERCEPT 217 amino acid sequences (SEQ ID NO: 93; made using BESTFIT software, BLOSUM62 scoring matrix, gap opening penalty=12, frameshift gap penalty=5, gap extension penalty=4). In this alignment, the human and murine amino acid sequences are 71.3% identical in the overlapping region. Alignment of human and murine INTERCEPT 217 ORFs indicated 79.9% nucleotide sequence identity in the overlapping region.

The signal peptide prediction program SIGNALP (Nielsen et al. (1997) Protein Engineering 10:1–6) predicted that human INTERCEPT 217 protein includes an approximately 20 (i.e., 18, 19, 20, 21, or 22) amino acid residue signal peptide (amino acid residues 1 to 20 of SEQ ID NO: 3; SEQ ID NO: 4) preceding the mature INTERCEPT 217 protein (i.e., approximately amino acid residues 21 to 455 of SEQ ID NO: 3; SEQ ID NO: 5). In one embodiment, human INTERCEPT 217 protein includes an extracellular domain (amino acid residues 21 to 383 of SEQ ID NO: 3; SEQ ID NO: 6); a transmembrane domain (amino acid residues 384 to 403 of SEQ ID NO: 3; SEQ ID NO: 7); and a cytoplasmic domain (amino acid residues 404 to 455 of SEQ ID NO: 3; SEQ ID NO: 8). In an alternative embodiment, human INTERCEPT 217 protein includes a cytoplasmic domain (amino acid residues 21 to 383 of SEQ ID NO: 3; SEQ ID NO: 6); a transmembrane domain (amino acid residues 384 to 403 of SEQ ID NO: 3; SEQ ID NO: 7); and an extracellular domain (amino acid residues 404 to 455 of SEQ ID NO: 3; SEQ ID NO: 8).

The SIGNALP program predicted that murine INTERCEPT 217 protein includes an approximately 15 (i.e., 13, 14, 15, 16, or 17) amino acid residue signal peptide (amino acid residues 1 to 16 of SEQ ID NO: 93; SEQ ID NO: 94) preceding the mature INTERCEPT 217 protein (i.e., approximately amino acid residues 16 to 320 of SEQ ID NO: 93; SEQ ID NO: 95). In one embodiment, murine INTERCEPT 217 protein includes an extracellular domain (amino acid residues 16 to 213 of SEQ ID NO: 93; SEQ ID NO: 96); a transmembrane domain (amino acid residues 214 to 233 of SEQ ID NO: 93; SEQ ID NO: 97); and a cytoplasmic domain (amino acid residues 234 to 320 of SEQ ID NO: 93; SEQ ID NO: 98). In an alternative embodiment, murine INTERCEPT 217 protein includes a cytoplasmic domain (amino acid residues 16 to 213 of SEQ ID NO: 93; SEQ ID NO: 96); a transmembrane domain (amino acid residues 214 to 233 of SEQ ID NO: 93; SEQ ID NO: 97); and an extracellular domain (amino acid residues 234 to 320 of SEQ ID NO: 93; SEQ ID NO: 98).

Figure 1L:
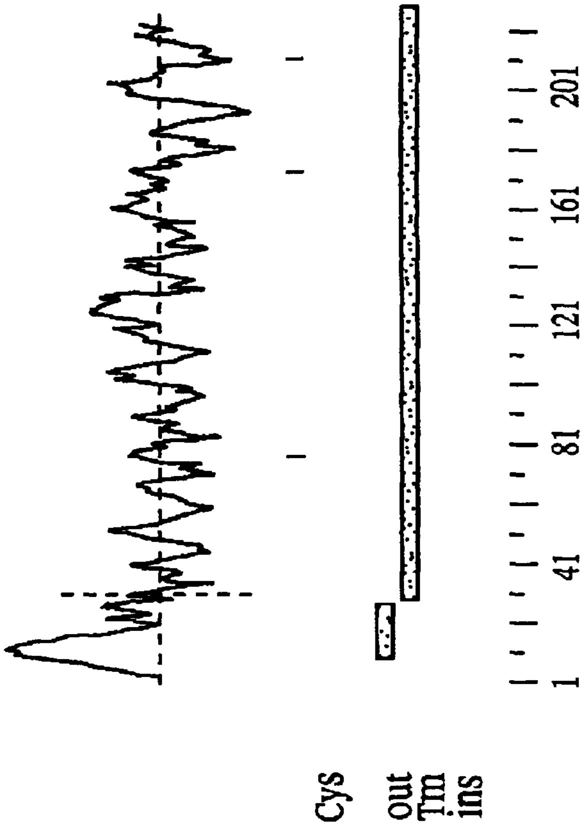
FIG. 1L is a hydrophilicity plot of murine INTERCEPT 217 protein, in which the locations of cysteine residues ("Cys") and potential N-glycosylation sites ("Ngly") are indicated by vertical bars and the predicted extracellular ("out"), intracellular ("ins"), or transmembrane ("TM") locations of the protein backbone is indicated by a horizontal bar. An alignment of the amino acid sequences of human INTERCEPT 217 protein ("H"; SEQ ID NO: 3) and murine INTERCEPT 217 protein ("M"; SEQ ID NO: 93) is shown in FIG. 1M, wherein identical amino acid residues are indicated by "|" and similar amino acid residues are indicated by ".". These alignments were made using the BESTFIT software (BLOSUM62 scoring matrix, gap opening penalty=12, frameshift gap penalty=5, gap extension penalty=4).

FIG. 1F depicts a hydrophilicity plot of human INTERCEPT 217 protein. Relatively hydrophobic regions are above the dashed horizontal line, and relatively hydrophilic regions are below the dashed horizontal line. The hydrophobic region which corresponds to amino acid residues 1 to 20 of SEQ ID NO: 3 is the signal sequence of human INTERCEPT 217 (SEQ ID NO: 4). The hydrophobic region which corresponds to amino acid residues 384 to 403 of SEQ ID NO: 3 is the transmembrane domain of human INTERCEPT 217 (SEQ ID NO: 7). As described elsewhere herein, relatively hydrophilic regions are generally located at or near the surface of a protein, and are more frequently effective immunogenic epitopes than are relatively hydrophobic regions. For example, the region of human INTERCEPT 217 protein from about amino acid residue 355 to about amino acid residue 380 appears to be located at or near the surface of the protein, while the region from about amino acid residue 190 to about amino acid residue 210 appears not to be located at or near the surface. FIG. 1L depicts a hydrophilicity plot of murine INTERCEPT 217 protein.

The predicted molecular weight of human INTERCEPT 217 protein without modification and prior to cleavage of the signal sequence is about 49.8 kilodaltons. The predicted molecular weight of the mature human INTERCEPT 217 protein without modification and after cleavage of the signal sequence is about 47.4 kilodaltons.

The predicted molecular weight of murine INTERCEPT 217 protein, without modification and prior to cleavage of the signal sequence is about 35.5 kilodaltons. The predicted molecular weight of the mature human INTERCEPT 217 protein without modification and after cleavage of the signal sequence is about 33.8 kilodaltons.

Northern analysis experiments indicated that mRNA corresponding to the cDNA encoding INTERCEPT 217 is expressed in two forms, one having an apparent approximate size of about 6 kilobases and another having an apparent approximate size of about 3 kilobases (i.e., corresponding to the size of the INTERCEPT 217 cDNA). These experiments indicated that INTERCEPT 217 is expressed in the tissues listed in Table II, wherein "++" indicates strong expression, "+" indicates lower expression, and "+/−" indicates still lower expression.

TABLE II

| Animal | Tissue | Relative Level of Expression |
|---|---|---|
| Human | pancreas | ++ |
| | skeletal muscle | + |
| | heart | +/− |
| | brain | +/− |
| | placenta | +/− |
| | lung | +/− |
| | liver | +/− |
| | kidney | +/− |

An assay to detect possible secretion of INTERCEPT 217 protein was negative. This assay was performed as follows. About $8\times10^5$ 293T cells were incubated at 37° C. in wells containing growth medium (Dulbecco's modified Eagle's medium {DMEM} supplemented with 10% fetal bovine serum) under a 5% (v/v) $CO_2$, 95% air atmosphere to about 60–70% confluence. The cells were then transfected using a standard transfection mixture comprising 2 micrograms of DNA and 10 microliters of LIPOFECTAMINE™ (GIBCO/BRL Catalog no. 18342-012) per well. The transfection mixture was maintained for about 5 hours, and then replaced with fresh growth medium and maintained in an air atmosphere. Each well was gently rinsed twice with DMEM which did not contain methionine or cysteine (DMEM-MC; ICN Catalog no. 16-424-54). About 1 milliliter of DMEM-MC and about 50 microcuries of TRANS-$^{35}$S™ reagent (ICN Catalog no. 51006) were added to each well. The wells were maintained under the 5% $CO_2$ atmosphere described above and incubated at 37° C. for a selected period. Following incubation, 150 microliters of conditioned medium was removed, centrifuged to remove floating cells and debris, and combined with 150 microliters of 2×SDS sample buffer. The sample was boiled at 100° C. for 5 minutes, and about 40 microliters of sample was loaded onto a NOVEX™ 4–20% (w/v) SDS-containing polyacrylamide gel. Following electrophoresis, the gel was stained for protein and dried according to the NOVEX™ procedure. The dried gel was exposed to radiation-sensitive film in order to detect the position of secreted proteins.

Biological function of INTERCEPT 217 proteins, nucleic acids encoding them, and modulators of these molecules INTERCEPT 217 proteins are involved in disorders which affect both tissues in which they are normally expressed and tissues in which they are normally not expressed. Based on the observation that INTERCEPT 217 is expressed in pancreas, skeletal muscle, heart, brain, placenta, lung, liver, and kidney tissue, INTERCEPT 217 protein is involved in one or more biological processes which occur in these tissues. In particular, INTERCEPT 217 is involved in modulating binding of cells of one or more of these tissues with proteins of other cells or with secreted proteins which occur in the extracellular environment of one or more of these tissues. INTERCEPT 217 is especially implicated in disorders of skeletal muscle (e.g., protection of skeletal muscle cells during ischemia and in bruised tissue), and more especially those involving the pancreas (e.g., diabetes, pancreatitis, and the like).

Structural similarity of human INTERCEPT 217 protein with human GP-IB-alpha indicates that INTERCEPT 217 is involved in binding extracellular proteins and other ligands. INTERCEPT 217 protein is involved in binding of proteins which induce release of pancreatic digestive enzymes (e.g., amylases, lipases, proteases, and nucleases) from pancreatic cells, and in disorders associated with insufficient or inappropriate release of such enzymes. INTERCEPT 217 protein is also involved in binding of secreted pancreatic digestive enzymes in pancreatic tissue, thereby protecting pancreatic tissue from autodigestion. Thus, INTERCEPT 217 protein is involved in disorders such as diabetes, pancreatitis, and pancreatic carcinoma which involve acute and chronic autodigestive damage to pancreatic tissues. Homology of INTERCEPT 217 protein with porcine ribonuclease inhibitor protein is a further indication of this involvement.

The presence of LRR domains in human INTERCEPT 217 protein and detection of its expression in a variety of tissues indicate that the tissue protective functions of INTERCEPT 217 are not limited to pancreatic tissues, but are involved in protection of other tissues as well (e.g., skeletal muscle, heart, brain, placenta, lung, liver, prostate, and kidney tissues). INTERCEPT 217 is therefore involved in protection of these (and likely other tissues) from the effects of inflammation, autoimmunity, infection, and acute and chronic traumas.

Presence in INTERCEPT 217 protein of multiple SH3 domain binding sites indicates that INTERCEPT 217 protein interacts with one or more SH3 domain-containing proteins. Thus, INTERCEPT 217 protein mediates binding of proteins (i.e., binding of proteins to INTERCEPT 217 and to one another to form protein complexes) in cells in which it is expressed. INTERCEPT 217 is also involved in transduction of signals between the exterior environment of cells (i.e., including from other cells) and the interior of cells in which it is expressed. INTERCEPT 217 mediates regulation of cell growth and proliferation, endocytosis, activation of respiratory burst, and other physiological processes triggered by transmission of a signal via a protein with which INTERCEPT 217 interacts.

INTERCEPT 217-related molecules can be used to modulate one or more of the activities in which INTERCEPT 217 is involved and can also be used to prevent, diagnose, or treat one or more of the disorders in which INTERCEPT 217 is involved.

INTERCEPT 217 polypeptides, nucleic acids, and modulators thereof, can, for example, be used to treat pancreatic disorders, such as pancreatitis (e.g., acute hemorrhagic pancreatitis and chronic pancreatitis), pancreatic cysts (e.g., congenital cysts, pseudocysts, and benign or malignant neoplastic cysts), pancreatic tumors (e.g., pancreatic carcinoma and adenoma), diabetes mellitus (e.g., insulin- and non-insulin-dependent types, impaired glucose tolerance, and gestational diabetes), and islet cell tumors (e.g., insulinomas, adenomas, Zollinger-Ellison syndrome, glucagonomas, and somatostatinoma). INTERCEPT 217 polypeptides, nucleic acids, and modulators thereof can be used to prognosticate, diagnose, inhibit, prevent, or alleviate one or more of these disorders.

In another example, INTERCEPT 217 polypeptides, nucleic acids, and modulators thereof, can be used to treat disorders of skeletal muscle, such as muscular dystrophy (e.g., Duchenne muscular dystrophy, Becker muscular dystrophy, Emery-Dreifuss muscular dystrophy, limb-girdle muscular dystrophy, facioscapulohumeral muscular dystrophy, myotonic dystrophy, oculopharyngeal muscular dystrophy, distal muscular dystrophy, and congenital muscular dystrophy), motor neuron diseases (e.g., amyotrophic lateral sclerosis, infantile progressive spinal muscular atrophy, intermediate spinal muscular atrophy, spinal bulbar muscular atrophy, and adult spinal muscular atrophy), myopathies (e.g., inflammatory myopathies {e.g., dermatomyositis and polymyositis}, myotonia congenita, paramyotonia congenita, central core disease, nemaline myopathy, myotubular myopathy, and periodic paralysis), and metabolic diseases of muscle (e.g., phosphorylase deficiency, acid maltase deficiency, phosphofructokinase deficiency, debrancher enzyme deficiency, mitochondrial myopathy, camitine deficiency, camitine palmityl transferase deficiency, phosphoglycerate kinase deficiency, phosphoglycerate mutase deficiency, lactate dehydrogenase deficiency, and myoadenylate deaminase deficiency). INTERCEPT 217 polypeptides, nucleic acids, and modulators thereof can be used to prognosticate, diagnose, inhibit, prevent, or alleviate one or more of these disorders.

Because INTERCEPT 217 exhibits expression in heart tissue, INTERCEPT 217 nucleic acids, proteins, and modulators thereof can be used to treat heart disorders (e.g., ischemic heart disease, atherosclerosis, hypertension, angina pectoris, hypertrophic cardiomyopathy, and congenital heart disease). INTERCEPT 217 polypeptides, nucleic acids, and modulators thereof can be used to prognosticate, diagnose, inhibit, prevent, or alleviate one or more of these disorders.

In another example, INTERCEPT 217 polypeptides, nucleic acids, and modulators thereof, can be used to treat disorders of the brain, such as cerebral edema, hydrocephalus, brain herniations, iatrogenic disease (due to, e.g., infection, toxins, or drugs), inflammations (e.g., bacterial and viral meningitis, encephalitis, and cerebral toxoplasmosis), cerebrovascular diseases (e.g., hypoxia, ischemia, and infarction, intracranial hemorrhage and vascular malformations, and hypertensive encephalopathy), and tumors (e.g., neuroglial tumors, neuronal tumors, tumors of pineal cells, meningeal tumors, primary and secondary lymphomas, intracranial tumors, and medulloblastoma), and to treat injury or trauma to the brain. INTERCEPT 217 polypeptides, nucleic acids, and modulators thereof can be used to prognosticate, diagnose, inhibit, prevent, or alleviate one or more of these disorders.

In another example, INTERCEPT 217 polypeptides, nucleic acids, and modulators thereof, can be used to treat placental disorders, such as toxemia of pregnancy (e.g., preeclampsia and eclampsia), placentitis, and spontaneous abortion. INTERCEPT 217 polypeptides, nucleic acids, and modulators thereof can be used to prognosticate, diagnose, inhibit, prevent, or alleviate one or more of these disorders.

In another example, INTERCEPT 217 polypeptides, nucleic acids, and modulators thereof, can be used to treat pulmonary (i.e., lung) disorders, such as atelectasis, cystic fibrosis, rheumatoid lung disease, pulmonary congestion, pulmonary edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), and tumors (e.g., bronchogenic carcinoma, bronchioloalveolar carcinoma, bronchial carcinoid, hamartoma, and mesenchymal tumors). INTERCEPT 217 polypeptides, nucleic acids, and modulators thereof can be used to prognosticate, diagnose, inhibit, prevent, or alleviate one or more of these disorders.

In another example, INTERCEPT 217 polypeptides, nucleic acids, and modulators thereof, can be used to treat cardiovascular disorders, such as ischemic heart disease (e.g., angina pectoris, myocardial infarction, and chronic ischemic heart disease), hypertensive heart disease, pulmonary heart disease, valvular heart disease (e.g., rheumatic fever and rheumatic heart disease, endocarditis, mitral valve prolapse, and aortic valve stenosis), congenital heart disease (e.g., valvular and vascular obstructive lesions, atrial or ventricular septal defect, and patent ductus arteriosus), and myocardial disease (e.g., myocarditis, congestive cardiomyopathy, and hypertrophic cariomyopathy). INTERCEPT 217 polypeptides, nucleic acids, and modulators thereof can be used to prognosticate, diagnose, inhibit, prevent, or alleviate one or more of these disorders.

In yet another example, INTERCEPT 217 polypeptides, nucleic acids, and modulators thereof, can be used to treat hepatic (i.e., liver) disorders, such as jaundice, hepatic failure, hereditary hyperbiliruinemias (e.g., Gilbert's syndrome, Crigler-Naijar syndromes and Dubin-Johnson and Rotor's syndromes), hepatic circulatory disorders (e.g., hepatic vein thrombosis and portal vein obstruction and thrombosis), hepatitis (e.g., chronic active hepatitis, acute viral hepatitis, and toxic and drug-induced hepatitis), cirrhosis (e.g., alcoholic cirrhosis, biliary cirrhosis, and hemochromatosis), and malignant tumors (e.g., primary carcinoma, hepatoblastoma, and angiosarcoma). INTERCEPT 217 polypeptides, nucleic acids, and modulators thereof can be used to prognosticate, diagnose, inhibit, prevent, or alleviate one or more of these disorders.

In still another example, INTERCEPT 217 polypeptides, nucleic acids, and modulators thereof, can be used to treat renal (i.e., kidney) disorders, such as glomerular diseases (e.g., acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (e.g., acute tubular necrosis and acute renal failure, polycystic renal disease, medullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy), acute and rapidly progressive renal failure, chronic renal failure, nephrolithiasis, vascular diseases (e.g., hypertension and nephrosclerosis, microangiopathic hemolytic anemia, atheroembolic renal disease, diffuse cortical necrosis, and renal infarcts), and tumors (e.g., renal cell carcinoma and nephroblastoma). INTERCEPT 217 polypeptides, nucleic acids, and modulators thereof can be used to prognosticate, diagnose, inhibit, prevent, or alleviate one or more of these disorders.

INTERCEPT 297

A cDNA clone (designated jthsa085g01) encoding at least a portion of human INTERCEPT 297 protein was isolated from a human fetal spleen cDNA library. The human INTERCEPT 297 protein is predicted by structural analysis to be a transmembrane protein.

The full length of the cDNA encoding human INTERCEPT 297 protein (FIG. 2; SEQ ID NO: 9) is 1518 nucleotide residues. The ORF of this cDNA, nucleotide residues 40 to 1152 of SEQ ID NO: 9 (i.e., SEQ ID NO: 10), encodes a 371-amino acid transmembrane protein (FIG. 2; SEQ ID NO: 11).

The invention thus includes purified human INTERCEPT 297 protein, both in the form of a 371 amino acid residue protein (SEQ ID NO: 11) in which the 'signal sequence' (i.e., the portion of INTERCEPT 297 protein corresponding to amino acid residues 1 to 18) described in this section is not cleaved and in the form of a 353 amino acid residue protein (SEQ ID NO: 13) in which the 'signal sequence' is cleaved. Human INTERCEPT 297 protein can exist with or without the signal sequence polypeptide at the amino terminus thereof. It is likely that the 'signal sequence' is not cleaved, but is instead a transmembrane domain of the protein.

In addition to full length human INTERCEPT 297 proteins, the invention includes fragments, derivatives, and variants of these INTERCEPT 297 proteins, as described herein. These proteins, fragments, derivatives, and variants are collectively referred to herein as INTERCEPT 297 polypeptides of the invention or INTERCEPT 297 proteins of the invention.

The invention also includes nucleic acid molecules which encode an INTERCEPT 297 polypeptide of the invention. Such nucleic acids include, for example, a DNA molecule having the nucleotide sequence listed in SEQ ID NO: 9 or some portion thereof, such as the portion which encodes mature INTERCEPT 297 protein, immature INTERCEPT 297 protein, or a domain of INTERCEPT 297 protein. These nucleic acids are collectively referred to as INTERCEPT 297 nucleic acids of the invention.

INTERCEPT 297 proteins and nucleic acid molecules encoding them comprise a family of molecules having certain conserved structural and functional features.

A common domain present in INTERCEPT 297 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a INTERCEPT 297 protein contains a signal sequence corresponding to about amino acid residues 1 to 18 of SEQ ID NO: 11 (SEQ ID NO: 12). The signal sequence can be cleaved during processing of the mature protein, but it is likely that amino acid residues 1 to 18 of SEQ ID NO: 11 represent a (non-cleaved) transmembrane region of the protein.

INTERCEPT 297 proteins can include one or more extracellular domains. In one embodiment of the human INTERCEPT 297 protein, extracellular domains are located from about amino acid residues 19 to 47, from about amino acid residues 110 to 118, from about amino acid residues 162 to 175, from about amino acid residues 234 to 260, and from about amino acid residues 313 to 319 of SEQ ID NO: 11 (SEQ ID NOs: 14–18, respectively). In an alternative embodiment, extracellular domains are located from about amino acid residue 69 to 88, from about amino acid residue 138 to 144, from about amino acid residue 193 to 215, from about amino acid residue 284 to 292, and from about amino acid residue 337 to 371 of SEQ ID NO: 11 (SEQ ID NOs: 28–32, respectively).

In addition, INTERCEPT 297 includes one or more transmembrane domains. In one embodiment, a INTERCEPT 297 protein of the invention contains transmembrane domains corresponding to about amino acid residues 48 to 68, about amino acid residues 89 to 109, about amino acid residues 119 to 137, about amino acid residues 145 to 161, about amino acid residues 176 to 192, about amino acid residues 216 to 233, about amino acid residues 261 to 283, about amino acid residues 293 to 312, and about amino acid residues 320 to 336 of SEQ ID NO: 11 (SEQ ID NOs: 19–27, respectively). As indicated above, it is likely that the 'signal sequence' of INTERCEPT 297 is an additional (and non-cleaved) transmembrane region.

The present invention includes INTERCEPT 297 proteins having one or more cytoplasmic domains. In one embodiment of the human INTERCEPT 297 protein, cytoplasmic domains are located from about amino acid residue 69 to 88, from about amino acid residue 138 to 144, from about amino acid residue 193 to 215, from about amino acid residue 284 to 292, and from about amino acid residue 337 to 371 of SEQ ID NO: 11 (SEQ ID NOs: 28–32, respectively). In an alternative embodiment, cytoplasmic domains are located from about amino acid residues 19 to 47, from about amino acid residues 110 to 118, from about amino acid residues 162 to 175, from about amino acid residues 234 to 260, and from about amino acid residues 313 to 319 of SEQ ID NO: 11 (SEQ ID NOs: 14–18, respectively).

INTERCEPT 297 proteins typically comprise a variety of potential post-translational modification sites (often within an extracellular domain), such as those described herein in Table III, as predicted by computerized sequence analysis of INTERCEPT 297 proteins using amino acid sequence comparison software (comparing the amino acid sequence of INTERCEPT 297 with the information in the PROSITE database {rel. 12.2; February, 1995} and the Hidden Markov Models database {Rel. PFAM 3.3 }). In certain embodiments, a protein of the invention has at least 1, 2, 4, 6, 10, 15, or 20 or more of the post-translational modification sites listed in Table III.

TABLE III

| Type of Potential Modification Site or Domain | Amino Acid Residues of SEQ ID NO: 11 | Amino Acid Sequence |
|---|---|---|
| N-glycosylation site | 110 to 113 | NMTS |
| | 269 to 272 | NISS |
| Protein kinase C phosphorylation site | 24 to 26 | SAK |
| | 290 to 292 | TTR |
| | 297 to 299 | SLR |
| Casein kinase II phosphorylation site | 78 to 81 | SSVD |
| | 165 to 168 | SKHD |
| | 245 to 248 | TLED |
| | 354 to 357 | SEQE |
| N-myristoylation site | 18 to 23 | GSINTL |
| | 35 to 40 | GCGGSK |
| | 53 to 58 | GMFLGE |
| | 74 to 79 | GQSDSS |
| | 147 to 152 | GILATI |
| | 236 to 241 | GSFSGN |
| | 268 to 273 | GNISSI |
| | 280 to 285 | GISVTK |
| Amidation site | 136 to 139 | LGRR |
| DUF6 domain | 44 to 171 | See FIG. 2 |

Among the domains that occur in INTERCEPT 297 protein is a DUF6 domain. In one embodiment, the protein of the invention has at least one domain that is at least 55%, preferably at least about 65%, more preferably at least about 75%, yet more preferably at least about 85%, and most preferably at least about 95% identical to this DUF6 domain.

The DUF6 domain is a transmembrane domain that is highly conserved among eukaryote, prokaryote, and archae kingdoms. This high degree of domain sequence conservation indicates that proteins of the class which includes INTERCEPT 297 are involved in fundamental membrane physiology of living cells. INTERCEPT 297 protein is therefore involved in disorders which are associated with aberrant membrane function including, for example, disorders involving abnormal membrane fluidity, disorders involving aberrant transmembrane transport, disorders involving abnormal membrane organization, disorders involving abnormal membrane synthesis, disorders involving aberrant cell division, and the like.

The signal peptide prediction program SIGNALP (Nielsen et al. (1997) Protein Engineering 10:1–6) predicted that human INTERCEPT 297 protein includes an approximately 18 (i.e., 16, 17, 18, 19, or 20) amino acid residue signal peptide (amino acid residues 1 to 18 of SEQ ID NO: 11; SEQ ID NO: 12) preceding the mature INTERCEPT 297 protein (i.e., approximately amino acid residues 19 to 371 of SEQ ID NO: 11; SEQ ID NO: 13). In one embodiment, human INTERCEPT 297 protein includes about five extracellular domains (amino acid residues 19 to 47, 110 to 118, 162 to 175, 234 to 260, and 313 to 319 of SEQ ID NO: 11); about nine transmembrane domains (amino acid residues 48 to 68, 89 to 109, 119 to 137, 145 to 161, 176 to 192, 216 to 233, 261 to 283, 293 to 312, and 320 to 326 of SEQ ID NO: 11); and about five cytoplasmic domains (amino acid residues 69 to 88, 138 to 144, 193 to 215, 284 to 292, and 337 to 371 of SEQ ID NO: 11). In an alternative embodiment, human INTERCEPT 297 protein includes about five cytoplasmic domains (amino acid residues 19 to 47, 110 to 118, 162 to 175, 234 to 260, and 313 to 319 of SEQ ID NO: 11); about nine transmembrane domains (amino acid residues 48 to 68, 89 to 109, 119 to 137, 145 to 161, 176 to 192, 216 to 233, 261 to 283, 293 to 312, and 320 to 326 of SEQ ID NO: 11); and about five extracellular domains (amino acid residues 69 to 88, 138 to 144, 193 to 215, 284 to 292, and 337 to 371 of SEQ ID NO: 11).

Figure 2D:
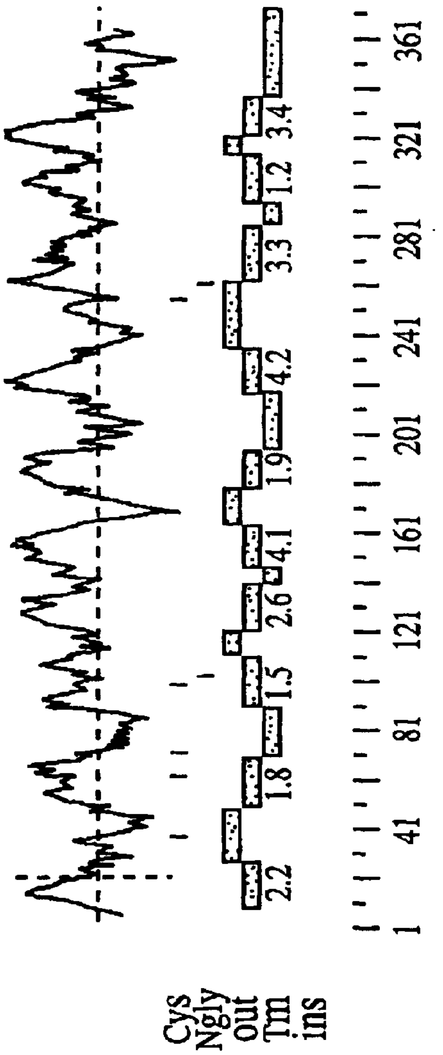
FIG. 2D is a hydrophilicity plot of human INTERCEPT 297 protein.

FIG. 2D depicts a hydrophilicity plot of human INTERCEPT 297 protein. Relatively hydrophobic regions are above the dashed horizontal line, and relatively hydrophilic regions are below the dashed horizontal line. Hydrophobic region corresponding to the signal sequence and the transmembrane domains are observed in this figure. As described elsewhere herein, relatively hydrophilic regions are generally located at or near the surface of a protein, and are more frequently effective immunogenic epitopes than are relatively hydrophobic regions. For example, the region of human INTERCEPT 297 protein from about amino acid residue 165 to about amino acid residue 175 appears to be located at or near the surface of the protein.

The predicted molecular weight of human INTERCEPT 297 protein without modification and prior to cleavage of the signal sequence is about 40.2 kilodaltons. The predicted molecular weight of the mature human INTERCEPT 297 protein without modification and after cleavage of the signal sequence is about 38.2 kilodaltons.

Biological function of INTERCEPT 297 proteins, nucleic acids encoding them, and modulators of these molecules INTERCEPT 297 proteins are involved in disorders which affect both tissues in which they are normally expressed and tissues in which they are normally not expressed. Based on the observation that INTERCEPT 297 is expressed in human fetal spleen, INTERCEPT 297 protein is involved in one or more biological processes which occur in fetal and spleen tissues. In particular, INTERCEPT 297 is involved in modulating growth, proliferation, survival, differentiation, and activity of cells including, but not limited to, spleen and fetal cells of the animal in which it is normally expressed. Thus, INTERCEPT 297 has a role in disorders which affect these cells and their growth, proliferation, survival, differentiation, and activity (e.g., hematologic and immune disorders). Expression of INTERCEPT 297 in an animal is also involved in modulating growth, proliferation, survival, differentiation, and activity of cells and viruses which are foreign to the host (i.e., bacterial, fungal, and viral infections).

INTERCEPT 297 bears amino acid sequence similarity to *Caenorhabditis elegans* protein C2G12.12, and therefore exhibits one or more activities analogous to that protein.

INTERCEPT 297 nucleic acids, proteins, and modulators thereof can be used to modulate the proliferation, differentiation, or function of cells of the spleen (e.g., cells of the splenic connective tissue, splenic smooth muscle cells, and endothelial cells of the splenic blood vessels). INTERCEPT 297 nucleic acids, proteins, and modulators thereof can also be used to modulate the proliferation, differentiation, and function of cells that are processed within the spleen (e.g., regenerated or phagocytized within the spleen, erythrocytes, B and T lymphocytes, and macrophages). Thus, INTERCEPT 297 nucleic acids, proteins, and modulators thereof can be used to treat disorders of the spleen (including disorders of the fetal spleen). Examples of splenic disorders include, splenic lymphoma, splenomegaly, and phagocytotic disorders (e.g., those in which macrophage engulfment of bacteria and viruses in the bloodstream is inhibited). INTERCEPT 297 polypeptides, nucleic acids, and modulators thereof can be used to prognosticate, diagnose, inhibit, prevent, or alleviate one or more of these disorders.

Structural analysis of INTERCEPT 297 and the presence of a DUF6 domain therein indicate that INTERCEPT 297 is involved in disorders which affect membrane structure and function. INTERCEPT 297 can be used to affect development and persistence of disorders involving inappropriate membrane structure and function, such as atherogenesis, arteriosclerosis, and various transmembrane transport disorders. Other exemplary disorders for which INTERCEPT 297 is useful include disorders involving generation and persistence of an immune response to bacterial, fungal, and viral infections. INTERCEPT 297 polypeptides, nucleic acids, and modulators thereof can be used to prognosticate, diagnose, inhibit, prevent, or alleviate one or more of these disorders.

The structure of INTERCEPT 297 is analogous to the structures of integral membrane proteins responsible for transmembrane transport of molecules such as sugars, ions, and the like. INTERCEPT 297 is thus involved in one or more transmembrane transport-related disorders such as cystic fibrosis, nerve conduction disorders (e.g., pain and loss or failure of sensation), muscle contraction disorders (e.g., cardiac insufficiency), metal ion uptake disorders (e.g., hemochromatosis), and the like. INTERCEPT 297 polypeptides, nucleic acids, and modulators thereof can be used to prognosticate, diagnose, inhibit, prevent, or alleviate one or more of these disorders.

TANGO 276

A cDNA clone (designated jthsa006e01) encoding at least a portion of human TANGO 276 protein was isolated from a human fetal spleen cDNA library. The human TANGO 276 protein is predicted by structural analysis to be a secreted protein.

The full length of the cDNA encoding human TANGO 276 protein (FIG. 3; SEQ ID NO: 33) is 2811 nucleotide residues. The ORF of this cDNA, nucleotide residues 58 to 786 of SEQ ID NO: 33 (i.e., SEQ ID NO: 34), encodes a 243-amino acid secreted protein (FIG. 3; SEQ ID NO: 35).

The invention thus includes purified human TANGO 276 protein, both in the form of the immature 243 amino acid residue protein (SEQ ID NO: 35) and in the form of the mature, approximately 223 amino acid residue protein (SEQ ID NO: 37). Mature human TANGO 276 protein can be synthesized without the signal sequence polypeptide at the amino terminus thereof, or it can be synthesized by generating immature TANGO 276 protein and cleaving the signal sequence therefrom.

In addition to full length mature and immature human TANGO 276 proteins, the invention includes fragments, derivatives, and variants of these TANGO 276 proteins, as described herein. These proteins, fragments, derivatives, and variants are collectively referred to herein as TANGO 276 polypeptides of the invention or TANGO 276 proteins of the invention.

The invention also includes nucleic acid molecules which encode a TANGO 276 polypeptide of the invention. Such nucleic acids include, for example, a DNA molecule having the nucleotide sequence listed in SEQ ID NO: 33 or some portion thereof, such as the portion which encodes mature TANGO 276 protein, immature TANGO 276 protein, or a domain of TANGO 276 protein. These nucleic acids are collectively referred to as TANGO 276 nucleic acids of the invention.

TANGO 276 proteins and nucleic acid molecules encoding them comprise a family of molecules having certain conserved structural and functional features, as indicated by the conservation of amino acid sequence between human TANGO 276 protein and the murine protein designated M-Sema-F (see Inagaki et al. (1995) FEBS Lett. 370:269–272), as shown in FIGS. 3F to 3H.

A common domain present in TANGO 276 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45%-hydrophobic residues. A signal sequence serves to direct a protein containing such a sequence to a lipid bilayer. Thus, in one embodiment, a TANGO 276 protein contains a signal sequence corresponding to about amino acid residues 1 to 20 of SEQ ID NO: 35 (SEQ ID NO: 36). The signal sequence is cleaved during processing of the mature protein.

TANGO 276 proteins can exist in a secreted form, such as a mature protein having the amino acid sequence of amino acid residues 21 to 243 of SEQ ID NO: 35 (SEQ ID NO: 37).

TANGO 276 proteins typically comprise a variety of potential post-translational modification sites (often within an extracellular domain), such as those described herein in, Table IV, as predicted by computerized sequence analysis of TANGO 276 proteins using amino acid sequence comparison software (comparing the amino acid sequence of TANGO 276 with the information in the PROSITE database {rel. 12.2; February, 1995} and the Hidden Markov Models database {Rel. PFAM 3.3 }). In certain embodiments, a protein of the invention has at least 1, 2, 4, 6, or all 8 of the post-translational modification sites listed in Table IV.

TABLE IV

| Type of Potential Modification Site or Domain | Amino Acid Residues of SEQ ID NO: 35 | Amino Acid Sequence |
|---|---|---|
| N-glycosylation site | 106 to 109 | NQTE |
| | 121 to 124 | NASH |
| cAMP- or cGMP-dependent protein kinase phosphorylation site | 43 to 46 | RRFS |
| Protein kinase C phosphorylation site | 194 to 196 | SLK |
| Casein kinase II phosphorylation site | 34 to 37 | SSGE |
| | 57 to 60 | TLTE |
| N-myristoylation site | 16 to 21 | GLGIGA |
| | 68 to 73 | GAREAL |
| Sema domain | 53 to 141 | See FIG. 3 |

A Sema domain occurs in human TANGO 276 protein. In one embodiment, the protein of the invention has at least one domain that is at least 55%, preferably at least about 65%, more preferably at least about 75%, yet more preferably at least about 85%, and most preferably at least about 95% identical to this Sema domain.

Sema domains occur in semaphorin proteins. Semaphorins are a large family of secreted and transmembrane proteins, some of which function as repellent signals during neural axon guidance. The Sema domain and a variety of semaphorin proteins in which it occurs are described, for example, in Winberg et al. (1998 Cell 95:903–916). Sema domains also occur in human hepatocyte growth factor receptor (SwissProt Accession no. P08581) and the similar neuronal and epithelial transmembrane receptor protein (SwissProt Accession no. P51805). The presence of a Sema domain in human TANGO 276 protein indicates that TANGO 276 is involved in one or more physiological processes in which the semaphorins are involved, has biological activity in common with one or more of the semaphorins, or both.

Human TANGO 276 protein exhibits considerable sequence similarity to murine M-Sema F protein (GenBank Accession no. S79463), as indicated herein in FIGS. 3F to 3H. FIGS. 3F to 3H depict an alignment of the amino acid sequences of human TANGO 276 protein (SEQ ID NO: 35) and murine M-Sema F protein (SEQ ID NO: 65). In this alignment (pam120. mat scoring matrix, gap opening penalty=12, gap extension penalty=4), the amino acid sequences of the proteins are 76.1% identical. FIGS. 3I through 3R depict an alignment of the nucleotide sequences of cDNA encoding human TANGO 276 protein (SEQ ID NOs: 33) and murine cDNA encoding M-Sema F protein (SEQ ID NO: 66). In this alignment (pam120. mat scoring matrix, gap opening penalty=12, gap extension penalty=4), the nucleic acid sequences of the cDNAs are 79.7% identical. Thus, TANGO 276 is related to murine M-Sema F and shares functional similarities to that protein.

It is known that semaphorins are bi-functional, capable of functioning either as attractive axonal guidance proteins or as repellent axonal guidance proteins (Wong et al. (1997) Development 124:3597–3607). Furthermore, semaphorins bind with neuronal cell surface proteins designated plexins, which are expressed on both neuronal cells and cells of the immune system (Comeau et al. (1998) Immunity 8:473–482; Jin and Strittmatter (1997) J. Neurosci. 17:6256–6263).

The signal peptide prediction program SIGNALP (Nielsen et al. (1997) Protein Engineering 10:1–6) predicted that human TANGO 276 protein includes an approximately 20 (i.e., 18, 19, 20, 21, or 22) amino acid signal peptide (amino acid residues 1 to 20 of SEQ ID NO: 35; SEQ ID NO: 36) preceding the mature TANGO 276 protein (i.e., approximately amino acid residues 21 to 243 of SEQ ID NO: 34; SEQ ID NO: 37). Human TANGO 276 protein is a secreted protein.

Figure 3E:
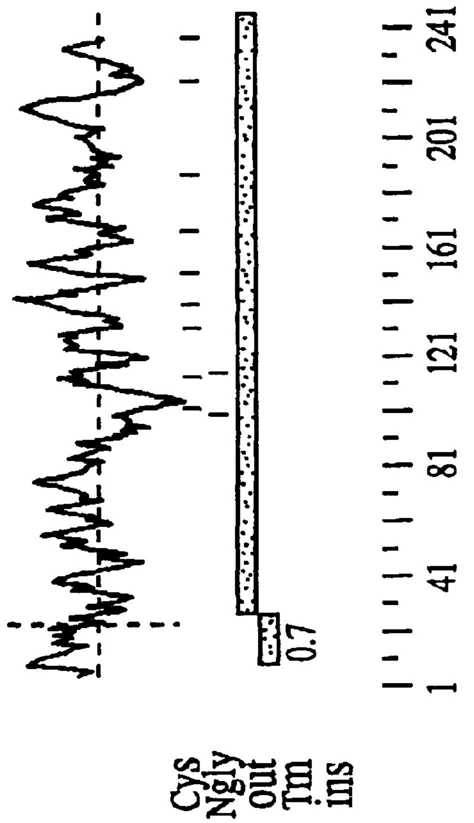
FIG. 3E is a hydrophilicity plot of TANGO 276 protein. An alignment of the amino acid sequences of human TANGO 276 protein ("H"; SEQ ID NO: 35) and murine protein M-Sema-F ("M"; SEQ ID NO: 65) is shown in FIGS. 3F to 3H.

FIG. 3E depicts a hydrophilicity plot of human TANGO 276 protein. Relatively hydrophobic regions are above the dashed horizontal line, and relatively hydrophilic regions are below the dashed horizontal line. The hydrophobic region which corresponds to about amino acid residues 1 to 20 of SEQ ID NO: 35 is the signal sequence of human TANGO 276. As described elsewhere herein, relatively hydrophilic regions are generally located at or near the surface of a protein, and are more frequently effective immunogenic epitopes than are relatively hydrophobic regions. For example, the region of human TANGO 276 protein from about amino acid residue 90 to about amino acid residue 105 appears to be located at or near the surface of the protein, while the region from about amino acid residue 170 to about amino acid residue 180 appears not to be located at or near the surface.

The predicted molecular weight of human TANGO 276 protein without modification and prior to cleavage of the signal sequence is about 27.1 kilodaltons. The predicted molecular weight of the mature human TANGO 276 protein without modification and after cleavage of the signal sequence is about 24.8 kilodaltons.

Northern analysis experiments indicated that mRNA corresponding to the cDNA encoding TANGO 276 is expressed in the tissues listed in Table V, wherein "++" indicates a greater level of expression and "+" indicates a lower level of expression.

TABLE V

| Animal | Tissue | Relative Level of Expression |
|---|---|---|
| Human | heart | ++ |
| | placenta | ++ |
| | brain | + |
| | lung | + |
| | liver | + |
| | skin | + |
| | kidney | + |
| | pancreas | + |

Biological function of TANGO 276 proteins, nucleic acids encoding them, and modulators of these molecules TANGO 276 proteins are involved in disorders which affect both tissues in which they are normally expressed and tissues in which they are normally not expressed. Based on the observation that TANGO 276 is expressed in human heart and placenta tissues, to a lesser extent in brain, lung, liver, skin, kidney, and pancreas tissues, and in fetal spleen tissue, TANGO 276 protein is involved in one or more biological processes which occur in these tissues. In particular, TANGO 276 is involved in modulating growth, proliferation, survival, differentiation, and activity of cells including, but not limited to, heart, placenta, spleen, brain, lung, liver, skin, kidney, and pancreas cells of the animal in which it is normally expressed. Thus, TANGO 276 has a role in disorders which affect these cells and their growth, proliferation, survival, differentiation, and activity.

Because TANGO 276 exhibits expression in the heart, TANGO 276 nucleic acids, proteins, and modulators thereof can be used to treat heart disorders. Examples of heart disorders with which TANGO 276 can be involved include ischemic heart disease, atherosclerosis, hypertension, angina pectoris, hypertrophic cardiomyopathy, and congenital heart disease. TANGO 276 polypeptides, nucleic acids, or modulators thereof can be used to prognosticate, diagnose, inhibit, prevent, or alleviate one or more of these disorders.

In another example, TANGO 276 polypeptides, nucleic acids, and modulators thereof can be used to treat placental disorders, such as toxemia of pregnancy (e.g., preeclampsia and eclampsia), placentitis, and spontaneous abortion. TANGO 276 polypeptides, nucleic acids, and modulators thereof can be used to prognosticate, diagnose, inhibit, prevent, or alleviate one or more of these disorders.

In another example, TANGO 276 polypeptides, nucleic acids, or modulators thereof, can be used to treat disorders of the brain, such as cerebral edema, hydrocephalus, brain herniations, iatrogenic disease (due to, e.g., infection, toxins, or drugs), inflammations (e.g., bacterial and viral meningitis, encephalitis, and cerebral toxoplasmosis), cerebrovascular diseases (e.g., hypoxia, ischemia, and infarction, intracranial hemorrhage and vascular malformations, and hypertensive encephalopathy), and tumors (e.g., neuroglial tumors, neuronal tumors, tumors of pineal cells, meningeal tumors, primary and secondary lymphomas, intracranial tumors, and medulloblastoma), and to treat injury or trauma to the brain. TANGO 276 polypeptides, nucleic acids, and modulators thereof can be used to prognosticate, diagnose, inhibit, prevent, or alleviate one or more of these disorders.

TANGO 276 polypeptides, nucleic acids, and modulators thereof can be associated with pulmonary (i.e., lung) disorders, such as atelectasis, cystic fibrosis, rheumatoid lung disease, pulmonary congestion, pulmonary edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), and tumors (e.g., bronchogenic carcinoma, bronchioloalveolar carcinoma, bronchial carcinoid, hamartoma, and mesenchymal tumors). TANGO 276 polypeptides, nucleic acids, or modulators thereof can be used to prognosticate, diagnose, inhibit, prevent, or alleviate one or more of these disorders.

In another example, TANGO 276 polypeptides, nucleic acids, and modulators thereof, can be used to treat hepatic (i.e., liver) disorders, such as jaundice, hepatic failure, hereditary hyperbiliruinemias (e.g., Gilbert's syndrome, Crigler-Naijar syndromes and Dubin-Johnson and Rotor's syndromes), hepatic circulatory disorders (e.g., hepatic vein thrombosis and portal vein obstruction and thrombosis) hepatitis (e.g., chronic active hepatitis, acute viral hepatitis, and toxic and drug-induced hepatitis) cirrhosis (e.g., alcoholic cirrhosis, biliary cirrhosis, and hemochromatosis), and malignant tumors (e.g., primary carcinoma, hepatoblastoma, and angiosarcoma). TANGO 276 polypeptides, nucleic acids, and modulators thereof can be used to prognosticate, diagnose, inhibit, prevent, or alleviate one or more of these disorders.

Exemplary skin disorders with which TANGO 276 can be associated include, by way of example, psoriasis, infections, wounds (and healing of wounds), inflammation, dermatitis, acne, benign and malignant dermatological tumors, and the like. TANGO 276 proteins, nucleic acids encoding them, and agents that modulate activity or expression of either of these can be used to prognosticate, diagnose, treat, and inhibit one or more of these disorders.

In another example, TANGO 276 polypeptides, nucleic acids, or modulators thereof, can be used to treat renal (i.e., kidney) disorders, such as glomerular diseases (e.g., acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (e.g., acute tubular necrosis and acute renal failure, polycystic renal disease, medullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy) acute and rapidly progressive renal failure, chronic renal failure, nephrolithiasis, vascular diseases (e.g., hypertension and nephrosclerosis, microangiopathic hemolytic anemia, atheroembolic renal disease, diffuse cortical necrosis, and renal infarcts), and tumors (e.g., renal cell carcinoma and nephroblastoma). TANGO 276 polypeptides, nucleic acids, and modulators thereof can be used to prognosticate, diagnose, inhibit, prevent, or alleviate one or more of these disorders.

Pancreatic disorders in which TANGO 276 can be involved include pancreatitis (e.g., acute hemorrhagic pancreatitis and chronic pancreatitis), pancreatic cysts (e.g., congenital cysts, pseudocysts, and benign or malignant neoplastic cysts), pancreatic tumors (e.g., pancreatic carcinoma and adenoma), diabetes mellitus (e.g., insulin- and non-insulin-dependent types, impaired glucose tolerance, and gestational diabetes), and islet cell tumors (e.g., insulinomas, adenomas, Zollinger-Ellison syndrome, glucagonomas, and somatostatinoma). TANGO 276 polypeptides, nucleic acids, or modulators thereof can be used to prognosticate, diagnose, inhibit, prevent, or alleviate one or more of these disorders.

The presence of the Sema domain in TANGO 276 indicates that this protein is involved in development of neuronal and epithelial tissues and also functions as a repellant protein which guides axonal development. TANGO 276 modulates nerve growth and regeneration and also modulates growth and regeneration of other epithelial tissues. TANGO 276 is thus involved in a variety of neuronal disorder including, but not limited to, one or more of seizure, epilepsy, (regeneration of) neuronal damage, pain (including, for example, migraine, headache, and other chronic pain), infections of the central nervous system, multiple sclerosis, sleep disorders, psychological disorders, nerve root disorders, and the like. Presence of a Sema domain in TANGO 276 further indicates that TANGO 276 has one or more physiological roles in common with other proteins (e.g., secreted and transmembrane semaphorins, collapsins, neuropilins, plexins, and the like) in which the Sema domain occurs. Thus, TANGO 276 is implicated in development, maintenance, and regeneration of neuronal connections and networks, in modulating differentiation of cells of the immune system, in modulating cytokine production by cells of the immune system, in modulating reactivity of cells of the immune system toward cytokines, in modulating initiation and persistence of an inflammatory response, and in modulating proliferation of epithelial cells. Sema domain-containing proteins have also been implicated in development and progression of small cell lung cancer, in normal brain development, and immune system regulation. This indicates that TANGO 276 is also involved in one or more of these processes and in disorders relating to these processes (e.g., small cell lung cancer, brain development disorders, and immune and auto-immune disorders). TANGO 276 polypeptides, nucleic acids, and modulators thereof can be used to prognosticate, diagnose, inhibit, prevent, or alleviate one or more of these disorders.

The observation that TANGO 276 shares identity with the murine semaphorin protein designated M-Sema F suggests that TANGO 276 has activity identical or analogous to the activity of this protein. These observations indicate that TANGO 276 modulates growth, proliferation, survival, differentiation, and activity of neuronal cells. Thus, TANGO 276 protein is useful, for example, for modulating and guiding neural axon development and for modulating establishment and maintenance of neuronal networks.

TANGO 292

A cDNA clone (designated jthkf040b11) encoding at least a portion of human TANGO 292 protein was isolated from a human normal embryonic keratinocyte cDNA library. A corresponding gerbil cDNA clone (designated jtiba040e12) was also isolated, and encoded at least a portion of gerbil TANGO 292 protein. The human and TANGO 292 proteins are predicted by structural analysis to be transmembrane proteins.

Figure 4D:
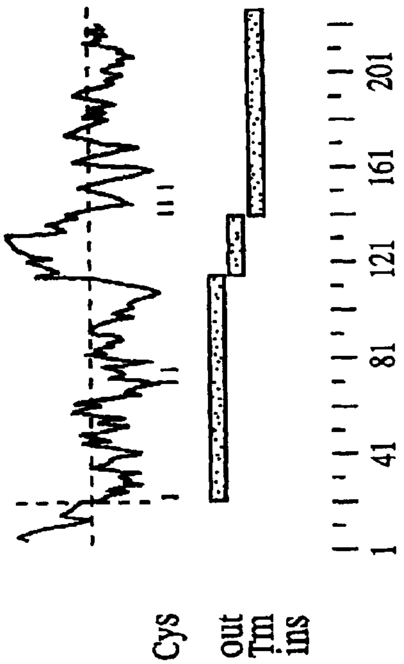
FIG. 4D is a hydrophilicity plot of human TANGO 292 protein. The nucleotide sequence (SEQ ID NO: 81) of a cDNA encoding the gerbil TANGO 292 protein described herein is listed in FIGS. 4E to 4H. The ORF (residues 89 to 763; SEQ ID NO: 82) of the cDNA is indicated by nucleotide triplets, below which the amino acid sequence (SEQ ID NO: 83) of gerbil TANGO 292 is listed.

The full length of the cDNA encoding human TANGO 292 protein (FIG. 4; SEQ ID NO: 38) is 2498 nucleotide residues. The ORF of this cDNA, nucleotide residues 205 to 882 of SEQ ID NO: 38 (i.e., SEQ ID NO: 39), encodes a 226-amino acid residue transmembrane protein (FIG. 4; SEQ ID NO: 40). The full length of the cDNA encoding gerbil TANGO 292 protein (FIG. 4; SEQ ID NO: 81) is 2002 nucleotide residues. The ORF of this cDNA, nucleotide residues 89 to 763 of SEQ ID NO: 81 (i.e., SEQ ID NO: 82), encodes a 225-amino acid transmembrane protein (FIG. 4; SEQ ID NO: 83).

The invention thus includes purified human TANGO 292 protein, both in the form of the immature 226 amino acid residue protein (SEQ ID NO: 40) and in the form of the mature, approximately 209 amino acid residue protein (SEQ ID NO: 42). The invention also includes purified gerbil TANGO 292 protein, both in the form of the immature 225-amino acid residue (SEQ ID NO: 83) protein and in the form of the mature, approximately 208-amino acid residue protein (SEQ ID NO: 85). Mature human or gerbil TANGO 292 protein can be synthesized without the signal sequence polypeptide at the amino terminus thereof, or it can be synthesized by generating immature TANGO 292 protein and cleaving the signal sequence therefrom.

In addition to full length mature and immature human and gerbil TANGO 292 proteins, the invention includes fragments, derivatives, and variants of these TANGO 292 proteins, as described herein. These proteins, fragments, derivatives, and variants are collectively referred to herein as TANGO 292 polypeptides of the invention or TANGO 292 proteins of the invention.

The invention also includes nucleic acid molecules which encode a TANGO 292 polypeptide of the invention. Such nucleic acids include, for example, a DNA molecule having the nucleotide sequence listed in SEQ ID NO: 38 or 81 or some portion thereof, such as the portion which encodes mature human or gerbil TANGO 292 protein, immature human or gerbil TANGO 292 protein, or a domain of human or gerbil TANGO 292 protein. These nucleic acids are collectively referred to as TANGO 292 nucleic acids of the invention.

TANGO 292 proteins and nucleic acid molecules encoding them comprise a family of molecules having certain conserved structural and functional features. This family includes, for example, human and gerbil TANGO 292 proteins and nucleic acid molecules described herein.

A common domain present in TANGO 292 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 292 protein contains a signal sequence corresponding to about amino acid residues 1 to 17 of SEQ ID NO: 40 (SEQ ID NO: 41) or to about amino acid residues 1 to 17 of SEQ ID NO: 83 (SEQ ID NO: 84). The signal sequence is cleaved during processing of the mature protein.

TANGO 292 proteins can include an extracellular domain. The human TANGO 292 protein extracellular domain is located from about amino acid residue 18 to about amino acid residue 113 of SEQ ID NO: 40 (SEQ ID NO: 43). The gerbil TANGO 292 protein extracellular domain includes at least about amino acid residues 18 to 112 of SEQ ID NO: 83 (SEQ ID NO: 86).

In addition, TANGO 292 include a transmembrane domain. In one embodiment, a human TANGO 292 protein contains a transmembrane domain corresponding to about amino acid residues 114 to 138 of SEQ ID NO: 40 (SEQ ID NO: 44). Gerbil TANGO 292 protein includes a transmembrane domain corresponding to about amino acid residues 113 to 137 of SEQ ID NO: 83 (SEQ ID NO: 87).

The present invention includes TANGO 292 proteins having a cytoplasmic domain, particularly including proteins having a carboxyl-terminal cytoplasmic domain. The human TANGO 292 cytoplasmic domain is located from about amino acid residue 139 to amino acid residue 226 of SEQ ID NO: 40 (SEQ ID NO: 45). The gerbil TANGO 292 cytoplasmic domain is located from about amino acid residue 138 to amino acid residue 225 of SEQ ID NO: 83 (SEQ ID NO: 88).

TANGO 292 proteins typically comprise a variety of potential post-translational modification sites (often within an extracellular domain), such as those described herein in Table VIa as predicted by computerized sequence analysis of human TANGO 292. protein, or in Table VIb as predicted by computerized sequence analysis of gerbil TANGO 292 protein, using amino acid sequence comparison software (comparing the amino acid sequence of TANGO 292 with the information in the PROSITE database {rel. 12.2; February, 1995} and the Hidden Markov Models database {Rel. PFAM 3.3 }). In certain embodiments, a protein of the invention has at least 1, 2, 4, 6, or all of the post-translational modification sites listed in Table VIa or in Table VIb.

TABLE VIa

| Type of Potential Modification Site or Domain | Amino Acid Residues of SEQ ID NO: 40 | Amino Acid Sequence |
|---|---|---|
| cAMP- or cGMP-dependent protein kinase phosphorylation site | 197 to 200 | RKHS |
| Protein kinase C phosphorylation site | 37 to 39 | TSK |
| | 97 to 99 | SAK |
| | 102 to 104 | TTK |
| | 196 to 198 | TRK |
| Casein kinase II phosphorylation site | 37 to 40 | TSKE |
| | 103 to 106 | TKSD |
| | 180 to 183 | SVED |
| N-myristoylation site | 116 to 121 | GLLTGL |
| Vitamin K-dependent carboxylation domain | 56 to 98 | See FIG. 4 |

TABLE VIb

| Type of Potential Modification Site or Domain | Amino Acid Residues of SEQ ID NO: 83 | Amino Acid Sequence |
|---|---|---|
| cAMP- or cGMP-dependent protein kinase phosphorylation site | 196 to 199 | RKHS |
| Protein kinase C phosphorylation site | 23 to 25 | SLK |
| | 37 to 39 | SKK |
| | 96 to 98 | SVK |
| | 101 to 103 | TTR |
| | 155 to 157 | TRR |
| | 195 to 197 | TRK |
| Casein kinase II phosphorylation site | 74 to 77 | SYEE |
| | 102 to 105 | TRSD |
| | 155 to 157 | THEE |
| | 195 to 197 | SSSE |
| N-myristoylation site | 33 to 38 | GVFASK |
| | 115 to 120 | GLLTGL |
| Vitamin K-dependent carboxylation domain | 55 to 92 | See FIG. 4 |

Among the domains that occur in TANGO 292 protein is a vitamin K-dependent carboxylation domain. In one embodiment, the protein of the invention has at least one domain that is at least 55%, preferably at least about 65%, more preferably at least about 75%, yet more preferably at least about 85%, and most preferably at least about 95% identical to this vitamin K-dependent carboxylation domain.

The vitamin K-dependent carboxylation domain has the following consensus sequence, wherein standard single-letter amino acid codes are used and 'X' refers to any amino acid residue.

$-X_{12}$-E-$X_3$-E-X-C-$X_6$-(D or E or N)-X-(L or I or V or M or F or Y)-$X_9$-(F or Y or W)-

Glutamic acid residues within this consensus region are potential vitamin K-dependent carboxylation sites. Human TANGO 292 has 9 glutamic acid residues in the vitamin K-dependent carboxylation domain located from about amino acid residue 56 to 98 of SEQ ID NO: 40, namely at amino acid residues 58, 66, 68, 71, 72, 77, 78, 81, and 86 of SEQ ID NO: 40, and gerbil TANGO 292 has 10 glutamic acid residues in the vitamin K-dependent carboxylation domain located from about amino acid residue 55 to 92 of SEQ ID NO: 83, namely at amino acid residues 57, 65, 67, 70, 71, 76, 77, 80, 86, and 87 of SEQ ID NO: 83. In one embodiment, the protein of the invention is carboxylated at one or more of these glutamic acid residues. In some proteins in which a vitamin K-dependent carboxylation domain occurs, many of the glutamic acid residues which occur from the amino terminus of the protein through the conserved aromatic residue at the carboxyl terminal end of the domain are carboxylated. Human TANGO 292 has 13 glutamic acid residues in the region from the amino terminus of (both the immature and mature forms of) the protein and the tryptophan residue at amino acid residue 93 of SEQ ID NO: 40, and also has another glutamic acid residue at position 95 of SEQ ID NO: 40 which can also be carboxylated. In addition, human TANGO 292 protein has four sets of paired (i.e., adjacent) glutamic acid residues, at residues 33–34, 40–41, 71–72, and 77–78 and a pair of glutamic acid residues (66 and 68) which are separated by a single residue. Similarly, gerbil TANGO 292 has 12 glutamic acid residues in the region from the amino terminus of (both the immature and mature forms of) the protein and the tryptophan residue at amino acid residue 92 of SEQ ID NO: 83, and also has another glutamic acid residue at position 94 of SEQ ID NO: 83 which can also be carboxylated. In addition, gerbil TANGO 292 protein has three sets of glutamic acid residues, at residues 70–71, 76–77, and 86–87, and a pair of glutamic acid residues (65 and 67) which are separated by a single residue. The protein of the invention includes proteins which are carboxylated at one or more of the individual or paired glutamic acid residues.

TANGO 292, like other vitamin K-dependent carboxylation domain-containing proteins, is involved in binding, uptake, and response to metal cations such as calcium, to proteins, and to small molecules. Other proteins in which a vitamin K-dependent carboxylation domain occurs include, for example, osteocalcin (bone-Gla protein), matrix Gla protein, various plasma proteins such as prothrombin, coagulation factors VII, IX, and X, proline rich Gla domain-containing proteins PRGP1 and PRGP2, and proteins C, S, and Z. Thus, TANGO 292 is involved in physiological processes in which one or more of these other vitamin K-dependent carboxylation domain-containing proteins is involved.

The signal peptide prediction program SIGNALP (Nielsen et al. (1997) Protein Engineering 10:1–6) predicted that human TANGO 292 protein includes an approximately 17 (i.e., 15, 16, 17, 18, or 19) amino acid residue signal peptide (amino acid residues 1 to 17 of SEQ ID NO: 40; SEQ ID NO: 41) preceding the mature TANGO 292 protein (i.e., approximately amino acid residues 18 to 226 of SEQ ID NO: 40; SEQ ID NO: 42). In one embodiment, human TANGO 292 protein includes an extracellular domain (amino acid residues 18 to 113 of SEQ ID NO: 40; SEQ ID NO: 43); a transmembrane domain (amino acid residues 114 to 138 of SEQ ID NO: 40; SEQ ID NO: 44); and a cytoplasmic domain (amino acid residues 139 to 225 of SEQ ID NO: 40; SEQ ID NO: 45). In an alternative embodiment, human TANGO 292 protein includes a cytoplasmic domain (amino acid residues 18 to 113 of SEQ ID NO: 40; SEQ ID NO: 43); a transmembrane domain (amino acid residues 114 to 138 of SEQ ID NO: 40; SEQ ID NO: 44); and an extracellular domain (amino acid residues 139 to 225 of SEQ ID NO: 40; SEQ ID NO: 45).

The SignalP program predicted that gerbil TANGO 292 protein includes an approximately 17 (i.e., 15, 16, 17, 18, or 19) amino acid residue amino acid signal peptide (amino acid residues 1 to 17 of SEQ ID NO: 83; SEQ ID NO: 84) preceding the mature TANGO 292 protein (i.e., approximately amino acid residues 18 to 225 of SEQ ID NO: 83; SEQ ID NO: 85). In one embodiment, gerbil TANGO 292 protein includes an extracellular domain (amino acid residues 18 to 112 of SEQ ID NO: 83; SEQ ID NO: 86); a transmembrane domain (amino acid residues 113 to 137 of SEQ ID NO: 83; SEQ ID NO: 87); and a cytoplasmic domain (amino acid residues 138 to 225 of SEQ ID NO: 83; SEQ ID NO: 88). In an alternative embodiment, gerbil TANGO 292 protein includes a cytoplasmic domain (amino acid residues 18 to 112 of SEQ ID NO: 83; SEQ ID NO: 86); a transmembrane domain (amino acid residues 113 to 137 of SEQ ID NO: 83; SEQ ID NO: 87); and an extracellular domain (amino acid residues 138 to 225 of SEQ ID NO: 83; SEQ ID NO: 88).

FIG. 4E depicts a hydrophilicity plot of human TANGO 292 protein. Relatively hydrophobic regions are above the dashed horizontal line, and relatively hydrophilic regions are below the dashed horizontal line. The hydrophobic region which corresponds to amino acid residues 1 to 17 of SEQ ID NO: 40 is the signal sequence of human TANGO 292. The hydrophobic region which corresponds to amino acid residues 114 to 138 of SEQ ID NO: 40 is the transmembrane domain of human TANGO 292. As described elsewhere herein, relatively hydrophilic regions are generally located at or near the surface of a protein, and are more frequently effective immunogenic epitopes than are relatively hydrophobic regions. For example, the region of human TANGO 292 protein from about amino acid residue 90 to about amino acid residue 110 appears to be located at or near the surface of the protein, while the region from about amino acid residue 190 to about amino acid residue 195 appears not to be located at or near the surface.

Figure 4M:
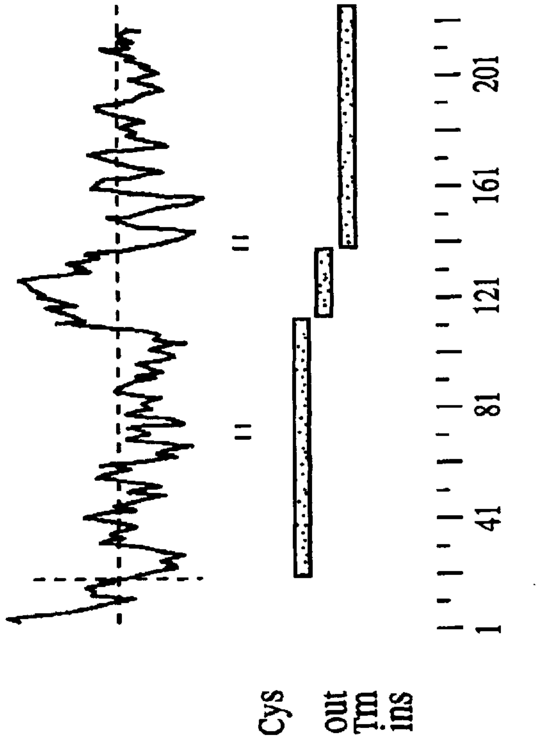
FIG. 4M is a hydrophilicity plot of gerbil TANGO 292 protein.

FIG. 4M depicts a hydrophilicity plot of gerbil TANGO 292 protein. Relatively hydrophobic regions are above the dashed horizontal line, and relatively hydrophilic regions are below the dashed horizontal line. The hydrophobic region which corresponds to amino acid residues 1 to 17 of SEQ ID NO: 83 is the signal sequence of gerbil TANGO 292. The hydrophobic region which corresponds to amino acid residues 113 to 137 of SEQ ID NO: 40 is the transmembrane domain of gerbil TANGO 292. As described elsewhere herein, relatively hydrophilic regions are generally located at or near the surface of a protein, and are more frequently effective immunogenic epitopes than are relatively hydrophobic regions. For example, the region of gerbil TANGO 292 protein from about amino acid residue 90 to about amino acid residue 110 appears to be located at or near the surface of the protein.

An alignment of the human (H) and gerbil (G) ORF sequences encoding TANGO 292 protein is shown in FIGS. 4I–4K. This alignment was made using the ALIGN software {Myers and Miller (1989) CABIOS, ver. 2.0}; pam120.mat scoring matrix; gap opening penalty=12, gap extension penalty=4), and indicates about 64.1% identity between these two cDNA sequences. An alignment of the amino acid sequences of gerbil (G) and human (H) TANGO 292 proteins is shown in FIG. 4L. In this alignment (made using the ALIGN software {Myers and Miller (1989) CABIOS, ver. 2.0}; pam120.mat scoring matrix; gap opening penalty=12, gap extension penalty=4), the proteins are about 77.7% identical and about 80% similar.

The predicted molecular weight of human TANGO 292 protein without modification and prior to cleavage of the signal sequence is about 25.4 kilodaltons. The predicted molecular weight of the mature human TANGO 292 protein without modification and after cleavage of the signal sequence is about 23.6 kilodaltons. The predicted molecular weight of gerbil TANGO 292 protein without modification and prior to cleavage of the signal sequence is about 25.4 kilodaltons. The predicted molecular weight of the mature human TANGO 292 protein without modification and after cleavage of the signal sequence is about 23.5 kilodaltons.

Northern analysis experiments indicated that human mRNA corresponding to the cDNA encoding TANGO 292 is expressed in the tissues listed in Table VIc, wherein "++" indicates strong expression, "+" indicates lower expression, "+/−" indicates still lower expression, and "−" indicates that expression could not be detected in the corresponding tissue.

TABLE VIc

| Animal | Tissue | Relative Level of Expression |
|---|---|---|
| Human | placenta | ++ |
| | liver | ++ |
| | kidney | ++ |
| | lung | + |
| | pancreas | + |
| | heart | +/− |
| | brain | − |
| | skeletal muscle | − |

Biological function of TANGO 292 proteins, nucleic acids encoding them, and modulators of these molecules TANGO 292 proteins are involved in disorders which affect both tissues in which they are normally expressed and tissues in which they are normally not expressed. Based on the observation that TANGO 292 is expressed in human embryonic keratinocytes, and in placenta, liver, kidney, lung, pancreas, and heart tissues, TANGO 292 protein is involved in one or more biological processes which occur in these tissues. In particular, TANGO 292 is involved in modulating growth, proliferation, survival, differentiation, and activity of cells including, but not limited to, keratinocytes and cells with which keratinocytes interact in the animal in which TANGO 292 is normally expressed. TANGO 292 is also involved in modulating growth, proliferation, survival, differentiation, and activity of placenta, liver, kidney, lung, pancreas, and heart cells. Thus, TANGO 292 has a role in disorders which affect these cells and their growth, proliferation, survival, differentiation, and activity. TANGO 292 polypeptides, nucleic acids, and modulators thereof can be used to prognosticate, diagnose, inhibit, prevent, or alleviate one or more of these disorders.

In another example, TANGO 292 polypeptides, nucleic acids, and modulators thereof can be used to treat placental disorders, such as toxemia of pregnancy (e.g., preeclampsia and eclampsia), placentitis, and spontaneous abortion. TANGO 292 polypeptides, nucleic acids, and modulators thereof can be used to prognosticate, diagnose, inhibit, prevent, or alleviate one or more of these disorders.

In another example, TANGO 292 polypeptides, nucleic acids, and modulators thereof, can be used to treat hepatic (i.e., liver) disorders, such as jaundice, hepatic failure, hereditary hyperbiliruinemias (e.g., Gilbert's syndrome, Crigler-Naijar syndromes and Dubin-Johnson and Rotor's syndromes), hepatic circula and portal vein obstruction and thrombosis) hepatitis (e.g., chronic active hepatitis, acute viral hepatitis, and toxic and drug-induced hepatitis) cirrhosis (e.g., alcoholic cirrhosis, biliary cirrhosis, and hemochromatosis), and malignant tumors (e.g., primary carcinoma, hepatoblastoma, and angiosarcoma). TANGO 292 polypeptides, nucleic acids, and modulators thereof can be used to prognosticate, diagnose, inhibit, prevent, or alleviate one or more of these disorders.

In another example, TANGO 292 polypeptides, nucleic acids, or modulators thereof, can be used to treat renal (i.e., kidney) disorders, such as glomerular diseases (e.g., acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (e.g., acute tubular necrosis and acute renal failure, polycystic renal disease, medullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy) acute and rapidly progressive renal failure, chronic renal failure, nephrolithiasis, vascular diseases (e.g., hypertension and nephrosclerosis, microangiopathic hemolytic anemia, atheroembolic renal disease, diffuse cortical necrosis, and renal infarcts), and tumors (e.g., renal cell carcinoma and nephroblastoma). TANGO 292 polypeptides, nucleic acids, and modulators thereof can be used to prognosticate, diagnose, inhibit, prevent, or alleviate one or more of these disorders.

TANGO 292 polypeptides, nucleic acids, and modulators thereof can be associated with pulmonary (i.e., lung) disorders, such as atelectasis, cystic fibrosis, rheumatoid lung disease, pulmonary congestion, pulmonary edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, Goodpasture's syndrome, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), and tumors (e.g., bronchogenic carcinoma, bronchioloalveolar carcinoma, bronchial carcinoid, hamartoma, and mesenchymal tumors). TANGO 292 polypeptides, nucleic acids, or modulators thereof can be used to prognosticate, diagnose, inhibit, prevent, or alleviate one or more of these disorders.

Pancreatic disorders in which TANGO 292 can be involved include pancreatitis (e.g., acute hemorrhagic pancreatitis and chronic pancreatitis), pancreatic cysts (e.g., congenital cysts, pseudocysts, and benign or malignant neoplastic cysts), pancreatic tumors (e.g., pancreatic carcinoma and adenoma), diabetes mellitus (e.g., insulin- and non-insulin-dependent types, impaired glucose tolerance, and gestational diabetes), and islet cell tumors (e.g., insulinomas, adenomas, Zollinger-Ellison syndrome, glucagonomas, and somatostatinoma). TANGO 292 polypeptides, nucleic acids, or modulators thereof can be used to prognosticate, diagnose, inhibit, prevent, or alleviate one or more of these disorders.

Because TANGO 292 exhibits expression in the heart, TANGO 292 nucleic acids, proteins, and modulators thereof can be used to treat heart disorders. Examples of heart disorders with which TANGO 292 can be involved include ischemic heart disease, atherosclerosis, hypertension, angina pectoris, hypertrophic cardiomyopathy, and congenital heart disease. TANGO 292 polypeptides, nucleic acids, or modulators thereof can be used to prognosticate, diagnose, inhibit, prevent, or alleviate one or more of these disorders.

Presence in TANGO 292 of a vitamin K-dependent carboxylation (Gla) domain indicates that TANGO 292 is involved in physiological functions identical or analogous to the functions performed by other proteins having such domains. For example, like other Gla domain-containing proteins, TANGO 292 modulates binding and uptake of calcium and other metal ions by cells which express it and the response of those cells to the presence and uptake of such ions. Human matrix Gla protein, for example, is involved in Keutel syndrome, an autosomal recessive disorder characterized by abnormal cartilage calcification, peripheral pulmonary stenosis, and midfacial hypoplasia (Munroe et al. (1999) Nat. Genet. 21:142–144). Other proteins containing a Gla domain include, for example, two human proline-rich Gla proteins designated PRGP1 and PRGP2, human G domain-containing protein Gas6, and several human blood coagulation factors ( Kulman et al. (1997) Proc. Natl. Acad. Sci. USA 94:9058–9062; Mark et al., (1996) J. Biol. Chem. 271:9785–9786; Cancela et al. (1990) J. Biol. Chem. 265:15040–15048). These proteins are involved in binding of mineral ions such as calcium, phosphate, and hydroxyapatite, binding of proteins, binding of vitamins and small molecules, and mediation of blood coagulation. Thus, TANGO 292 is involved in numerous physiological processes which are influenced by levels of calcium and other metal ions in body fluids or by the presence of proteins, vitamins, or small molecules. Such processes include, for example, bone uptake, maintenance, and deposition, formation, maintenance, and repair of cartilage, formation and maintenance of extracellular matrices, movement of cells through extracellular matrices, coagulation and dissolution of blood components (e.g., blood cells and proteins), and deposition of materials (e.g., lipids, cells, calcium, and the like) in arterial walls. TANGO 292 polypeptides, nucleic acids, and modulators thereof can be used to prognosticate, diagnose, inhibit, prevent, or alleviate one or more of these disorders.

TANGO 292 is involved in disorders which affect the tissues in which it is normally expressed and upon which it normally acts. Thus, TANGO 292 is involved in disorders which involve aberrant binding or aberrant failure to bind of keratinocytes or similar cells with a tissue affected by the disorder. Such disorders include, by way of example and not limitation, osteoporosis, (repair of) traumatic bone injuries, rickets, osteomalacia, Paget's disease, and other bone disorders, osteoarthritis, rheumatoid arthritis, ankylosing spondylitis, Keutel syndrome, and other disorders of the joints and cartilage, iron deficiency anemia, hemophilia, inappropriate blood coagulation, stroke, arteriosclerosis, atherosclerosis, aneurysm, and other disorders related to blood and blood vessels, metastasis and other disorders related to inappropriate movement of cells through extracellular matrices, and the like. TANGO 292 polypeptides, nucleic acids, and modulators thereof can be used to prognosticate, diagnose, inhibit, prevent, or alleviate one or more of these disorders.

TANGO 325

A cDNA clone (designated jthdc071a12) encoding at least a portion of human TANGO 325 protein was isolated from a human aortic endothelial cell cDNA library. The human TANGO 325 protein is predicted by structural analysis to be a transmembrane protein.

The full length of the cDNA encoding human TANGO 325 protein (FIG. 5; SEQ ID NO: 46) is 2169 nucleotide residues. The ORF of this cDNA, nucleotide residues 135 to 2000 of SEQ ID NO: 46 (i.e., SEQ ID NO: 47), encodes a 622-amino acid transmembrane protein (FIG. 5; SEQ ID NO: 48).

The invention thus includes purified human TANGO 325 protein, both in the form of the immature 622 amino acid residue protein (SEQ ID NO: 48) and in the form of the mature, approximately 591 amino acid residue protein (SEQ ID NO: 50). Mature human TANGO 325 protein can be synthesized without the signal sequence polypeptide at the amino terminus thereof, or it can be synthesized by generating immature TANGO 325 protein and cleaving the signal sequence therefrom.

In addition to full length mature and immature human TANGO 325 proteins, the invention includes fragments, derivatives, and variants of these TANGO 325 proteins, as described herein. These proteins, fragments, derivatives, and variants are collectively referred to herein as TANGO 325 polypeptides of the invention or TANGO 325 proteins of the invention.

The invention also includes nucleic acid molecules which encode a TANGO 325 polypeptide of the invention. Such nucleic acids include, for example, a DNA molecule having the nucleotide sequence listed in SEQ ID NO: 46 or some portion thereof, such as the portion which encodes mature TANGO 325 protein, immature TANGO 325 protein, or a domain of TANGO 325 protein. These nucleic acids are collectively referred to as TANGO 325 nucleic acids of the invention.

TANGO 325 proteins and nucleic acid molecules encoding them comprise a family of molecules having certain conserved structural and functional features.

A common domain present in TANGO 325 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 325 protein contains a signal sequence corresponding to about amino acid residues 1 to 31 of SEQ ID NO: 48 (SEQ ID NO: 49). The signal sequence is cleaved during processing of the mature protein.

TANGO 325 proteins can include an extracellular domain. The human TANGO 325 protein extracellular domain is located from about amino acid residue 32 to about amino acid residue 529 of SEQ ID NO: 48 (SEQ ID NO: 51).

In addition, TANGO 325 include a transmembrane domain. In one embodiment, a TANGO 325 protein of the invention contains a transmembrane domain corresponding to about amino acid residues 530 to 547 of SEQ ID NO: 48 (SEQ ID NO: 52).

The present invention includes TANGO 325 proteins having a cytoplasmic domain, particularly including proteins having a carboxyl-terminal cytoplasmic domain. The human TANGO 325 cytoplasmic domain is located from about amino acid residue 548 to amino acid residue 622 of SEQ ID NO: 48 (SEQ ID NO: 53).

TANGO 325 proteins typically comprise a variety of potential post-translational modification sites (often within an extracellular domain), such as those described herein in Table VII, as predicted by computerized sequence analysis of TANGO 325 proteins using amino acid sequence comparison software (comparing the amino acid sequence of TANGO 325 with the information in the PROSITE database {rel. 12.2; February, 1995} and the Hidden Markov Models database {Rel. PFAM 3.3}). In certain embodiments, a protein of the invention has at least 1, 2, 4, 6, 10, 15, or 20 or more of the post-translational modification sites listed in Table VII.

TABLE VII

| Type of Potential Modification Site or Domain | Amino Acid Residues of SEQ ID NO: 48 | Amino Acid Sequence |
|---|---|---|
| N-glycosylation site | 71 to 74 | NISY |
| | 76 to 79 | NESE |
| | 215 to 218 | NLTK |
| | 266 to 269 | NVTR |
| | 317 to 320 | NDTF |
| | 331 to 334 | NLSF |
| | 336 to 339 | NLTA |
| | 400 to 403 | NITN |
| | 410 to 413 | NVSR |
| | 451 to 454 | NITF |
| | 579 to 582 | NVTA |
| cAMP- or cGMP-dependent protein kinase phosphorylation site | 231 to 234 | RRLS |
| Protein kinase C phosphorylation site | 40 to 42 | TGR |
| | 229 to 231 | SLR |
| | 326 to 328 | SLK |
| | 390 to 392 | SMR |
| | 510 to 512 | SGK |
| | 575 to 577 | SAR |
| Casein kinase II phosphorylation site | 284 to 287 | SHND |
| | 442 to 445 | SPLE |
| | 447 to 450 | TETE |
| | 453 to 456 | TFWE |
| N-myristoylation site | 3 to 8 | GLQFSL |
| | 69 to 74 | GNNISY |
| | 126 to 131 | GIFKGL |
| | 174 to 179 | GTFVGM |
| ATP/GTP-binding site motif A (P-loop) | 506 to 513 | AASMSGKT |
| Leucine rich repeat amino terminal domain (LLRNT) | 32 to 60 | See FIG. 5 |
| Leucine rich repeat (LRR) domain | 61 to 84 | See FIG. 5 |
| | 85 to 108 | See FIG. 5 |
| | 109 to 132 | See FIG. 5 |
| | 133 to 156 | See FIG. 5 |
| | 157 to 180 | See FIG. 5 |
| | 181 to 204 | See FIG. 5 |
| | 205 to 228 | See FIG. 5 |
| | 229 to 252 | See FIG. 5 |
| | 253 to 276 | See FIG. 5 |
| | 277 to 300 | See FIG. 5 |
| | 301 to 324 | See FIG. 5 |
| | 326 to 349 | See FIG. 5 |
| Leucine rich repeat carboxyl terminal domain (LRRCT) | 359 to 405 | See FIG. 5 |

Among the domains that occur in TANGO 325 protein are leucine rich repeat (LRR) domains, including amino terminal and carboxyl terminal LRR domains, and a P-loop domain. In one embodiment, the protein of the invention has at least one domain that is at least 55%, preferably at least about 65%, more preferably at least about 75%, yet more preferably at least about 85%, and most preferably at least about 95% identical to one of these domains. In another embodiment, the protein has at least on amino terminal LRR domain, at least one carboxyl terminal LRR domain, and a plurality of LRR domains interposed therebetween. In yet another embodiment, the protein has at least one P-loop domain, and a plurality (e.g., 2, 3, 4, or more) of the LRR domains described herein in Table VII.

One or more LRR domains is present in a variety of proteins involved in protein-protein interactions. Such proteins include, for example, proteins involved in signal transduction, cell-to-cell adhesion, cell-to-extracellular matrix adhesion, cell development, DNA repair, RNA processing, and cellular molecular recognition processes. Specialized LRR domains, designated LRR amino terminal (LRRNT) domains and LRR carboxyl terminal (LRRCT) domains often occur near the amino and carboxyl, respectively, ends of a series of LRR domains. TANGO 325 protein has fourteen clustered LRR domains, including (from the amino terminus toward the carboxyl terminus of TANGO 325) an LRRNT domain, twelve LRR domains, and an LRRCT domain. TANGO 325 is thus involved in one or more physiological processes in which these other LRR domain-containing proteins are involved, namely binding of cells with extracellular proteins such as soluble extracellular proteins and cell surface proteins of other cells.

The fact that TANGO 325 has an ATP/GTP-binding domain (i.e., a P-loop domain) within the extracellular domain of the protein indicates that this protein is involved in transmembrane signaling events. Considered in combination with the protein-binding LRR domains present in the extracellular domain of the, the presence of the ATP-GTP-binding domain indicates that TANGO 325 protein is capable of sensing extracellular proteins, including ATP-binding proteins and GTP-binding proteins, and extracellular nucleotides (e.g., ATP, ADP, and AMP). Thus, TANGO 325 protein is involved in translating information (e.g., environmental conditions or signaling molecules provided to the environment by other cells) from the extracellular environment of the cell in which it is expressed to one or more intracellular biochemical systems.

TANGO 325 exhibits amino acid sequence and nucleic acid sequence homology with human Slit-1 protein. An alignment of the amino acid sequences of TANGO 325 and human Slit-1 protein is shown in FIGS. 5G to 5L. In this alignment (made using the ALIGN software {Myers and Miller (1989) CABIOS, ver. 2.0}; pam120.mat scoring matrix; gap opening penalty=12, gap extension penalty=4), the proteins are 35.4% identical (i.e., 35.4% of the residues of TANGO 325 correspond to identical residues in Slit-1). An alignment of the nucleotide sequences of the ORFs encoding TANGO 325 and human Slit-1 protein is shown in FIGS. 5M-1 through 5M-18. The two ORFs are 65.7% identical, as assessed using the same software and parameters.

The signal peptide prediction program SIGNALP (Nielsen et al. (1997) Protein Engineering 10:1–6) predicted that human TANGO 325 protein includes an approximately 31 (i.e., 29, 30, 31, 32, or 33) amino acid residue signal peptide (amino acid residues 1 to 31 of SEQ ID NO: 48; SEQ ID NO: 49) preceding the mature TANGO 325 protein (i.e., approximately amino acid residues 42 to 622 of SEQ ID NO: 48; SEQ ID NO: 50). In one embodiment, human TANGO 325 protein includes an extracellular domain (amino acid residues 32 to 529 of SEQ ID NO: 48; SEQ ID NO: 51); a transmembrane domain (amino acid residues 530 to 547 of SEQ ID NO: 48; SEQ ID NO: 52); and a cytoplasmic domain (amino acid residues 548 to 622 of SEQ ID NO: 48; SEQ ID NO: 53). In an alternative embodiment, human TANGO 325 protein includes a cytoplasmic domain (amino acid residues 32 to 529 of SEQ ID NO: 48; SEQ ID NO: 51); a transmembrane domain (amino acid residues 530 to 547 of SEQ ID NO: 48; SEQ ID NO: 52); and an extracellular domain (amino acid residues 548 to 622 of SEQ ID NO: 48; SEQ ID NO: 53).

Figure 5F:
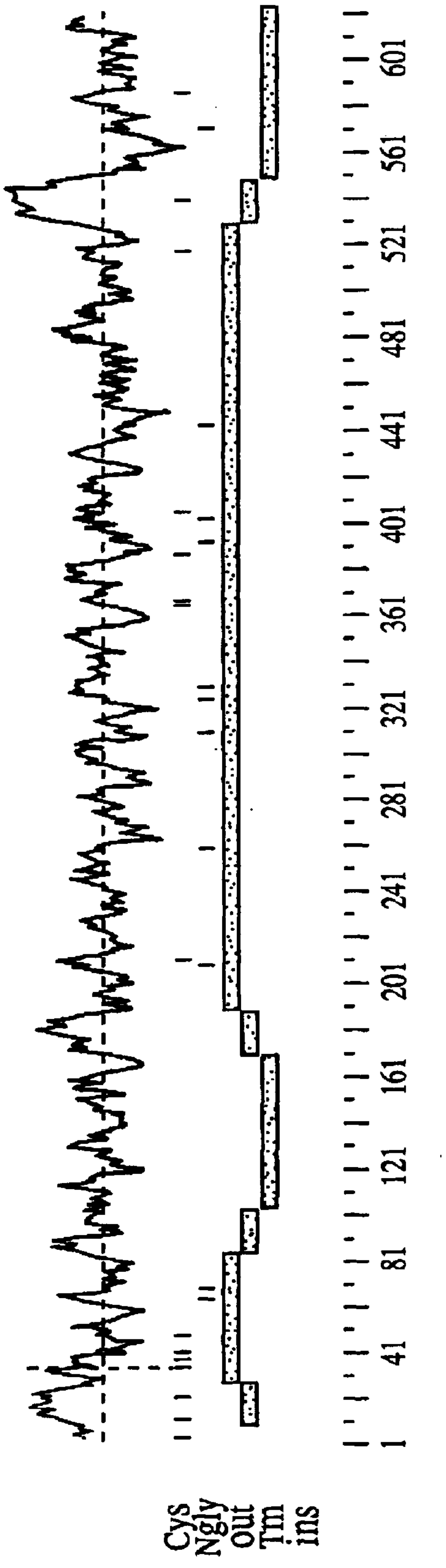
FIG. 5F is a hydrophilicity plot of TANGO 325 protein. An alignment of the amino acid sequences of TANGO 325 ("325"; SEQ ID NO: 48) and Slit-1 protein ("Slit"; SEQ ID NO: 67) protein is shown in FIGS. 5G to 5L.

FIG. 5F depicts a hydrophilicity plot of human TANGO 325 protein. Relatively hydrophobic regions are above the dashed horizontal line, and relatively hydrophilic regions are below the dashed horizontal line. The hydrophobic region which corresponds to amino acid residues 1 to 31 of SEQ ID NO: 48 is the signal sequence of TANGO 325 (SEQ ID NO: 49). The hydrophobic region which corresponds to amino acid residues 530 to 547 of SEQ ID NO: 48 is the transmembrane domain of human TANGO 325 (SEQ ID NO: 52). As described elsewhere herein, relatively hydrophilic regions are generally located at or near the surface of a protein, and are more frequently effective immunogenic epitopes than are relatively hydrophobic regions. For example, the region of human TANGO 325 protein from about amino acid residue 550 to about amino acid residue 565 appears to be located at or near the surface of the protein, while the region from about amino acid residue 168 to about amino acid residue 185 appears not to be located at or near the surface.

The predicted molecular weight of human TANGO 325 protein without modification and prior to cleavage of the signal sequence is about 70.3 kilodaltons. The predicted molecular weight of the mature human TANGO 325 protein without modification and after cleavage of the signal sequence is about 66.8 kilodaltons.

Northern analysis experiments indicated that mRNA corresponding to the cDNA encoding TANGO 325 is expressed in the tissues listed in Table VIIA, wherein "+" indicates expression and "−" indicates that expression could not be detected in the corresponding tissue.

TABLE VIIA

| Animal | Tissue | Relative Level of Expression |
|---|---|---|
| Human | placenta | + |
| | liver | + |
| | kidney | + |
| | pancreas | + |
| | heart | + |
| | brain | − |
| | skeletal muscle | − |
| | lung | − |

Biological function of TANGO 325 proteins, nucleic acids encoding them, and modulators of these molecules TANGO 325 proteins are involved in disorders which affect both tissues in which they are normally expressed and tissues in which they are normally not expressed. Based on the observation that TANGO 325 is expressed in human aortic endothelial tissue and in placenta, liver, kidney, pancreas, and heart tissues, TANGO 325 protein is involved in one or more biological processes which occur in these tissues. In particular, TANGO 325 is involved in modulating growth, proliferation, survival, differentiation, and activity of endothelial cells including, but not limited to, vascular and cardiac (including valvular) endothelial cells of the animal in which it is normally expressed. TANGO 325 also modulates growth, proliferation, survival, differentiation, and activity of placenta, liver, kidney, and pancreas cells. Thus, TANGO 325 has a role in disorders which affect these cells and their growth, proliferation, survival, differentiation, and activity. TANGO 325 polypeptides, nucleic acids, or modulators thereof can be used to prognosticate, diagnose, inhibit, prevent, or alleviate one or more of these disorders.

In one example, TANGO 325 polypeptides, nucleic acids, and modulators thereof can be used to treat placental disorders, such as toxemia or pregnancy (e.g., preeclampsia and eclampsia), placentitis, and spontaneous abortion. TANGO 325 polypeptides, nucleic acids, or modulators thereof can be used to prognosticate, diagnose, inhibit, prevent, or alleviate one or more of these disorders.

In another example, TANGO 325 polypeptides, nucleic acids, and modulators thereof, can be used to treat hepatic (i.e., liver) disorders, such as jaundice, hepatic failure, hereditary hyperbiliruinemias (e.g., Gilbert's syndrome, Crigler-Naijar syndromes and Dubin-Johnson and Rotor's syndromes), hepatic circulatory disorders (e.g., hepatic vein thrombosis and portal vein obstruction and thrombosis) hepatitis (e.g., chronic active hepatitis, acute viral hepatitis, and toxic and drug-induced hepatitis) cirrhosis (e.g., alcoholic cirrhosis, biliary cirrhosis, and hemochromatosis), and malignant tumors (e.g., primary carcinoma, hepatoblastoma, and angiosarcoma). TANGO 325 polypeptides, nucleic acids, or modulators thereof can be used to prognosticate, diagnose, inhibit, prevent, or alleviate one or more of these disorders.

In another example, TANGO 325 polypeptides, nucleic acids, or modulators thereof, can be used to treat renal (i.e., kidney) disorders, such as glomerular diseases (e.g., acute and chronic glomerulonephritis, rapidly progressive glomerulonephritis, nephrotic syndrome, focal proliferative glomerulonephritis, glomerular lesions associated with systemic disease, such as system lupus erythematosus, Goodpasture's syndrome, multiple myeloma, diabetes, neoplasia, sickle cell disease, and chronic inflammatory diseases), tubular diseases (e.g., acute tubular necrosis and acute renal failure, polycystic renal disease, medullary sponge kidney, medullary cystic disease, nephrogenic diabetes, and renal tubular acidosis), tubulointerstitial diseases (e.g., pyelonephritis, drug and toxin induced tubulointerstitial nephritis, hypercalcemic nephropathy, and hypokalemic nephropathy) acute and rapidly progressive renal failure, chronic renal failure, nephrolithiasis, vascular diseases (e.g., hypertension and nephrosclerosis, microangiopathic hemolytic anemia, atheroembolic renal disease, diffuse cortical necrosis, and renal infarcts), and tumors (e.g., renal cell carcinoma and nephroblastoma). TANGO 325 polypeptides, nucleic acids, or modulators thereof can be used to prognosticate, diagnose, inhibit, prevent, or alleviate one or more of these disorders.

Pancreatic disorders in which TANGO 325 can be involved include pancreatitis (e.g., acute hemorrhagic pancreatitis and chronic pancreatitis), pancreatic cysts) e.g., congenital cysts, pseudocysts, and benign or malignant neoplastic cysts), pancreatic tumors (e.g., pancreatic carcinoma and adenoma), diabetes mellitus (e.g., insulin- and non-insulin-dependent types, impaired glucose tolerance, and gestation diabetes), and islet cell tumors (e.g., insulinomas, adenomas, Zollinger-Ellison syndrome, glucagonomas, and somatostatinoma). TANGO 325 polypeptides, nucleic acids, or modulators thereof can be used to prognosticate, diagnose, inhibit prevent, or alleviate one or more of these disorders.

Because TANGO 325 exhibits expression in the heart, TANGO 325 nucleic acids, proteins, and modulators thereof can be used to treat heart disorders. Examples of heart disorders with which TANGO 325 can be involved include ischemic heart disease, atherosclerosis, hypertension, angino pectoris, hypertrophic cardiomyopathy, and congenital heart disease. TANGO 325 polypeptides, nucleic acids, or modulators thereof can be used to prognosticate, diagnose, hihibit, prevent, or alleviate one or more of these disorders.

It is known that serum nucleotide levels (e.g., ATP) affect cardiac contractility and vasomotor tone. Presence in TANGO 325 of an ATP/GTP binding domain in the extracellular portion thereof implicates this transmembrane protein in sensing of serum nucleotide levels and transmission of the sensed level by mechanisms not yet fully understood to myocytes underlying the epithelium. Thus, TANGO 325 is involved in disorders such as cardiovascular insufficiency, hypertension, hypotension, shock, and the like.

Leukocytes are known to bind with vascular endothelial surfaces in a reversible manner prior to penetrating the vascular endothelium in route to an underlying tissue. Although a few proteins have previously been implicated in the leukocyte-endothelium binding process, the identities of all of the proteins involved remain unknown. The presence of numerous LRR domains on the exterior portion of TANGO 325 protein implicates this protein in reversible binding of leukocytes to vascular endothelium. Thus, TANGO 325 is involved in physiological processes and disorders which involve leukocyte-endothelium binding. Such processes and disorders include, by way of example, cellular aspects of immune responses, autoimmune responses and disorders, and migration of leukocytes to lymph nodes.

The aortic endothelium, as well as other vascular endothelia, are known to be involved in detection of signals (e.g., metabolites, proteins, and the like) in the blood stream. Mammalian Slit-1 protein is known to be involved in the human endocrine system (Itoh et al. (1998) Brain Res. Mol. Brain Res. 62:175–186). Amino acid and nucleic acid sequence similarity of TANGO 325 with human Slit-1 protein, as described herein, indicates that TANGO 325 is involved in sensing physiological signals by the endocrine system. Thus, TANGO 325 is involved in one or more human endocrine disorders such as pituitary disorders (e.g., diabetes insipidus), thyroid disorders (e.g., hyperthyroidism, hypothyroidism, diabetes, goiter, and growth and developmental disorders), adrenal disorders (e.g., Addison's disease, Cushing's syndrome, hyperaldosteronism, and pheochromocytoma), and the like.

Human Slit-1 protein is also known to be involved in guidance of neuronal growth. The sequence similarity of TANGO 325 with Slit-1, as described herein, implicates TANGO 325 in growth, development, maintenance, and regeneration of neurons. TANGO 325 can thus be used to prevent, diagnose, and treat a variety of neurological disorders.

TANGO 331

A cDNA clone (designated jthvb042g08) encoding at least a portion of human TANGO 331 protein was isolated from a human mammary epithelium cDNA library. A corresponding cDNA clone (designated jchrc045a03) was isolated from a human heart library. The human TANGO 331 protein is predicted by structural analysis to be a secreted protein.

The full length of the cDNA encoding human TANGO 331 protein (FIG. 6; SEQ ID NO: 54) is 1432 nucleotide residues. The ORF of this cDNA, nucleotide residues 114 to 1172 of SEQ ID NO: 54 (i.e., SEQ ID NO: 55), encodes a 353-amino acid secreted protein (FIG. 6; SEQ ID NO: 56).

The invention thus includes purified human TANGO 331 protein, both in the form of the immature 353 amino acid residue protein (SEQ ID NO: 56) and in the form of the mature, approximately 329 amino acid residue protein (SEQ ID NO: 58). Mature human TANGO 331 protein can be synthesized without the signal sequence polypeptide at the amino terminus thereof, or it can be synthesized by generating immature TANGO 331 protein and cleaving the signal sequence therefrom.

In addition to full length mature and immature human TANGO 331 proteins, the invention includes fragments, derivatives, and variants of these TANGO 331 proteins, as described herein. These proteins, fragments, derivatives, and variants are collectively referred to herein as TANGO 331 polypeptides of the invention or TANGO 331 proteins of the invention.

The invention also includes nucleic acid molecules which encode a TANGO 331 polypeptide of the invention. Such nucleic acids include, for example, a DNA molecule having the nucleotide sequence listed in SEQ ID NO: 54 or some portion thereof, such as the portion which encodes mature TANGO 331 protein, immature TANGO 331 protein, or a domain of TANGO 331 protein. These nucleic acids are collectively referred to as TANGO 331 nucleic acids of the invention.

TANGO 331 proteins and nucleic acid molecules encoding them comprise a family of molecules having certain conserved structural and functional features, as indicated by the conservation of amino acid sequence between human TANGO 331 protein and the Chinese hamster (*Cricetulus griseus*) protein designated HT and having GenBank Accession number U48852, as shown in FIG. 6E, and the conservation of nucleotide sequence between the ORFs encoding human TANGO 331 protein and Chinese hamster protein HT, as shown in FIGS. 6F through 6J.

A common domain present in TANGO 331 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 331 protein contains a signal sequence corresponding to about amino acid residues 1 to 24 of SEQ ID NO: 56 (SEQ ID NO: 57). The signal sequence is cleaved during processing of the mature protein.

TANGO 331 proteins can include an extracellular domain. The human TANGO 331 protein is a secreted protein, and thus includes an 'extracellular domain' consisting of the entire mature protein (i.e., approximately residues 25 to 353 of SEQ ID NO: 56; SEQ ID NO: 58).

TANGO 331 proteins typically comprise a variety of potential post-translational modification sites (often within an extracellular domain), such as those described herein in Table VIII, as predicted by computerized sequence analysis of TANGO 331 proteins using amino acid sequence comparison software (comparing the amino acid sequence of TANGO 331 with the information in the PROSITE database {rel. 12.2; February, 1995} and the Hidden Markov Models database {Rel. PFAM 3.3}). In certain embodiments, a protein of the invention has at least 1, 2, 4, 6, 10, 15, or 20 or more of the post-translational modification sites listed in Table VIII.

TABLE VIII

| Type of Potential Modification Site or Domain | Amino Acid Residues of SEQ ID NO: 56 | Amino Acid Sequence |
|---|---|---|
| N-glycosylation site | 190 to 193 | NETH |
| | 251 to 254 | NGSY |
| cAMP- or cGMP-dependent protein kinase phosphorylation site | 26 to 29 | KKPT |
| Protein kinase C phosphorylation site | 48 to 50 | TAK |
| | 123 to 125 | TLK |
| | 144 to 146 | SQR |
| | 165 to 167 | SCR |
| | 187 to 189 | SLR |
| | 202 to 204 | SCK |
| | 210 to 212 | TNR |
| Casein kinase II phosphorylation site | 58 to 61 | TAWE |
| | 66 to 69 | SKYE |
| | 86 to 89 | SDFE |
| | 197 to 200 | TACD |
| | 210 to 213 | TNRD |
| | 255 to 258 | TCEE |
| | 295 to 298 | SLAE |
| | 339 to 342 | TEGE |
| | 349 to 352 | SRED |
| Tyrosine kinase phosphorylation site | 303 to 309 | RKNENCY |
| N-myristoylation site | 44 to 49 | GMVDTA |
| | 54 to 59 | GGGNTA |
| | 81 to 86 | GLCESS |
| | 150 to 155 | GNGHCS |
| | 158 to 163 | GSRQGD |
| | 164 to 169 | GSCRCH |
| | 252 to 257 | GSYTCE |
| | 313 to 318 | GSYVCV |
| Aspartic acid and asparagine hydroxylation site | 308 to 319 | See FIG. 6 |
| EGF-like domain cysteine pattern signature | 166 to 177 | See FIG. 6 |
| EGF domain | 140 to 177 | See FIG. 6 |
| | 234 to 263 | See FIG. 6 |
| | 301 to 330 | See FIG. 6 |
| Laminin-like EGF domain | 153 to 199 | See FIG. 6 |
| TNFR/NGFR cysteine-rich region domain | 180 to 214 | See FIG. 6 |
| Vertebrate metallothionein-like domain | 229 to 298 | See FIG. 6 |
| Leucine Zipper domain | 94 to 115 | See FIG. 6 |

Among the domains that occur in TANGO 331 protein are EGF domains, including a laminin-like EGF domain, a TNFR/NGFR cysteine-rich domain, a metallothionein-like domain, and a leucine zipper domain.

EGF-like domains are about 30 to 40 amino acid residues in length and comprise several conserved cysteine residues in one of several patterns. EGF-like domains occur in a large number of proteins including, for example, human epidermal growth factor (EGF), murine adipocyte differentiation inhibitor, human agrin, human growth factor amphiregulin, human growth factor betacellulin, sea urchin blastula tissue patterning proteins BP10 and Span, cattle tick glycoprotein BM86, human bone morphogenic protein 1, sea urchin suBMP, Drosophila tolloid protein, *Caenorhabditis elegans* developmental proteins lin-12 and glp-1, *C. elegans* tissue patterning protein APX-1, human calcium-dependent serine proteinase, human cartilage matrix protein, human cartilage oligomeric matrix protein, human cell surface antigen 114/A10, rat cell surface glycoprotein complex transmembrane subunit ASGP-2, human coagulation associated proteins C, Z, and S, human coagulation factors VII, IX, X, and XII, human complement components Clr, Cls, C6, C7, C8alpha, C8beta, and C9, human complement-activating components of Ra-reactive factor, Drosophila epithelial development protein Crumbs, sea urchin exogastrula-inducing peptides A, C, D, and X, Drosophila cadherin-related tumor suppressor protein Fat, human fetal antigen 1 (a neuroendocrine differentiation protein derived from the delta-like protein), human fibrillins 1 and 2, sea urchin fibropellins IA, IB, IC, II, and III, human extracellular matrix proteins fibulin-1 and -2, Drosophila cell determination/axon guidance protein Argos, various poxvirus growth factor-related proteins, Drosophila developmental protein Gurken, human heparin-binding EGF-like growth factor, human transforming growth factor-alpha, human growth factors Lin-3 and Spitz, human hepatocyte growth factor activator, human LDL and VLDL receptors, human LDL receptor-related protein, human leukocyte antigen CD97, human cell surface glycoprotein EMR1, human cell surface glycoprotein F4/80, Japanese horseshoe crab limulus clotting factor C, mammalian membrane-bound endopeptidase Meprin A alpha subunit, murine milk fat globule-EGF factor 8, human glial growth factors neuregulin GGF-I and GGF-II, mammalian neurexins, human neurogenic proteins Notch, Xotch, Tan-1, and Delta, *C. elegans* differentiation protein Lag-2, Drosophila differentiation proteins Serrate and Slit, chordate basement membrane protein Nidogen, Plasmodium ookinete 24, 25, and 28 kilodalton surface proteins, human pancreatic secretory granule membrane glycoprotein GP2, human non-specific cell lysis protein Perforin, human proteoglycans aggrecan, versican, perlecan, brevican, and chondroitin sulfate, human endoplasmic reticulum prostaglandin G/H synthases 1 and 2, human extracellular protein S1–5, human autocrine growth factor Schwannoma-derived growth factor, human E-, P-, and L-selectins, Arabidopsis thaliana chlorophyll complex assembly protein serine/threonine-protein kinase homolog, guinea pig sperm-egg fusion proteins PH-30alpha and beta, murine stromal cell derived protein-1, human teratocarcinoma-derived growth factor, mammalian extracellular protein tenascin, chicken extracellular protein TEN-A, human tenascin-X, Drosophila tenascin-like proteins TEN-A and TEN-M, human protein C activator thrombomodulin, human adhesive glycoproteins thrombospondins 1, 2, 3, and 4, human thyroid peroxidases 1 and 2, human transforming growth factor beta-1 binding protein, human tyrosine-protein kinase receptors Tek and Tie, human urokinase-type plasminogen activator, human tissue plasminogen activator, human uromodulin, human vitamin K-dependent anticoagulant proteins C and S (and the related human single-chain plasma glycoprotein Z), the sea urchin 63 kilodalton sperm flagellar membrane protein, chicken Nel protein, and the hypothetical *C. Elegans* protein T20G5.3. Although these proteins have a variety of activities and sites of expression, a common characteristic of most of them is that they are involved in protein-to-protein binding in the extracellular space—either to a secreted protein, a component of the extracellular matrix, or to an extracellular portion of an integral membrane protein. Based on this shared characteristic, the presence of multiple EGF-like domains in TANGO 331 indicates that TANGO 331 is involved in binding to proteins extracellularly.

Post-translational hydroxylation of aspartic acid or asparagine to form erythro-beta-hydroxyaspartic acid or erythro-beta-hydroxyasparagine occurs in various proteins having one or more EGF-like domains (e.g., blood coagulation protein factors VII, IX, and X, blood coagulation proteins C, S, and Z, the LDL receptor, thrombomodulin, and the like). TANGO 331 has a signature sequence which is characteristic of hydroxylation of the asparagine residue at amino acid residue 310. The invention thus includes TANGO 331 proteins having a hydroxylated asparagine residue at position 310 of SEQ ID NO: 56.

TNFR/NGFR (tumor necrosis factor receptor/nerve growth factor receptor) cysteine-rich region domains are about 30 to 40 amino acid residues in length, and generally exhibit a conserved pattern of six or more cysteine residues. These domains occur in several soluble and transmembrane proteins which are known to be receptors for growth factors or for cytokines. Examples of TNFR/NGFR cysteine-rich region domain-containing proteins are human tumor necrosis factor (TNF) cysteine-rich region domains type I and type II receptors, Shope fibroma virus soluble TNF receptor, human lymphotoxin -alpha-beta, human low-affinity nerve growth factor receptor, human CD40L (cytokine) receptor CD40, human CD27L (cytokine) receptor CD27, human CD3OL (cytokine) receptor CD30, human T-cell cytokine receptor 4–1BB, human apoptotic FASL protein receptor FAS, human T-cell OX40L (cytokine) receptor OX40, human apoptosis-related receptor Wsl-1, and Vaccinia protein A53. Presence of a TNFR/NGFR cysteine-rich region domain in TANGO 331 is an indication that TANGO 331 is involved in one or more physiological processes involving extracellular binding with a cytokine or growth factor. Such processes include, for example, growth, homeostasis, regeneration, and proliferation of cells and tissues, immune (including autoimmune) responses, host defenses against infection, and the like.

Metallothioneins are cysteine-rich proteins which are capable of binding heavy metals such as calcium, zinc, copper, cadmium, cobalt, nickel, and the like. Proteins which have a domain which resembles a metal-binding domain of a metallothionein are also capable of binding such metals. TANGO 331 comprises a metallothionein-like domain, and is capable of binding one or more heavy metals. This is an indication that TANGO 331 is involved in one or more physiological processes which involve metal binding. Such processes include, by way of example and not limitation, nutritional supply of metals to cells on a controlled basis, removal of toxic metal species from body tissues, storage of metals, and the like.

TANGO 331 comprises a leucine zipper region at about amino acid residue 94 to about amino acid residue 115 (i.e., 94 LeaqeehLeawwlqLkseypdL 115). Leucine zipper regions are known to be involved in dimerization of proteins. Leucine zipper regions interact with one another, leading to formation of homo- or hetero-dimers between proteins, depending on their identity. The presence in TANGO 331 of a leucine zipper region is a further indication that this protein is involved in protein-protein interactions.

TANGO 331 shares amino acid and nucleic acid homology with a Chinese hamster protein designated HT, and thus is involved in corresponding physiological processes in humans. An alignment of the amino acid sequences of (human) TANGO 331 and Chinese hamster protein HT is shown in FIG. 6E. In this alignment (made using the ALIGN software {Myers and Miller (1989) CABIOS, ver. 2.0}; pam120.mat scoring matrix; gap opening penalty=12, gap extension penalty=4), the proteins are 71.9% identical. An alignment of the nucleotide sequences of the ORFs encoding (human) TANGO 331 and Chinese hamster protein HT is shown in FIGS. 6F through 6J. The two ORFs are 74.5% identical, as assessed using the same software and parameters.

The signal peptide prediction program SIGNALP (Nielsen et al. (1997) Protein Engineering 10:1–6) predicted that human TANGO 331 protein includes an approximately 24 (i.e., 22, 23, 24, 25, or 26) amino acid residue signal peptide (amino acid residues 1 to 24 of SEQ ID NO: 56; SEQ ID NO: 57) preceding the mature TANGO 331 protein (i.e., approximately amino acid residues 25 to 353 of SEQ ID NO: 56; SEQ ID NO: 58). Mature human TANGO 331 is a secreted protein.

Figure 6D:
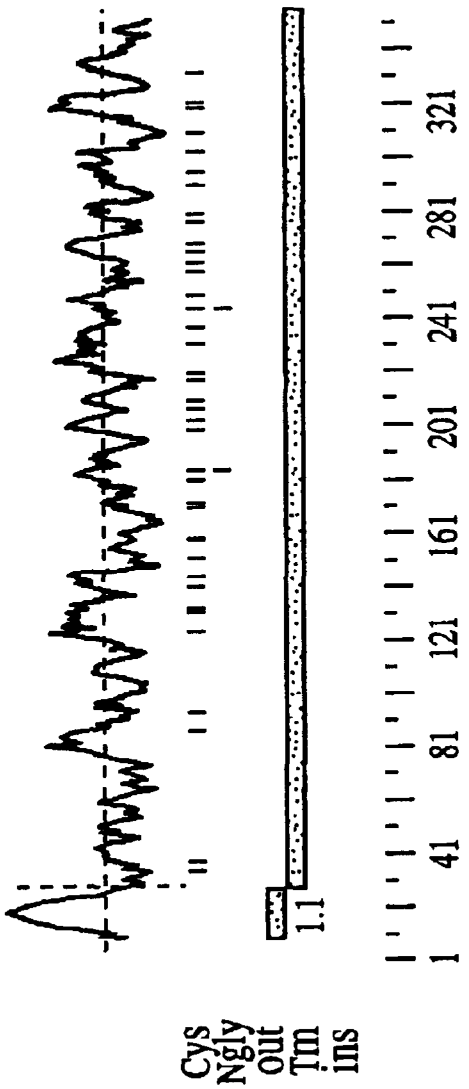
FIG. 6D is a hydrophilicity plot of TANGO 331 protein. An alignment of the amino acid sequences of human TANGO 331 protein ("H"; SEQ ID NO: 56) and Chinese hamster protein HT ("C"; SEQ ID NO: 69; GenBank Accession No. U48852) is shown in FIG. 6E.

FIG. 6D depicts a hydrophilicity plot of human TANGO 331 protein. Relatively hydrophobic regions are above the dashed horizontal line, and relatively hydrophilic regions are below the dashed horizontal line. The hydrophobic region which corresponds to amino acid residues 1 to 24 of SEQ ID NO: 56 is the signal sequence of human TANGO 331 (SEQ ID NO: 57). As described elsewhere herein, relatively hydrophilic regions are generally located at or near the surface of a protein, and are more frequently effective immunogenic epitopes than are relatively hydrophobic regions. For example, the region of human TANGO 331 protein from about amino acid residue 140 to about amino acid residue 170 appears to be located at or near the surface of the protein, while the region from about amino acid residue 115 to about amino acid residue 130 appears not to be located at or near the surface.

The predicted molecular weight of human TANGO 331 protein without modification and prior to cleavage of the signal sequence is about 38.2 kilodaltons. The predicted molecular weight of the mature human TANGO 331 protein without modification and after cleavage of the signal sequence is about 35.6 kilodaltons.

Tissue distribution of TANGO 331 mRNA was determined by Northern blot hybridization. Northern blot hybridizations with the various RNA samples were performed using standard Northern blotting conditions and washing under stringent conditions (i.e., 0.2×SSC at 65° C.). The DNA probe used in the Northern Blot experiments was radioactively labeled with 32P-dCTP using the PRIME-IT™ kit (Stratagene, La Jolla, Calif.) according to the instructions of the supplier. Filters having human mRNA disposed thereon (MULTITISSUE™ Northern I and MULTITISSUE™ Northern II obtained from Clontech, Palo Alto, Calif.) were probed in EXPRESSHYB™ hybridization solution (Clontech) and washed at high stringency according to the manufacturer's recommendations.

Two isoforms of human TANGO 331 were identified using this Northern blot analysis, indicating that TANGO 331 can have a splice variant. One isoform (corresponding to the larger message) can be a transmembrane protein (frizzled-like) and the other (i.e., smaller) isoform can be a secreted form. The two isoforms exhibit a clear pattern of tissue specificity. On the multiple tissue blot from Clontech, the large transcript is found in almost all tissues, whereas the smaller message is expressed mainly in heart, skeletal muscle, placenta, and pancreas tissues.

TANGO 331 can be expressed as a recombinant glutathione-S-transferase (GST) fusion polypeptide in *E. coli* and the fusion polypeptide is isolated and characterized. Specifically, TANGO 331 can be fused with GST and this fusion polypeptide can expressed in *E. coli*, e.g., in strain PEB199. Expression of the GST-TANGO 331 fusion protein in PEB199 is induced with IPTG. The recombinant fusion polypeptide can be purified from crude bacterial lysates of the induced PEB 199 strain by affinity chromatography, e.g., using glutathione-substituted beads. Using polyacrylamide gel electrophoretic analysis of the polypeptide purified from the bacterial lysates, the molecular weight of the resultant fusion polypeptide can be determined.

To express the TANGO 331 gene in COS cells, the pcDNA/Amp vector by Invitrogen Corporation (San Diego, Calif.) can be used. This vector contains an SV40 origin of replication, an ampicillin resistance gene, an *E. coli* replication origin, a CMV promoter followed by a polylinker region, and an SV40 intron and polyadenylation site. A DNA fragment encoding the entire TANGO 331 protein and an HA tag (Wilson et al. (1984) Cell 37:767) or a FLAG tag fused in-frame to its 3' end of the fragment can be cloned into the polylinker region of the vector, thereby placing the expression of the recombinant protein under the control of the CMV promoter.

To construct the plasmid, the TANGO 331 DNA sequence is amplified by PCR using two primers. The 5' primer contains the restriction site of interest followed by approximately twenty nucleotides of the TANGO 331 coding sequence starting from the initiation codon; the 3' end sequence contains complementary sequences to the other restriction site of interest, a translation stop codon, the HA tag or FLAG tag and the last 20 nucleotides of the TANGO 331 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the TANGO 331 gene is inserted in the correct orientation. The ligation mixture is transformed into *E. coli* cells (e.g., one or more of strains HB 101, DH5a, SURE, available from Stratagene Cloning Systems, La Jolla, Calif.), the transformed culture is plated on ampicillin media plates, and resistant colonies are selected. Plasmid DNA is isolated from transformants and examined by restriction analysis for the presence of the correct fragment.

COS cells are subsequently transfected using the TANGO 331 -pcDNA/Amp plasmid DNA using the calcium phosphate or calcium chloride co-precipitation methods, DEAE-dextran-mediated transfection, lipofection, or electroporation. Other suitable methods of transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the TANGO 331 polypeptide can be detected by radiolabeling ($^{35}$S-methionine or $^{35}$S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 millimolar NaCl, 1% NP-40, 0.1% SDS, 0.5% DOC, 50 millimolar Tris, pH 7.5). Both the cell lysate and the culture media are precipitated with an HA specific monoclonal antibody. Precipitated polypeptides are then analyzed by SDS-PAGE.

Alternatively, DNA containing the TANGO 331 coding sequence can be cloned directly into the polylinker of the pcDNA/Amp vector using the appropriate restriction sites. The resulting plasmid is transfected into COS cells in the manner described above, and the expression of the TANGO 331 polypeptide can be detected by radiolabeling and immunoprecipitation using an TANGO 331 specific monoclonal antibody.

The human TANGO 331 gene was mapped using the Genebridge 4 Human Radiation hybrid mapping panel with ATTATTCAGAAGGATGTCCCGTGG (SEQ ID NO: 99) as the forward primer and CCTCCTGATTACCTACAATGGTC (SEQ ID NO: 100) as the reverse primer. The human TANGO 331 gene maps to human 22q 11-q13. Flanking markers for this region are WI-4572 and WI-8917. The schizophrenia 4 (sczd4) locus also maps to this region of the human chromosome. Also mapping to this region of the human chromosome are the following genes: transcription factor 20 (tcf20), Benzodiazepine receptor, peripheral type (bzrp), Arylsulfatase A (arsa), diaphorase (NADH); cytochrome b-5 reductase (dia1), and Solute carrier family 5 (sodium/glucose transporter), member 1 (slca1). This region is syntenic to mouse chromosome 15. The stargazer (stg), gray tremor (gt), brachyury modifier 2 (Brm2), bronchial hyper-responsiveness 2 (Bhr2), loss of righting induced by ethanol 5 (Lore5), fluctuating asymmetry QTL 8 (Faq8), jerky (Jrk), belted (bt), and koala (Koa) loci also map to this region of the mouse chromosome, several of which are neuromuscular related.

Biological function of TANGO 331 proteins, nucleic acids encoding them, and modulators of these molecules TANGO 331 proteins are involved in disorders which affect both tissues in which they are normally expressed and tissues in which they are normally not expressed. Based on the observation that TANGO 331 is expressed in human mammary epithelial tissue and human heart tissue, TANGO 331 protein is involved in one or more biological processes which occur in mammary epithelial tissue, in other epithelial tissues, and in heart tissue. In particular, TANGO 331 is involved in modulating growth, proliferation, survival, differentiation, and activity of cells including, but not limited to, epithelial cells (e.g., mammary epithelial cells) of the animal in which it is normally expressed. Thus, TANGO 331 has a role in disorders which affect these cells and their growth, proliferation, survival, differentiation, and activity. TANGO 331 is therefore involved in physiological processes such as maintenance of epithelia, carcinogenesis, modulation and storage of protein factors and metals, and lactation. Furthermore, because TANGO 331 is expressed in human mammary epithelial cells, it also has a role in nutrition of human infants (e.g., providing nutrients such as minerals to infants and providing protein factors not synthesized by infants) and in disorders which affect them. Thus, TANGO 331 is involved in a number of disorders such as breast cancer, insufficient lactation, infant nutritional and growth disorders, and the like. TANGO 331 polypeptides, nucleic acids, or modulators thereof can be used to prognosticate, diagnose, inhibit, prevent, or alleviate one or more of these disorders.

Because TANGO 331 exhibits expression in the heart, TANGO 331 nucleic acids, proteins, and modulators thereof can be used to treat heart disorders. Examples of heart disorders with which TANGO 331 can be involved include ischemic heart disease, atherosclerosis, hypertension, angina pectoris, hypertrophic cardiomyopathy, and congenital heart disease. TANGO 331 polypeptides, nucleic acids, or modulators thereof can be used to prognosticate, diagnose, inhibit, prevent, or alleviate one or more of these disorders.

In another example, TANGO 331 polypeptides, nucleic acids, and modulators thereof, can be involved in normal and aberrant functioning of skeletal muscle tissue, and can thus be involved in disorders of such tissue. Examples of skeletal muscle disorders include muscular dystrophy (e.g., Duchenne muscular dystrophy, Becker muscular dystrophy, Emery-Dreifuss muscular dystrophy, limb-girdle muscular dystrophy, facioscapulohumeral muscular dystrophy, myotonic dystrophy, oculopharyngeal muscular dystrophy, distal muscular dystrophy, and congenital muscular dystrophy), motor neuron diseases (e.g., amyotrophic lateral sclerosis, infantile progressive spinal muscular atrophy, intermediate spinal muscular atrophy, spinal bulbar muscular atrophy, and adult spinal muscular atrophy), myopathies (e.g., inflammatory myopathies (e.g., dermatomyositis and polymyositis), myotonia congenita, paramyotonia congenita, central core disease, nemaline myopathy, myotubular myopathy, and periodic paralysis), and metabolic diseases of muscle (e.g., phosphorylase deficiency, acid maltase deficiency, phosphofructokinase deficiency, debrancher enzyme deficiency, mitochondrial myopathy, camitine deficiency, camitine palmityl transferase deficiency, phosphoglycerate kinase deficiency, phosphoglycerate mutase deficiency, lactate dehydrogenase deficiency, and myoadenylate deaminase deficiency). TANGO 331 polypeptides, nucleic acids, or modulators thereof can be used to prognosticate, diagnose, inhibit, prevent, or alleviate one or more of these disorders.

In another example, TANGO 331 polypeptides, nucleic acids, and modulators thereof can be used to treat placental disorders, such as toxemia of pregnancy (e.g., preeclampsia and eclampsia), placentitis, and spontaneous abortion. TANGO 331 polypeptides, nucleic acids, or modulators thereof can be used to prognosticate, diagnose, inhibit, prevent, or alleviate one or more of these disorders.

In another example, TANGO 331 polypeptides, nucleic acids, and modulators thereof can be used to treat placental disorders, such as toxemia of pregnancy (e.g., preeclampsia and eclampsia), placentitis, and spontaneous abortion.

Presence in TANGO 331 of numerous EGF-like domains, including the laminin-like EGF-like domain indicates that TANGO 331 is involved in extracellular binding of proteins, including both other secreted proteins (e.g., growth factors and cytokines) and cell-surface proteins. Binding of TANGO 331 to other secreted proteins modulates their activity, their rate of uptake by cells, and their rate of degradation. Binding of TANGO 331 to cell surface proteins modulates their activity, including, for example, their ability to bind with other secreted proteins, and transmits a signal to the cell expressing the cell-surface protein. Presence in TANGO 331 of a TNFR/NGFR cysteine-rich region domain is further indicative of the ability of TANGO 331 to bind with growth factors and cytokines. Thus, TANGO 331 is involved in a number of proliferative and immune disorders including, but not limited to, cancers (e.g., breast cancer), autoimmune disorders, insufficient or inappropriate host responses to infection, acquired immune deficiency syndrome, and the like. TANGO 331 polypeptides, nucleic acids, or modulators thereof can be used to prognosticate, diagnose, inhibit, prevent, or alleviate one or more of these disorders.

The fact that TANGO 331 has a metallothionein-like region is indicative of the ability of TANGO 331 to bind with metal ions, including nutritionally required metal ions (e.g., calcium, magnesium, zinc, manganese, cobalt, iron, and the like). Thus, TANGO 331 is involved in binding with essential minerals and in delivering them to their proper body locations. TANGO 331 is also involved in binding excess or toxic metal ions so that they can be excreted. TANGO 331 is thus involved in disorders involving insufficient or inappropriate localization of metal ions. Such disorders include, but are not limited to, malnutrition and mineral deficiency disorders, hemochromatosis, inappropriate calcification of body tissues, bone disorders such as osteoporosis, and the like. TANGO 331 polypeptides, nucleic acids, or modulators thereof can be used to prognosticate, diagnose, inhibit, prevent, or alleviate one or more of these disorders.

Mapping of the human TANGO 331 gene to chromosomal region 22q11-q13 is an indication of disorders with which its expression (or non- or aberrant-expression) can be associated. For example, arylsulfatase A is associated with Metachromatic leukodystrophy. Diaphorase (NADH:cytochrome b-5 reductase) is associated with methemoglobinemia, types I and II. Solute carrier family 5 (sodium/glucose transporter), member 1 is associated with glucose/galactose malabsorption. The gene designated schizophrenia 4 is associated with schizophrenia and velocardiofacial syndrome, as described in Online Mendelian Inheritance in Man, Johns Hopkins University, Baltimore, Md. MIM Number: 600850: Dec. 7, 1998. (World Wide Web URL: http://www.ncbi.nlm.nih.gov/omim/). These mapping data indicate that TANGO 331 polypeptides, nucleic acids, and modulators thereof can be used to prognosticate, diagnose, inhibit, prevent, or alleviate one or more of these disorders.

TANGO 332

A cDNA clone (designated jlhbab463g12) encoding at least a portion of human TANGO 332 protein was isolated from a human adult brain cDNA library. The human TANGO 332 protein is predicted by structural analysis to be a secreted protein.

The full length of the cDNA encoding human TANGO 332 protein (FIG. 7; SEQ ID NO: 59) is 2730 nucleotide residues. The ORF of this cDNA, nucleotide residues 173 to 2185 of SEQ ID NO: 59 (i.e., SEQ ID NO: 60), encodes a 671-amino acid transmembrane protein (FIG. 7; SEQ ID NO: 61).

The invention thus includes purified human TANGO 332 protein, both in the form of the immature 671 amino acid residue protein (SEQ ID NO: 61) and in the form of the mature, approximately 649 amino acid residue protein (SEQ ID NO: 63). Mature human TANGO 332 protein can be synthesized without the signal sequence polypeptide at the amino terminus thereof, or it can be synthesized by generating immature TANGO 332 protein and cleaving the signal sequence therefrom.

In addition to full length mature and immature human TANGO 332 proteins, the invention includes fragments, derivatives, and variants of these TANGO 332 proteins, as described herein. These proteins, fragments, derivatives, and variants are collectively referred to herein as TANGO 332 polypeptides of the invention or TANGO 332 proteins of the invention.

The invention also includes nucleic acid molecules which encode a TANGO 332 polypeptide of the invention. Such nucleic acids include, for example, a DNA molecule having the nucleotide sequence listed in SEQ ID NO: 59 or some portion thereof, such as the portion which encodes mature TANGO 332 protein, immature TANGO 332 protein, or a domain of TANGO 332 protein. These nucleic acids are collectively referred to as TANGO 332 nucleic acids of the invention.

TANGO 332 proteins and nucleic acid molecules encoding them comprise a family of molecules having certain conserved structural and functional features, as indicated by the conservation of amino acid sequence between human TANGO 332 protein, human brain-enriched hyaluronan-binding factor (BEF), as shown in FIGS. 7G and 7H, and murine brevican protein, as shown in FIGS. 7I to 7K. This conservation is further indicated by conservation of nucleotide sequence between the ORFs encoding human TANGO 332 protein and murine brevican protein, as shown in FIGS. 7L through 7U.

A common domain present in TANGO 332 proteins is a signal sequence. As used herein, a signal sequence includes a peptide of at least about 10 amino acid residues in length which occurs at the amino terminus of membrane-bound proteins and which contains at least about 45% hydrophobic amino acid residues such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35–60%, more preferably 40–50%, and more preferably at least about 45% hydrophobic residues. A signal sequence serves to direct a protein containing such a sequence to a lipid bilayer. Thus, in one embodiment, a TANGO 332 protein contains a signal sequence corresponding to about amino acid residues 1 to 22 of SEQ ID NO: 61 (SEQ ID NO: 62). The signal sequence is cleaved during processing of the mature protein.

TANGO 332 proteins are secreted proteins. The mature form of human TANGO 332 protein has the amino acid sequence of approximately amino acid residues 23 to 671 of SEQ ID NO: 61.

TANGO 332 proteins typically comprise a variety of potential post-translational modification sites (often within an extracellular domain), such as those described herein in Table IX, as predicted by computerized sequence analysis of TANGO 332 proteins using amino acid sequence comparison software (comparing the amino acid sequence of TANGO 332 with the information in the PROSITE database {rel. 12.2; February, 1995} and the Hidden Markov Models database {Rel. PFAM 3.3}). In certain embodiments, a protein of the invention has at least 1, 2, 4, 6, 10, 15, or 20 or more of the post-translational modification sites listed in Table IX.

TABLE IX

| Type of Potential Modification Site or Domain | Amino Acid Residues of SEQ ID NO: 61 | Amino Acid Sequence |
|---|---|---|
| N-glycosylation site | 130 to 133 | NDSG |
| | 337 to 340 | NQTG |
| Protein kinase C phosphorylation site | 67 to 69 | SRR |
| | 74 to 76 | SPR |
| | 165 to 167 | SAR |
| | 212 to 214 | TVR |
| | 219 to 221 | TPR |
| | 310 to 312 | SVR |
| | 319 to 321 | SQR |
| | 545 to 547 | TPR |
| | 615 to 617 | SGR |
| Casein kinase II phosphorylation site | 29 to 32 | SSED |
| | 116 to 119 | SLTD |
| | 219 to 222 | TPRE |
| | 269 to 272 | TLEE |
| | 382 to 385 | TVTE |
| | 386 to 389 | TLEE |
| | 397 to 400 | TESE |
| | 419 to 422 | STPE |
| | 430 to 433 | TLLE |
| | 446 to 449 | SEEE |
| | 545 to 548 | TPRE |
| | 558 to 561 | TLVE |
| Tyrosine kinase phosphorylation site | 128 to 135 | RPNDSGIY |
| | 451 to 459 | KALEEEEKY |
| N-myristoylation site | 47 to 52 | GVLGGA |
| | 133 to 138 | GIYRCE |
| | 142 to 147 | GIDDSS |
| | 174 to 179 | GAQEAC |
| | 183 to 188 | GAHIAT |
| | 281 to 286 | GAEIAT |
| | 288 to 293 | GQLYAA |
| | 297 to 302 | GLDHCS |
| | 324 to 329 | GGLPGV |
| | 403 to 408 | GAIYSI |
| | 414 to 419 | GGGGSS |
| | 576 to 581 | GVPRGE |
| | 586 to 591 | GSSEGA |
| Immunoglobulin-/major histocompatibility protein-like (Ig-/MHC-like) domain | 50 to 141 | See FIG. 7 |
| Extracellular link domain | 156 to 251 | See FIG. 7 |
| | 257 to 353 | See FIG. 7 |

Among the domains that occur in TANGO 332 protein are an Ig-/MHC-like domain and a pair of extracellular link domains. In one embodiment, the protein of the invention has at least one domain that is at least 55%, preferably at least about 65%, more preferably at least about 75%, yet more preferably at least about 85%, and most preferably at least about 95% identical to one of these domains. In other embodiments, the protein has at least one Ig-/MHC-like domain and one extracellular link domain described herein in Table IX. In other embodiments, the protein has at least one Ig-/MHC-like domain and at least two extracellular link domains.

Ig-/MHC-like domains are conserved among immunoglobulin (Ig) constant (CL) regions and one of the three extracellular domains of major histocompatibility proteins (MHC). The presence in TANGO 332 of an Ig-/MHC-like domain indicates that the corresponding region of TANGO 332 is structurally similar to this conserved extracellular region.

Extracellular link domains occur in hyaluronan- (HA-) binding proteins. Proteins having this domain include cartilage link protein, proteoglycans such as aggrecan, brevican, neurocan, and versican, CD44 antigen (the primary cell surface receptor for HA), and tumor necrosis factor-inducible protein TSG-6. Presence of a pair of extracellular link domains in TANGO 332 indicates that this protein is also involved in HA-binding, and therefore is involved in physiological processes such as cartilage (and other tissue) organization, extracellular matrix organization, neural growth and branching, and cell-to-cell and cell-to-matrix interactions. Involvement of TANGO 332 in these processes implicates this protein in disorders such as tumor growth and metastasis, movement of cells (e.g., leukocytes) through extracellular matrix, inappropriate inflammation, and the like.

Brevican is a murine nervous system-specific chondroitin sulfate proteoglycan which binds in a calcium-dependent manner with two classes of sulfated glycolipids, namely sulfatides and HNK-1-reactive sulfoglucuronylglycolipids (Miura et al. (1999) J. Biol. Chem. 274:11431–11438). A human orthologue, designated BEF ('Brain-Enriched hyaluronan-binding Factor'), of murine brevican is expressed by human glioma cells, but not by brain tumors of non-glial origin (P.C.T. application publication number WO98/31800; Zhang et al. (1998) J. Neurosci. 18:2370–2376). Those authors suggested that cleavage of that human orthologue mediates glioma cell invasion in vivo.

An alignment of the amino acid sequences of TANGO 332 and BEF protein is shown in FIGS. 7G and 7H. In this alignment (made using the ALIGN software {Myers and Miller (1989) CABIOS, ver. 2.0}; pam120.mat scoring matrix; gap opening penalty=12, gap extension penalty=4), the proteins are 75.7% identical, although it is seen that TANGO 332 includes two domains (one from about amino acid residue 152 to about residue 208, and the other near the carboxyl terminus of TANGO 332) which do not occur in BEF protein. It is likely that these two regions account for the differences between the physiological roles of TANGO 332 and BEF.

An alignment of the amino acid sequences of (human) TANGO 332 and murine brevican protein is shown in FIGS. 7I through 7K. In this alignment (made using the ALIGN software {Myers and Miller (1989) CABIOS, ver. 2.0}; pam120.mat scoring matrix; gap opening penalty=12, gap extension penalty=4), the proteins are 75.5% identical, although it is seen that murine brevican protein includes a domain which does not occur in TANGO 332 protein, this domain is present from about amino acid residue 626 to the carboxyl terminus of murine brevican protein. An alignment of the nucleotide sequences of the ORFs encoding (human) TANGO 332 and murine brevican protein is shown in FIGS. 7L through 7U. The two ORFs are 62.6% identical, as assessed using the same software and parameters.

TANGO 332 exhibits many of the same properties as BEF. TANGO 332 is also related to murine brevican protein, and thus is involved with corresponding physiological processes (i.e., such as those described above) in humans. For example, TANGO 332 modulates intracellular binding and migration of cells in a tissue or extracellular matrix. However, the absence from BEF of one of the two extracellular link domains present in TANGO 332 indicates that one or more of the subunit structure, the tissue specificity, and the binding specificity of TANGO 332 and BEF proteins differ. Thus, TANGO 332 is involved in many of the physiological processes and disorders in which BEF protein is involved. Like murine brevican and other proteoglycans, TANGO 332 acts in vivo as a tissue organizing protein, influences growth and maturation of tissues in which it is expressed, modulates growth factor-mediated activities, modulates structural features of tissues (e.g., collagen fibrillogenesis), modulates tumor cell growth and invasivity, and influences neurite growth and branching.

The signal peptide prediction program SIGNALP (Nielsen et al. (1997) Protein Engineering 10:1–6) predicted that human TANGO 332 protein includes an approximately 22 (i.e., 20, 21, 22, 23, or 24) amino acid residue signal peptide (amino acid residues 1 to 22 of SEQ ID NO: 61; SEQ ID NO: 62) preceding the mature TANGO 332 protein (i.e., approximately amino acid residues 23 to 671 of SEQ ID NO: 61; SEQ ID NO: 63). Human TANGO 332 protein is a secreted protein, as assessed using the secretion assay described herein. Secreted TANGO 332 proteins having approximate sizes of 148 kilodaltons and 100 kilodaltons could be detected using this assay.

Figure 7F:
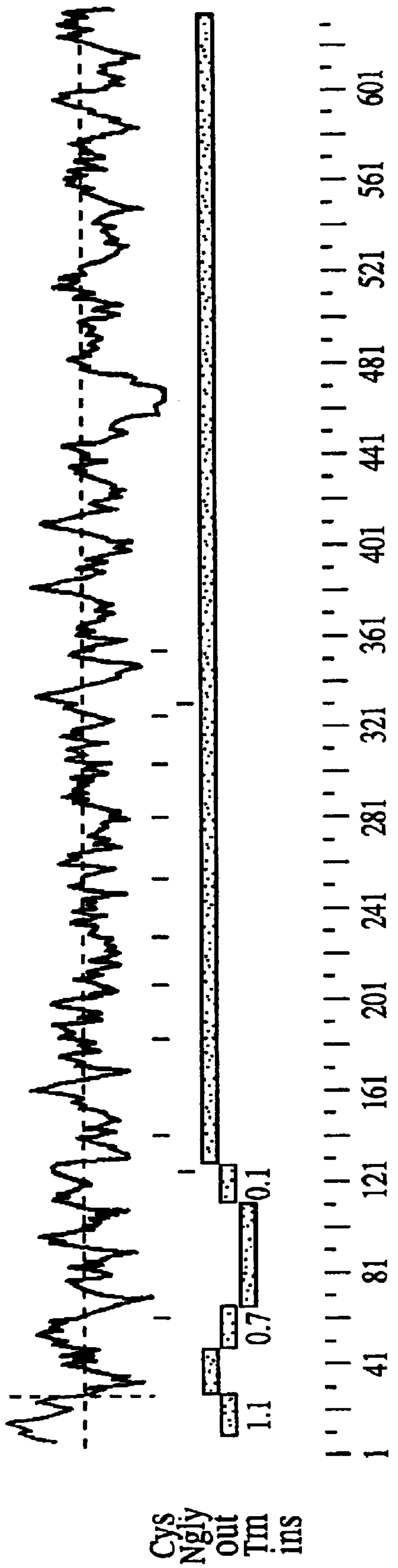
FIG. 7F is a hydrophilicity plot of TANGO 332 protein. An alignment of the amino acid sequences of TANGO 332 protein ("332"; SEQ ID NO: 61) and BEF protein ("BEF"; SEQ ID NO: 71) is shown in FIGS. 7G and 7H. An alignment of the amino acid sequences of human TANGO 332 protein ("H"; SEQ ID NO: 61) and murine brevidin protein ("M"; SEQ ID NO: 72) is shown in FIGS. 7I to 7K.

FIG. 7F depicts a hydrophilicity plot of human TANGO 332 protein. Relatively hydrophobic regions are above the dashed horizontal line, and relatively hydrophilic regions are below the dashed horizontal line. The hydrophobic region which corresponds to amino acid residues 1 to 22 of SEQ ID NO: 61 is the signal sequence of human TANGO 332 (SEQ ID NO: 62). As described elsewhere herein, relatively hydrophilic regions are generally located at or near the surface of a protein, and are more frequently effective immunogenic epitopes than are relatively hydrophobic regions. For example, the region of human TANGO 332 protein from about amino acid residue 445 to about amino acid residue 475 appears to be located at or near the surface of the protein, while the region from about amino acid residue 45 to about amino acid residue 62 appears not to be located at or near the surface.

The predicted molecular weight of human TANGO 332 protein without modification and prior to cleavage of the signal sequence is about 71.7 kilodaltons. The predicted molecular weight of the mature human TANGO 332 protein without modification and after cleavage of the signal sequence is about 69.5 kilodaltons.

Biological function of TANGO 332 proteins, nucleic acids encoding them, and modulators of these molecules TANGO 332 proteins are involved in disorders which affect both tissues in which they are normally expressed and tissues in which they are normally not expressed. Based on the observation that TANGO 332 is expressed in human adult brain tissue, TANGO 332 protein is involved in one or more biological processes which occur in these tissues. In particular, TANGO 332 is involved in modulating growth, proliferation, survival, differentiation, and activity of cells including, but not limited to, adult brain cells of the animal in which it is normally expressed. Thus, TANGO 332 has a role in disorders which affect these cells and their growth, proliferation, survival, differentiation, interaction, and activity. Examples of such disorders include, by way of example and not limitation, disorders of neural connection establishment or maintenance, impaired cognitive function, dementia, senility, Alzheimer's disease, mental retardation, brain tumors (e.g., gliomas such as astrocytomas, endophytic and exophytic retinoblastomas, ependymomas, gangliogliomas, mixed gliomas, nasal gliomas, optic gliomas, and Schwannomas, and other brain cell tumors such as medulloblastomas, pituitary adenomas, teratomas, etc.), and the like.

Homology of human TANGO 332 with murine brevican protein and with human brevican homolog BEF indicates that TANGO 332 has physiological functions in humans analogous to the functions of these proteins. Brevican is a member of the aggrecan/versican family of proteoglycans, and has a hyaluronic acid-binding domain in its amino terminal region and a lectin-like domain in its carboxyl terminal region. Expression of brevican is highly specific to brain tissue, and increases as the mammalian brain develops. Thus, brevican is involved in maintaining the extracellular environment of mature brain tissue and is a constituent of adult brain extracellular matrix. TANGO 332 is involved in modulating cell-to-cell adhesion, tissue and extracellular matrix invasivity of cells, and the like. Thus, TANGO 332 is involved in disorders in which these physiological processes are relevant. Such disorders include, for example, loss of control of cell growth, tumor metastasis, malformation of neurological connections, inflammation, immune and autoimmune responses, and the like.

In addition, presence in TANGO 332 of extracellular link domains indicates that this protein is involved in physiological processes involving structure and function of extracellular matrices and interaction of cells with such matrices and with each other. This is further evidence that TANGO 332 is involved in disorders such as inappropriate inflammation, tumor metastasis, inappropriate leukocyte extravasation, localization, and reactivity, and the like.

TANGO 332-related molecules can be used to modulate one or more of the activities in which TANGO 332 is involved and can also be used to prevent, diagnose, or treat one or more of the disorders in which TANGO 332 is involved.

Tables A and B summarize sequence data corresponding to the human proteins herein designated INTERCEPT 217, INTERCEPT 297, TANGO 276, TANGO 292, TANGO 325, TANGO 331, and TANGO 332.

TABLE A

| Protein | SEQ ID NOs | | | Depicted in | ATCC ® |
|---|---|---|---|---|---|
| Designation | cDNA | ORF | Protein | FIGURE # | Accession # |
| INTERCEPT 217 | 1 | 2 | 3 | 1 | PTA-147 |
| INTERCEPT 297 | 9 | 10 | 11 | 2 | PTA-147 |
| TANGO 276 | 33 | 34 | 35 | 3 | PTA-150 |
| TANGO 292 | 38 | 39 | 40 | 4 | 207230 |
| TANGO 325 | 46 | 47 | 48 | 5 | PTA-147 |
| TANGO 331 | 54 | 55 | 56 | 6 | PTA-147 |
| TANGO 332 | 59 | 60 | 61 | 7 | PTA-151 |

TABLE B

| Protein Desig. | Signal Sequence | | Mature Protein | | Extracellular Domain(s) | | Transmembrane Domain(s) | | Cytoplasmic Domain(s) | |
|---|---|---|---|---|---|---|---|---|---|---|
| | | | | | SEQ ID NOs | | | | | |
| INTERCEPT 217 | 1–20 | 4 | 21–455 | 5 | 21–383 | 6 | 384–403 | 7 | 404–455 | 8 |
| INTERCEPT 297 | (1–18) | (12) | 19–371 | 13 | 19–47 | 14 | (1–18) | (12) | 69–88 | 28 |
| | | | | | 110–118 | 15 | 48–68 | 19 | 138–144 | 29 |
| | | | | | 162–175 | 16 | 89–109 | 20 | 193–215 | 30 |
| | | | | | 234–260 | 17 | 119–137 | 21 | 284–292 | 31 |
| | | | | | 313–319 | 18 | 145–161 | 22 | 337–371 | 32 |
| | | | | | | | 176–192 | 23 | | |
| | | | | | | | 216–233 | 24 | | |
| | | | | | | | 261–283 | 25 | | |
| | | | | | | | 293–312 | 26 | | |
| | | | | | | | 320–336 | 27 | | |
| TANGO 276 | 1–20 | 36 | 21–243 | 37 | 21–243 | 37 | N/A | | N/A | |
| TANGO 292 | 1–17 | 41 | 18–226 | 42 | 18–113 | 43 | 114–138 | 44 | 139–226 | 45 |
| TANGO 325 | 1–31 | 49 | 32–622 | 50 | 32–529 | 51 | 530–547 | 52 | 548–622 | 53 |
| TANGO 331 | 1–24 | 57 | 25–353 | 58 | 25–353 | 58 | N/A | | N/A | |
| TANGO 332 | 1–22 | 62 | 23–671 | 63 | 23–671 | 63 | N/A | | N/A | |
| | | | | Amino Acid Residues | | | | | | |

Various aspects of the invention are described in further detail in the following subsections.

Isolated Nucleic Acid Molecules

One aspect of the invention pertains to isolated nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kilobases, 4 kilobases, 3 kilobases, 2 kilobases, 1 kilobases, 0.5 kilobases, or 0.1 kilobases of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of all or a portion of SEQ ID NO: 1, 2, 9, 10, 33, 34, 38, 39, 46, 47, 54, 55, 59, 60, 81, 82, and 92, or a complement thereof, or which has a nucleotide sequence comprising one of these sequences, can be isolated using standard molecular biology techniques and the sequence information provided herein. Using all or a portion of the nucleic acid sequences of SEQ ID NO: 1, 2, 9, 10, 33, 34, 38, 39, 46, 47, 54, 55, 59, 60, 81, 82, or 92 as a hybridization probe, nucleic acid molecules of the invention can be isolated using standard hybridization and cloning techniques (e.g., as described in Sambrook et al., eds., Molecular Cloning: A Laboratory Manual, 2nd ed., Cold Spring Harbor Laboratory, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of SEQ ID NO: 1, 2, 9, 10, 33, 34, 38, 39, 46, 47, 54, 55, 59, 60, 81, 82, or 92, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence encoding a full length polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and/or cloning homologs in other cell types, e.g., from other tissues, as well as homologs from other mammals. The probe/primer typically comprises substantially purified oligonucleotide. The oligonucleotide typically comprises a region of nucleotide sequence that hybridizes under stringent conditions to at least about 15, preferably about 25, more preferably about 50, 75, 100, 125, 150, 175, 200, 250, 300, 350, or 400 or more consecutive nucleotides of the sense or anti-sense sequence of one of any of SEQ ID NOs: 1, 2, 9, 10, 33, 34, 38, 39, 46, 47, 54, 55, 59, 60, 81, 82, and 92, or of a naturally occurring mutant of one of SEQ ID NO: 1, 2, 9, 10, 33, 34, 38, 39, 46, 47, 54, 55, 59, 60, 81, 82, and 92.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a biologically active portion of a polypeptide of the invention can be prepared by isolating a portion of one of SEQ ID NO: 2, 10, 34, 39, 47, 55, 60, 82, and 92, expressing the encoded portion of the polypeptide protein (e.g., by recombinant expression in vitro), and assessing the activity of the encoded portion of the polypeptide.

The invention further encompasses nucleic acid molecules that differ from the nucleotide sequence of SEQ ID NO: 1, 2, 9, 10, 33, 34, 38, 39, 46, 47, 54, 55, 59, 60, 81, 82, or 92 due to degeneracy of the genetic code and thus encode the same protein as that encoded by the nucleotide sequence of SEQ ID NO: 2, 10, 34, 39, 47, 55, 60, 82, or 92.

In addition to the nucleotide sequences of SEQ ID NOs: 2, 10, 34, 39, 47, 55, 60, 82, and 92, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus.

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologs), which have a nucleotide sequence which differs from that of the specific proteins described herein are intended to be within the scope of the invention. Nucleic acid molecules corresponding to natural allelic variants and homologs of a cDNA of the invention can be isolated based on their identity to human nucleic acid molecules using the cDNAs described herein, or a portion thereof, as a hybridization probe according to standard hybridization techniques under stringent hybridization conditions. For example, a cDNA encoding a soluble form of a membrane-bound protein of the invention isolated based on its hybridization to a nucleic acid molecule encoding all or part of the membrane-bound form. Likewise, a cDNA encoding a membrane-bound form can be isolated based on its hybridization to a nucleic acid molecule encoding all or part of the soluble form.

Accordingly, in another embodiment, an isolated nucleic acid molecule of the invention is at least 15 (25, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or 4928) nucleotides in length and hybridizes under stringent conditions to the nucleic acid molecule comprising the nucleotide sequence, preferably the coding sequence, of SEQ ID NO: 1, 2, 9, 10, 33, 34, 38, 39, 46, 47, 54, 55, 59, 60, 81, 82, or 92, or a complement thereof. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO: 1, 2, 9, 10, 33, 34, 38, 39, 46, 47, 54, 55, 59, 60, 81, 82, or 92, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a nucleic acid molecule of the invention sequence that can exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from SEQ ID NO: 3–8, 11–32, 35–37, 40–45, 48–53, 56–58, 61–63, 83–88, and 93–98, yet retain biological actitivity in one embodiment, the isolated nucleic acid molecule includes a nucleotide sequence encoding a protein that includes an amino acid sequence that is at least about 40% identical, 50%, 60%, 70%, 80%, 90%, 95%, or 98% identical to the amino acid sequence of one of SEQ ID NO: 3–8, 11–32, 35–37, 40–45, 48–53, 56–58, 61–63, 83–88, and 93–98.

An isolated nucleic acid molecule encoding a variant protein can be created by introducing one or more nucleotide substitutions, additions or deletions into the nucleotide sequence of SEQ ID NO: 1, 2, 9, 10, 33, 34, 38, 39, 46, 47, 54, 55, 59, 60, 81, 82, or 92, such that one or more amino acid residue substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In a preferred embodiment, a mutant polypeptide that is a variant of a polypeptide of the invention can be assayed for: (1) the ability to form protein:protein interactions with the polypeptide of the invention; (2) the ability to bind a ligand of the polypeptide of the invention (e.g., another protein identified herein); (3) the ability to bind to a modulator or substrate of the polypeptide of the invention; or (4) the ability to modulate a physiological activity of the protein, such as one of those disclosed herein.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' un-translated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N_6$-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al. (1987) Nucleic Acids Res.

15:6625–6641). The antisense nucleic acid molecule can also comprise a 2'-o-methylribonucleotide-(Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach (1988) Nature 334:585–591) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) Science 261:1411–1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) Anticancer Drug Des. 6(6):569–84; Helene (1992) Ann. N.Y. Acad. Sci. 660:27–36; and Maher (1992) Bioassays 14(12):807–15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. USA 93: 14670–675.

PNAs can be used in therapeutic and diagnostic applications. For example, PNAs can be used as antisense or anti-gene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) Proc. Natl. Acad. Sci. USA 93: 14670–675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) Nucleic Acids Res. 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) Nucleic Acids Res. 17:5973–88). PNA monomers are then coupled in a step-wise manner to produce a chimeric molecule with a 5' PNA segment and a 3' DNA segment (Finn et al. (1996) Nucleic Acids Res. 24(17):3357–63). Alternatively, chimeric molecules can be synthesized with a 5' DNA segment and a 3' PNA segment (Peterser et al. (1975) Bioorganic Med. Chem. Lett. 5:1119–11124).

In other embodiments, the oligonucleotide can include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide can be conjugated to another molecule, e.g., a peptide, hybridization triggered cross-linking agent, transport agent, hybridization-triggered cleavage agent, etc.

Isolated Proteins and Antibodies

One aspect of the invention pertains to isolated proteins, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence shown in any of SEQ ID NOs: 3–8, 11–32, 35–37, 40–45, 48–53, 56–58, 61–63, 83–88, and 93–98), which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of one of SEQ ID NOs: 3–8, 11–32, 35–37, 40–45, 48–53, 56–58, 61–63, 83–88, and 93–98. Other useful proteins are substantially identical (e.g., at least about 40%, preferably 50%, 60%, 70%, 80%, 90%, 95%, or 99%) to any of SEQ ID NO: 3–8, 11–32, 35–37, 40–45, 48–53, 56–58, 61–63, 83–88, and 93–98, and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264–2268, modified as in Karlin and Altschul (1993) Proc. Natl. Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389–3402. Alternatively, PSI-Blast can be used to perform an iterated search which detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) CABIOS 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides chimeric or fusion proteins. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which the polypeptide of the invention is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a polypeptide of the invention can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative and differentiative disorders and for modulating (e.g., promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention (e.g., the signal sequence in one of SEQ ID NO: 3, 4, 11, 12, 35, 36, 40, 41, 48, 49, 56, 57, 61, 62, 83, 84, 93, and 94) can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, the nucleic acids which flank the signal sequence on its amino-terminal side are likely regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence; Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, re-naturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811–7815; Delgrave et al. (1993) Protein Engineering 6(3):327–331).

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of SEQ ID NOs: 3–8, 11–32, 35–37, 40–45, 48–53, 56–58, 61–63, 83–88, and 93–98, and encompasses an epitope of the protein such that an antibody raised against the peptide forms a specific immune complex with the protein.

Preferred epitopes encompassed by the antigenic peptide are regions that are located on the surface of the protein, e.g., hydrophilic regions. FIGS. 1F, 1M, 2D 3E, 4E, 4M, 5F, 6D, and 7F are hydrophobicity plots of the proteins of the invention. These plots or similar analyses can be used to identify hydrophilic regions.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and $F(ab')_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. Preferred polyclonal antibody compositions are ones that have been selected for antibodies directed against (i.e., which bind specifically with) one or more polypeptides of the invention. Particularly preferred polyclonal antibody preparations are ones that contain only antibodies directed against one or more polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be harvested or isolated from the subject (e.g., from the blood or serum of the subject) and further purified by well-known techniques, such as protein A chromatography to obtain the IgG fraction. Alternatively, antibodies which bind specifically with a protein or polypeptide of the invention can be selected (e.g., partially purified) or purified using chromatographic methods, such as affinity chromatography. For example, a recombinantly expressed and purified (or partially purified) protein of the invention can be produced as described herein, and covalently or non-covalently coupled with a solid support such as, for example, a chromatography column. The column thus exhibits specific affinity for antibody substances which bind specifically with the protein of the invention, and these antibody substances can be purified from a sample containing antibody substances directed against a large number of different epitopes, thereby generating a substantially purified antibody substance composition, i.e., one that is substantially free of antibody substances which do not bind specifically with the protein. By a substantially purified antibody composition is meant, in this context, that the antibody sample contains at most only 30% (by dry weight) of contaminating antibodies directed against epitopes other than those on the desired protein or polypeptide of the invention, preferably at most 20%, more preferably at most 10%, most preferably at most 5% (by dry weight), of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol. Today 4:72), the EBV-hybridoma technique (Cole et al. (1985), Monoclonal Antibodies and Cancer Therapy, Alan R. Liss, Inc., pp. 77–96) or trioma techniques. The technology for producing hybridomas is well known (see generally Current Protocols in Immunology (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SURFZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372;

Hay et al. (1992) Hum. Antibod. Hybridomas 3:81–85; Huse et al. (1989) Science 246:1275–1281; Griffiths et al. (1993) EMBO J. 12:725–734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions of the antibody amino acid sequence are derived from different animal species, such as those having a variable region derived from a murine monoclonal antibody and a constant region derived from a human immunoglobulin. (See, e.g., Cabilly et al., U.S. Pat. No. 4,816,567; and Boss et al., U.S. Pat. No. 4,816,397). Humanized antibodies are antibody molecules which are obtained from non-human species, which have one or more complementarity-determining regions (CDRs) derived from the non-human species, and which have a framework region derived from a human immunoglobulin molecule. (See, e.g., Queen, U.S. Pat. No. 5,585,089). Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Cancer Res. 47:999–1005; Wood et al. (1985) Nature 314:446–449; and Shaw et al. (1988) J. Natl. Cancer Inst. 80:1553–1559); Morrison (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, Bio/technology 12:899–903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetyleholinesterase; examples of suitable prosthetic group complexes include streptavidinibiotin and avidinibiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Further, an antibody substance can be conjugated with a therapeutic moiety such as a cytotoxin, a therapeutic agent, or a radioactive metal ion. Cytotoxins and cytotoxic agents include any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, and analogs or homologs of these compounds. Therapeutic agents include, antimetabolites (e.g., methotrexate, 6-mercaptopurine, 6-thioguanine, cytarabine, 5-fluorouracil, and decarbazine), alkylating agents (e.g., mechlorethamine, thioepa chlorambucil, melphalan, carmustine {BSNU}, lomustine {CCNU}, cyclothosphamide, busulfan, dibromomannitol, streptozotocin, mitomycin C, and cis-dichlorodiamine platinum (II) (DDP) cisplatin), anthracyclines (e.g., daunorubicin {formerly daunomycin} and doxorubicin), antibiotics (e.g., dactinomycin {formerly actinomycin}, bleomycin, mithramycin, and anthramycin {AMC}), and anti-mitotic agents (e.g., vincristine and vinblastine).

The conjugates of the invention can be used to modify a biological response; the drug moiety is not to be construed as limited to classical chemical therapeutic agents. For example, the drug moiety can be a protein or polypeptide which exhibits a desired biological activity. Such proteins include, for example, toxins such as abrin, ricin A, pseudomonas exotoxin, or diphtheria toxin; proteins such as tumor necrosis factor, alpha-interferon, beta-interferon, nerve growth factor, platelet derived growth factor, tissue plasminogen activator; and biological response modifiers such as lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), and other growth factors.

Techniques for conjugating a therapeutic moiety with an antibody substance are well known (see, e.g., Amon et al., "Monoclonal Antibodies For Immunotargeting Of Drugs In Cancer Therapy", in Monoclonal Antibodies and Cancer Therapy, Reisfeld et al., eds., pp. 243–256, Alan R. Liss, Inc., 1985; Hellstrom et al., "Antibodies For Drug Delivery", in Controlled Drug Delivery, 2nd Ed., Robinson et al., eds., pp. 623–653, Marcel Dekker, Inc., 1987; Thorpe, "Antibody Carriers Of Cytotoxic Agents In Cancer Therapy: A Review", in Monoclonal Antibodies '84: Biological and Clinical Applications, Pinchera et al., eds., pp. 475–506, 1985; "Analysis, Results, And Future Prospective Of The Therapeutic Use Of Radiolabeled Antibody In Cancer Therapy", in Monoclonal Antibodies for Cancer Detection and Therapy, Baldwin et al., eds., pp. 303–316, Academic Press, 1985; and Thorpe et al., "The Preparation And Cytotoxic Properties Of Antibody-Toxin Conjugates", Immunol. Rev. 62:119–58, 1982). Alternatively, an antibody can be conjugated with a second antibody to form an antibody heteroconjugate as described by Segal in U.S. Pat. No. 4,676,980.

Accordingly, in one aspect, the invention provides substantially purified antibodies or fragment thereof, and non-human antibodies or fragments thereof, which antibodies or fragments specifically bind with a polypeptide having an amino acid sequence which comprises a sequence selected from the group consisting of (i) SEQ ID NOs: 3–8, 11–32, 35–37, 40–45, 48–53, 56–58, 61–63, 83–88, and 93–

(ii) the amino acid sequence encoded by a cDNA of a clone deposited as ATCC® PTA-147, PTA-150, 207230, or PTA-151;

(iii) a fragment of at least 15 amino acid residues of the amino acid sequence of SEQ ID NO: 3–8, 11–32, 35–37, 40–45, 48–53, 56–58, 61–63, 83–88, or 93–98;

(iv) an amino acid sequence which is at least 95% identical to the amino acid sequence of SEQ ID NO: 3–8, 11–32, 35–37, 40–45, 48–53, 56–58, 61–63, 83–88, or 93–98, percent identity is determined using the ALIGN program of the GCG software package with a PAM120 weight residue table, a gap length penalty of 12, and a gap penalty of 4; and (v) an amino acid sequence which is encoded by a nucleic acid molecule, the complement of which hybridizes with a nucleic acid molecule having the sequence of SEQ ID NO: 1, 2, 9, 10, 33, 34, 38, 39, 46, 47, 54, 55, 59, 60, 81, 82, or 92, or with a cDNA of a clone deposited as ATCC® PTA-147, PTA-150, 207230, or PTA-151, under conditions of hybridization of 6×SSC (standard saline citrate buffer) at 45° C. and washing in 0.2×SSC, 0.1% SDS at 65° C.

In another aspect, the invention provides non-human antibodies or fragments thereof, which antibodies or fragments specifically bind with a polypeptide having an amino acid sequence which comprises a sequence selected from the group consisting of:

(i) SEQ ID NOs: 3–8, 11–32, 35–37, 40–45, 48–53, 56–58, 61–63, 83–88, and 93–98;

(ii) the amino acid sequence encoded by a cDNA of a clone deposited as ATCC® PTA-147, PTA-150, 207230, or PTA-151;

(iii) a fragment of at least 15 amino acid residues of the amino acid sequence of SEQ ID NO: 3–8, 11–32, 35–37, 40–45, 48–53, 56–58, 61–63, 83–88, or 93–98;

(iv) an amino acid sequence which is at least 95% identical to the amino acid sequence of SEQ ID NO: 3–8, 11–32, 35–37, 40–45, 48–53, 56–58, 61–63, 83–88, or 93–98, wherein the percent identity is determined using the ALIGN program of the GCG software package with a PAM120 weight residue table, a gap length penalty of 12, and a gap penalty of 4; and (v) an amino acid sequence which is encoded by a nucleic acid molecule, the complement of which hybridizes with a nucleic acid molecule having the sequence of SEQ ID NO: 1, 2, 9, 10, 33, 34, 38, 39, 46, 47, 54, 55, 59, 60, 81, 82, or 92, or with a cDNA of a clone deposited as ATCC® PTA-147, PTA-150, 207230, or PTA-151, under conditions of hybridization of 6× SSC (standard saline citrate buffer) at 45° C. and washing in 0.2×SSC, 0.1% SDS at 65° C. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind with a polypeptide having an amino acid sequence which comprises a sequence selected from the group consisting of:

(i) SEQ ID NOs: 3–8, 11–32, 35–37, 40–45, 48–53, 56–58, 61–63, 83–88, and 93–98;

(ii) the amino acid sequence encoded by a cDNA of a clone deposited as ATCC® PTA-147, PTA-150, 207230, or PTA-151;

(iii) a fragment of at least 15 amino acid residues of the amino acid sequence of SEQ ID NO: 3–8, 11–32, 35–37, 40–45, 48–53, 56–58, 61–63, 83–88, or 93–98;

(iv) an amino acid sequence which is at least 95% identical to the amino acid sequence of SEQ ID NO: 3–8, 11–32, 35–37, 40–45, 48–53, 56–58, 61–63, 83–88, or 93–98, percent identity is determined using the ALIGN program of the GCG software package with a PAM120 weight residue table, a gap length penalty of 12, and a gap penalty of 4; and (v) an amino acid sequence which is encoded by a nucleic acid molecule, the complement of which hybridizes with a nucleic acid molecule having the sequence of SEQ ID NO: 1, 2, 9, 10, 33, 34, 38, 39, 46, 47, 54, 55, 59, 60, 81, 82, or 92, or with a cDNA of a clone deposited as ATCC® PTA-147, PTA-150, 207230, or PTA-151, under conditions of hybridization of 6× SSC (standard saline citrate buffer) at 45° C. and washing in 0.2×SSC, 0.1% SDS at 65° C. The monoclonal antibodies can be human, humanized, chimeric and/or non-human antibodies.

The substantially purified antibodies or fragments thereof can specifically bind with a signal peptide, a secreted sequence, an extracellular domain, a transmembrane or a cytoplasmic domain cytoplasmic membrane of a polypeptide of the invention. In a particularly preferred embodiment, the substantially purified antibodies or fragments thereof, the non-human antibodies or fragments thereof, and/or the monoclonal antibodies or fragments thereof, of the invention specifically bind with a secreted sequence or with an extracellular domain of one of INTERCEPT 217, INTERCEPT 297, TANGO 276, TANGO 292, TANGO 325, TANGO 331, and TANGO 332. Preferably, the extracellular domain with which the antibody substance binds has an amino acid sequence selected from the group consisting of SEQ ID NOs: 6, 14–18, 37, 43, 51, 58, or 63.

Any of the antibody substances of the invention can be conjugated with a therapeutic moiety or to a detectable substance. Non-limiting examples of detectable substances that can be conjugated with the antibody substances of the invention include an enzyme, a prosthetic group, a fluorescent material (i.e., a fluorophore), a luminescent material, a bioluminescent material, and a radioactive material (e.g., a radionuclide or a substituent comprising a radionuclide).

The invention also provides a kit containing an antibody substance of the invention conjugated with a detectable substance, and instructions for use. Still another aspect of the invention is a pharmaceutical composition comprising an antibody substance of the invention and a pharmaceutically acceptable carrier. In preferred embodiments, the pharmaceutical composition contains an antibody substance of the invention, a therapeutic moiety (preferably conjugated with the antibody substance), and a pharmaceutically acceptable carrier.

Still another aspect of the invention is a method of making an antibody that specifically recognizes one of INTERCEPT 217, INTERCEPT 297, TANGO 276, TANGO 292, TANGO 325, TANGO 331, and TANGO 332. This method comprises immunizing a vertebrate (e.g., a mammal such as a rabbit, goat, or pig) with a polypeptide. The polypeptide used as an immunogen has an amino acid sequence that comprises a sequence selected from the group consisting of:

(i) SEQ ID NOs: 3–8, 11–32, 35–37, 40–45, 48–53, 56–58, 61–63, 83–88, and 93–98;

(ii) the amino acid sequence encoded by a cDNA of a clone deposited as ATCC® PTA-147, PTA-150, 207230, or PTA-151;

(iii) a fragment of at least 15 amino acid residues of the amino acid sequence of SEQ ID NO: 3–8, 11–32, 35–37, 40–45, 48–53, 56–58, 61–63, 83–88, or 93–98;

(iv) an amino acid sequence which is at least 95% identical to the amino acid sequence of SEQ ID NO: 3–8, 11–32, 35–37, 40–45, 48–53, 56–58, 61–63, 83–88, or 93–98, wherein the percent identity is determined using the ALIGN program of the GCG software package with a PAM120 weight residue table, a gap length penalty of 12, and a gap penalty of 4; and (v) an amino acid sequence which is encoded by a nucleic acid molecule, the complement of which hybridizes with a nucleic acid molecule having the sequence of SEQ ID NO: 1, 2, 9, 10, 33, 34, 38, 39, 46, 47, 54, 55, 59, 60, 81, 82, or 92, or with a cDNA of a clone deposited as ATCC® PTA-147, PTA-150, 207230, or PTA-151, under conditions of hybridization of 6× SSC (standard saline citrate buffer) at 45° C. and washing in 0.2× SSC, 0.1% SDS at 65° C.

After immunization, a sample is collected from the vertebrate that contains an antibody that specifically recognizes the polypeptide with which the vertebrate was immunized. Preferably, the polypeptide is recombinantly produced using a non-human host cell. Optionally, an antibody substance can be further purified from the sample using techniques well known to those of skill in the art. The method can further comprise making a monoclonal antibody-producing cell from a cell of the vertebrate. Optionally, antibodies can be collected from the antibody-producing cell.

Recombinant Expression Vectors and Host Cells

Another aspect of the invention pertains to vectors, preferably expression vectors, containing a nucleic acid encoding a polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) Gene 69:301–315) and pET 1d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident lambda prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) Nucleic Acids Res. 20:2111–2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374–379) and the alpha-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous nucleic acid within a cell, cell line, or microorganism (e.g., a INTERCEPT 217, INTERCEPT 297, TANGO 276, TANGO 292, TANGO 325, TANGO 331, or TANGO 332 nucleic acid, as described herein) can be modified by inserting a heterologous DNA regulatory element (i.e., one that is heterologous with respect to the endogenous gene) into the genome of the cell, stable cell line, or cloned microorganism. The inserted regulatory element can be operatively linked with the endogenous gene (e.g., INTERCEPT 217, INTERCEPT 297, TANGO 276, TANGO 292, TANGO 325, TANGO 331, or TANGO 332) and thereby control, modulate, or activate the endogenous gene. For example, an endogenous INTERCEPT 217, INTERCEPT 297, TANGO 276, TANGO 292, TANGO 325, TANGO 331, or TANGO 332 gene which is normally "transcriptionally silent" (i.e., a INTERCEPT 217, INTERCEPT 297, TANGO 276, TANGO 292, TANGO 325, TANGO 331, or TANGO 332 gene which is normally not expressed, or is normally expressed only at only a very low level) can be activated by inserting a regulatory element which is capable of promoting expression of the gene in the cell, cell line, or microorganism. Alternatively, a transcriptionally silent, endogenous INTERCEPT 217, INTERCEPT 297, TANGO 276, TANGO 292, TANGO 325, TANGO 331, or TANGO 332 gene can be activated by inserting a promiscuous regulatory element that works across cell types.

A heterologous regulatory element can be inserted into a stable cell line or cloned microorganism such that it is operatively linked with and activates expression of an endogenous INTERCEPT 217, INTERCEPT 297, TANGO 276, TANGO 292, TANGO 325, TANGO 331, or TANGO 332 gene, using techniques, such as targeted homologous recombination, which are well known to those of skill in the art (described e.g., in Chappel, U.S. Pat. No. 5,272,071; PCT publication No. WO 91/06667, published May 16, 1991).

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce non-human transgenic animals. For example, in one embodiment, a host cell of the invention is a fertilized oocyte or an embryonic stem cell into which a sequences encoding a polypeptide of the invention have been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986), and in Wakayama et al., 1999, Proc. Natl. Acad. Sci. USA 96:14984–14989. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create a homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of *Saccharomyces cerevisiae* (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication NOS. WO 97/07668 and WO 97/07669.

Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

The agent which modulates expression or activity can, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents and protein or polypeptide agents depends upon a number of factors within the ken of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g., about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having one or more monoclonal antibodies incorporated therein or thereon; e.g., liposomes comprising a monoclonal antibody which binds specifically with a virus antigen) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Uses and Methods of the Invention

The nucleic acid molecules, proteins, protein homologs, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). For example, polypeptides of the invention can to used for all of the purposes identified herein in portions of the disclosure relating to individual types of protein of the invention (e.g., INTERCEPT 217 proteins, INTERCEPT 297 proteins, TANGO 276 proteins, TANGO 292 proteins, TANGO 325 proteins, TANGO 331 proteins, and TANGO 332 proteins). The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the and modulate activity of a protein of the invention.

This invention further pertains to novel agents identified by the above-described screening assays and uses thereof for treatments as described herein.

Screening Assays

The invention provides a method (also referred to herein as a "screening assay") for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds can be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865–1869) or phage (Scott and Smith (1990) Science 249:386–390; Devlin (1990) Science 249:404–406; Cwirla et al. (1990) Proc. Natl. Acad. Sci. USA 87:6378–6382; and Felici (1991) J. Mol. Biol. 222:301–310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radio-emission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, the assay involves assessment of an activity characteristic of the polypeptide, wherein binding of the test compound with the polypeptide or a biologically active portion thereof alters (i.e., increases or decreases) the activity of the polypeptide.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide to bind to or interact with a target molecule or to transport molecules across the cytoplasmic membrane.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., an mRNA, intracellular $Ca^{2+}$, diacylglycerol, IP3, and the like), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic activity, the enzymatic activity, or both, of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it can be desirable to utilize a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methylglucamide; decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl) dimethyl ammonio]-2-hydroxy-1-propane sulfonate (CHAPSO), or N-dodecyl-N,N-dimethyl-3-ammonio-1-propane sulfonate.

In one or more embodiments of the above assay methods of the present invention, it can be desirable to immobilize either the polypeptide of the invention or its target molecule to facilitate separation of complexed from non-complexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione Sepharose beads (Sigma Chemical; St. Louis, Mo.) or glutathione derivatized microtiter plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (i.e., statistically significantly greater) in the presence of the candidate compound than in its absence, the candidate compound is identified as a stimulator of the selected mRNA or protein expression. Alternatively, when expression of the selected mRNA or protein is less (i.e., statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15–25 base pairs in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al. ((1983) Science 220:919–924).

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sub-localization can be achieved with panels of fragments from specific chromosomes. Other mapping strategies which can similarly be used to map a gene to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries. Fluorescence in situ hybridization (FISH) of a DNA sequence to a metaphase chromosomal spread can further be used to provide a precise chromosomal location in one step. For a review of this technique, see Verma et al. (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to non-coding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature 325:783–787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Furthermore, the nucleic acid sequences disclosed herein can be used to perform searches against "mapping databases", e.g., BLAST-type search, such that the chromosome position of the gene is identified by sequence homology or identity with known sequence fragments which have been mapped to chromosomes.

A polypeptide and fragments and sequences thereof and antibodies which bind specifically with such polypeptides/fragments can be used to map the location of the gene encoding the polypeptide on a chromosome. This mapping can be performed by specifically detecting the presence of the polypeptide/fragments in members of a panel of somatic cell hybrids between cells obtained from a first species of animal from which the protein originates and cells obtained from a second species of animal, determining which somatic cell hybrid(s) expresses the polypeptide, and noting the chromosome(s) of the first species of animal that it contains. For examples of this technique (see Pajunen et al., 1988, Cytogenet. Cell Genet. 47:37–41 and Van Keuren et al., 1986, Hum. Genet. 74:34–40). Alternatively, the presence of the polypeptide in the somatic cell hybrids can be determined by assaying an activity or property of the polypeptide (e.g., enzymatic activity, as described in Bordelon-Riser et al., 1979, Som. Cell Genet. 5:597–613 and Owerbach et al., 1978, Proc. Natl. Acad. Sci. USA 75:5640–5644).

Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the non-coding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the non-coding regions, fewer sequences are necessary to differentiate individuals. The non-coding sequences of SEQ ID NO: 1, 9, 33, 38, 46, 54, 59, and 81 can comfortably provide positive individual identification with a panel of perhaps 10 to 1,000 primers which each yield a non-coding amplified sequence of 100 bases. If predicted coding sequences, such as those in SEQ ID NO: 2, 10, 34, 39, 47, 55, 60, 82, and 92 are used, a more appropriate number of primers for positive individual identification would be 500–2,000.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

Use of Partial Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to non-coding regions are particularly appropriate for this use as greater numbers of polymorphisms occur in the non-coding regions, making it easier to differentiate individuals using this technique. Examples of polynucleotide reagents include the nucleic acid sequences of the invention or portions thereof, e.g., fragments derived from non-coding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining expression of a polypeptide or nucleic acid of the invention and/or activity of a polypeptide of the invention, in the context of a biological sample (e.g., blood, serum, cells, tissue) to thereby determine whether an individual is afflicted with a disease or disorder, or is at risk of developing a disorder, associated with aberrant expression or activity of a polypeptide of the invention. The invention also provides for prognostic (or predictive) assays for determining whether an individual is at risk of developing a disorder associated with aberrant expression or activity of a polypeptide of the invention. For example, mutations in a gene of the invention can be assayed in a biological sample. Such assays can be used for prognostic or predictive purpose to thereby prophylactically treat an individual prior to the onset of a disorder characterized by or associated with aberrant expression or activity of a polypeptide of the invention.

As an alternative to making determinations based on the absolute expression level of a selected gene, determinations can be based on normalized expression levels of the gene. A gene expression level is normalized by correcting the absolute expression level of the gene (e.g., an INTERCEPT 217, INTERCEPT 297, TANGO 276, TANGO 292, TANGO 325, TANGO 331, or TANGO 332 gene as described herein) by comparing its expression to expression of a gene for which expression is not believed to be co-regulated with the gene of interest, e.g., a housekeeping gene that is constitutively expressed. Suitable genes for normalization include housekeeping genes such as the actin gene. Such normalization allows comparison of the expression level in one sample, e.g., a patient sample, with the expression level in another sample, e.g., a sample obtained from a patient known not to be afflicted with a disease or condition, or between samples obtained from different sources.

Alternatively, the expression level can be assessed as a relative expression level. To assess a relative expression level for a gene (e.g., an INTERCEPT 217, INTERCEPT 297, TANGO 276, TANGO 292, TANGO 325, TANGO 331, or TANGO 332 gene, as described herein), the level of expression of the gene is determined for 10 or more samples (preferably 50 or more samples) of different isolates of cells in which the gene is believed to be expressed, prior to assessing the level of expression of the gene in the sample of interest. The mean expression level of the gene detected in the large number of samples is determined, and this value is used as a baseline expression level for the gene. The expression level of the gene assessed in the test sample (i.e., its absolute level of expression) is divided by the mean expression value to yield a relative expression level. Such a method can identify tissues or individuals which are afflicted with a disorder associated with aberrant expression of a gene of the invention.

Preferably, the samples used in the baseline determination are generated either using cells obtained from a tissue or individual known to be afflicted with a disorder (e.g., a disorder associated with aberrant expression of one of the INTERCEPT 217, INTERCEPT 297, TANGO 276, TANGO 292, TANGO 325, TANGO 331, or TANGO 332 genes) or using cells obtained from a tissue or individual known not to be afflicted with the disorder. Alternatively, levels of expression of these genes in tissues or individuals known to be or not to be afflicted with the disorder can be used to assess whether the aberrant expression of the gene is associated with the disorder (e.g., with onset of the disorder, or as a symptom of the disorder over time).

Another aspect of the invention provides methods for expression of a nucleic acid or polypeptide of the invention or activity of a polypeptide of the invention in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of a polypeptide of the invention in clinical trials. These and other agents are described in further detail in the following sections.

Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO: 1, 9, 33, 38, 46, 54, 59, 62, or 81, or a portion thereof, such as an oligonucleotide of at least 15, 30, 50, 100, 250 or 500 nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention (e.g., one of the disorders described in the section of this disclosure wherein the individual polypeptide of the invention is discussed). For example, the kit can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

Prognostic Assays

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention (e.g., one of the disorders described in the section of this disclosure wherein the individual polypeptide of the invention is discussed). Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in a gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. PCR and/or LCR can be desirable to use as a preliminary amplification step in conjunction with any of the techniques used for detecting mutations described herein.

Alternative amplification methods include: self-sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, (optionally) amplified, digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in a selected gene include methods in which protection from cleavage agents is used to detect mismatched bases in RNA/RNA or RNA/DNA heteroduplexes (Myers et al. (1985) Science 230:1242). In general, the technique of mismatch cleavage entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) Proc. Natl. Acad. Sci. USA 85:4397; Saleeba et al. (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called DNA mismatch repair enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) can be used to detect differences in electrophoretic mobility between mutant and wild type nucleic acids (Orita et al. (1989) Proc. Natl. Acad. Sci. USA 86:2766; see also Cotton (1993) Mutat. Res. 285:125–144; Hayashi (1992) Genet. Anal. Tech. Appl. 9:73–79). Single-stranded DNA fragments of sample and control nucleic acids will be denatured and allowed to re-nature. The secondary structure of single-stranded nucleic acids varies according to sequence, and the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a 'GC clamp' of approximately 40 base pairs of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers can be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization; Gibbs et al. (1989) Nucleic Acids Res. 17:2437–2448) or at the extreme 3' end of one primer where, under appropriate conditions, mismatching can prevent or reduce polymerase extension (Prossner (1993) Tibtech 11:238). In addition, it can be desirable to introduce a novel restriction site in the region of the mutation to create cleavage-based detection (Gasparini et al. (1992) Mol. Cell Probes 6:1). Amplification can also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

The methods described herein can be performed, for example, using pre-packaged diagnostic kits comprising at least one probe nucleic acid or antibody reagent described herein, which can be conveniently used, e.g., in clinical settings to diagnose patients exhibiting symptoms or family history of a disease or illness involving a gene encoding a polypeptide of the invention. Furthermore, any cell type or tissue, preferably peripheral blood leukocytes, in which the polypeptide of the invention is expressed can be utilized in the prognostic assays described herein.

Pharmacogenomics

Agents, or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses.

If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

Monitoring of Effects during Clinical Trials

Monitoring the influence of agents (e.g., drug compounds) on the expression or activity of a polypeptide of the invention (e.g., the ability to modulate aberrant cell proliferation chemotaxis, and/or differentiation) can be applied not only in basic drug screening, but also in clinical trials. For example, the effectiveness of an agent, as determined by a screening assay as described herein, to increase gene expression, protein levels, or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state can be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the pre-administration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent can be desirable to increase the expression or activity of the polypeptide to higher levels than detected, i.e., to increase the effectiveness of the agent. Alternatively, decreased administration of the agent can be desirable to decrease expression or activity of the polypeptide to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant expression or activity of a polypeptide of the invention and/or in which the polypeptide of the invention is involved. Disorders characterized by aberrant expression or activity of the polypeptides of the invention are described elsewhere in this disclosure.

Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrance, such that a disease or disorder is prevented or, alternatively, delayed in its progression. Depending on the type of aberrance, for example, an agonist or antagonist agent can be used for treating the subject. The appropriate agent can be determined based on screening assays described herein.

Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention.

Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., up-regulates or down-regulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or down-regulated and/or in which increased activity is likely to have a beneficial effect, e.g., in wound healing. Conversely, inhibition of activity is desirable in situations in which activity or expression is abnormally high or up-regulated and/or in which decreased activity is likely to have a beneficial effect.

The contents of all references, patents, and published patent applications cited throughout this application are hereby incorporated by reference.

Deposits of Clones

Clones encoding the proteins of the invention were deposited with the American Type Culture Collection (ATCC®, 10801 University Boulevard, Manassas, Va. 20110–2209) on Apr. 27, 1999 and May 27, 1999. These deposits will be maintained under the terms of the Budapest Treaty on the International Recognition of the Deposit of Microorganisms for the Purposes of Patent Procedure. Each of these deposits was made merely as a convenience to those of skill in the art. These deposits are not an admission that a deposit is required under 35 U.S.C. §112.

Clones comprising cDNA molecules encoding human INTERCEPT 217, human INTERCEPT 297, human TANGO 325, and human TANGO 331 were deposited with ATCC® on May 28, 1999, as part of a composite deposit representing a mixture of five strains, each carrying one recombinant plasmid harboring a particular cDNA clone. This deposit was assigned Accession Number PTA-147

To distinguish the strains and isolate a strain harboring a particular cDNA clone, an aliquot of the mixture is streaked out to single colonies on nutrient medium (e.g., Luria broth plates) supplemented with 100 micrograms per milliliter ampicillin, single colonies grown, and then plasmid DNA is extracted using a standard mini-preparation procedure. Next, a sample of the DNA mini-preparation is digested using a combination of the restriction enzymes SalI, NotI, and SmaI, and the resultant products are resolved on a 0.8% agarose gel using standard DNA electrophoresis conditions. The digest liberates fragments as follows:

1. human INTERCEPT 217 (clone EpT217): 2.9 kilobases
2. human INTERCEPT 297 (clone EpT297): 1.2 kilobases and 0.3 kilobases (human INTERCEPT 297 has a SmaI cut site at about base pair 1183).
3. human TANGO 325 (clone EpT325): 2.2 kilobases
4. human TANGO 331 (clone EpT331): 1.4 kilobases The identity of the strains can be inferred from the fragments liberated.

Human TANGO 276, human TANGO 292, and human TANGO 332 were each deposited as single deposits. Their clone names, deposit dates, and accession numbers are as follows:

1. human TANGO 276: clone EpT276 was deposited with ATCC® on May 28, 1999, and was assigned Accession Number PTA-150.
2. human TANGO 292: clone EpT292 was deposited with ATCC® on Apr. 28, 1999, and was assigned Accession Number 207230.
3. human TANGO 332: clone EpT332 was deposited with ATCC® on May 28, 1999, and was assigned Accession Number PTA-151.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polypeptide selected from the group consisting of:

a) a fragment of a polypeptide comprising the amino acid sequence of SEQ ID NO: 61, SEQ ID NO: 63, or the amino acid sequence encoded by the cDNA clone deposited with ATCC® as Accession number PTA-151, wherein the fragment comprises at least 200 contiguous amino acid residues of SEQ ID NO: 61, SEQ ID NO: 63, or the amino acid sequence encoded by the cDNA clone;

b) a polypeptide comprising an amino acid sequence which has at least 95% sequence identity to SEQ ID NO: 61, SEQ ID NO: 63, or the amino acid sequence encoded by the cDNA clone deposited with ATCC® as Accession number PTA-151; and c) a polypeptide which is encoded by a nucleic acid molecule comprising a nucleotide sequence which has at least 95% sequence identity to SEQ ID NO: 59, SEQ ID NO: 60, or the nucleotide sequence of the cDNA clone deposited with ATCC® as Accession number PTA-151;

wherein the polypeptide or fragment thereof has the ability to:

i) bind to hyaluronic acid;

ii) bind to extracellular matrix;

iii) bind to neural cells; or iv) bind to brain cells.

2. The isolated polypeptide of claim 1, wherein the polypeptide is a fragment of a polypeptide comprising the amino acid sequence of SEQ ID NO: 61, SEQ ID NO: 63, or the amino acid sequence encoded by the cDNA clone deposited with ATCC® as Accession number PTA-151, wherein the fragment comprises at least 200 contiguous amino acid residues of SEQ ID NO: 61, SEQ ID NO: 63, or the amino acid sequence encoded by the cDNA clone.

3. The isolated polypeptide of claim 1, wherein the polypeptide comprises the amino acid sequence of SEQ ID NO: 61, SEQ ID NO: 63, or the amino acid sequence encoded by a cDNA clone deposited with ATCC® as Accession number PTA-151.

4. The isolated polypeptide of claim 1, wherein the polypeptide comprises the amino acid sequence of SEQ ID NO: 61.

5. The isolated polypeptide of claim 1, wherein the polypeptide comprises the amino acid sequence of SEQ ID NO: 63.

6. The isolated polypeptide of claim 1, wherein the polypeptide is a polypeptide comprising an amino acid sequence which has at least 95% sequence identity to SEQ ID NO: 61, SEQ ID NO: 63, or the amino acid sequence encoded by the cDNA clone deposited with ATCC® as Accession number PTA-151.

7. The isolated polypeptide of claim 6, wherein the polypeptide comprises an amino acid sequence which has at least 98% sequence identity to SEQ ID NO: 61, SEQ ID NO: 63, or the amino acid sequence encoded by the cDNA clone deposited with ATCC® as Accession number PTA-151.

8. The isolated polypeptide of claim 1, wherein the polypeptide is encoded by a nucleic acid molecule comprising a nucleotide sequence which has at least 95% sequence identity to SEQ ID NO: 59, SEQ ID NO: 60, or the nucleotide sequence of the cDNA clone deposited with ATCC® as Accession number PTA-151.

9. The isolated polypeptide of claim 8, wherein the polypeptide is encoded by a nucleic acid molecule comprising a nucleotide sequence which has at least 98% sequence identity to SEQ ID NO: 59, SEQ ID NO: 60, or the nucleotide sequence of the cDNA clone deposited with ATCC® as Accession number PTA-151.

10. The isolated polypeptide of claim 9, wherein the polypeptide is encoded by a nucleic acid molecule comprising a nucleotide sequence comprising SEQ ID NO: 59, SEQ ID NO: 60, or the nucleotide sequence of the cDNA clone deposited with ATCC® as Accession number PTA-151.

11. The polypeptide of claim 1, wherein the amino acid sequence of the polypeptide further comprises heterologous amino acid residues.

12. The isolated polypeptide of claim 1, wherein the brain cells are glial cells.

13. The isolated polypeptide of claim 12, wherein the glial cells are cells of a glioma.

14. The isolated polypeptide of claim 13, wherein the glioma is selected from the group consisting of an astrocytoma, an endophytic retinoblastoma, an exophytic retinoblastoma, an ependymoma, a ganglioglioma, a nasal glioma, an optic glioma, a Schwannoma, and a mixed glioma.

15. A kit comprising a compound which selectively binds with a polypeptide of claim 1 and instructions for use.

* * * * *